(12) United States Patent
Suhy et al.

(10) Patent No.: US 12,060,613 B2
(45) Date of Patent: Aug. 13, 2024

(54) METHODS AND COMPOSITIONS FOR SYNTHETIC BIOMARKERS

(71) Applicant: EARLI Inc., South San Francisco, CA (US)

(72) Inventors: David Suhy, San Ramon, CA (US); Paul Escarpe, San Ramon, CA (US); Cyriac Roeding, Portola Valley, CA (US); Justin Lin, Simi Valley, CA (US); Alex Harwig, South San Francisco, CA (US); Shireen Rudina, South San Francisco, CA (US); Leland Harrison Hartwell, Seattle, WA (US)

(73) Assignee: EARLI Inc., South San Francisco, CA (US)

( * ) Notice: Subject to any disclaimer, the term of this patent is extended or adjusted under 35 U.S.C. 154(b) by 0 days.

(21) Appl. No.: 17/219,666

(22) Filed: Mar. 31, 2021

(65) Prior Publication Data

US 2021/0277474 A1    Sep. 9, 2021

Related U.S. Application Data

(63) Continuation-in-part of application No. PCT/US2020/026758, filed on Apr. 4, 2020.
(Continued)

(51) Int. Cl.
*C12Q 1/68* (2018.01)
*C12Q 1/28* (2006.01)
(Continued)

(52) U.S. Cl.
CPC ............ *C12Q 1/6883* (2013.01); *C12Q 1/28* (2013.01); *C12Q 1/42* (2013.01); *C12Q 1/66* (2013.01); *C12Q 1/6886* (2013.01); *C12Q 2600/112* (2013.01); *C12Q 2600/158* (2013.01); *C12Q 2600/178* (2013.01)

(58) Field of Classification Search
USPC ......... 435/6.1, 6.11, 91.1, 455; 436/94, 501; 536/23.1, 24.3, 24.33
See application file for complete search history.

(56) References Cited

U.S. PATENT DOCUMENTS

| 6,737,523 B1 | 5/2004 | Fisher et al. |
| 2004/0167381 A1* | 8/2004 | Lichter ................... G16Z 99/00 600/323 |

(Continued)

FOREIGN PATENT DOCUMENTS

| CN | 102191245 A | 9/2011 |
| EP | 3946470 A1 | 2/2022 |

(Continued)

OTHER PUBLICATIONS

Kotterman et al., Engineering adeno-associated viruses for clinical gene therapy. Nature Reviews, 15, 445-451, 2014.*
(Continued)

*Primary Examiner* — Frank W Lu
(74) *Attorney, Agent, or Firm* — Wilson Sonsini Goodrich & Rosati

(57) ABSTRACT

The present disclosure encompasses embodiments of nucleic acids comprising genetic elements which are useful for the detection of diseased cells.

13 Claims, 41 Drawing Sheets
(14 of 41 Drawing Sheet(s) Filed in Color)
Specification includes a Sequence Listing.

Related U.S. Application Data

(60) Provisional application No. 62/955,925, filed on Dec. 31, 2019, provisional application No. 62/830,279, filed on Apr. 5, 2019.

(51) Int. Cl.
    *C12Q 1/42*     (2006.01)
    *C12Q 1/66*     (2006.01)
    *C12Q 1/6883*   (2018.01)
    *C12Q 1/6886*   (2018.01)

(56) References Cited

U.S. PATENT DOCUMENTS

| | | |
|---|---|---|
| 2005/0059044 A1 | 3/2005 | Graham et al. |
| 2009/0311664 A1 | 12/2009 | Fong et al. |
| 2010/0076062 A1 | 3/2010 | Thompson et al. |
| 2011/0117608 A1 | 5/2011 | Graham et al. |
| 2012/0058562 A1 | 3/2012 | Thomson et al. |
| 2013/0171726 A1 | 7/2013 | Roelvink et al. |
| 2014/0127326 A1 | 5/2014 | Sood et al. |
| 2015/0071859 A1* | 3/2015 | Gambhir .......... C12Q 1/66 435/8 |
| 2016/0051704 A1 | 2/2016 | Morse et al. |
| 2016/0145582 A1 | 5/2016 | Yu |
| 2016/0215296 A1 | 7/2016 | Williams |
| 2016/0331845 A1 | 11/2016 | Mao et al. |
| 2017/0211066 A1 | 7/2017 | Croce et al. |
| 2018/0303952 A1 | 10/2018 | Sagert et al. |
| 2019/0010190 A1 | 1/2019 | Weinschenk et al. |
| 2019/0032083 A1 | 1/2019 | Kotin et al. |
| 2019/0211089 A1 | 7/2019 | Daugherty et al. |
| 2022/0275451 A1 | 9/2022 | Suhy et al. |

FOREIGN PATENT DOCUMENTS

| | | |
|---|---|---|
| WO | WO-2012058522 A2 | 5/2012 |
| WO | WO-2014035457 A1 | 3/2014 |
| WO | WO-2020206385 A1 | 10/2020 |
| WO | WO-2022212547 A1 | 10/2022 |

OTHER PUBLICATIONS

Shim et al., Nonviral Delivery Systems for Cancer Gene Therapy: Strategies and Challenges. Current Gene Therapy, 18, 3-20, 2018.*
Lenzi et al., NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16, 2014.*
Ronald et al., Detecting cancers through tumor-activatable minicircles that lead to a detectable blood biomarker. PNAS, 112, 3068-3073, 2015.*
Yaghoubi et al., Positron Emission Tomography Reporter Genes and Reporter Probes: Gene and Cell Therapy Applications. Theranostics, 2, 374-391, 2012.*
Curtin et al., Short Communication: Bidirectional promoter interference between two widely used internal heterologous promoters. Gene Therapy, 15, 384-390, 2008.*
Shearwin et al., Transcriptional interference—a crash course. Trends in Genetics, 21, 339-345, 2005.*
"Positron emission tomography" from Wikipedia. Printed on Oct. 12, 2023.*
Adams et al. Visualization of advanced human prostate cancer lesions in living mice by a targeted gene transfer vector and optical imaging. Nature Medicine, vol. 8, No. 8, pp. 891-896 (2002). Published online Jul. 22, 2002.
Bao et al. Activation of cancer-specific gene expression by the survivin promoter. Journal of the National Cancer Institute, vol. 94, No. 7, pp. 522-528, Apr. 3, 2002.
Chen, et al., Minicircle DNA vectors devoid of bacterial DNA result in persistent and high-level transgene expression in vivo. Molecular therapy, Sep. 1, 2003; 8(3): 495-500.
Chen et al. Promoter-Operating Targeted Expression of Gene Therapy in Cancer: Current Stage and Prospect. Molecular Therapy: Nucleic Acids, vol. 11, pp. 508-514 (Jun. 2018).
Chen et al. Use of the XRCC2 promoter for in vivo cancer diagnosis and therapy. Cell Death and Disease (2018) 9:420. 12 pages.
Darquet et al., Minicircle: an improved DNA molecule for in vitro and in vivo gene transfer (1999) Gene Therapy 6: 209-218.
Dent et al., Exhaled breath analysis for lung cancer. J Thorac Dis. Oct. 2013; 5(Suppl 5): S540-S550. doi: 10.3978/j.issn.2072-1439.2013.08.44.
EP20785373.0 European Partial Exam Report dated Dec. 20, 2022.
Fukazawa et al. Development of a Cancer-Targeted Tissue-Specific Promoter System. Cancer Research 64:363-369 (Jan. 1, 2004).
Jacobs et al. Positron-emission tomography of vector-mediated gene expression in gene therapy for gliomas. Lancet 2001; 358: 727-29.
Johansen et al. Increased in vitro and in vivo transgene expression levels mediated through cis-acting elements. The Journal of Gene Medicine, vol. 5, pp. 1080-1089, 2003.
Johnson et al. Selectively replicating adenoviruses targeting deregulated E2F activity are potent, systemic antitumor agents. Cancer Cell, vol. 1, pp. 325-337 (May 2002).
Kang et al. Molecular-Genetic Imaging Based on Reporter Gene Expression. J Nucl Med, vol. 49, No. 6 (Suppl) (Jun. 2008).
Komata et al. Treatment of Malignant Glioma Cells with the Transfer of Constitutively Active Caspase-6 Using the Human Telomerase Catalytic Subunit (Human Telomerase Reverse Transcriptase) Gene Promoter. Cancer Research 61:5796-5802 (Aug. 1, 2001).
Lan et al. In Vivo Selective Gene Expression and Therapy Mediated by Adenoviral Vectors for Human Carcinoembryonic Antigen-producing Gastric Carcinoma. Cancer Research 57:4279-4284 (Oct. 1, 1997).
Luke et al., Poster 112: Novel nonviral plasmid vectors with minimalized bacterial backbones dramatically increase transgene expression level in vivo, 17th annual meeting of the American Society of Gene and cell therapy, May 21, 2014, p. 1 of 1. Retrieved from the internet: https://bit.ly/3hY6gFM on Jun. 10, 2020.
Mazzone et al., Diagnosis of lung cancer by the analysis of exhaled breath with a colorimetric sensor array. Thorax. Jul. 2007;62(7):565-8. doi: 10.1136/thx.2006.072892. Epub Feb. 27, 2007.
PCT/US2020/026758 International Search Report and Written Opinion dated Jul. 9, 2020.
PCT/US2022/022603 International Search Report and Written Opinion dated Jul. 22, 2022.
Richter et al. A Dual-Reporter, Diagnostic Vector for Prostate Cancer Detection and Tumor Imaging. Gene Ther. Oct. 2014; 21(10): 897-902.
Ronald J A et al: "Artificial MicroRNAs as Novel Secreted Reporters for Cell Monitoring in Living Subjects", PLoS One, vol. 11, No. 7, Jul. 21, 2016 (Jul. 21, 2016), p. e0159369, XP055603160.
Ueki et al. A novel gene expression system for detecting viable bladder cancer cells. International Journal of Oncology 41:135-140 (2012).
Wang et al. Adenovirus-mediated suicide gene therapy under the control of Cox-2 promoter for colorectal cancer. Cancer Biology & Therapy 8:15, 1480-1488; Aug. 1, 2009.
Warram et al., A Genetic Strategy for Combined Screening and Localized Imaging of Breast Cancer (2011) Mal. Imaging Biol. 13: 452-461. Published Online: Jul. 24, 2010.
Wu et al. Transcriptionally targeted gene therapy to detect and treat cancer. Trends Mol Med. Oct. 2003 ; 9(10): 421.
Zhang et al. Interrogating Androgen Receptor Function in Recurrent Prostate Cancer. Cancer Research 63:4552-4560 (Aug. 1, 2003).
Zuo et al., Minicircle-oriP-IFNγ: A Novel Targeted Gene Therapeutic System for EBV Positive Human Nasopharyngeal Carcinoma (2011) PLoS One 6: e19407.
Bhang et al., Tumor-specific imaging through progression elevated gene-3 promoter-driven gene expression (2011) Nat. Med. 17: 123-129.

(56) References Cited

OTHER PUBLICATIONS

Dragulescu-Andrasi, A. et al., Bioluminescence resonance energy transfer (BRET) imaging of protein-protein interactions within deep tissues of living subjects. PNAS. Jul. 19, 2011, vol. 108 No. 29, 12060-12065.
Kay et al. A robust system for production of minicircle DNA vectors. Nature Biotechnol 28:1287-1289 (2010).
Ray et al., Noninvasive Imaging of Therapeutic Gene Expression Using a Bidirectional Transcriptional Amplification Strategy (2008) Mal. Therapy: J_ Am. Soc. Gene Therapy 16:1848-1856.
Zugates, G.T. et al., Rapid optimization of Gene delivery by parallel end-modification of Poly (B-amino ester)s. Molecular Therapy, Jul. 2007, vol. 15 Issue 7; pp. 1306-1312.
EP20785373.0 Extended European Search Report dated Apr. 26, 2023.
EP20785373.0 Extended European Search Report dated Apr. 4, 2023.
EP20785373.0 Partial Supplementary European Search Report dated Dec. 20, 2022.
Griffiths, et al., Reagents and Methods for PET Using Bispecific Antibody Pretargeting and 68Ga-Radiolabeled Bivalent Hapten-Peptide-Chelate Conjugates. The Journal of Nuclear Medicine, Jan. 2004; vol. 45, No. 1: pp. 30-39.
Jansen, et al., Molecular Drug Imaging: 89Zr-Bevacizumab PET in Children with Diffuse Intrinsic Pontine Glioma. J Nucl Med 2017; 58:711-716.
Jemal et al., Higher Lung Cancer Incidence in Young Women Than Young Men in the United States, (2018), N Engl J Med 2018; 378:1999-2009.
Le Fur, et al., Yttrium-86 PET imaging in rodents to better understand the biodistribution and clearance of gadolinium-based contrast agents used in MRI. Journal of Nuclear Medicine, May 2019, 60 (supplement 1) 346.
Melling M, The influence of SUMOylation on the adenoviral early region 4 protein Orf6/7, (2018), Dissertation, Department of Biology of the University of Hamburg, Jul. 6, 2018.
U.S. Appl. No. 18/452,504 Office Action dated Jan. 9, 2024.
Bahce, I. et al., Pilot study of (89)Zr-bevacizumab positron emission tomography in patients with advanced non-small cell lung cancer. EJNMMI Res. Dec. 2014;4(1):35. doi: 10.1186/s13550-014-0035-5. Epub Aug. 2, 2014.
Branchini, et al. Red-emitting luciferases for bioluminescence reporter and imaging applications. Anal Biochem. Jan. 15, 2010;396(2):290-7. doi: 10.1016/j.ab.2009.09.009. Epub Sep. 11, 2009.
Co-pending U.S. Appl. No. 18/452,504, inventors Suhy; David et al., filed on Aug. 18, 2023.
Co-pending U.S. Appl. No. 18/455,209, inventors Suhy; David et al., filed on Aug. 24, 2023.
Daughtry, et al. Tailoring encodable lanthanide-binding tags as MRI contrast agents. Chembiochem. Nov. 26, 2012;13(17):2567-74. doi: 10.1002/cbic.201200448. Epub Nov. 13, 2012.
Fernandez-Retana, J. et al., Gene signature based on degradome-related genes can predict distal metastasis in cervical cancer patients, Tumour Biol. 2017;39(6):1010428317711895. doi: 10.1177/1010428317711895.PMID: 28639897.
Kaczkowski, B. et al., Transcriptome Analysis of Recurrently Deregulated Genes across Multiple Cancers Identifies New Pan-Cancer Biomarkers. Cancer Res Jan. 15, 2016; 76 (2): 216-226. https://doi.org/10.1158/0008-5472.CAN-15-0484.
Kawasaki, K. et al., FAM111B enhances proliferation of KRAS-driven lung adenocarcinoma by degrading p16. Cancer Sci. Jul. 2020;111(7):2635-2646. doi: 10.1111/cas.14483. Epub Jun. 3, 2020. PMID: 32418298; PMCID: PMC7385341.
Mercier, S. et al., FAM111B Mutation Is Associated With Pancreatic Cancer Predisposition. Pancreas. May/Jun. 2019;48(5):e41-e42. doi: 10.1097/MPA.0000000000001303.PMID: 31090666.
Penheiter, A. R. et al., The sodium iodide symporter (NIS) as an imaging reporter for gene, viral, and cell-based therapies. Curr Gene Ther. Feb. 1, 2012;12(1):33-47. doi: 10.2174/156652312799789235.
Sun, H. et al., FAM111B, a direct target of p53, promotes the malignant process of lung adenocarcinoma. Onco Targets Ther. Apr. 17, 2019;12:2829-2842. doi: 10.2147/OTT.S190934. PMID: 31114230; PMCID: PMC6489872.
Yaghoubi et al., "PET imaging of herpes simplex virus type 1 thymidine kinase (HSV1-tk) or mutant HSV1-sr39tk reporter gene expression in mice and humans using [18F]FHBG." Nat Protoc. 2006;1(6):3069-3075.
Akamatsu et al.: Common variants at 11q12, 10q26 and 3p11.2 are associated with prostate cancer susceptibility in Japanese. Nature Genetics 44(4):426-430 (2012).

\* cited by examiner

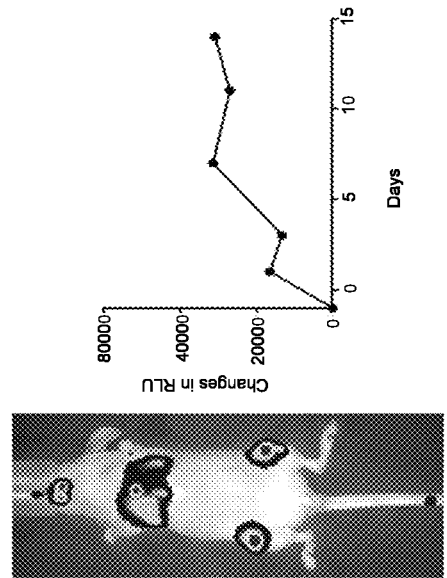
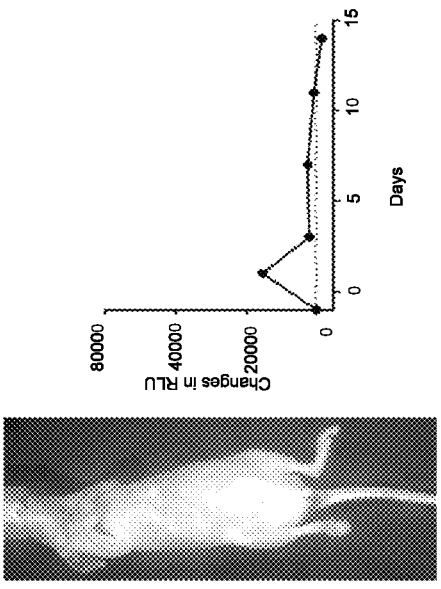
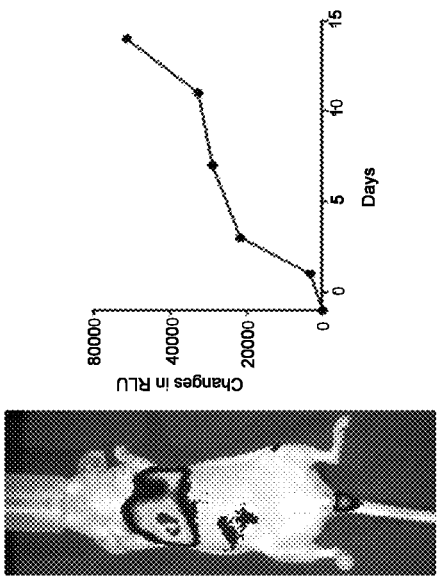
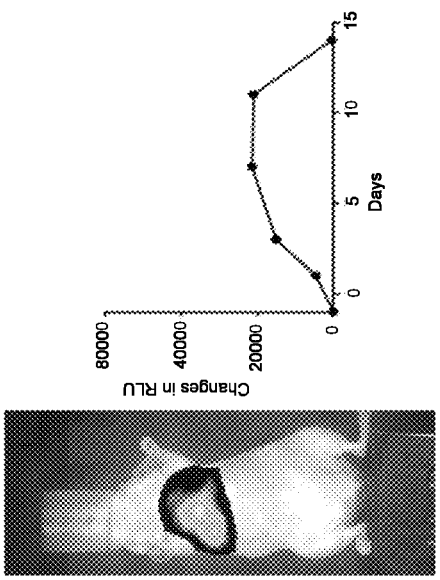
Fig. 9

MC-pSurv-SEAP-WPRE-pA (SEQ ID NO: 1)
cccaactggggtaacctttgggctcccgggcgcgactagtaataaaatatctttattttcatta
catctgtgtgttggtttttgtgtgaatcgatagtactaacatacgctctccatcaaaacaaaacg
aaacaaaacaaactagcaaaataggctgtcccagtgcaagtgcaggtgccagaacatttctctac
tagtgccatagaaccagagaagtgagtggatgtgatgccagctccagaagtgactccagaacac
ctgttccaaagcagaggacacactgatttttttttttaataggctgcaggacttactgttggtggga
cgcctgctttgcgaagggaaaggaggagttttgccctgagcacaggcccccacctccactgggct
ttccccagctcccttgtcttctatcacggtagtggcccagtccctggcccctgactccagaaggt
ggcctcctggaaaccaggtcgtgcagtcaacgatgtactcgccgggacagcgatgtctgctgca
ctccatccctccctgttcatttgtccttcatgcccgtctggagtagatgcttttgcagaggtgg
cacctgtaaagctctcctgtctgactttttttttttttttagactgagttttgctcttgttgcct
aggctggagtgcaatggcacaatctcagctcactgcaccctctgcctcccggttcaagcgattct
cctgcctcagcctcccgagtagttgggattacaggcatgcaccaccacgcccagctaattttttgta
tttttagtagagacaaggtttcaccgtgatggccaggctggtcttgaactccaggactcaagtgat
gctcctgcctaggcctctcaaagtgttgggattacaggcgtgagccactgcacccggcctgcacgc
gttcttttgaaagcagtcgagggggcgctaggtgtgggcaggacgagctggcgcggcgtcgctggg
tgcacgcgcgaccacgggcagagccacgcggcgggaggactacaactcccggcacaccgcgccgc
ccgcctctactcccagaaggccgcgggggtggacgcctaagagggcgtgcgctccgacatgc
ccgcggcgcgccattaaccgccagatttgaatcgcgggacccgttggcagaggtgggaattcacc
ggtcaccatggttctgggccctgcatgctgctgctgctgctgctgggcctgaggctacagct
ctccctgggcatcatcccagttgaggaggagaacccggacttctggaaccgcgaggcagccgaggc
cctgggtgccgccaagaagctgcagcctgcacagacagccgccaagaacctcatcatcttcctggg
cgatgggatggggtgtctacggtgacagctgccaggatcctaaaagggcagaagaaggacaaact
ggggcctgagatacccctggctatggaccgcttcccatatgtggctctgtccaagacatacaatgt
agacaaacatgtgccagacagtggagccacagccacggcctacctgtgcgggggtcaagggcaactt
ccagaccattggcttgagtgcagccgccgcttaaccagtgcaacacgacacgcgggcaacgaggt
catctccgtgatgaatcgggccaagaaagcagggaagtcagtgggagtggtaaccaccacacgagt
gcagcacgcctcgccagccggcacctacgccacacggtgaaccgcaactggtactcggacgccga
cgtgcctgcctcggccgccaggaggggtgccaggacatcgctacgcagctcatctccaacatgga
cattgatgtgatcctgggtggaggccgaaagtacatgttcgcatgggaaccccagaccctgagta
cccagatgactacagccaaggtgggaccaggctggacgggaagaatctggtgcaggaatggctggc
gaagcgccaggggtgccggtatgtgtggaaccgcactgagctcatgcaggcttccctggaccgtc
tgtgacccatctcatgggtctctttgagcctggagacatgaaatacgagatccaccgagactccac
actggacccctccctgatggagatgacagaggctgccctgcgcctgctgagcaggaaccccgcgg
cttcttcctcttcgtggagggtggtcgcatcgaccacggtcatcacgaaagcagggcttaccgggc
actgactgagacgatcatgttcgacgacgccattgagagggcgggccagctcaccagcgaggagga
cacgctgagcctgtcactgccgaccactccacgtcttctccttcggaggctacccctgcgagg
gagctccatcttcgggctggccctggcaaggccgggacaggaaggcctacacggtcctcctata
cggaaacggtccaggctatgtgctcaaggacggcgccggccggatgttaccgagagcgagagcgg
gagcccgagtatcggcagcagtcagcagtgcccctggacgaagagaccacgcaggcgaggacgt
ggcggtgttcgcgcgcggcccgcaggcgcacctggttcacggcgtgcaggacagaccttcatagc
gcacgtcatggccttcgccgcctgctggagccctacaccgctgcgacctggcgcccccgcgg
caccaccgacgccgcgcacccggggcggtcccggtccaagcgtctggattgagctagcttcgaatt
taaatcggatccctgcaggagctcgtcgacaatcaacctctggattacaaaat ttgtgaaagattgactggtattcttaactatgttgctccttttacgctatgtggatacgctgctt
taatgcctttgtatcatgctattgcttcccgtatggctttcattttctcctccttgtataaatcc
tggttgctgtctctttatgaggagttgtggcccgttgtcaggcaacgtggcgtggtgtgcactgt
gttgctgacgcaacoccactggttggggcattgccaccactgtcagctcctttccgggactt
tcgctttccccctccctattgccacggcggaactcatcgccgctgccttgcccgctgctggaca
gcgcggtcggctgttgggcactgacaattccgtggtgttgtcggggaaatcatcgtccttccttg
gctgctcgcctgtgttgccacctggattctgcgcgggacgtccttctgctacgtccttcggccc
tcaatccagcggacccttccttcccgcggcctgctgccggctctgcggcctcttccgcgtcttcgc
cttcgccctcagacgagtcggatctcccttgggcgcctcccgcctggtaccttaagaccaa
tgacttacaaggcagctgtagatcttagccactttttaaaagaaaagggggactggaaggcta
attcactcccaacgaaaataagatctgcttttttgcttgtactgggtctctctggttagaccagat
ctgagcctggagctctctggctaactagggaaccoactgcttaagcctcaataaagcttgcctt
gagtgcttcaagtagtgtgtgccogtctgttgtgtgactctggtaactagagatccctcagacc
ttttagtcagtgtggaaaatctctagcagtagtagttcatgtcatcttattattcagtatttata
acttgcaaagaaatgaatatcagagagtgagaggaacttgtttattgcagcttataatggttaca
aataaagcaatagcatcacaaatttcacaaataaagcatttttttcactgcattctagttgtggt
ttgtccaaactcatcaatgtatcttatcatgtctggctctagctatcccgcccctaactccgccc
agttccgcccattctccgccctcccgcccctaactccgcccaatggctgactaattttttttat
ttatgcagaggccgaggccgcctcggcctctgagctattccagaagtagtgaggaggcttttttg
gaggcctagactttgcagatcgaccatggggcccg MC-pSurv-Luc2-WPRE-pA (SEQ ID NO: 2)
cccaactggggtaaccttttgggctcccggqcgcgactagtaataaaatatctttattttcat
tacatctgtgtgttggttttttgtgtgaatcgatagtactaacatacgctctccatcaaaacaa
aacgaaacaaaacaaactagcaaaataggctgtccccagtgcaagtgcaggtgccagaacattt
ctctactagtgaattgatgccatagaaccagagaagtgagtggatgtgatgccagctccagaa
gtgactccagaacacctgttccaagcagaggacacactgattttttttttaataggctgcag
gacttactgttggtgggacgcctgctttgcaagggaaaggaggagtttgccctgagcacagg
cccccacctcactgggctttcccagctcccttgtcttctatcacggtagtggcccagtcc
ctggcccctgactccagaaggtggccctcctggaaaccaggtcgtgcagtcaacgatgtactc
gccgggacagcgatgtctgctgcactccatccctccctgttcatttgtcttcatgccgtct
ggagtagatgcttttgcagaggtggcaccctgtaaagctctcctgtctgactttttttttttt
tttagactgagtttgtcttgttgcctaggctggagtgcaatggcacaatctcagctcactgc
acctctgcctcccgggttcaagcgattctcctgcctcagcctcccgagtagttgggattacag
gcatgcaccaccacgcccagctaatttttgtatttttagtagagacaaggtttcaccgtgatgg
ccaggctggtcttgaactccaggactcaagtgatgctcctgcctaggcctctcaaagtgttggg
attacaggcgtgagccactgcaccggcctgcacgcgttctttgaaagcagtcgaggggcgct
aggtgtgggcagggacgagctggcgcggcgtcgctgggtgcaccgcgaccacgggcagagccac
ggggcgggaggactacaactcccggcacaccccgcgccgcccgcctctactcccagaaggccg
cggggggtggaccgcctaagagggcgtgcgctcccgacatgcccgcggcgcgccattaaccgc
cagatttgaatcgcgggacccgttgcagaggtggaagcttggcaatccggtactgttggtaaa
gccaccatggaagatgccaaaaacattaagaagggcccagcgccattctacccactcgaagacg
ggaccgccggcgagcagctgcacaaagccatgaagcgctacgccctggtgcccggcaccatcgc
cttaccgacgcacatatcgaggtggacattacctacgccgagtacttcgagatgagcgttcgg
ctggcagaagctatgaagcgctatggctgaatacaaaccatcggatcgtggtgtgcagcgaga
atagcttgcagttcttcatgcccgtgttgggtgccctgttcatcggtgtggctgtggcccagc
taacgacatctacaacgagcgcgagctgctgaacagcatgggcatcagccagcccaccgtcgta
ttcgtgagcaagaaagggctgcaaaagatcctcaacgtgcaaaagaagctaccgatcatacaaa
agatcatcatcatggatagcaagaccgactaccagggcttccaaagcatgtacacattcgtgac
ttcccatttgccacccggcttcaacgagtacgacttcgtgcccgagagcttcgaccgggacaaa
accatcgccctgatcatgaacagtagtggcagtaccggattgcccaaggggcgtagcctaccgc
acgcaccgttgtgtccgattcagtcatgcccgcgaccccatcttggcaaccagatcatccc
cgacaccgctatcctcagcgtggtgccatttcaccacggcttcggcatgttcaccacgctggc
tacttgatctgcggcttcgggtgtgtgctcatgtaccgcttcgaggaggagctattcttgcgca
gcttgcaagactataagattcaatctgccctgctggtgccacactatttagcttcttcgctaa
gagcactctcatcgacaagtacgacctaagcaacttgcacgagatcgccagcggcggggcgccg
ctcagcaaggaggtaggtgaggccgtggcaaacgcttccacctaccaggcatccgcaggct
acggcctgacagaaacaaccagcgccattctgatcaccccccgaagggacgacaagcctggcgc
agtaggcaaggtggtgccttctcgaggctaaggtggtggactggacacggtaagacactg
ggtgtgaaccagcgcggcgagctgtgcgtccgtggccccatgatcatgagcggctacgttaaca
acccgaggctacaaacgctctcatcgacaaggacggctggctgcacagcggcgacatcgccta
ctggacgaggacgagcacttcttcatcgtggaccggctgaagagcctgatcaaatacaagggc
taccaggtagccccagccgaactggagagcatcctgctgcaacacccaacatcttcgacgccg
gggtcgccggcctgcccgacgacgatgc

```
cggcgagctgcccgccgcagtcgtcgtgctggaacacggtaaaaccatgaccgagaaggaga
tcgtggactatgtggccagccaggttacaaccgccaagaagctgccgcggtggtgttgtgttc
gtggacgaggtgcctaaaggactgaccggcaagttggacgccgcaagatccgcgagattct
cattaaggccaagaagggcggcaagatccgcgtgtaatctagagctagcgaattcagatctg
atatctagagtcgagctagcttcgaatttaaatcggatccctgcaggagctcgtcgacaa
tcaacctctggattacaaaatttgtgaaagattgactggtattcttaactatgttgctcctt
ttacgctatgtggatacgctgctttaatgcctttgtatcatgctattgcttcccgtatggct
ttcattttctcctccttgtataaatcctggttgctgtctctttatgaggagttgtggcccgt
tgtcaggcaacgtggcgtggtgtgcactgtgtttgctgacgcaacccccactggttggggca
ttgccaccacctgtcagctccttccgggactttcgctttccccctccctattgccacggcg
gaactcatcgccgcctgccttgcccgctgctggacagggctcggctgttgggcactgacaa
ttccgtggtgttgtcggggaaatcatcgtcctttccttggctgctcgcctgtgttgccacct
ggattctgcgcgggacgtccttctgctacgtcccttcggccctcaatccagcggaccttcct
tcccgcggcctgctgccggctctgcggcctcttccgcgtcttcgccttcgccctcagacgag
tcggatctccctttgggccgcctccccgcctggtaccttaagaccaatgacttacaaggca
gctgtagatcttagccacttttttaaaagaaaaggggggactggaagggctaattcactccca
acgaaataagatctgctttttgcttgtactgggtctctctggttagaccagatctgagcct
gggagctctctggctaactagggaacccactgcttaagcctcaataaagcttgccttgagtg
cttcaagtagtgtgtgcccgtctgttgtgtgactctggtaactagagatccctcagaccctt
ttagtcagtgtggaaaatctctagcagtagtagttcatgtcatcttattattcagtatttat
aacttgcaaagaaatgaatatcagagagtgagaggaacttgtttattgcagcttataatggt
tacaaataaagcaatagcatcacaaatttcacaaataaagcatttttttcactgcattctag
ttgtggtttgtccaaactcatcaatgtatcttatcatgtctggctctagctatcccgcccct
aactccgcccagttccgcccattctccgccccctcccgcccctaactccgcccaatggctgac
taatttttttattatgcagaggccgaggccgcctcggcctctgagctattccagaagtag
tgaggaggcttttttggaggcctagacttttgcagatcgaccatggggcccg
```

*Fig. 14-cont'd*

In Vivo BLI

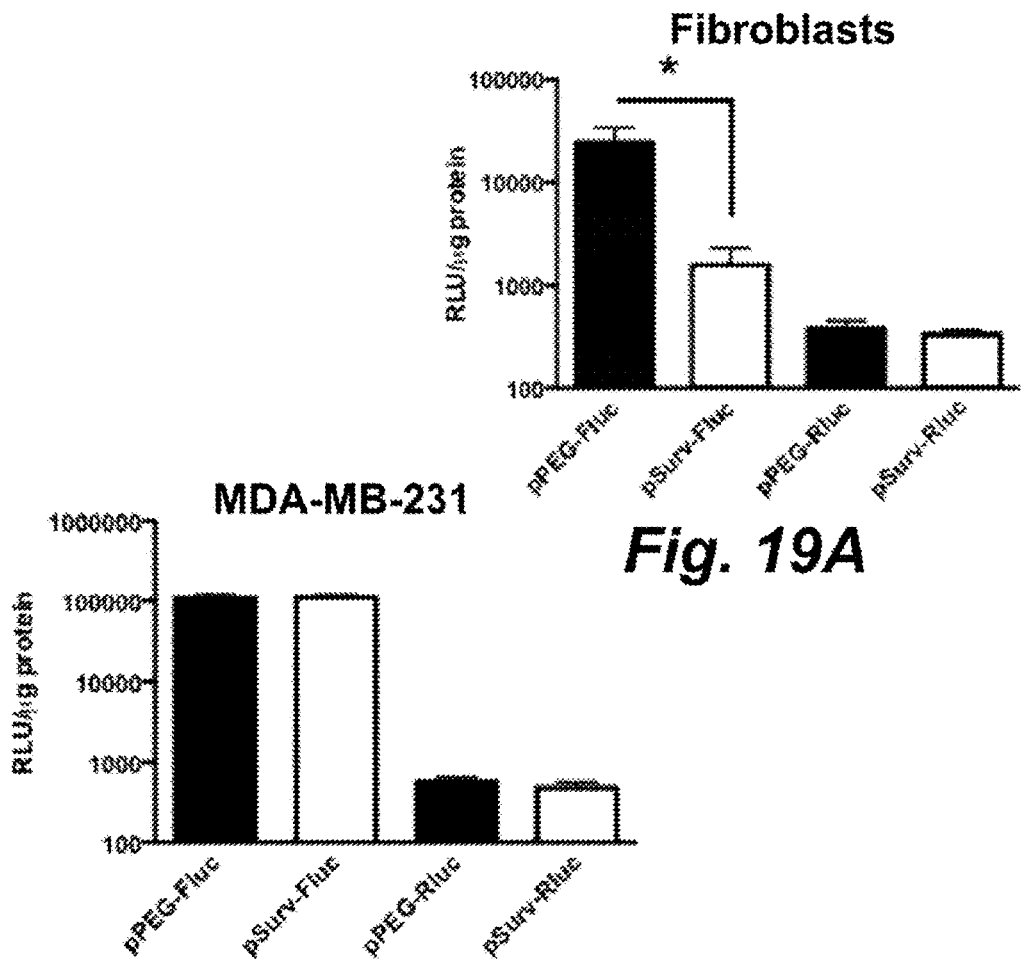
Fig. 19A
Fig. 19B
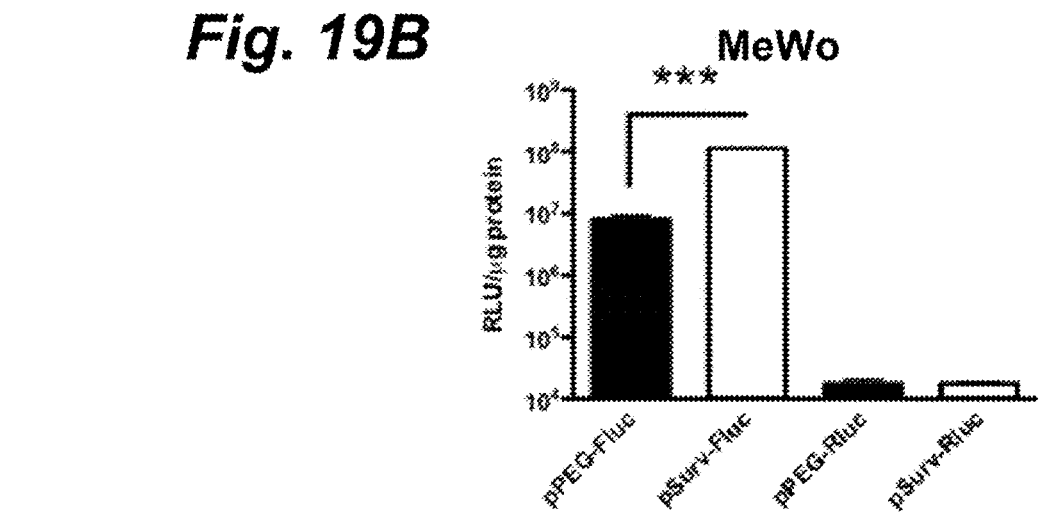
Fig. 19C

| mg SEAP in 25 ml plasma | % CV |
| --- | --- |
| 3e-02 | 2.16 |
| 3e-03 | 3.10 |
| 3e-04 | 1.47 |
| 3e-05 | 0.91 |
| 3e-06 | 1.09 |
| 3e-07 | 3.82 |

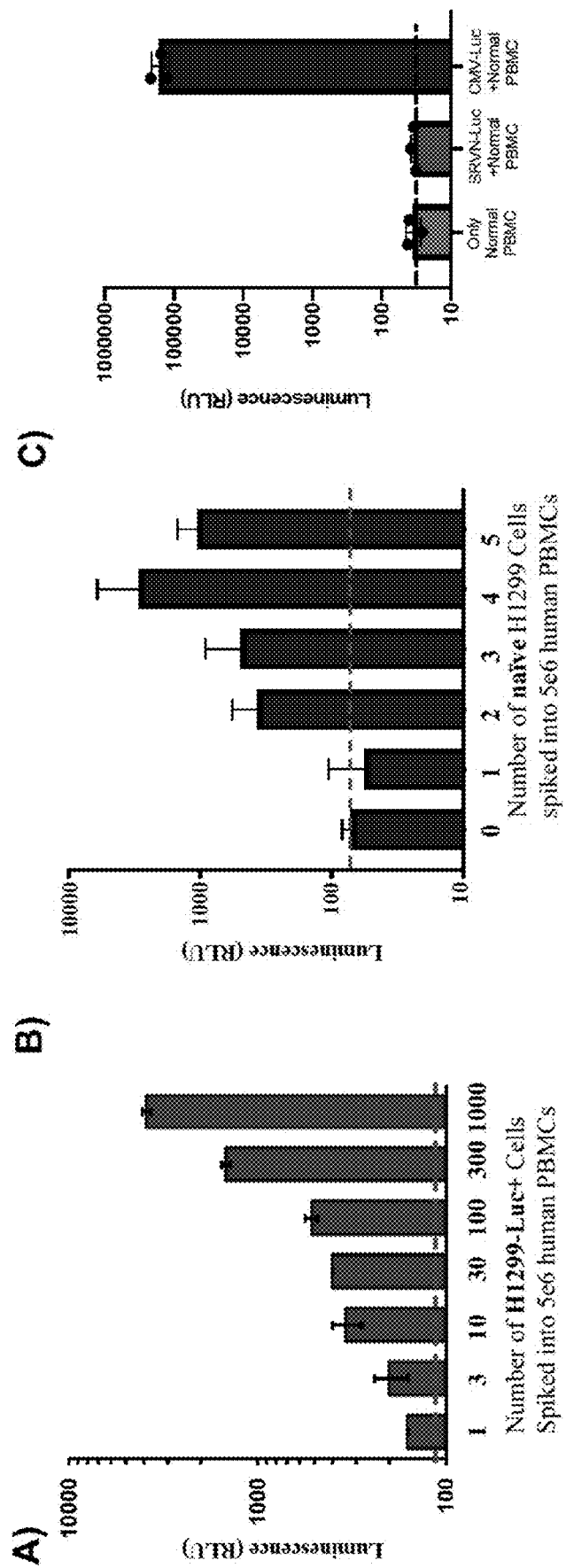
FIGS. 30A-C

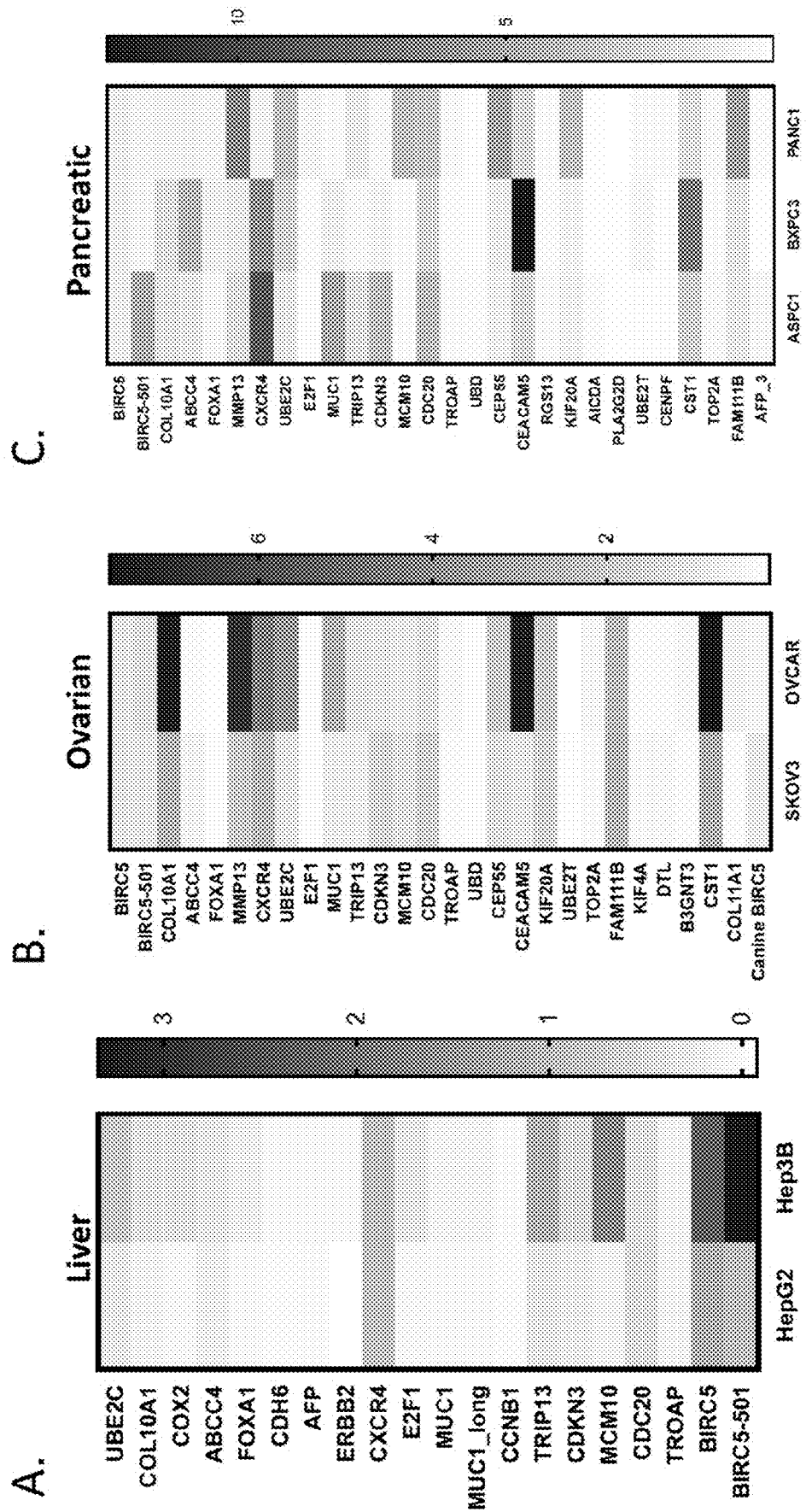
FIGS 33A, 33B, and 33C

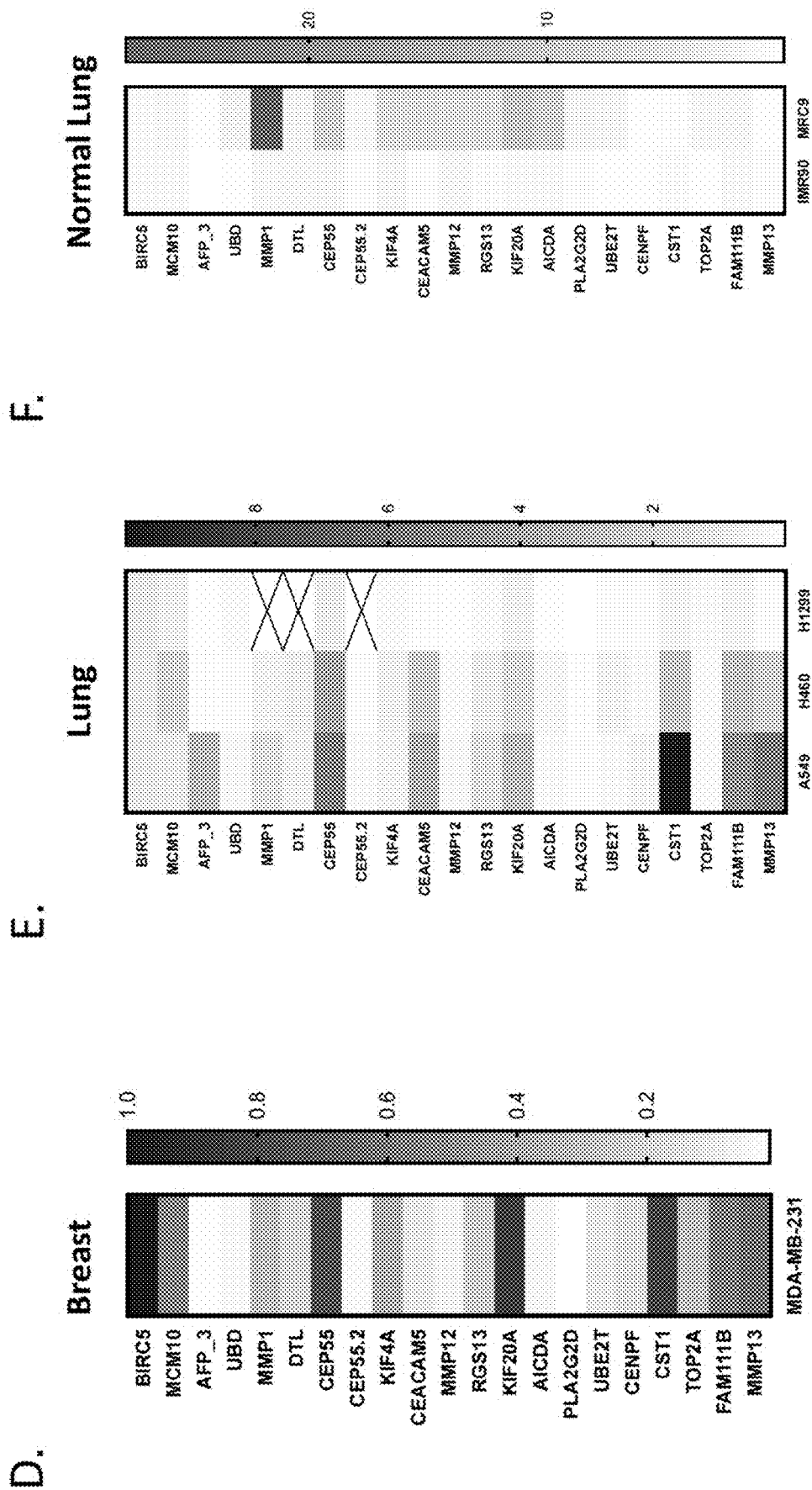
FIGS 33D, 33E, and 33F

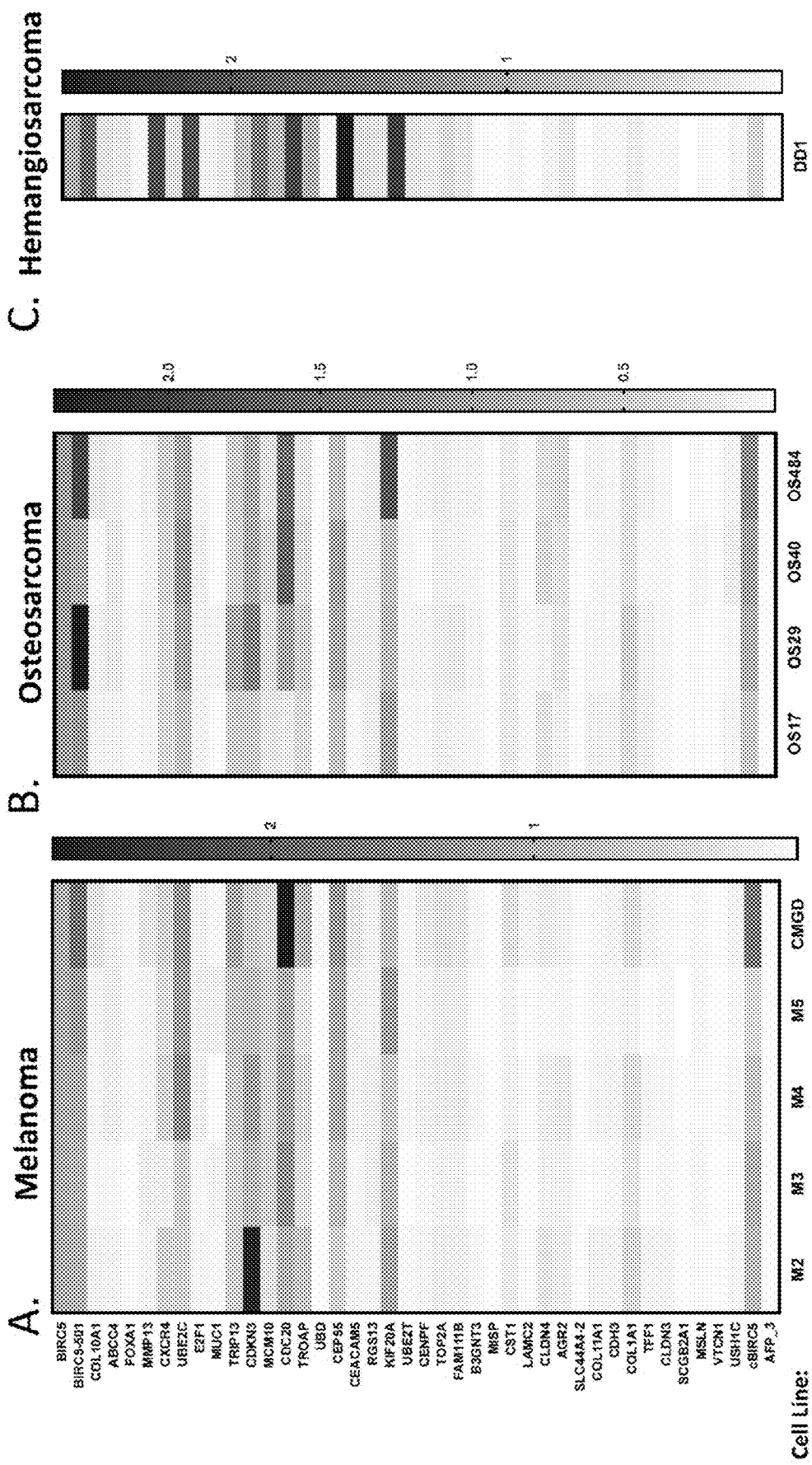
FIGS 34A, 34B, and 34C

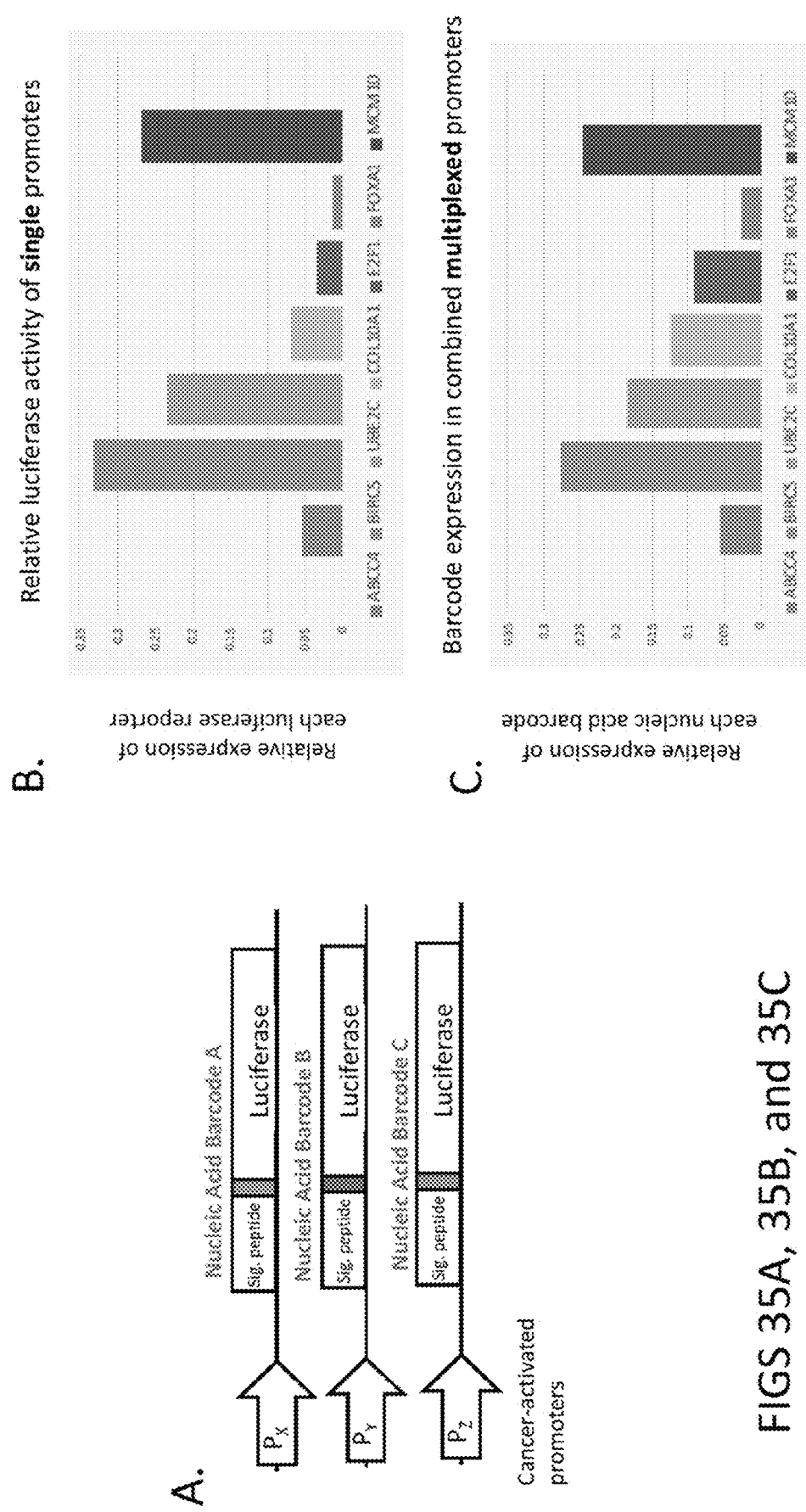
FIGS 35A, 35B, and 35C

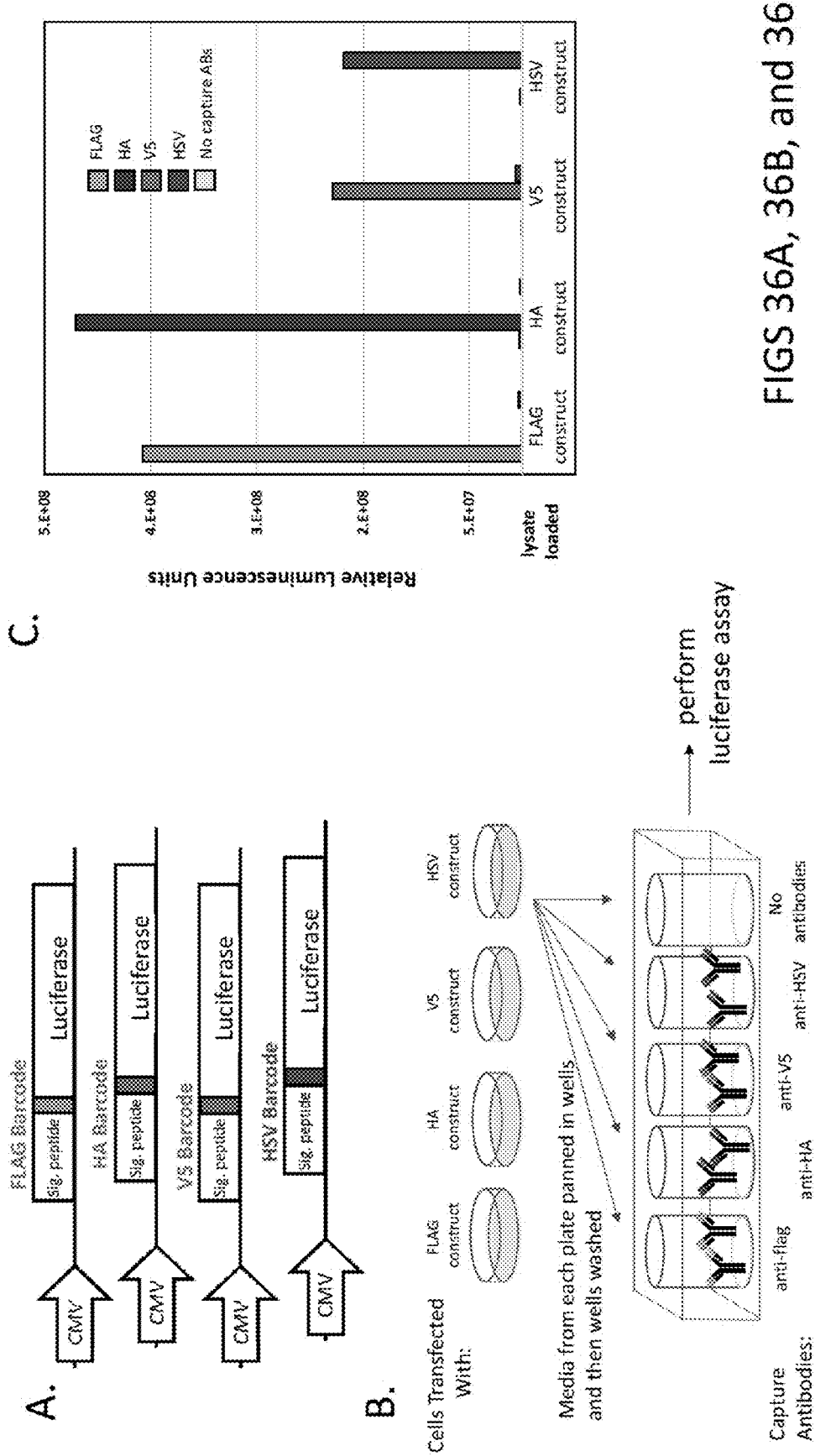
FIGS 36A, 36B, and 36C

METHODS AND COMPOSITIONS FOR SYNTHETIC BIOMARKERS

CROSS-REFERENCE

This application is a continuation-in-part of International Application No. PCT/US2020/026758, which was filed on Apr. 4, 2020, which claims the priority of U.S. Provisional Application 62/830,279, entitled "IMPROVED METHODS AND COMPOSITIONS FOR SYNTHETIC BIOMARKERS", which was filed on Apr. 5, 2019 and U.S. Provisional Application 62/955,925, entitled "IMPROVED METHODS AND COMPOSITIONS FOR SYNTHETIC BIOMARKERS", which was filed on Dec. 31, 2019, each of which is entirely incorporated herein by reference.

SEQUENCE LISTING

The instant application contains a Sequence Listing which has been submitted in ASCII format via EFS-Web and is hereby incorporated by reference in its entirety. Said ASCII copy, created Mar. 22, 2021, is named 53531_707_501 SL.txt and is 18,345 bytes in size.

BACKGROUND

Cancer is an enormous global health problem. The World Health Organization estimates that in 2018 alone there were an estimated 18.1 million new diagnoses of cancer and 9.6 million deaths due to cancer. The time at which cancer is detected, both prior to initial cancer diagnosis and during tumor recurrence, is one of the most important factors affecting patient outcome since if detected early, current treatments are likely to be more effective. Unfortunately, the majority of cancers are detected relatively late, leading to high mortality rates. These rates are expected to double by 2030 unless more effective detection strategies and treatments are developed. To stem the tremendous loss of life due to this terrible disease, a broadly applicable tool capable of detecting cancer in its earliest stages is urgently needed.

Two current paradigms for improving cancer detection include the development of blood-based assays that detect endogenous cancer biomarkers (e.g. protein, microRNA, circulating tumor DNA, circulating tumor cells, etc.) that are shed or released into the bloodstream, and molecular imaging assays that utilize biomarker-targeted imaging probes to better visualize tumors that are undetectable with conventional anatomical imaging.

Blood assays are highly attractive as they facilitate affordable cancer screening programs but often suffer from sensitivity and specificity issues due to low blood biomarker concentrations (Nagrath et al., (2007) Nature 450: 1235-1239), rapid in vivo and ex vivo biomarker degradation (Haun et al., (2011) Sci. Translational Med. 3: 71ra16), and highly variable background expression in non-malignant tissues (Diamandis E P (2010) J. National Cancer Inst. 102: 1462-1467). Using current clinical biomarker assays, it has been estimated that a tumor can grow for 10-12 years and reach a spherical diameter greater than 2.5 cm before endogenous blood biomarker amounts reach sufficient levels to indicate disease (Hori & Gambhir (2011) Sci. Translational Med. 3: 109ra116). Of the thousands of potential blood biomarkers reported, less than 1% are used in the clinic (7), and the implementation of new blood biomarkers into the clinical setting is decreasing due to their lack of validated specificity and diagnostic value (Haun et al., (2011) Sci. Translational Med. 3: 71ra16; Kern S E (2012) Cancer Res. 72: 6097-6101). Overall, while enormous effort has been devoted to developing tools for detecting endogenous cancer blood biomarkers, there have been very few successes. Thus, new strategies and tools capable of sensitive and specific cancer detection are urgently needed.

SUMMARY

In some aspects, the present disclosure provides for a method comprising: (a) administering to a subject a composition, wherein the composition induces expression of a biomarker in a diseased cell preferentially over expression of the biomarker in non-diseased cells in the subject such that a relative ratio of the biomarker expressed in the diseased cell over the non-diseased cells is greater than 1.0; (b) detecting the biomarker; and (c) using the biomarker detected in (b) to determine that the subject has the diseased cell at an accuracy of at least 70%.

In some aspects, the present disclosure provides for a method treating a subject having or suspected of having a disease, comprising administering to the subject a composition that induces expression of a therapeutically effective agent by a diseased cell associated with the disease preferentially over expression of the therapeutically effective agent by non-diseased cells in the subject such that a relative concentration of the therapeutically effective agent expressed by the diseased cell over the non-diseased cells is greater than 1.0, which therapeutically effective agent treats the subject at a therapeutic efficacy of at least 10% as determined by a decrease in a cell population of the diseased cells.

In some aspects, the present disclosure provides for a composition comprising a first nucleic acid sequence encoding a first polypeptide or nucleic acid biomarker and a second nucleic acid sequence encoding a second polypeptide or second nucleic acid biomarker, wherein the composition is configured such that when the composition is in a cell: the second polypeptide or nucleic acid biomarker is expressed in an amount that reflects delivery of the first and the second nucleic acids to the cell, and the first polypeptide or nucleic acid biomarker is expressed differentially in a diseased cell versus a non-diseased cell.

In some aspects, the present disclosure provides for a method of detecting diseased cells in a subject, comprising administering a composition to the subject, wherein the composition comprises: a first nucleic acid sequence encoding a first polypeptide or nucleic acid biomarker and a second nucleic acid sequence encoding a second polypeptide or second nucleic acid biomarker, wherein the composition is configured such that when the composition is in a cell: (i) the cell induces expression of the first nucleic acid sequence in a diseased cell preferentially over expression of the first nucleic acid sequence in non-diseased cells, wherein the first polypeptide is a detectable biomarker or a therapeutic agent; and (ii) the cell induces equivalent expression of the second nucleic acid sequence equally in diseased and in non-diseased cells and the second nucleic acid sequence yields the second polypeptide that is not the detectable biomarker or the therapeutic agent, such that a level of expression of the second polypeptide provides a control for assessing the relative level of the nucleic acid sequences in the cell.

In some aspects, the present disclosure provides for a composition comprising a first nucleic acid sequence encoding a first polypeptide and a second nucleic acid sequence encoding a second polypeptide, wherein the composition is configured such that when the composition is in a cell: (i) the cell expresses the first nucleic acid sequence to yield the first polypeptide; (ii) the cell expresses the second nucleic acid sequence to yield the second polypeptide; and (iii) the first polypeptide and the second polypeptide expressed by the cell are configured to combine to form a heterodimer protein.

In some aspects, the present disclosure provides for a method of detecting or treating a diseased cell, comprising administering the composition above comprising a first nucleic acid sequence encoding a first polypeptide and a second nucleic acid sequence encoding a second polypeptide, wherein the first and the second polypeptide are selectively transcribed or translated in the diseased cell.

In some aspects, the present disclosure provides for a composition comprising a non-naturally occurring recombinant genetic construct comprising a sequence encoding a polypeptide or nucleic acid sequence, and wherein the sequence comprises a first promoter that selectively drives expression of the polypeptide or nucleic acid biomarker sequence in a plurality of different types of cells isolated from a subject when transduced into the cells ex vivo.

In some aspects, the present disclosure provides for a method for detecting a diseased or disordered cell ex-vivo, comprising delivering ex vivo a non-naturally occurring recombinant genetic construct to a population of cells isolated from a subject, wherein the non-naturally occurring recombinant genetic construct comprises: a sequence encoding a polypeptide or nucleic acid biomarker sequence, wherein the sequence comprises a first promoter that selectively drives expression of the polypeptide or nucleic acid biomarker sequence in a plurality of different types of cells isolated from a subject when transduced into the cells.

In some aspects, the present disclosure provides for a composition comprising a vector, wherein the vector comprises a plurality of different promoters operably linked to a plurality of different nucleic acid sequences, wherein each the promoter drives expression of the plurality of nucleic acid sequences in a cell to yield a plurality of polypeptides or nucleic acid biomarker sequences, wherein levels of individual polypeptides or nucleic acid biomarker sequences of the plurality of nucleic acid sequences are indicative of a stage of a disease of the cell, or a tissue from which the cell originates.

In some aspects, the present disclosure provides for a method for detecting a stage of disease, comprising administering to a subject a composition comprising a vector, wherein the vector comprises a plurality of different promoters operably linked to a plurality of different nucleic acid sequences, wherein each the promoter drives expression of the plurality of nucleic acid sequences in a cell to yield a plurality of polypeptides or nucleic acid biomarker sequences, wherein levels of individual polypeptides of the plurality of nucleic acid sequences are indicative of a stage of a disease of the cell, or a tissue from which the cell originates.

In some aspects, the present disclosure provides for a composition comprising an engineered nucleic acid encoding an expressible reporter gene that exhibits about 10% or less expression in normal cells versus diseased cells when compared to a recombinant nucleic acid comprising a reporter gene comprising a nucleic acid sequence of SEQ ID NO: 1 or SEQ ID NO: 2.

In some aspects, the present disclosure provides for a method comprising administering to a subject the composition comprising the engineered nucleic acid encoding an expressible reporter gene above.

In some aspects, the present disclosure provides for a composition that exhibits about 10% or less expression in normal cells versus diseased cells and comprises a recombinant nucleic acid comprising a nucleic acid sequence encoding a reporter gene that includes one or more miRNA binding sequences in a 3' untranslated region of the reporter gene.

In some aspects, the present disclosure provides for a method of detecting a diseased cell comprising administering to a subject the composition that exhibits about 10% or less expression in normal cells versus diseased cells above.

In some aspects, the present disclosure provides for a composition exhibiting significantly longer expression of synthetic biomarker versus plasmid DNA or minicircle DNA comprising a linear vector comprising a double-stranded nucleic acid comprising a promoter operatively linked to a DNA sequence encoding a synthetic biomarker, wherein a forward and a reverse strand of the double-stranded nucleic acid are covalently linked on each of their terminal ends, wherein the promoter induces expression of the synthetic biomarker in a diseased cell preferentially over expression of the synthetic biomarker in a non-diseased cell such that a relative concentration of the synthetic biomarker expressed in the diseased cell over the non-diseased cell is greater than 1.0.

In some aspects, the present disclosure provides for a method of identifying a diseased cell, comprising administering to a subject the composition exhibiting significantly longer expression of synthetic biomarker versus plasmid DNA or minicircle DNA above, and detecting the synthetic biomarker, wherein the synthetic biomarker is expressed in a diseased cell preferentially over expression of the synthetic biomarker in non-diseased cells in the subject such that a relative concentration of the synthetic biomarker expressed in the diseased cell over the non-diseased cells is greater than 1.0.

In some aspects, the present disclosure provides for a composition exhibiting significantly longer expression of synthetic biomarker versus plasmid DNA or minicircle DNA comprising a linear vector comprising a double-stranded nucleic acid comprising a promoter operatively linked to a DNA sequence encoding a therapeutically effective agent, wherein a forward and a reverse strand of the double-stranded nucleic acid are covalently linked on each of their terminal ends, wherein the promoter induces expression of the therapeutically effective agent in a diseased cell preferentially over expression of the synthetic biomarker in a non-diseased cell such that a relative concentration of the therapeutically effective agent expressed in the diseased cell over the non-diseased cell is greater than 1.0.

In some aspects, the present disclosure provides for a method of treating a diseased cell, comprising administering to a subject the composition above, and detecting the synthetic biomarker, wherein the synthetic biomarker is expressed in a diseased cell preferentially over expression of the synthetic biomarker in non-diseased cells in the subject such that a relative concentration of the synthetic biomarker expressed in the diseased cell over the non-diseased cells is greater than 1.0.

In some aspects, the present disclosure provides for a composition comprising a non-viral vector expressing a synthetic biomarker, wherein the synthetic biomarker exhibits about 10% or less expression in normal organ cells versus diseased cells.

In some aspects, the present disclosure provides for an engineered particle that mimics one or many functions of a biological cell or macrophage including inducing the expression of a biomarker in a diseased cell preferentially over expression of the biomarker in non-diseased cells such that the relative concentration ratio of the biomarker expressed in the diseased cell over the non-diseased cells is greater than 1.0.

In some aspects, the present disclosure provides for at least one vector, wherein the at least one vector comprises: a plurality of different promoters operably linked to a plurality of different nucleic acid sequences, wherein the promoters drive expression of the plurality of nucleic acid sequences in a cell to yield a plurality of polypeptides or nucleic acid biomarker sequences, wherein the promoters induce expression of the plurality of polypeptides or nucleic acid biomarker sequences in a diseased cell preferentially over expression of the plurality of polypeptides or nucleic acid biomarker sequences in non-diseased cells in a subject such that a relative ratio of the plurality of polypeptides or nucleic acid biomarker sequences expressed in the diseased cell over the non-diseased cells is greater than 1.0.

In some aspects, the present disclosure provides for a method for detecting a disease in a subject, comprising: administering to a subject a composition comprising the at least one vector comprising a plurality of different promoters operably linked to a plurality of different nucleic acid sequences above; detecting the plurality of polypeptides or nucleic acid biomarker sequences to obtain an expression profile; and detecting the diseased cell based expression profile, thereby detecting the disease.

In some aspects, the present disclosure provides for methods for detecting a subject's disease or absence thereof, comprising contacting one or more cells of said subject with a genetic construct ex-vivo, wherein: said genetic construct comprises a disease-activated promoter operably linked to a barcode molecule and said disease-activated promoter drives expression of said barcode molecule in a cell affected by said disease; quantifying an expression level of said barcode molecule; and detecting said disease or absence thereof based on said expression level.

By ascribing an exclusive label to a unique member within a larger group, barcodes afford the opportunity to identify and quantify that member (e.g. expression of a reporter under the control of a particular cancer specific promoter) within the context of a larger and more complex mixture of many members (e.g. multiple promoter-reporter constructs expressed within the same cell), as well as offering the opportunity to isolate a single member from the complex mixture. For instance, in the case of barcodes based on nucleic acids, hybridization of barcodes based on base pairing complementarity may be used to capture and isolate or otherwise reduce the complexity of a mixture by said capture event. For barcodes based on peptides, unique features including immunocapture or interactions of ligands and receptors may be used to capture and isolate or otherwise reduce the complexity of a mixture by said capture event.

In some aspects, the present disclosure provides for methods for generating a profile of a subject's disease, comprising contacting one or more cells of said subject with a plurality of genetic constructs, wherein: said plurality of genetic constructs comprises a plurality of disease-activated promoters respectively operably linked to a plurality of barcode molecules and said disease-activated promoter drives expression of said corresponding barcode molecule in a cell affected by said disease; and quantifying expression levels of said plurality of barcode molecules to generate said profile.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The patent or application file contains at least one drawing executed in color. Copies of this patent or patent application publication with color drawings will be provided by the Office upon request and payment of the necessary fee. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (denoted "FIGURE" or "FIG.") of which:

FIG. 2A illustrates vector maps of both Survivin promoter (pSurv)-driven parental plasmids (PP; top) and MCs (bottom). These constructs encoded the reporter protein secreted embryonic alkaline phosphatase (SEAP). The PP and MC have the identical transcription unit (pSurv-SEAP-WPRE-polyA) but the MC lacks the prokaryotic backbone (light grey). WPRE (Woodchuck Hepatitis virus posttranscriptional regulatory element (WPRE). FIG. 2B illustrates agarose gel electrophoresis con-firming the ability to generate both PP (7.9 kb) and MC (4.1 kb).

FIG. 9 illustrates representative mouse blood SEAP activity after systemic administration of tumor-specific SEAP minicircles.

FIG. 13 illustrates the nucleic acid sequence of minicircle MC-pSurv-SEAP-WPRE-pA.

FIG. 14 illustrates the nucleic acid sequence of minicircle MC-pSurv-Luc2-WPRE-pA.

FIGS. 16A-16C illustrate human melanoma tumor development following intravenous cell administration in nude mice (n=7) monitored using bioluminescence imaging (BLI) (left images). Representative BLI images showed tumor growth primarily within the lung and individual mice had a wide range of tumor burden within 3 days prior to MC administration. The BLI scales in FIGS. 16A and 16B are the same, but that of FIG. 16C is one order of magnitude lower. Tumor-activatable MCs were administered systemically, and SEAP levels were measured before (Day 0) and up to 14 days following administration (right graphs). Varying SEAP concentrations were detected in tumor-bearing mice over the 14-day period. FIG. 16D illustrates healthy (tumor-free) mice that received either MC (Control+MC; n=7) or 5% glucose carrier only (Control-MC; n=5). No statistically significant differences in plasma SEAP levels were detected between these two groups. Importantly, across all mice regardless of tumor burden, significantly higher plasma SEAP concentration was detected in tumor-bearing mice receiving MC between days 3 to 14 compared to both control groups (#*$p<0.05$; ##**$p<0.01$). Data is expressed as mean±SEM.

FIG. 17A: Area under the curve (AUC) analysis of plasma SEAP measurements over 2 weeks revealed significant differences between tumor-bearing mice receiving MCs (n=7) compared to both healthy mice receiving MCs (n=7) or 5% glucose (n=5) (*$p<0.05$; $p<0.01$). Data is expressed as meant SD. FIG. 17B: ROC (receiver operating characteristic curve) analysis revealed a significant ability of the tumor-activatable MC system to differentiate tumor-bearing from healthy subjects by measuring and computing plasma SEAP AUC. FIG. 17C**: Correlational analysis of SEAP AUC measurements and lung tumor burden (as measured by BLI lung average radiance). Across 6 mice a significant positive correlation was noted between these two measures, showing the ability of our tool to assess tumor burden provided that the tumor is in one location. One mouse was removed from analysis (square symbol) since this mouse had tumors in both the lungs and multiple metastatic foci outside the lungs (BLI measurement was taken from just within lung explaining overall low BLI signal in this mouse). This mouse had a higher SEAP AUC level than would be expected based on its lung tumor burden.

FIG. 18A illustrates representative BLI images 48 hours post-injection. Image scale for the pCMV mouse is 2 orders of magnitude higher than all other mice. BLI signal, primarily in the lungs, was seen in all mice receiving Luc2 plasmid. FIG. 18B illustrates region-of-interest analysis over the entire mouse performed on BLI images, revealing significantly higher (*$p<0.05$; about 100-fold) BLI signal in mice receiving pCMV-Luc2 plasmids compared to all other mice (*$p<0.05$). A significantly higher (*$p<0.05$) BLI signal was also observed in pPEG mice compared to mock-injected mice. Although qualitatively higher BLI signal was notable in pSury mice compared to mock-injected mice, quantitative measures only revealed a trend ($p=0.16$) towards higher BLI signal. Thus, in this mouse strain, Luc2 expression in normal tissues was lowest with the tumor-specific pSurv. FIG. 18C illustrates that 48 h after plasmid injection, ex vivo analysis of Luc2 activity across numerous tissues revealed significantly higher (*$p<0.05$) expression with pCMV compared to all other groups. With pPEG, significantly higher (*$p<0.05$) Luc2 activity was found in the heart, lung and spleen compared to mock-injected animals. With pSurv, significantly higher (*$p<0.05$) Luc2 activity was in the spleen and a trend ($p=0.13$) towards higher activity in the lung. FIG. 18D illustrates that the only tissue showing higher hRluc activity above background was the lung (values presented are normalized to average background values from mock-injected mice). Due to this, Luc2 values determined from both imaging (FIG. 18B) and ex vivo tissue analysis (FIG. 18C) are not normalized by hRluc values. No significant differences in hRluc values within the lungs were seen across the 3 promoter mouse groups. Thus, differences Luc2 measurements across the 3 groups are unlikely to be related to differences in transfection efficiency but to differences in promoter activity. Data is expressed as mean±SD.

FIGS. 19A-19C illustrate a comparison of tumor-specific promoter activities in primary human fibroblasts and human cancer cell lines. Primary human fibroblasts, MDA-MB-231 cells (human breast cancer) and MeWo cells (human melanoma) were transfected with pPEG- or pSurv-driven plasmids (1 lig) expressing Luc2 and co-transfected with a promoterless plasmid expressing hRluc (50 ng) to normalize for transfection efficiency. No differences in Rluc transfection efficiency were noted in any of the 3 cell types. pPEG-driven plasmids led to significantly higher Luc2 activity in fibroblasts than pSury ($*p<0.05$). pSurv-driven plasmids led to significantly higher Luc2 activity in MeWo cells ($***p<0.001$) and equivalent activity in MDA-MB-231 cells. Data is expressed as mean±SD.

FIG. 21A illustrates mice that received systemic administration of either MCs (n=4) or PPs (n=5) expressing hRluc driven by the strong constitutive EF1 promoter after complexation with PEI (40 lig; N/P=8). BLI imaging was performed on days 1, 2, 3, 5 and 7 using the substrate coelenterazine. Representative images show higher BLI signal in MC-administered mice at all time points examined. Signal from a mouse receiving a 5% glucose injection is shown for comparison (signal in liver is from oxidized coelenterazine). FIG. 21B illustrates a region-of-interest analysis over the lung region showing a significantly higher BLI signal in MC versus PP mice on days 1, 2, and 5 ($*p<0.05$; $**p<0.01$). Data is expressed as mean±SD.

FIG. 26A, shows an experiment where 40 µg of DNA encoding CMV-Luciferase was formulated in the polymeric formulations or was complexed with JetPEI followed by intravenous administration into Balb/C mice, D-luciferin was injected into the animals four days after transfection, after which the animals were sacrificed and lungs were harvested for ex vivo BLI analysis. For cytotoxicity assessments (FIGS. 26B, 26C, 26D, 26E, and 26F), polyplexes containing 250 ng of CMV-Luc DNA were added into each well of a 96-well plate with 10,000 cells plated per well the day before transfection. Each formulation was tested with 3 replicates. 48 hours later, cell morphology was recorded by microscope and cell viability was measured during the MTT assay; FIG. 26B shows blank cells; FIG. 26C shows in vivo delivery of construct with JetPEI; FIG. 26D shows delivery of DNA with high-molecular-weight, amine-terminated poly((3-amino ester) C32-122; FIG. 26E shows delivery of DNA with high-molecular-weight, amine-terminated poly((3-amino ester) C32-145; and FIG. 26F shows cell viability results by MTT assays.

FIGS. 30A-C illustrate sensitivity and specificity of Ad-survivin-FLuc in an ex vivo assay. A) H1299 cells, engineered to constitutively express the firefly luciferase protein, were spiked into 5e6 human normal PBMCs and then the entirety of the sample was processed and analyzed for luciferase expression. B) naïve H1299 cells, which had not been transduced, were spiked into the human PBMCs and then transduced with a recombinant adenovirus with an expression cassette of human survivin promoter driving the expression of firefly luciferase (Ad-Survivin-FLuc). After growth for 48 hours, the sample was processed and analyzed for luciferase expression. C) Samples with only human PBMCs with transduced with either Ad-Survivin-FLuc or Ad-CMV-FLuc, the latter, under control of a strong constitutive promoter. Following a 2-day incubation, luminescence assays were used to quantify FLuc expression.

FIGS. 33A, 33B, 33C, 33D, 33E, and 33F illustrate the activation of various promoter-reporter constructs in particular cell lines of varying tissue origin, where the gene labels denotes the source of promoters used in the construct. FIG. 33A shows various promoter-reporter constructs in cell lines of liver origin (e.g. HepG2 and Hep3B), demonstrating that CXCR4, TRIP13, MCM10, COL10A1, BIRC5, and BIRC5-501 are particularly activated in liver cancers.

FIG. 33B shows activation of various promoter-reporter constructs in immortalized cell lines of ovarian origin (e.g. SKOV3 and OVCAR), demonstrating that COL10A1, MMP13, UBE2C, MUC1, CEP55, CEACAM5, KIF20A, FAM111B, and CST1 are particularly activated in ovarian cancers. FIG. 33C shows activation of various promoter-reporter constructs in immortalized cell lines of pancreatic origin (e.g. ASPC1, BXPC3, and PANC1), demonstrating that BIRC5, ABCC4, MMP13, CXCR4, UBE2C, MUC1, CDKN3, MCM10, CDC20, CEP55, CEACAM5, KIF20A, CST1, and FAM111B are particularly activated in pancreatic cancers.

FIG. 33D shows activation of various promoter-reporter constructs in a cell line of breast origin (e.g. MDA-MB-231), demonstrating that BIRC5, MCM10, MMP1, DTL, CEP55, KIF4A, RGS13, KIF20A, UBE2T, CENPF, CST1, TOP2A, FAM111B, and MMP13 are particularly activated in breast cancers. FIG. 33E shows activation of various promoter-reporter constructs in cell lines of lung origin (e.g. A549, H460, and H1299), demonstrating that MCM10, AFP, MMP1, CEP55, CEACAM5, RGS13, KIF20A, CST1, FAM111B, and MMP13 are particularly activated in lung cancers. FIG. 33F shows a comparison of the same promoter-reporter constructs as 33E but in non-transformed breast cancer lines, demonstrating that genes other than MMP1 that are shown activated in 33E may be particularly useful for distinguishing breast cancer from normal tissue.

FIGS. 34A, 34B, and 34C illustrate the activation of a panel of promoter-reporter constructs in melanoma, osteosarcoma, and hemangiosarcoma cancer cell lines, where the gene labels denote promoters used in the construct. FIG. 34A shows activation of members of the panel in cell lines of melanoma origin (e.g. M2, M3, M4, M5, and CMGD), demonstrating that BIRC5, BIRC5-501, CXCR4, UBE2C, TRIP13, CDKN3, MCM10, CDC20, TROAP, CEP55, KIF20A, and cBIRC5 are particularly activated in melanoma cancer. FIG. 34B shows activation of members of the panel in cell lines of osteosarcoma origin (e.g. OS17, OS29, OS40, and OS484), demonstrating that BIRC5, BIRC5-501, CXCR4, UBE2C, TRIP13, CDKN3, MCM10, CDC20, TROAP, CEP55, KIF20A, and cBIRC5 are particularly activated in osteosarcoma. FIG. 34C shows activation of members of the panel in cell lines of hemangiosarcoma origin, showing that BIRC5, BIRC5-501, MMP13, CXCR4, UBE2C, TRIP13, CDKN3, MCM10, CDC20, TROAP, CEP55, KIF20A, and cBIRC5 are particularly activated in hemangiosarcoma cancer.

FIGS. 35A, 35B, and 35C show design of a multiplex detection assay using multiple different cancer-specific promoters and linked barcodes. 35A shows design of the multiplex constructs, wherein various cancer specific promoters (designated non-descriptively as Px, Py, and Pz) are used to drive expression of orthogonal reporters created by fusion of a signal peptide to luciferase with an intervening nucleic acid barcode sequence unique to the promoter being used to drive the construct (Barcodes A, B, and C for promoters Px, Py, and Pz, respectively).

FIG. 35B demonstrates relative expression of each promoter construct when individually transfected in equimolar amounts into H1299 cells and FIG. 35C shows relative expression of each promoter construct when combinatorially transfected in equimolar amounts into H1299 cells, demonstrating that co-transfection of multiple reporter-promoter constructs into the same cells does not appreciably alter the expression pattern of a given promoter in a given cell line, indicating that the multiplex format is a viable format for generating "profiles" of promoter activation in single cell types.

FIGS. 36A, 36B, and 36C show design of a multiplex detection assay using multiple different peptide epitopes to detect reporters driven from separate promoters. 36A shows design of the multiplex constructs, wherein different copies of the CMV promoter drive expression of orthogonal reporters created by fusion of a signal peptide to luciferase with an intervening epitope peptide (e.g. FLAG, HA, V5, or HSV peptide epitopes) barcode that is unique to the promoter being used to drive the construct (36A shows CMV promoter being used, but ultimately multiple distinct promoters such as the Px, Py, Pz, etc of FIG. 35 is envisioned). FIG. 36B demonstrates how the multiple epitope barcodes can be used with capture antibodies specific for the epitopes (e.g. anti-FLAG, anti-HA, anti-VS, or anti-HSV) to separate out the secreted reporter constructs to obtain independent measures of the activities for each promoter.

FIG. 36C shows an example using the FLAG/HA/V5/HSV-barcoded luciferase constructs co-transfected into cells, demonstrating that luciferase constructs tagged with each peptide epitope can be separated and used to independently read out promoter activation in a same cell.

to detect activation of a promoter-reporter construct in a cancer cell line, along with corresponding performance data. In this design, a cancer specific promoter (Px, in this case represented by the survivin promoter) is used to drive expression of a secretion-signal modified luciferase also fused to a human chorionic gonadotropin (hCG) epitope. FIG. 37B shows via transfection of various related constructs into H1299 cells that the hCG tag does not appreciably disrupt expression of luciferase from the survivin promoter. FIG. 37C shows that the supernatant from the transfected cells can be loaded onto a commercial lateral-flow immunoassay strip for hCG and that the lateral flow immunoassay can detect the hCG-tagged luciferase, showing the utility of using exiting epitope immunoassays to read out the expression of promoter-reporter constructs where the reporter is tagged with an epitope having a high-confidence off-the-shelf assay.

DETAILED DESCRIPTION OF THE INVENTION

Figure 1:
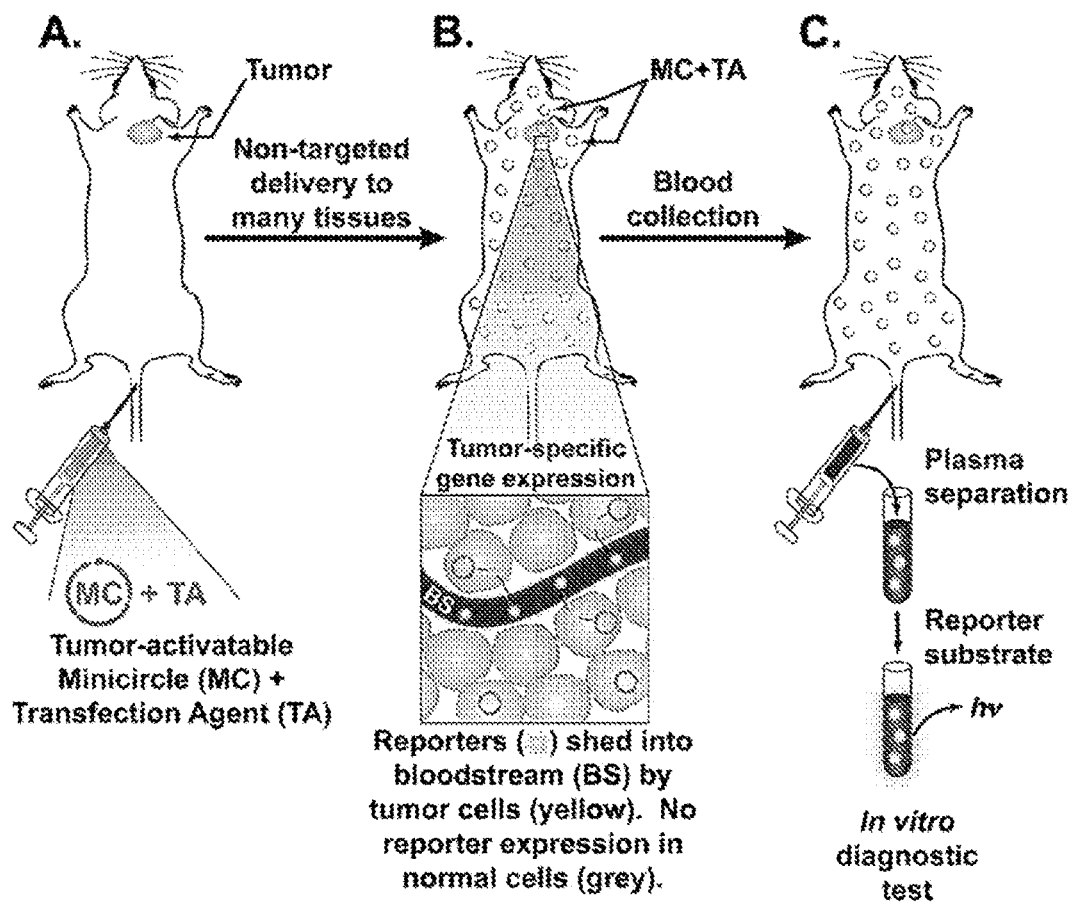
FIG. 1 schematically illustrates a blood-based tumor-activatable minicircle (MC) approach for cancer detection. (A) Tumor-activatable MCs driven by a tumor-specific promoter and encoding a secretable reporter protein are complexed with a non-targeted transfection agent (TA). These nanocomplexes are delivered systemically (via tail-vein). (B) MCs transfect many tissues, but reporter protein production occurs near-exclusively within tumor cells and the expressed reporter is secreted into the bloodstream (BS). Minimal protein expression should occur in tumor-free subjects due to promoter leakiness. (C) Collection of blood and detection of the secreted reporter in plasma enables differentiation between tumor-bearing (reporter-positive) and tumor-free (reporter-negative) subjects.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

The term "subject" can include human or non-human animals. Thus, the methods and compositions described herein are applicable to both human and veterinary disease and animal models. Preferred subjects are "patients," i.e., living humans that are receiving medical care for a disease or condition. This includes persons with no defined illness who are being investigated for signs of pathology. Also included are persons suspected of possessing or being at-risk for a defined illness. In some embodiments, the subject has at least one risk factor for cancer such as Li-Fraumeni syndrome, lynch syndrome, familial adenomatous polyposis, lung nodules, Von Hippel-Lindau disease, aplastic anemia, myelodysplastic syndrome, Cowden syndrome, hereditary breast and ovarian cancer syndrome (HBOC), or BRCA mutations; being a current smoker, ex-smoker, or exposed to heavy doses of second hand smoke; exposure to carcinogens, excessive sunlight, immunosuppressive agents, or hepatitis B, hepatitis C, or human papilloma virus; or obesity.

The term "gene," as used herein refers to all regulatory and coding sequences contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances, complexes of a plurality of protein or nucleic acids or other molecules, or of any two of the above, may be required for a gene's function. On the other hand, a gene's genetic function may require only RNA expression or protein production or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

The terms "episomally replicating vector" or "episomal vector" as used herein refer to a vector which is typically not integrated into the genome of the host cell but exists in parallel. An episomally replicating vector may be replicated during the cell cycle and in the course of this replication the vector copies are distributed statistically in the resulting cells depending on the number of the copies present before and after cell division. Replication may take place in the nucleus of the host cell, and preferably replicates during S-phase of the cell cycle. Moreover, the episomally replicating vector can be replicated at least once, i.e. one or multiple times, in the nucleus of the host cell during S-phase of the cell cycle.

The term "sample" is defined as any material to be tested in an analytical or experimental method as described herein. Samples are typically obtained from a subject as described herein. Samples include, but are not limited to, blood or blood fractions, saliva, urine, stool, cerebrospinal fluid, semen, vaginal secretions, sputum, sweat, breast milk, synovial fluid, mucus (including rheum), tears, bile, gastric fluid, interstitial fluid, biopsies of tissues or epithelial cells that are naturally shed or specifically collected from the body (such as cheek cell scrapings), aqueous humor, amniotic fluid, pleural fluid or breath exhalation from a subject. In some embodiments, the sample is obtained via a non-invasive method (e.g. is a non-invasive sample). Exemplary non-invasive methods include but are not limited to passive collection of bodily fluids, or non-injurious scrapings of tissues accessible to the external environment (e.g. of the epidermis, or mouth). Exemplary non-invasive samples include but are not limited to saliva, sputum, mucus, sweat, urine, stool, semen, cervicovaginal secretions, breast milk, rheum, tears, or cheek epithelial swabs. In some embodiments, the sample is obtained via a minimally-invasive method. Exemplary minimally-invasive methods include, but are not limited to, capillary collection, venipuncture, thoracentesis, amniocentesis, needle aspiration, or gastric lavage. Exemplary minimally-invasive samples include, but are not limited to, blood or blood fractions (e.g. plasma or PBMC preparations), interstitial fluid, bile, gastric fluid, and amniotic fluid. In some embodiments, the sample is obtained via biopsy. Exemplary biopsy samples include, but are not limited to, skin biopsy samples (e.g. obtained by punch, shave, saucerization, wedge, incisional, or excisional biopsy), a bone marrow samples (e.g. obtained by aspiration biopsy), a lymph node or breast biopsies (e.g. obtained by fine-needle aspiration, core needle biopsy, vacuum assisted biopsy, or image-guided biopsy), a surgical biopsy samples (e.g. of an internal organ obtained by excisional or incisional biopsy), or mouth, GI-tract, lung, bladder, or urinary tract biopsy samples (e.g. obtained by endoscopy).

The term "origin of replication" as used herein refers to a DNA sequence that is recognized by a replication initiation factor or a DNA replicase leading to replication of a plasmid containing the origin of replication. The expression "recognized by a replication initiation factor" is intended to mean that a replication initiation factor can physically interact with all or a portion of an origin of replication sequence, thereby causing or stimulating molecular mechanisms that ultimately cause all or a portion of the DNA molecule comprising the origin of replication to be replicated. The origin of replication, thus, typically comprises functionally required elements. One example for such functionally required elements are the family of repeats (FR) element or the dyad symmetry (DS) element of the EBV origin of replication (OriP). Further origin of replications comprising functionally required elements are well known in the art and are described for example in Bode et al., (2001) Gene Ther. Mol. Biol. 6: 33-46. The parental nucleic acid plasmid vectors of the dis-closure preferably comprise at least one origin of replication.

A "vector" is a nucleic acid sequence capable of transferring other operably-linked heterologous or recombinant nucleic acid sequences to target cells. In some examples, a vector is a minicircle, plasmid, nanoplasmid, yeast artificial chromosome (YAC), bacterial artificial chromosome (BAC), cosmid, phagemid, bacteriophage genome, or baculovirus genome. Suitable vectors also include vectors derived from bacteriophages or plant, invertebrate, or animal (including human) viruses such as CELiD vectors, adeno-associated viral vectors (e.g. AAV1, AAV2, AAV4, AAV5, AAV6, AAV7, AAV8, AAV9, or pseudotyped combinations thereof such as AAV2/5, AAV2/2, AAV-DJ, or AAV-DJ8), retroviral vectors (e.g. MLV or self-inactivating or SIN versions thereof, or pseudotyped versions thereof), herpesviral (e.g. HSV- or EBV-based), lentiviral vectors (e.g. HIV-, FIV-, or EIAV-based, or pseudotyped versions thereof), or adenoviral vectors (e.g. Ad5-based, including replication-deficient, replication-competent, or helper-dependent versions thereof). In some embodiments, a vector is a replication competent viral-derived vector. In some embodiments, a vector is a replication-incompetent viral-derived vector. In some cases, the vector may comprise an episomal maintenance element to facilitate replication in one or more target cell type, such as a Scaffold/Matrix Attachment Region (S/MAR). S/MAR elements are particularly useful to facilitate replication in the context of "naked" nucleic acid vectors such as minicircles. Exemplary suitable S/MAR elements include. but are not limited to, EnMAR from the immunoglobulin heavy chain locus, the apoB MAR from the human apolipoprotein B locus, the Ch-LysMAR from the chicken lysozyme locus, and the huIFM3 MAR from the human IFNβ-locus. A vector may comprise a coding sequence capable of being expressed in a target cell. Accordingly, as used herein, the terms "vector construct," "expression vector," and "gene transfer vector," may refer to any nucleic acid construct capable of directing the expression of a gene of interest and which is useful in transferring the gene of interest into target cells. Vectors as described herein may additionally comprise one or more cis-acting elements to stabilize or improve expression of mRNAs therefrom. Such cis-acting elements include but are not limited to any of the elements described e.g., in Johansen et al. The Journal of Gene Medicine. (5)12:1080-1089 or Vlasova-St. Louis and Sagarsky. Mammalian Cis-Acting RNA Sequence Elements (IntechOpen).

As one of the forms of vectors, the term "minicircle" as used herein refer to a small, double stranded circular DNA molecule that provides for persistent, high level expression of a sequence of interest that is present on the vector, which sequence of interest may encode a polypeptide, an shRNA, an anti-sense RNA, an siRNA, and the like. The sequence of interest is operably linked to regulatory sequences present on the minicircle vector, said regulatory sequences controlling its expression. Such minicircle vectors are described, for example in published U.S. Patent Application US20040214329, herein specifically incorporated by reference. As a different form of vectors, "nanoplasmid" refers to a vector that may comprise minimized bacterial ColE1 or R6K origin of replication (which provides for such nanoplasmids to be replicable in a bacterial host strain), a bacterial RNA-selectable marker, and a eukaryotic gene region. Such nanoplasmids can comprise the mini-R6K origin of SEQ ID NO: 3 and/or the RNA-OUT selectable marker of SEQ ID NO: 4. Further examples of such elements (nanoplasmid origins and RNA-out selectable markers) are described e.g., in U.S. Pat. No. 9,737,620B2, which is incorporated by reference herein for the purposes of describing nanoplasmid sequence elements.

The overall length of a minicircle vector is sufficient to include the desired elements as described below, but not so long as to prevent or substantially inhibit to an unacceptable level the ability of the vector to enter a target cell upon contact with the cell, e.g., via system administration to the host comprising the cell. As such, the minicircle vector can be generally at least about 0.3 kb long, often at least about 1.0 kb long, whereas the parental vector may be as long as 6 kb, 10 kb, or longer.

Minicircle vectors differ from bacterial plasmid vectors in that they lack an origin of replication or lack a natural origin of replication (e.g. may comprise a minimized synthetic bacterial origin of replication), and lack a selection marker commonly found in bacterial plasmids, e.g. p-lactamase, tetracycline-resistance (tet), kanamycin-resistance (kan), or other antibiotic selection markers. Consequently, a minicircle becomes smaller in size, allowing more efficient delivery. Minicircles lack the transgene expression silencing effect which is associated with the vector backbone nucleic acid sequences of parental plasmids from which the minicircle vectors are excised. The minicircle may be substantially free of vector sequences other than the recombinase hybrid product sequence, and the sequence of interest, i.e. a transcribed sequence and regulatory sequences required for expression.

The term "nanoplasmid" as used herein refer to a vector that may comprise minimized bacterial ColE1 or R6K origin of replication (which provides for such nanoplasmids to be replicable in a bacterial host strain), a bacterial RNA-selectable marker, and a eukaryotic gene region. Some embodiments of nanoplasmids are described in e.g. US20150275221A1. In some embodiments, the nanoplasmid may comprise a fusion bacterial-RNA-selectable marker/minimized origin of replication. In some embodiments, the fusion bacterial-RNA-selectable marker/minimized origin of replication may be located within a synthetic intron located within the eukaryotic gene region of the nanoplasmid.

An RNA selectable marker is a vector-borne expressed non translated RNA that regulates a chromosomally expressed target gene to afford selection of the vector. This may be a plasmid borne nonsense suppressing tRNA that regulates a nonsense suppressible selectable chromosomal target as described by Crouzet J and Soubrier F 2005 U.S. Pat. No. 6,977,174 included herein by reference. This may also be a plasmid borne antisense repressor RNA, an RNA-OUTgene that represses RNA-IN regulated targets, pMB1 plasmid origin encoded RNAI that represses RNAII regulated targets, IncB plasmid pMU720 origin encoded RNAI that represses RNA II regulated targets, ParB locus Sok of plasmid RI that represses Hok regulated targets, Flm locus FlmB of F plasmid that represses flmA regulated targets, another natural antisense repressor RNA such as those described in e.g. Wagner E G H, Altuvia S, Romby P. 2002. Adv Genet 46:361 and Franch T, and Gerdes K. 2000. Current Opin Microbiol 3: 159, or an engineered repressor RNA such as a small synthetic small RNA like the SgrS, MicC or MicF scaffolds as described in Park et al. Nature Biotechnology volume 31, pages 170-174 (2013).

A number of suitable methods for transfecting cells according to the disclosure are available. By "transfected" it is meant an alteration in a cell resulting from the uptake of foreign nucleic acid, usually DNA. Use of the term "transfection" is not intended to limit introduction of the foreign nucleic acid to any particular method. Thus, suitable methods include viral infection/transduction, conjugation, nanoparticle delivery, electroporation, particle gun technology, calcium phosphate precipitation, direct microinjection, and the like. The choice of method is dependent on the type of cell being transfected and the circumstances under which the transfection is taking place (i.e. in vitro, ex vivo, or in vivo). A general discussion of these methods can be found in Ausubel, et al., Short Protocols in Molecular Biology, 3rd ed., Wiley & Sons, 1995, which are hereby incorporated by reference.

The term "transfection agent" may encompass any compound that mediates incorporation of DNA or RNA into a host cell, e.g., a liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), Ausubel, et al., Short Protocols in Molecular Biology, 3rd ed., Wiley & Sons, 1995, and other laboratory manuals, which are hereby incorporated by reference. Examples of suitable transfection agents include, but are not limited to, linear or branched polyethylenimines, nanoparticles, liposomes, lipophilic particles, solid nanoparticles, amphipathic peptides, micelles, dendrimers, polymeric compositions, hydrogels, synthetic or naturally derived exosomes, virus-like particles, or any combination thereof.

The term "EXOmotif", as used herein, refers to an RNA sequence controlling loading of a miRNA into an exosome. In some embodiments, an EXOmotif may mediate the binding of a miRNA to heterogeneous ribonucleoprotein A2B1 (hnRNPA2B1), which has been described as controlling the loading of miRNAs into exosomes. Such sequences include, but are not limited to, 5'-GGAG-3' and 5'-CCCU-3'.

The terms "nucleic acid molecule" and "polynucleotide" as used herein refer polymeric forms of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "promoter" is a DNA sequence that directs the transcription of a polynucleotide. Typically, a promoter can be located in the 5' region of a polynucleotide to be transcribed, proximal to the transcriptional start site of such polynucleotide. More typically, promoters are defined as the region upstream of the first exon; more typically, as a region upstream of the first of multiple transcription start sites. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include upstream activator regions (UARs) and optionally, other DNA sequences that affect transcription of a polynucleotide such as a synthetic upstream element.

The terms "coding sequence" and "encodes" when used in reference to a polypeptide herein refer to a nucleic acid molecule that is transcribed (in the case of DNA) and translated (in the case of mRNA) into a polypeptide, for example, when the nucleic acid is present in a living cell (in vivo) and placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral, eukaryotic, or prokaryotic DNA, and synthetic DNA sequences. A transcription termination sequence may be located 3' to the coding sequence, and a promoter may be located 5' to the coding sequence; along with additional control sequences if desired, such as enhancers, introns, poly adenylation site, etc. A DNA sequence encoding a polypeptide may be optimized for expression in a selected cell by using the codons preferred by the selected cell to represent the DNA copy of the desired polypeptide coding sequence.

The term "barcode" or "barcode molecule" as used herein generally refers to a label, or an identifier, that conveys or is capable of conveying information about a molecule to which the barcode/barcode molecule is attached. A barcode/barcode molecule may be unique. Barcodes/barcode molecules may have a variety of different formats. For example, barcodes/barcode molecules can include polynucleotide barcodes; random nucleic acid and/or amino acid sequences; and synthetic nucleic acid and/or amino acid sequences. A barcode/barcode molecule can be attached to a molecule in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "operably linked" as used herein refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "expression cassette" as used herein refers to any nucleic acid construct capable of directing the expression of any RNA transcript including gene/coding sequence of interest as well as non-translated RNAs, such as shRNAs, microRNAs, siRNAs, anti-sense RNAs, and the like. Such cassettes can be constructed into a "vector," "vector construct," "expression vector," or "gene transfer vector," in order to transfer the expression cassette into target cells. Thus, the term includes cloning and expression vehicles, as well as viral vectors.

The term "target cell" as used herein refers to a cell that in which a genetic modification is desired. Target cells can be isolated (e.g., in culture) or in a multicellular organism (e.g., in a blastocyst, in a fetus, in a postnatal animal, and the like).

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as pea-nut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "detectable" refers to the ability to detect a signal over the background signal. The detectable signal is defined as an amount sufficient to yield an acceptable image using equipment that is available for pre-clinical use. A detectable signal maybe generated by one or more administrations of the probes of the present disclosure. The amount administered can vary according to factors such as the degree of susceptibility of the individual, the age, sex, and weight of the individual, idiosyncratic responses of the individual, the dosimetry, and the like. The amount administered can also vary according to instrument and digital processing related factors.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The "imaging moiety" may be detected either externally to a subject human or non-human animal body or via use of detectors designed for use in vivo, such as intravascular radiation or optical detectors such as endoscopes, or radiation detectors designed for intra-operative use. The imaging moiety is preferably but is not limited to a reporter suitable for in vivo optical imaging.

The term "bioluminescence" as used herein refers to a type of chemiluminescent emission of light by biological molecules, particularly proteins. The essential condition for bioluminescence is molecular oxygen, either bound or free in the presence of an oxygenase, a luciferase, which acts on a substrate, a luciferin in the presence of molecular oxygen and transforms the substrate to an excited state, which upon return to a lower energy level releases the energy in the form of light.

The term "luciferase" as used herein refers to oxygenases that catalyze a light emitting reaction. For instance, bacterial luciferases catalyze the oxidation of flavin mono-nucleotide and aliphatic aldehydes, which reaction produces light. Another class of luciferases, found among marine arthropods, catalyzes the oxidation of Cypridina luciferin, and another class of luciferases catalyzes the oxidation of Coleoptera luciferin. Thus, "luciferase" refers to an enzyme or photoprotein that catalyzes a bioluminescent reaction. The luciferases such as firefly and *Renilla* luciferases are enzymes that act catalytically and are unchanged during the bioluminescence generating reaction. The luciferase photoproteins, such as the aequorin and obelin photoproteins to which luciferin is non-covalently bound, are changed by release of the luciferin, during bioluminescence generating reaction. The luciferase is a protein that occurs naturally in an organism or a variant or mutant thereof, such as a variant produced by mutagenesis that has one or more properties, such as thermal or pH stability, that differ from the naturally-occurring protein. Luciferases and modified mutant or variant forms thereof are well known. Reference, for example, to "*Renilla* luciferase" means an enzyme isolated from member of the genus *Renilla* or an equivalent molecule obtained from any other source, such as from another Anthozoa, or that has been prepared synthetically.

"Bioluminescent protein" refers to a protein capable of acting on a bioluminescent initiator molecule substrate to generate or emit bioluminescence.

"Bioluminescent initiator molecule" is a molecule that can react with a bioluminescent donor protein to generate bioluminescence. The bioluminescence initiator molecule includes, but is not limited to, coelenterazine, analogs thereof, and functional derivatives thereof. Derivatives of coelenterazine include, but are not limited to, coelenterazine 400a, coelenterazine cp, coelenterazine f, coelenterazine fcp, coelenterazine h, coelenterazine hcp; coelenterazine ip, coelenterazine n, coelenterazine 0, coelenterazine c, coelenterazine c, coelenterazine i, coelenterazine icp, coelenterazine 2-methyl, benzyl-coelenterazine bisdeoxycoelenterazine, and deep blue coelenterazine (DBC) (described in more detail in U.S. Pat. Nos. 6,020,192; 5,968,750 and 5,874,304).

In general, coelenterazines are known to luminesce when acted upon by a wide variety of bioluminescent proteins, specifically luciferases. Useful, but non-limiting, coelenterazines are disclosed in U.S. patent application Ser. No. 10/053,482, filed Nov. 2, 2001, the disclosure of which is hereby incorporated by reference in its entirety. Coelenterazines are available from Promega Corporation, Madison, Wis. and from Molecular Probes, Inc., Eugene, Oreg. Coelentera-zines may also be synthesized as described for example in Shimomura et al., (1989) Biochem. J. 261: 913-920; Inouye et al., (1997) Biochem. Biophys. Res. Comm. 233: 349-353, 1997; and Teranishi et al., (1997) Anal. Biochem. 249: 37-43.

The term "Survivin" as used herein refers to a protein also called baculoviral inhibitor of apoptosis repeat-containing 5 or BIRC5, is a protein that, in humans, is encoded by the BIRC5 gene. (NCBI Reference Sequence: NG 029069. 1). Survivin is a member of the inhibitor of apoptosis (IAP) family. The survivin protein inhibits caspase activation, thereby leading to negative regulation of apoptosis or programmed cell death. This has been shown by disruption of survivin induction pathways leading to an increase in apoptosis and decrease in tumor growth. The survivin protein is expressed highly in most human tumors and fetal tissue but is completely absent in terminally differentiated cells. Survivin expression is also highly regulated by the cell cycle and is only expressed in the G2-M phase. It is known that survivin localizes to the mitotic spindle by interaction with tubulin during mitosis and may play a contributing role in regulating mitosis. Regulation of survivin seems to be linked to the p53 protein. It also is a direct target gene of the Wnt pathway and is upregulated by 0-catenin.

It is contemplated, however, that the minicircles of the disclosure may utilize any tumor-specific promoter operably linked to a reporter or other heterologous nucleic acid sequence desired to be expressed in a target cell. For example, but not intended to be limiting, suitable promoters known in the art include: CXCR4 promoter tumor-specific in melanomas; Hexokinase type II promoter tumor-specific in lung cancer; TRPM4 (Transient Receptor Potential-Melastatin 4) promoter is preferentially active in prostate cancer; stromelysin 3 promoter is specific for breast cancer cells (Basset et al., (1990) Nature 348: 699); surfactant protein A promoter specific for non-small cell lung cancer cells (Smith et al., 1994) Hum. Gene Ther. 5: 29-35); secretory leukoprotease inhibitor (SLPI) promoter specific for SLPI-expressing carcinomas (Garver et al., (1994) Gene Ther. 1: 46-50); tyrosinase promoter specific for melanoma cells (Vile et al., (1994) Gene Ther. 1: 307); stress-inducible grp78/BiP promoter specific for fibrosarcoma/tumorigenic cells (Gazit et al., (1995) Cancer Res. 55: 1660); interleukin-10 promoter specific for glioblastoma multiform cells (Nitta et al., (1994) Brain Res. 649: 122); a-B-crystallin/heat shock protein 27 promoter specific for brain tumor cells (Aoyama et al., (1993) Int. J. Cancer 55: 760); epidermal growth factor receptor promoter specific for squamous cell carcinoma, glioma, and breast tumor cells (Ishii et al., (1993) Proc. Natl. Acad. Sci. U.S.A. 90: 282); mucin-like glycoprotein (DF3, MUC1) promoter specific for breast carcinoma cells (Abe et al., (1993) Proc. Natl. Acad. Sci. U.S.A. 90: 282); mts 1 promoter specific for metastatic tumors (Tulchinsky et al., (1992) Proc. Natl. Acad. Sci. U.S.A. 89: 9146); NSE promoter specific for small-cell lung cancer cells (Forss-Petter et al., (1990) Neuron 5: 187); somatostatin receptor promoter specific for small cell lung cancer cells (Bombardieri et al., (1995) Eur. J. Cancer 31A: 184; Koh et al., (1995) Int. J. Cancer 60: 843); c-erbB-3 and c-erbB-2 promoters are specific for breast cancer cells (Quin et al., (1994) Histopathology 25: 247); c-erbB4 promoter specific for breast and gastric cancer cells (Rajkumar et al., (1994) Breast Cancer Res. Trends 29: 3); thyroglobulin promoter specific for thyroid carcinoma cells (Mariotti et al., (1995) J. Clin.

Endocrinol. Meth. 80: 468); a-fetoprotein promoter specific for hepatoma cells (Zuibel et al., (1995) J. Cell. Phys. 162: 36); villin promoter specific for gastric cancer cells (Osborn et al., (1988) Virchows Arch. A. Pathol. Anat. Histopathol. 413: 303); and albumin promoter specific for hepatoma cells (Huber, (1991) Proc. Natl. Acad. Sci. U.S.A. 88: 8099), which are all hereby incorporation by reference. Other examples of promoters are an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/ nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, a functional fragment thereof, or any combination thereof.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Abbreviations

SEAP, Secreted Embryonic Alkaline Phosphatase; MRI, magnetic resonance imaging; SPECT, Single-photon emission computed tomography; MC, mini-circle; PP, parental plasmid; WPRE, Woodchuck Hepatitis Virus (WHP) Post-transcriptional Regulatory Element (WPRE; Luc, luciferase; BLI, bioluminescence imaging; ROI, region of interest;

AUC, area under the curve; RG, reporter gene; TS, tumor-specific; Fluc (FLUC), firefly luciferase, ROC (receiver operator-characteristic)

INTRODUCTION

Early detection of cancer can dramatically improve the efficacy of available treatment strategies. Yet, despite decades of effort on blood-based biomarker cancer detection, many promising endogenous biomarkers have failed clinically due to intractable problems such as highly variable background expression from non-malignant tissues. Strategies for improved cancer diagnosis have traditionally relied on measurement of endogenous molecules that are over-expressed in cancer cells either via molecular imaging or blood-based assays. A challenge of these strategies is often significant expression within non-cancerous tissues, leading to high background levels and confounding results. An alternative strategy is to utilize promoters of tumor-specific (TS) proteins in exogenously-delivered gene vectors in order to drive the expression of unique reporter genes (RGs) strictly within tumors. For this strategy to become a reality, safety, specificity, and sensitivity are of utmost importance. While safer than viral vectors, two drawbacks of non-viral vectors have been low gene transfer rates and transient expression profiles. Minicircles (MCs) are plasmids that lack a bacterial backbone and are advantageous to overcome the above key issues.

The present disclosure provides embodiments of an alternative and advantageous detection strategy based on systemic administration of safe, tumor-activatable minicircles that utilize the pan-tumor-specific Survivin promoter to drive expression of a secretable reporter gene that is detectable in the blood near-exclusively in tumor-bearing subjects. After systemic administration a robust ability to differentiate mice bearing experimental human melanoma metastases from tumor-free subjects for up to 2 weeks simply by measuring blood reporter levels has been shown. Cumulative changes in reporter levels also identified tumor-bearing subjects, and a receiver operator-characteristic curve analysis highlighted this test's performance with an AUC of $0.918 \pm 0.084$. Lung tumor burden correlated ($r2=0.714$; $p<0.05$) with cumulative reporter levels indicating that a determination of disease extent was possible. Continued development of our system could dramatically improve tumor detectability due to temporally-controlled, high reporter expression in tumors and near-zero background from healthy tissues is possible.

Tumor-specific nanoplasmid vectors driving the expression of either secreted embryonic alkaline phosphatase (SEAP) or firefly luciferase (FLUC) have been developed and their utility validated for detecting tumors after systemic administration using blood- and/or imaging-based assays. For gene vectors to be used for cancer screening purposes, challenges include efficient tumor delivery, achieving potent expression for maximum sensitivity, stringent control of expression to attain tumor specificity, and minimization of safety concerns. Tumor-specific minicircle vectors can overcome all of these challenges and it is now shown that systemically administered tumor-specific minicircle vectors can be assayed via serum and non-invasive imaging to differentially identify tumor-bearing subjects from normal subjects. Importantly, the tumor-specific minicircle vectors of the disclosure advantageously have broad applicability in many patient populations since the Survivin promoter drives expression across many different tumor types of tumor cell. The tumor-specific minicircle vectors of the disclosure provide a novel cancer management paradigm that involves tumor detection via an initial blood-based assay, tumor localization via molecular-genetic imaging, and tumor treatment using theranostic tumor-specific minicircle vectors.

The present disclosure encompasses embodiments of nucleic acid nanoplasmid vectors most advantageous for the detection of tumor cells. In particular, the minicircles of the disclosure incorporate a tumor-specific promoter operably linked to a nucleotide sequence desired to be selectively expressed in a tumor cell or a tissue comprising a population of tumor cells. In some embodiments of the disclosure, the minicircle vectors comprise a tumor-specific promoter operably linked to a nucleotide sequence encoding a polypeptide useful as a reporter. Accordingly, when expressed by a recipient tumor cell, the reporter may be detectable, thereby providing information such as a visual image of the tumor cell and/or its location in a tissue of the subject human or non-human animal.

In some embodiments, the nanoplasmid vectors according to the disclosure can advantageously deliver an expressible reporter gene to a tumor cell. It is within the scope of the disclosure for the reporter gene to be detectable by such non-invasive detection methods as MRI imaging, PET imaging, SPECT imaging, luminescence imaging and the like. For example, but not intended to be limiting, MRI reporter genes encode for creatine kinase; tyrosinase; transferrin receptor; ferritin; Mag A. PET imaging reporter genes include, but are not limited to such as Herpes simplex virus 1 thymidine kinase (HSV1-TK); hypoxanthine phosphoribosyl transferase; L-amino acid decarboxylase; dopamine 2 receptor (D2R, including the mutant D2RA80); somatostatin receptor; estrogen receptor (hERL); dopamine transporter; sodium iodide symporter; catecholamine transporter; β-galactosidase. PET/SPECT imaging reporter genes include, but are not limited to, Herpes simplex virus Type 1 thymidine kinase and multiple optimized mutants, such as HSV1-sr39tk; dopamine type 2 receptor; sodium iodide symporter; somatostatin type 2 receptor; human norepinephrine transporter; human estrogen receptor a; mutants of human deoxycytidine kinase; and recombinant carcinoembryonic antigen. Bioluminescence reporter genes include, but are not limited to, firefly luciferase (fl); synthetic *Renilla* luciferase (hrl); Enhanced Green Fluorescence protein (egfp); Red Fluorescence Protein (rfp); monomeric Red Fluorescence Protein (mrfp 1), and the like. It is further possible for the reporter genes suitable for incorporation into the minicircles of the disclosure to provide multi-modality methods of imaging. For example, but not intended to be limiting, a reporter gene suitable for photoacoustic, MRI, and PET imaging, is the gene encoding human tyrosinase, as described by Qin et al., (2013), Sci. Rpts. 3: Art. No.: 1490, incorporated herein by reference its entirety.

In addition to the advantageous use of the nanoplasmids of the disclosure for selectively detecting a recipient tumor cell, the nucleotide sequence operably linked to the tumor-specific promoter may encode a polypeptide useful for modulating the proliferation or metabolic activity of a recipient tumor cell for the purpose of reducing or eliminating the targeted tumor cell from the subject human or non-human animal.

For example, but not intended to be limiting, therapeutically effective polypeptides that are advantageous for targeting and therapeutically challenging a tumor cell include HSVtk; cytosine deaminase; DT diaphorase; nitroreductase; guanine phosphoribosyl transferase; purine nucleoside phosphorylase; thymidine phorphorylase; carboxylesterase; folylpolyglutamyl synthetase; carboxypeptidase A1; carboxypeptidase G2; cytochrome P-450 (CYP2B1), and the like. The activities of these polypeptides for the conversion of a prodrug to an effective therapeutic composition are described in, for example, Harrington et al., (2002) Clinical Oncology 14: 148-169 incorporated herein by reference in its entirety.

In further embodiments of the disclosure, it is contemplated that the nucleotide sequence tumor-specifically expressed from the minicircle may not be translated into a heterologous polypeptide but rather may be expressed as a short interfering ribonucleotide sequence (siRNA) that may interact with at least one gene regulatory element of the recipient tumor cell, again modulating the proliferation or metabolic activity of a recipient tumor cell. Alternatively, it is contemplated that the nucleotide sequence may be expressed as a microRNA sequence (miRNA) or as a synthetic RNA sequence that does not correspond to any known endogenous sequence and only serves the purpose of being an agent detectable by nucleic acid hybridization or amplification-based techniques (a nucleic acid biomarker).

Accordingly, it is contemplated to be within the scope of the disclosure to provide embodiments of nucleic acid minicircle vectors (and the parental plasmids thereof) useful for selectively targeting tumor cells cultured in vitro or, most advantageously, in vivo to obtain detectable signals identifying and/or locating a cancerous cell or population of tumor cells in the subject as well as for delivering a therapeutic agent (peptide, polypeptide, nucleic acid) to the targeted tumor cells.

Figure 3:
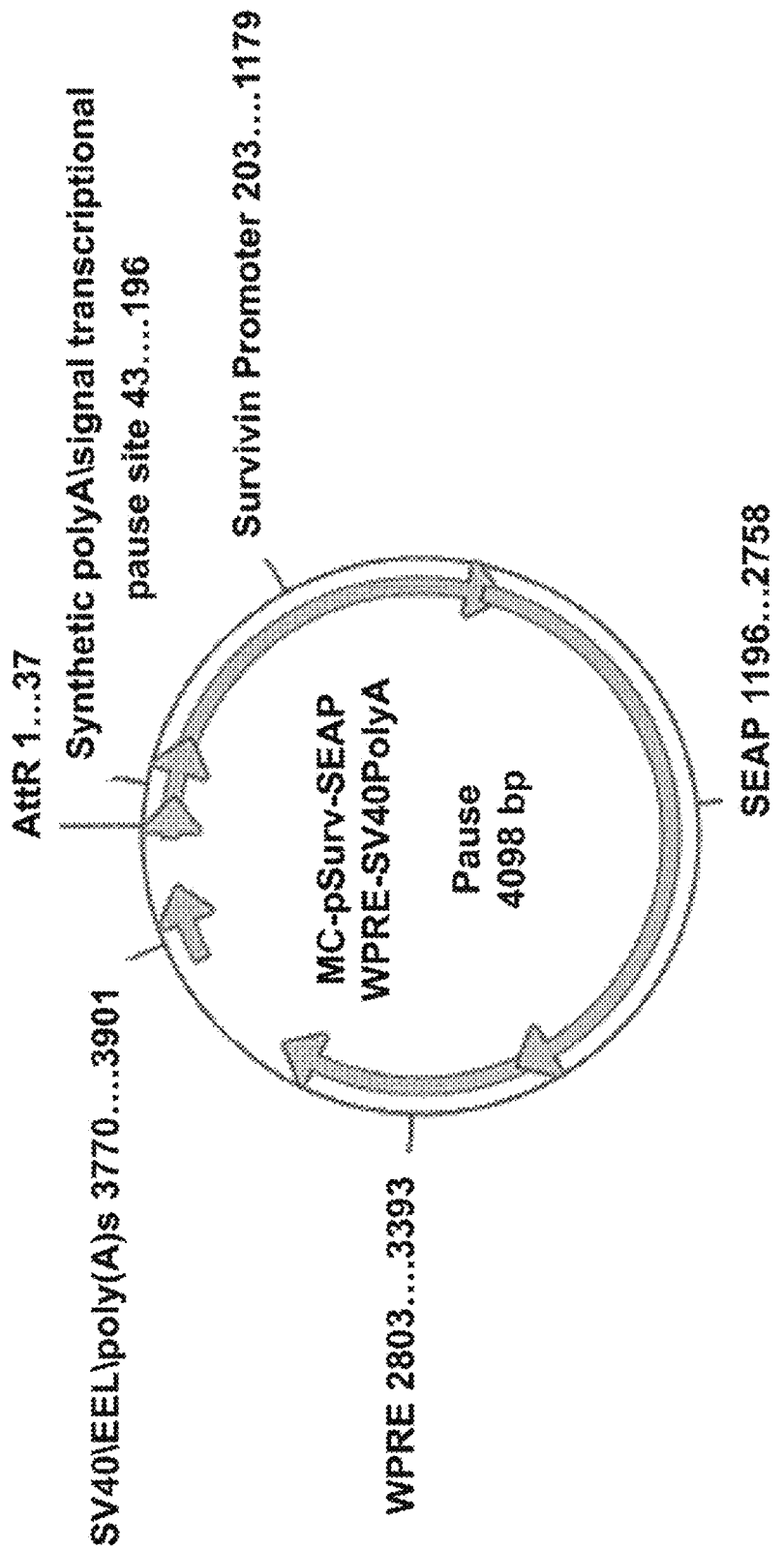
FIG. 3 is a schematic map of minicircle vector construct MC-pSurv-SEAP-WPRE-SV40PolyA-pause.

The present disclosure provides nucleic acid minicircle vectors useful for administering to a subject human or non-human animal for the purpose of detecting the presence of a targeted tumor cell or cells (including a tumor tissue). For example, the minicircle construct MC-pSurv-SEAP-WPRE-SV40PolyA as shown in FIG. 3 and having the nucleotide sequence SEQ ID NO: 1 as shown in FIG. 13, comprises a nucleic acid fragment encoding the detectable polypeptide secreted embryonic alkaline phosphatase (SEAP) operably linked to the tumor-specific promoter pSurvivin.

Figure 4:
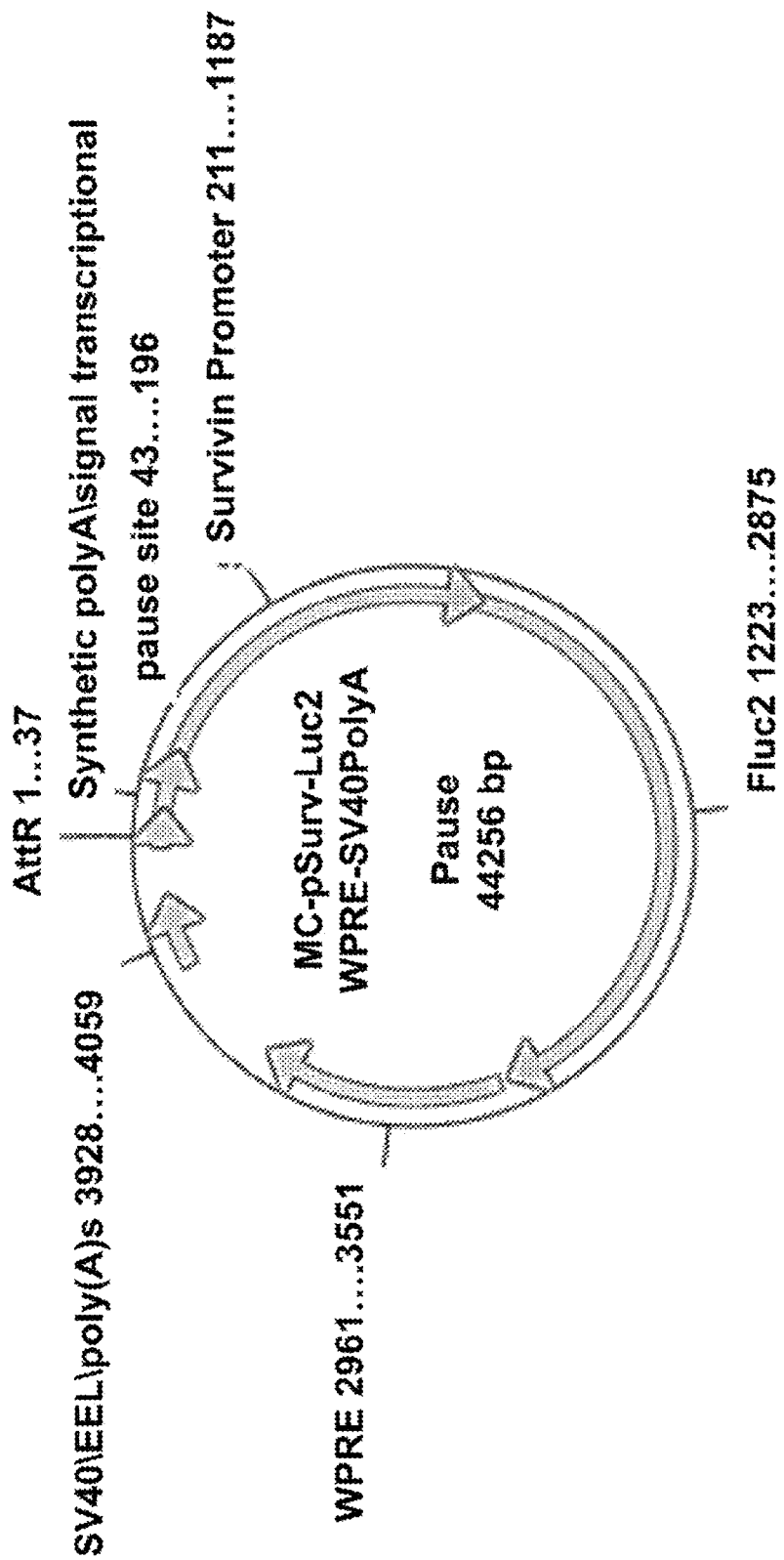
FIG. 4 is a schematic map of minicircle vector construct MC-pSurv-Luc2-WPRE-SV40PolyA-pause.
Figure 5:
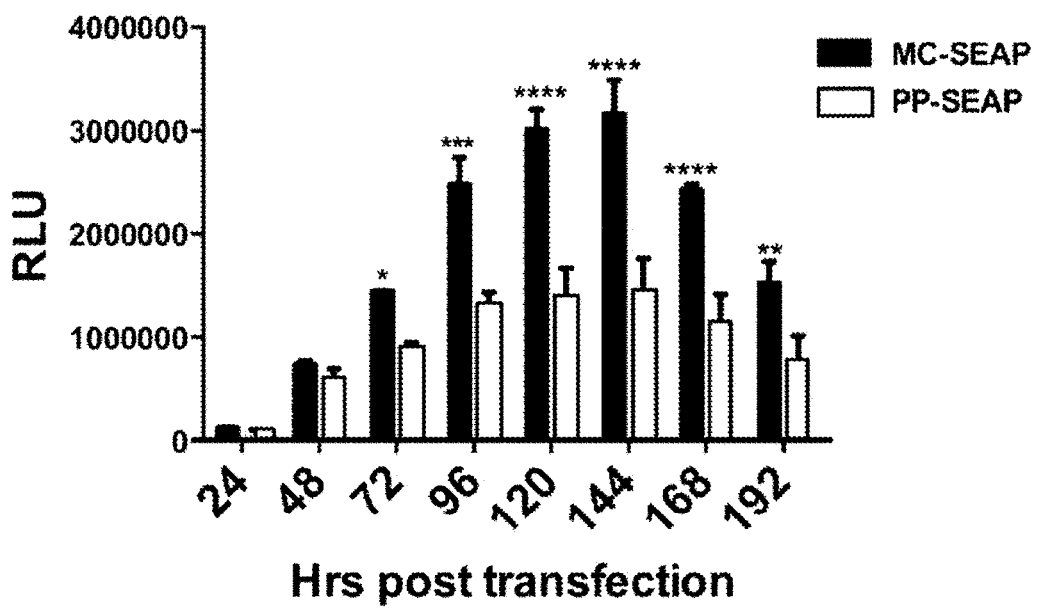
FIG. 5 is a graph illustrating a comparison of tumor-specific plasmids (PP-SEAP) and minicircles (MC-SEAP) in MeWo human melanoma cancer cells.
Figure 6:
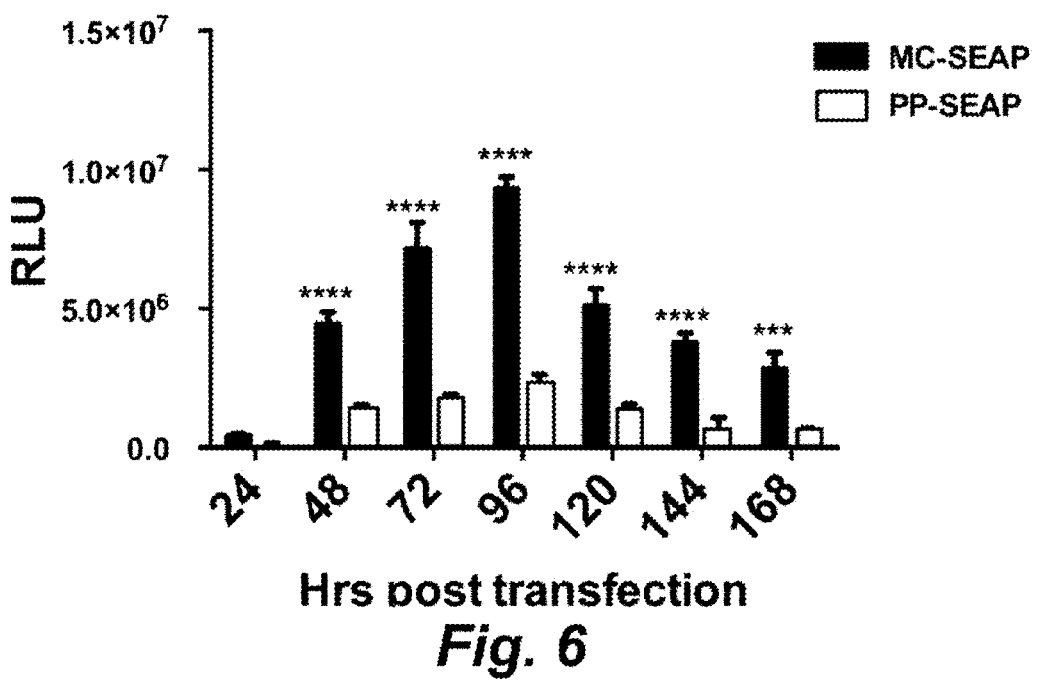
FIG. 6 is a graph illustrating a comparison of tumor-specific plasmids (PP-SEAP) and minicircles (MC-SEAP) in SK-MEL-28 human melanoma cancer cells.

When delivered to cultured melanoma cells, to subcutaneous melanoma xenografts, or intravenously to animals that have a developed tumor, the minicircle vectors of the disclosure provide detectable signals, either as a serum secreted alkaline phosphatase polypeptide or as a bioluminescent signal in the minicircle vector construct where SEAP had been replaced by a luciferase reporter, as shown in FIG. 4 (and having the nucleotide sequence SEQ ID NO: 2 as shown in FIG. 14). Accordingly, it has been demonstrated that the minicircle constructs of the disclosure can identify, in the recipient animal or human, both metastatic tumor cells or a localized tumor.

The present disclosure further provides methods of modulating the physiology or proliferation of a targeted tumor cell by delivering a minicircle nucleic acid to said tumor cell, allowing the targeted cell to express the nucleotide sequence from the nucleic acid sequence operably linked to the tumor-specific promoter, and allowing the expressed product to interact with the targeted cell, thereby modifying the physiological status of the cell or cells.

In a first instance, the disclosure provides embodiments of nucleic acid minicircles wherein a tumor-specific promoter is such as, but not limited to, the Survivin promoter.

Accordingly, to overcome the limitations of endogenous biomarker detection, the disclosure provides embodiments of a strategy based on identification of tumor-bearing individuals using blood-based detection of exogenously delivered genetically-encoded reporters, which produce tumor-driven biomarkers. The main advantage of this strategy is the ability to tailor biomarker expression exclusively in cells of a particular phenotype (i.e. tumor cells), thereby reducing the number of false positives due to protein production from non-malignant tissues. Thus, systemic administration of a tumor-activatable vector encoding a secretable reporter gene can be utilized to identify tumor-bearing subjects provided that transgene expression was transcriptionally targeted to cancer cells using a tumor-specific promoter (a promoter of a gene expressing a protein that is only present in tumors), as shown in FIG. 1. For this strategy to be translated into the clinic, the safety, specificity, sensitivity, and broad applicability are important and each component of the systems of the disclosure were chosen to offer maximum translational potential. Specifically, the present disclosure provides non-viral tumor-activatable minicircles (MCs) encoding a reporter gene including, but not limited to, human secreted embryonic alkaline phosphatase (SEAP) that attain tumor specificity through the use of a tumor-specific promoter such as, but not limited to, the Survivin promoter (pSurv).

While safer than viral vectors, two drawbacks of traditional non-viral vectors (i.e. plasmids) are low gene transfer rates and transient expression profiles. MCs are essentially plasmids that lack the prokaryotic backbone required only for expansion in bacteria. MCs have repeatedly shown to demonstrate improved expression profiles (months in non-dividing, and weeks in dividing, cells) compared to their plasmid counterparts due to their smaller size and reduced promoter silencing (Darquet et al., (1997) Gene Therapy 4: 1341-1349; Darquet et al., (1999) Gene Therapy 6: 209-218; Chen et al., (2003) Mol. Therapy: J. Am. Soc. Gene Therapy 8: 495-500; Chen et al., (2004) Gene Therapy 11: 856-864). MCs also conform to regulatory "plasmids free of antibiotic resistance genes" (pFAR) principles (Marie et al., (2010) J. Gene Med. 12: 323-332) which are known to be safer for human administration than constructs containing antibiotic resistance genes. Moreover, while producing MCs was traditionally very labor-intensive and time-consuming, more recent advances in MC production schemes have made it possible to produce large quantities in short periods of time with relative ease and reduced costs (Kay et al., (2010) Nat. Biotech. 28: 1287-1289). Finally, while integration is a safety concern with many gene (particularly viral) vectors, even with effective in vivo delivery methods like direct local injection and electroporation, the integration rates of non-viral vectors are approximately 1-3 orders of magnitude below the rate of spontaneous gene-inactivating mutations (Wang et al., (2004) Gene Therapy 11: 711-721; Nichols et al., (1995) Annals New York Acad. Sci. 772: 30-39; Ledwith et al., (2000) Develop. Biologicals 104: 33-43; Ledwith et al., (2000)Intervirology 43: 258-272). Hence, MCs have become one of the most useful non-viral vector platforms in terms of translational potential, potency and safety.

SEAP is a commonly used secretable reporter protein and has many ideal characteristics. It is an artificial, C-terminal truncated, secretable form of human placental alkaline phosphatase (PLAP) that is only expressed during embryogenesis; thus, it is a unique reporter not normally found in the blood and should have near-zero background (Berger et al., (1988) Gene 66: 1-10). Compared to PLAP, SEAP is unusually heat-stable; thus, heating samples to 65° C. allows SEAP to be specifically assayed (Bronstein et al., (1994) BioTechniques 17: 172-174, 76-177). Commercial SEAP detection assays are extremely sensitive over at least a 4-log order concentration range, with detection limits in the picogram/ml range. SEAP is also an advantageous protein-based reporter for translation into the clinic since: 1) it has shown effective longitudinal monitoring of non-viral gene transfer in mice and large animals (Brown et al., (2008) Methods Mol. Biol. 423: 215-224); 2) its human origin implies it can have reduced or zero immunogenic potential in patients similar to what has been shown with murine SEAP (mu-SEAP) in immunocompetent mice (Wang et al., (2001) Gene 279: 99-108); and 3) SEAP has been used in the clinic to monitor antibody levels following administration of an HPV16/18 ASO4-adjuvanted vaccine (Kemp et al., (2008) Vaccine 26: 3608-3616).

The systems of the disclosure utilize pSurv to drive the expression of SEAP. Survivin is a member of the apoptosis inhibitor family that helps control mitotic progression and prevent cell death and is over-expressed in many cancers such as melanoma, liver, lung, breast, colon and ovarian, but not in healthy adult tissues (Ito et al., (2000) Hepatology 31: 1080-1085; Chen et al., (2004) Cancer Gene Therapy 11: 740-747; Lu et al., (2005) Gene Therapy 12: 330-338). pSurv, therefore, is advantageous for transcriptional targeting of tumors as demonstrated in models of lung, melanoma, colon, breast, ovarian, and liver cancer (Lu et al., (2005) Gene Therapy 12: 330-338; Li et al., (2006) J. Gene Med. 8: 1232-1242; van Houdt et al., (2006) J. Neurosurgery 104: 583-592; Ahn et al., (2011) Gene Therapy 18: 606-612; Ray et al., (2008) Mol. Therapy: J. Am. Soc. Gene Therapy 16: 1848-1856). Thus, the tumor-specific promoter-driven tumor-activatable MCs of the disclosure offer broad applicability for effective cancer screening across numerous tumor types and patient populations.

Accordingly, diagnostic tumor-activatable MCs have been developed and tested for the ability to distinguish tumor-bearing subjects from healthy subjects after systemic administration of the MCs by measuring blood levels of a genetically-encoded cancer biomarker. For delivery, the MCs were compared with a non-targeted transfection agent that has been shown to have no immunogenicity (Bonnet et al., (2008) Pharmaceut. Res. 25: 2972-2982), the ability to repeatedly dose animals, and the ability efficiently transfect both primary and metastatic tumors in mice after systemic (tail-vein) administration (Yang et al., (2013) Proc. Nat. Acad. Sci. U.S.A. 110: 14717-14722; Bhang et al., (2011) Nat. Med. 17: 123-129). The results indicate that use of tumor-activatable MCs is an advantageous promising platform technology for safe and efficacious cancer screening. This system is useful for monitoring patients at high-risk for tumor recurrence, followed by screening high-risk populations prior to tumor diagnosis, and can be advantageous for screening for the general population.

An exogenously delivered genetically-encoded cancer blood biomarker vector strategy according to the disclosure can overcome some of the inherent limitations of cancer screening targeting endogenous cancer blood biomarkers such as high background expression in healthy tissues and random fluctuations in biomarker expression over time. The present disclosure provides embodiments of a tumor-activatable MC system that can be administered systemically to identify tumor-bearing subjects using a simple and relatively inexpensive blood-based assay. The assay showed reliable detection capabilities and assessment of disease extent, indicating the feasibility of tumor-activatable MCs as a highly robust and safe cancer screening system.

Research in cancer gene therapy has sought methods for expressing a therapeutic transgenes specifically within tumors to avoid undesirable effects in non-target or normal cells. To reach this goal several strategies have been explored including transcriptional targeting of tumors using tumor-specific promoters (Aim et al., (2011) Gene Therapy 18: 606-612; Ye et al., (2003) Biochem. Biophys. Res. Comms. 307: 759-764; Iyer et al., (2005) Transgenic Res. 14:47-55), transcriptional silencing or repression in healthy tissues using endogenous miRNA regulation (Cawood et al., (2009) PLoS Pathogens 5: e 1 000440; Ronald et al., (2013) Gene Therapy 20: 1006-1013), enhanced tumor tropism of both viral (transduction targeting) and non-viral vectors (Chisholm et al., (2009) Cancer Res. 69: 2655-2662; Bachtarzi et al., (2008) Expert Opinion Drug Delivery 5: 1231-1240), or combinations of these strategies (Tsuruta et al., (2008) Clin. Cancer Res. 14: 3582-3588; Sugio et al., (2011) Clin. Cancer Res 17: 2807-2818). The systems of the disclosure provide a means of expressing a secretable reporter gene for the purposes of cancer detection. With this application of gene vectors comes the additional challenge of overcoming heightened safety concerns, since as a potential screening tool the vectors could be used in patients without any clearly visible evidence of cancer. Therefore, all components of this type of system need to be safe including the delivery vehicle (if needed), the DNA vector itself, and the transgene (if expressed).

While many delivery formulations are known in the art and contemplated for use with the MC systems of the disclosure, an in vivo transfection agent that has a desirable safety profile (i.e. no immunostimulation) (Bonnet et al., (2008) Pharmaceut. Res. 25: 2972-2982) and is in phase I/II clinical trials (Lisziewicz et al., (2012) PLoS ONE 7:e35416) was particularly preferred. Furthermore, while non-viral vectors are much safer than viral vectors (i.e. low/nearly zero integration rates, lowered immunogenic potential), there is still a concern regarding immunostimulatory prokaryotic CpG motifs in the backbone of traditional plasmids. This concern is alleviated in MCs and/or nanoplasmids since these vectors lack a prokaryotic backbone or have a small bacterial region size (less than 500 bp). SEAP was selected since it is of human origin so it should not cause an immunogenic reaction (Wang et al., (2001) Gene 279: 99-108), and has already shown promise in the clinic (Kemp et al., (2008) Vaccine 26: 3608-3616).

Previously, viral infection has been used to drive cancer-specific gene constructs, such as MC-OriP-IFNy (Zuo et al., (2011) PLoS ONE 6: e19407) which uses the viral OriP promoter/origin of replication to drive interferon-y expression in Epstein-Barr virus (EBV) infected nasopharyngeal carcinomas (NPC). In contrast, the MC systems of the disclosure can be broadly applicable for many different tumor types beyond viral-infected cells. The non-viral MC vectors of the present disclosure were developed for use in cancer screening using a blood-based assay.

Although tumor-activatable reporter gene-expressing vectors for cancer detection have been developed (Bhang et al., (2011) Nat. Med. 17: 123-129; Chaudhuri et al., (2003) Technol. In Cancer Res. & Treat. 2: 171-180; Warram et al., (2011) Mol. Imaging Biol. 13: 452-461; Warram et al., (2012) Cancer Gene Therapy 19: 545-552; Browne et al., (2011) PLoS ONE 6: e19530). The vector systems used in these cases (adenoviruses, Herpes simplex viruses, and plasmids); however, have safety issues that hamper clinical translation. Viruses are highly immunogenic and pre-existing viral immunity in humans is a widespread problem (Browne et al., (2011) PLoS ONE 6: e19530; Sumida et al., (2005) J. Immunol. 174: 7179-7185; Schirmbeck et al., (2008) Mol. Therapy 16: 1609-1616). Plasmids can be immunogenic due to unmethylated CpG sequences in the prokaryotic backbone (necessary only for plasmid production) (Tan et al., (1999) Human Gene Therapy 10: 2153-

2161), as well as typically bearing coded antibiotic resistance genes to endogenous flora (Marie et al., (2010) J. Gene Med. 12: 323-332). Thus, the tumor-activatable MCs of the present disclosure have advantages over these other vectors and offer translational potential primarily due to easier manufacturing practices (compared to viruses) and a more desirable profile.

The MC and/or nanoplasmid systems of the disclosure can provide improved specificity through two mechanisms: 1) the uniqueness of the biomarker in the blood since no SEAP is detectable prior to MC administration; and 2) the ability to drive expression strictly within the tumor, thereby alleviating signal in healthy tumor-free subjects. A slight SEAP signal from tumor-free mice receiving MC likely is from leakiness of pSurv. It is contemplated, however, that the MC systems of the disclosure are not limited to this particular promoter and alternative tumor-activatable promoters such as, but not limited to, the Id1 or hTERT promoters (Warram et al., (2011) Mol. Imaging Biol. 13: 452-461; Zhang et al., (2008) Life sciences 82: 1154-1161) and the like are useful in the MCs of the disclosure. Also, sensitivity using endogenous biomarkers is inherently limited by the amount of biomarker produced by the tumor (Hori & Gambhir (2011) Sci. Translational Med. 3: 109ra116). In contrast, the sensitivity of the MC systems of the disclosure can be modified.

One of the advantages of endogenous blood biomarkers is that they can be used to determine what type of cancer a person may harbor (e.g. a high PSA level may indicate prostate cancer). However, the MC systems provided by the present disclosure are also advantageous for screening for all cancer, not a particular tumor type. It is further contemplated that alternative promoters useful for screening patients at high-risk for a particular cancer, such as variants of the prostate-specific antigen enhancer/promoter for prostate cancer (Iyer et al., (2005) Transgenic Res. 14: 47-55; Iyer et al., (2004) Mol. Therapy 10: 545-552; Iyer et al., (2006) Human Gene Therapy 17: 125-132) or the mucin-1 promoter for breast cancer (Huyn et al., (2009) Clin. Cancer Res. 15: 3126-3134) and the like can be incorporated into the MC systems of the disclosure.

Another limitation of exogenous biomarkers (i.e. reporter) is the inability to localize the site(s) in the body where the biomarker originated. By replacing or co-expressing SEAP with an imaging reporter gene (e.g., herpes simplex virus thymidine kinase 1 for positron emission tomography (PET), which is described in e.g. Yaghoubi S S and Gambhir S S (2006) Nat Protoc. 1(6):3069-75.) the systems of the disclosure can also allow tumor location to be visualized. Bhang et al. recently described the ability to image tumors using both BLI and single photon emission computed tomography (SPECT) following systemic administration of tumor-activatable plasmids expressing the appropriate imaging reporter gene (Bhang et al., (2011) Nat. Med. 17: 123-129). This strategy was also pursued with the SEAP-expressing viral vectors described to date since these vectors co-expressed fluorescent proteins for cancer visualization using fluorescence stereomicroscopy (Chaudhuri et al., (2003) Technol. In Cancer Res. & Treat. 2: 171-180; Warram et al., (2011) Mol. Imaging Biol. 13: 452-461; Warram et al., (2012) Cancer Gene Therapy 19: 545-552). Rather than one vector system expressing two reporters. It is further contemplated to be possible to deliver two different vectors designed for specific applications; one for cancer screening expressing a secretable reporter, and one for tumor localization expressing an imaging reporter.

One aspect of the disclosure, therefore, encompasses embodiments of a recombinant nucleic acid minicircle vector comprising a nucleotide sequence operably linked to a tumor-specific gene expression promoter and results in expression at a level greater by a recipient tumor cell than by a non-tumor cell.

In the embodiments of this aspect of the disclosure the tumor-specific gene expression promoter may be selected from the group consisting of: Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyl-transferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member Cl (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

In some embodiments of this aspect of the disclosure, the nucleotide sequence operably linked to the tumor-specific promoter can be expressed as a polypeptide.

In some embodiments of this aspect of the disclosure, the nucleotide sequence operably linked to the tumor-specific promoter can encode a reporter polypeptide.

In some embodiments of this aspect of the disclosure, the reporter polypeptide may be an MRI reporter, a PET reporter; a SPECT reporter, a photoacoustic reporter, a bioluminescent reporter, or any combination thereof.

In some embodiments of this aspect of the disclosure, the polypeptide can be secreted embryonic alkaline phosphatase (SEAP).

In some embodiments of this aspect of the disclosure, the recombinant nucleic acid minicircle vector can have the nucleic acid sequence according to SEQ ID NO: 1.

In some embodiments of this aspect of the disclosure, the polypeptide can be a bioluminescent reporter.

In some embodiments of this aspect of the disclosure, the recombinant nucleic acid minicircle vector can have the nucleic acid sequence according to SEQ ID NO: 2.

In some embodiments of this aspect of the disclosure, the nucleotide sequence operably linked to the tumor-specific promoter can be expressed as a small interfering RNA (siRNA) or a therapeutically effective polypeptide.

Another aspect of the disclosure encompasses embodiments of a pharmaceutically acceptable composition comprising a recombinant nucleic acid minicircle vector comprising a nucleotide sequence operably linked to a tumor-specific gene expression promoter and expressible at a level greater by a recipient tumor cell than by a non-tumor cell, and a pharmaceutically acceptable carrier, wherein: (i) the tumor-specific gene expression promoter can be selected from the group consisting of: a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member Cl (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof and (ii) the nucleotide sequence operably linked to the tumor-specific promoter can be expressed as a polypeptide encoding an MRI reporter, a PET reporter, a SPECT reporter, a photoacoustic reporter, a bioluminescent reporter, or any combination thereof.

In some embodiments of this aspect of the disclosure, the recombinant nucleic acid minicircle vector can have the nucleic acid sequence according to SEQ ID NO: 1 or SEQ ID NO: 2.

Yet another aspect of the disclosure encompasses embodiments of a method of detecting a tumor cell in a human or non-human subject, comprising the steps of: (i) delivering to a first subject human or non-human animal a pharmaceutically acceptable composition comprising a recombinant nucleic acid minicircle vector comprising a nucleotide sequence operably linked to a tumor-specific gene expression promoter and expressible at a level greater by a recipient tumor cell than by a non-tumor cell, and a pharmaceutically acceptable carrier, wherein: (a) the tumor-specific gene expression promoter can be selected from the group consisting of: Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyl-transferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof and (b) the nucleotide sequence operably linked to the tumor-specific promoter can be expressed as a polypeptide encoding an MRI reporter, a PET reporter, a SPECT reporter, a photoacoustic reporter, a bioluminescent reporter, or any combination thereof; and (ii) detecting an expression product in the first subject, wherein said expression product is generated from the nucleotide sequence operably linked to the tumor-specific gene expression promoter of the minicircle vector, and wherein the detection of said expression product indicates the presence of a tumor cell in the first subject.

In some embodiments of this aspect of the disclosure, the expression product can be a serum polypeptide and step (ii) can comprise obtaining a serum sample from the first subject and determining the serum level of the expression product generated from the minicircle vector.

In some embodiments of this aspect of the disclosure, the detected expression product can be secreted embryonic alkaline phosphatase (SEAP).

In some embodiments of this aspect of the disclosure, the minicircle vector can have the nucleic acid sequence according to SEQ ID NO: 1.

In some embodiments of this aspect of the disclosure, the expression product can be a bioluminescent polypeptide and the step (ii) can comprise generating a detectable signal derived from the expression product, measuring the level of the detectable signal generated from the minicircle vector, and comparing the level of the signal from the first subject to that obtained from a second subject not receiving the minicircle vector, wherein an elevated level signal from the first subject compared to that level obtained from a second subject indicates that the first subject comprises a tumor cell or population of tumor cells.

In some embodiments of this aspect of the disclosure, the step (ii) can further comprise non-invasively detecting the detectable signal, converting said signal into an image, overlaying said image with an image of the first subject, and locating the detectable signal relative to the first subject, thereby determining the position of a tumor cell or population of tumor cells in the first subject.

In some embodiments of this aspect of the disclosure, the expression product can be a luciferase.

In some embodiments of this aspect of the disclosure, the minicircle vector can have the nucleic acid sequence according to SEQ ID NO: 2.

Improved Synthetic Biomarkers for Disease Diagnosis, Detection, and Monitoring

In some aspects, the present disclosure provides for a method comprising: (a) administering to a subject a composition, wherein the composition induces expression of a synthetic biomarker in a diseased cell preferentially over expression of the biomarker in non-diseased cells in the subject such that a relative concentration ratio of the biomarker expressed in the diseased cell over the non-diseased cells is greater than about 1.0; (b) detecting the synthetic biomarker; and (c) using the synthetic biomarker detected in (b) to detect that the subject has the diseased cell. In some embodiments, the detecting has an accuracy of at least 90%.

In some cases, the composition is administered intravenously, subcutaneously, intraventricularly, intrathecally, intracerebroventricularly, transdermally, intramuscularly, orally, by inhalation, nasally, rectally, intratumorally, or proxi-tumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g. Rojas-Solanoet al. J Bronchology Intery Pulmonol. 2018 July; 25(3): 168-17). In some embodiments, the composition is administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region.

In some cases, the detection of the diseased cell may have an accuracy at least about 50%, at least about 53%, at least about 55%, at least about 57%, at least about 60%, at least about 63%, at least about 65%, at least about 67%, at least about 70%, at least about 72%, at least about 75%, at least about 77%, at least about 78%, at least about 79%, at least about 80%, at least about 81%, at least about 82%, 83%, at least about 84%, 85%, at least about 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values. In some cases the detection of the diseased cell may have an accuracy of at most about 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

In some cases, the detection of the diseased cell may have a sensitivity of at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values. In some cases, the detection of the diseased cell may have a sensitivity of at most about 81%, 82%, 83%, 84%, 85%, 86%, 87%, 88%, 89%, 90%, 91%, 92%, 93%, 94%, 95%, 96%, 97%, 98%, or 99%, or any range in between these values.

In some cases, the detection of the diseased cell may have a specificity of at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values. In some cases, the detection of the diseased cell may have a specificity of at most about 81%, 82%, 83%, 84%, 85%, 86%, 87%, 88%, 89%, 90%, 91%, 92%, 93%, 94%, 95%, 96%, 97%, 98%, or 99%, or any range in between these values In some cases, the detection of the diseased cell may have a negative predictive value (NPV) of at least about 80%, 81%, 82%, 83%, 84%, 85%, 86%, 87%, 88%, 89%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. In some cases, the detection of the diseased cell may have a NPV of at least about 81%, 82%, 83%, 84%, 85%, 86%, 87%, 88%, 89%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values.

In some cases, the detection of the diseased cell may have a positive predictive value (PPV) of at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any range between these values. In some cases, the detection of the diseased cell may have a PPV of at most about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any range between these values.

In some embodiments, the composition may comprise a vector encoding the synthetic biomarker. Suitable vectors include vectors suitable for administration to cells in vivo, including but not limited to minicircles, plasmids, nanoplasmids, mini-intronic plasmids, yeast artificial chromosomes (YACs), bacterial artificial chromosomes (BACs), cosmids, phagemids, bacteriophages, and baculoviruses. Suitable vectors also include vectors derived from bacteriophages or plant, invertebrate, or animal (including human) viruses such as CELiD vectors, adeno-associated viral vectors (e.g. AAV1, AAV2, AAV4, AAV5, AAV6, AAV7, AAV8, AAV9, or pseudotyped combinations thereof such as AAV2/5, AAV2/2, AAV-DJ, or AAV-DJ8), retroviral vectors (e.g. MLV or self-inactivating or SIN versions thereof, or pseudotyped versions thereof), herpesvirus (e.g. HSV- or EBV-based), lentivirus vectors (e.g. HIV-, FIV-, or EIAV-based, or pseudotyped versions thereof), or adenoviral vectors (e.g.

Ad5-based, including replication-deficient, replication-competent, or helper-dependent versions thereof). In some cases, the vector may comprise an episomal maintenance element to facilitate replication in one or more target cell type, such as a Scaffold/Matrix Attachment Region (S/MAR). S/MAR elements are particularly useful to facilitate replication in the context of "naked" nucleic acid vectors such as minicircles. Exemplary suitable S/MAR elements include, but are not limited to, ERMAR from the immunoglobulin heavy chain locus, the apoB MAR from the human apolipoprotein B locus, the Ch-LysMAR from the chicken lysozyme locus, and the huIFM3 MAR from the human IFM3-locus. In some embodiments, the vector may be a non-viral vector.

In some cases, the composition may comprise a vector containing a sequence encoding the synthetic biomarker operably linked to a promoter. Suitable promoters include natural pan-tumor specific promoters, natural tissue specific promoters, natural disease-specific/disease-activated promoters, natural constitutive promoters, and any composites thereof. The promoter may be a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyl-transferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein O (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF) promoter, a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

In some cases, the synthetic biomarker may be a polypeptide or nucleic acid biomarker. Polypeptides include any of the reporter polypeptides described herein. Nucleic acids include natural or engineered miRNAs, RNA hairpins, and RNA aptamers or barcoded versions thereof. When the nucleic acid is an miRNA, the miRNA may be detected e.g. by standard library generation techniques such as degenerate primer-based annealing and ligation, poly(A) polymerase labeling followed by RT or ligation, or sequential adapter ligation coupled to q-PCR, sequencing, or an electrophoretic detection method. When the biomarker is a polypeptide, the polypeptide may comprise an N-terminal secretion signal sequence (e.g. the N-terminal signal peptide from CD33 or CD8a).

By ascribing an exclusive label to a unique member within a larger group, barcodes afford the opportunity to identify and quantify that member (e.g. expression of a reporter under the control of a particular cancer specific promoter) within the context of a larger and more complex mixture of many members (e.g. multiple promoter-reporter constructs expressed within the same cell), as well as offering the opportunity to isolate a single member from the complex mixture. For instance, in the case of barcodes based on nucleic acids, hybridization of barcodes based on base pairing complementarity may be used to capture and isolate or otherwise reduce the complexity of a mixture by said capture event. For barcodes based on peptides, unique features including immunocapture or interactions of ligands and receptors may be used to capture and isolate or otherwise reduce the complexity of a mixture by said capture event.

When the nucleic acid is an engineered miRNA, the nucleic acid may be the Sec-miR or miR-neg constructs described in Ronald et al. (Ronald et al. PLoS ONE 11(7): e0159369.) Such constructs comprise: (a) a coding sequence not expressed endogenously and not having any known vertebrate target (e.g. Sec-miR 5'-AAAUGUA-CUGCGCGUGGAGAC-3', SEQ ID NO:6); (b) miR backbone sequences providing processing of pre-miRNA to mature miRNA flanking the coding sequence (e.g. miR-155 or miR-130 backbone sequences); and (c) an EXOmotif enhancing loading into exosomes (e.g. GGAG). Such miRNA constructs may be expressed in e.g. the 3'-UTR of a gene encoding a reporter polypeptide, or from the 3'-UTR of a gene encoding a suitably non-toxic protein (e.g. an endogenous structural protein such as actin or tubulin, or a highly expressed protein such as ubiquitin). In some embodiments, multiple copies (e.g. at least 2, at least 4) of the engineered miRNA may be provided in tandem.

In some cases, the synthetic biomarker may be a polypeptide biomarker detectable by a non-invasive imaging method performed on the subject and/or the method comprises detecting the synthetic biomarker by non-invasive imaging. Such non-invasive imagine methods include MRI imaging, PET imaging, SPECT imaging, photoacoustic imaging, and bioluminescent imaging. Synthetic biomarkers detectable by MRI imaging include polypeptide contrast agents, such as ferritin (or mutants thereof, such as *Pyrococcus furiousus* ferritin mutants L55P, F57S, or F123S), or lanthanide-binding proteins (or engineered fusions thereof, such as the LBT-ubiquitin fusions described in Daughtry et al. ChemBioChem 2012, 13, 2567-2574). Synthetic biomarkers detectable by PET or SPECT imaging include the human sodium iodide symporter (e.g. in conjunction with administration of PET-active iodine/iodide isotopes, see e.g. Penheiter et al. Curr Gene Ther. 2012 February; 12(1): 33-47), HSV-tk or mutants thereof such as HSV-sr39tk (e.g. in conjunction with administration of positron-labeled acycloguanosine or pyrimidine analog PET reporters such as [18F]FHBG, see Yaghoubi S S et al. Nat Protoc. 2006; 1(6):3069-75), and the dopamine D2 receptor or mutants thereof such as D2R80A or D2R194A (e.g. in conjunction with administration of positron-labeled D2 binders such as 3-(2'-[18F]-fluoroethyl)-spiperone). Synthetic biomarkers detectable by photoacoustic imaging include the pigment-producing enzymes such as 0-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP 1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). Synthetic biomarkers detectable by bioluminescent imaging include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396(2010): 290-297). In some embodiments, the synthetic biomarker may be a contrast agent, an enzyme producing a detectable molecule, or a transporter driving accumulation of a detectable molecule. The synthetic biomarker may be measured in situ within subject's body.

In instances where the synthetic biomarker is a polypeptide biomarker detectable by a non-invasive imaging method, the method involving administering to a subject a composition inducing expression of a synthetic biomarker in a diseased cell may further comprise (d) localizing the diseased cell in the body of the subject. The localizing may be associated with a particular resolution, for example 10 mm to 10 cm, at least 10 mm, or at most 10 cm. The localizing may be associated with a particular minimum detectable tumor size, for example a tumor size between 3 mm$^3$ and 5 cm$^3$. In some cases, the particular minimum range may be 1 cm$^3$ to 5 cm$^3$, or 900 mm$^3$ to 1 cm$^3$, or 800 mm$^3$ to 900 mm$^3$, or 700 mm$^3$ to 800 mm$^3$, or 600 mm$^3$ to 700 mm$^3$, or 500 mm$^3$ to 600 mm$^3$, or 400 mm$^3$ to 500 mm$^3$, or 300 mm$^3$ to 400 mm$^3$, or 200 mm$^3$ to 300 mm$^3$, or 100 mm$^3$ to 200 mm$^3$, or 50 mm$^3$ to 100 mm$^3$, or 10 mm$^3$ to 50 mm$^3$, or 3 mm$^3$ to 10 mm$^3$ in size. In some cases, the localization occurs in a non-invasive imaging scan (e.g. PET, MRI, SPECT, etc). In some cases, the localization occurs during surgical intervention in situ, for example by the use of visual inspection (in the case of visual-range absorbing reporters) or by the use of visual inspection combined with fluorescent excitation.

In some cases, the additional localization step above may be followed by a surgical step to eliminate the detected and/or localized diseased cell. The surgical step may be performed by the same or different party to that which administers the biomarker-encoding composition and/or localizes the diseased cell. The surgical step may be surgical excision of the diseased cell or a tumor associated with the diseased cell. The surgical or nonsurgical elimination step may involve a minimally-invasive killing technique, such as a radiosurgery (including but not limited to Gamma Knife, Reflexion, CyberKnife, and related techniques using targeted ionizing radiation to kill diseased cells).

In some cases, the synthetic biomarker may be detected in biological sample from the subject to whom the composition inducing expression of the synthetic biomarker is administered. In some cases, the synthetic biomarker is detected in vivo and determines a location of the diseased cell.

In some cases, the composition administered to the subject may comprise a transfection agent. Suitable transfection agents include, but are not limited to, linear or branched polyethylenimines, nanoparticles, lipophilic particles, peptides, micelles, dendrimers, hydrogels, synthetic or naturally derived exosomes, polymeric composition, virus-like particles, and any combination thereof.

In some cases, the composition may further comprise a pharmaceutically acceptable carrier. Exemplary pharmaceutically acceptable carriers include, but are not limited to, water, peanut oil, soybean oil, mineral oil, sesame oil, saline, gum acacia, gelatin, starch paste, talc, keratin, colloidal silica, urea, aqueous dextrose, glycerol solution, glucose, lactose, sucrose, glycerol monostearate, sodium chloride solution, propylene, glycol, or ethanol, or any combination thereof.

The biological sample may be a sample collected by a non-invasive method from the subject. Exemplary non-invasive samples include, but are not limited to, saliva, sputum, sweat, urine, stool, semen, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy).

In some cases, the biological sample may be obtained a certain period of time after administration of the composition inducing expression of the synthetic biomarker. The biological sample may be obtained at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, or at least about 6 months after administration of the composition inducing expression of the synthetic biomarker. The biological sample may be obtained at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, or at most about 6 months after administration of the composition inducing expression of the synthetic biomarker. In some embodiments, the biological sample may be obtained, and any biomarker detection protocols performed multiple times post administration of the composition inducing expression of the synthetic biomarker (e.g. to monitor synthetic biomarker levels over time). The biological sample may be obtained at least about 1, 2, 3, 4, 5, 6, 7, 8, 9, 10, 15, 20, or 25 times post administration of the composition inducing expression of the synthetic biomarker. The biological sample may be obtained weekly or monthly following administration of the composition inducing expression of the synthetic biomarker.

In some cases, the diseased cell may be a cancerous cell, a cell indicative of an autoimmune disease (e.g. a T-cell or lymphocyte with self-directed activity, or a normal cell damaged by autoimmunity), a cell indicative of a neurodegenerative disease (e.g. a cell bearing a toxic amyloid or proximal to a toxic amyloid), or a cell that may have an altered gene expression profile because a subject from which the cell is obtained suffers a disease or is about to suffer from a disease. A cell population comprising cells that have an altered gene expression profile can be described as transcriptionally altered cells (TACs). In some cases, the diseased cell may be a cancerous cell. Exemplary cancers include, but are not limited to, carcinomas, sarcomas, lymphomas, leukemias, and adenomas. Carcinomas may arise from cells that cover internal and external parts of the body such as the lung, breast, and colon. Sarcomas may arise from cells that are located in bone, cartilage, fat, connective tissue, muscle, and other supportive tissues. Lymphomas may arise in the lymph nodes and immune system tissues. Leukemias may arise in the bone marrow and accumulate in the bloodstream. Adenomas may arise in the thyroid, the pituitary gland, the adrenal gland, and other glandular tissues. Specific exemplary examples of cancer types include suitable for detection with the methods according to the disclosure include acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

In some cases, the diseased cell may be a virally-infected cell. Exemplary viruses include, but are not limited to, HIV, hepatitis C virus, hepatitis B virus, hepatitis D virus, herpesviruses, Epstein-Barr virus, cytomegalovirus, and human T-lymphotropic virus type III.

In some cases, the diseased cell may be indicative of an autoimmune disease. Exemplary autoimmune diseases include, but are not limited to, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

In some cases, the diseased cell may be indicative of a neurodegenerative disease. Neurodegenerative diseases include, but are not limited to, Multiple sclerosis (MS), Alzheimer's disease (AD), Parkinson's disease (PD), Amyotrophic lateral sclerosis (ALS), or neurodegeneration due to infection by viruses of families Herpesviridae, Polyomaviridae, Bornaviridae, Orthomyxoviridae, Paramyxoviridae, Rhabdoviridae, Flaviviridae, Picornaviridae, or Retroviridae (see Zhou et al. Virol J. 2013; 10: 172).

Genetic/DNA-based Therapeutics for Diseased Cells

In some aspects, the present disclosure provides for a method of treating a subject having or suspected of having a disease, comprising administering to the subject a composition that induces expression of a therapeutically effective agent by a diseased cell associated with the disease preferentially over expression of the therapeutically effective agent by non-diseased cells in the subject such that a relative concentration of the therapeutically effective agent expressed by the diseased cell over the non-diseased cells is greater than 1.0, which therapeutically effective agent treats the subject at a therapeutic efficacy of at least 10% as determined by a decrease in a cell population of the diseased cell.

In some cases, the composition is administered intravenously, subcutaneously, intraventricularly, intrathecally, intracerebroventricularly, transdermally, intramuscularly, orally, inhalation, nasally, rectally, intratumorally, or proxitumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g. Rojas-Solano et al. J Bronchology Intery Pulmonol. 2018 July; 25(3): 168-175). In some embodiments, the composition is administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region.

In some cases, the composition administered for treating a subject having or suspected of having a disease may comprise a promoter operably linked to a nucleotide sequence encoding the therapeutically effective agent. The promoter may be a cancer-specific promoter. Suitable promoters include natural pan-tumor specific promoters, natural tissue specific promoters, natural disease-specific/disease-activated promoters, natural constitutive promoters, and any composites thereof. The promoter may be a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

In some cases, the promoter operably linked to a nucleotide sequence encoding the therapeutically effective agent may be present on a vector, which may be a component of the composition administered to the subject. Suitable vectors include vectors suitable for administration to cells in vivo, including but not limited to minicircles, plasmids, nanoplasmids, mini-intronic plasmids, yeast artificial chromosomes (YACs), bacterial artificial chromosomes (BACs), cosmids, phagemids, bacteriophages, and baculoviruses. Suitable vectors also include vectors derived from bacteriophages or plant, invertebrate, or animal (including human) viruses such as CELiD vectors, adeno-associated viral vectors (e.g. AAV1, AAV2, AAV4, AAV5, AAV6, AAV7, AAV8, AAV9, or pseudotyped combinations thereof such as AAV2/5, AAV2/2, AAV-DJ, or AAV-DJ8), retroviral vectors (e.g. MLV or self-inactivating or SIN versions thereof, or pseudotyped versions thereof), herpesvirus (e.g. HSV- or EBV-based), lentivirus vectors (e.g. HIV-, FIV-, or EIAV-based, or pseudotyped versions thereof), or adenoviral vectors (e.g. Ad5-based, including replication-deficient, replication-competent, or helper-dependent versions thereof). In some cases, the vector may comprise an episomal maintenance element to facilitate replication in one or more target cell type, such as a Scaffold/Matrix Attachment Region (S/MAR). S/MAR elements are particularly useful to facilitate replication in the context of "naked" nucleic acid vectors such as minicircles. Exemplary suitable S/MAR elements include, but are not limited to, EuMAR from the immunoglobulin heavy chain locus, the apoB MAR from the human apolipoprotein B locus, the Ch-LysMAR from the chicken lysozyme locus, and the huIF19 MAR from the human IFNβ-locus. In some embodiments, the vector may be a non-viral vector.

In some cases, the therapeutically effective agent may comprise a particular class of therapeutic. Exemplary classes of therapeutics suitable for use according to methods of the disclosure include, but are not limited to, therapeutically effective polypeptides (e.g. therapeutic antibodies, fragments, or derivatives thereof; cytokines; growth factors; engineered or replacement metabolic/catabolic enzymes, engineered short peptide agonists or antagonists, or prodrug activating enzymes), small activating RNAs (saRNAs), microRNAs (miRNAs), small interfering RNAs (siRNAs) or any combination thereof. In some cases, the therapeutically effective agent may be a prodrug-activating enzyme. Exemplary prodrug-activating enzymes include, but are not limited to, HSVtk, cytosine deaminase, DT diaphorase, nitroreductase, guanine phosphoribosyl transferase, purine nucleoside phosphorylase, thymidine phorphorylase, carboxylesterase, folylpolyglutamyl synthetase, carboxypeptidase A1, carboxypeptidase G2, and cytochrome P-450. In cases where the therapeutically effective agent is a prodrug-activating enzyme, the method may comprise an additional administration of the drug according to any of the routes described herein. When the therapeutically effective agent is a polypeptide, the polypeptide may comprise an N-terminal secretion signal sequence (e.g. the N-terminal signal peptide from CD33 or CD8a).

Improved Synthetic Biomarker Constructs and Methods to Normalize Across Individual Subjects' Transfection Rates In some aspects, the present disclosure provides for a composition comprising a first nucleic acid sequence encoding a first polypeptide or nucleic acid biomarker and a second nucleic acid sequence encoding a second polypeptide or second nucleic acid biomarker, wherein the composition is configured such that when the composition is in a cell: the second polypeptide or the second nucleic acid biomarker is expressed in an amount that reflects delivery of at least the first and the second nucleic acids to the cell, and the first polypeptide or nucleic acid biomarker is expressed differentially in a diseased cell versus a non-diseased cell. In some cases, (i) the cell induces expression of the first nucleic acid sequence in a diseased cell preferentially over expression of the first nucleic acid sequence in non-diseased cells, wherein the first polypeptide is a detectable biomarker or a therapeutic agent; and (ii) the cell induces expression of the second nucleic acid sequence equally in diseased and in non-diseased cells and the second nucleic acid sequence yields the second polypeptide that is not the detectable biomarker or the therapeutic agent, such that a level of expression of the second polypeptide provides a control for assessing the relative level of the nucleic acid sequences in the cell. In some cases, the first nucleic acid sequence encoding the first polypeptide and the second nucleic acid sequence encoding the second polypeptide may be on independent genetic constructs. In some cases, in the composition the sequences comprising the first nucleic acid sequence encoding the first polypeptide and the second nucleic acid sequence encoding the second polypeptide may be on independent genetic constructs. In some cases, the vector comprises: (a) a first promoter operably linked to the first nucleic acid sequence, wherein the promoter induces expression of the first nucleic acid sequence in a diseased cell preferentially over expression of the first nucleic acid sequence in non-diseased cells; and (b) a second promoter sequence that induces expression equally in diseased and in non-diseased cells and is operably linked to the second nucleic acid.

In some cases, the first polypeptide may be both a detectable biomarker and a therapeutic agent. In some cases, the first polypeptide is a therapeutic antibody, a therapeutic antibody fragment or derivative, or a prodrug-activating enzyme. Exemplary prodrug-activating enzymes include, but are not limited to, HSVtk, cytosine deaminase, DT diaphorase, nitroreductase, guanine phosphoribosyl transferase, purine nucleoside phosphorylase, thymidine phosphorylase, carboxylesterase, folylpolyglutamyl synthetase, carboxypeptidase A1, carboxypeptidase G2, and cytochrome P-450. The polypeptide may comprise an N-terminal secretion signal sequence (e.g. the N-terminal signal peptide from CD33 or CD8a).

In some cases, the first and/or second nucleic acid may be on a vector. Suitable vectors include vectors suitable for administration to cells in vivo, including but not limited to minicircles, plasmids, nanoplasmids, mini-intronic plasmids, yeast artificial chromosomes (YACs), bacterial artificial chromosomes (BACs), cosmids, phagemids, bacteriophages, and baculoviruses. Suitable vectors also include vectors derived from bacteriophages or plant, invertebrate, or animal (including human) viruses such as CELiD vectors, adeno-associated viral vectors (e.g. AAV1, AAV2, AAV4, AAV5, AAV6, AAV7, AAV8, AAV9, or pseudotyped combinations thereof such as AAV2/5, AAV2/2, AAV-DJ, or AAV-DJ8), retroviral vectors (e.g. MLV or self-inactivating or SIN versions thereof, or pseudotyped versions thereof), herpesvirus (e.g. HSV- or EBV-based), lentivirus vectors (e.g. HIV-, FIV-, or EIAV-based, or pseudotyped versions thereof), or adenoviral vectors (e.g. Ad5-based, including replication-deficient, replication-competent, or helper-dependent versions thereof). In some cases, the vector may comprise an episomal maintenance element to facilitate replication in one or more target cell type, such as a Scaffold/Matrix Attachment Region (S/MAR). S/MAR elements are particularly useful to facilitate replication in the context of "naked" nucleic acid vectors such as minicircles. Exemplary suitable S/MAR elements include, but are not limited to, ERMAR from the immunoglobulin heavy chain locus, the apoB MAR from the human apolipoprotein B locus, the Ch-LysMAR from the chicken lysozyme locus, and the huIF19 MAR from the human IF19-locus. In some embodiments, the vector may be a non-viral vector.

In some cases, the cell to which the first and the second nucleic acid are delivered may be a diseased cell. In some cases, the diseased cell may be a cancerous cell, a cell indicative of an autoimmune disease (e.g. a T-cell or lymphocyte with self-directed activity, or a normal cell damaged by autoimmunity), a TAC, or a cell indicative of a neurodegenerative disease (e.g. a cell bearing a toxic amyloid or proximal to a toxic amyloid). Exemplary cancers, autoimmune diseases, and neurodegenerative diseases which such a cell may be indicative of include any of the cancers, autoimmune diseases, and neurodegenerative diseases described herein. In some cases, the diseased cell may be a virally-infected cell. Exemplary viruses include, but are not limited to, HIV, hepatitis C virus, hepatitis B virus, hepatitis D virus, herpesviruses, Epstein-Barr virus, cytomegalovirus, and human T-lymphotropic virus type III.

In some cases, the first or the second nucleic acid may be detectable nucleic acid biomarkers. Exemplary detectable nucleic acids include, but are not limited to, natural or engineered miRNAs, RNA hairpins, and RNA aptamers or barcoded versions thereof. When the nucleic acid is an miRNA, the miRNA may be detected e.g. by standard library generation techniques such as degenerate primer-based annealing and ligation, poly(A) polymerase labeling followed by RT or ligation, or sequential adapter ligation coupled to q-PCR, sequencing, or an electrophoretic detection method. When the biomarker is a polypeptide, the polypeptide may comprise an N-terminal secretion signal sequence (e.g. the N-terminal signal peptide from CD33 or CD8a).

When the nucleic acid is an engineered miRNA, the nucleic acid may be the Sec-miR or miR-neg constructs described in Ronald et al. (Ronald et al. PLoS ONE 11(7): e0159369.) Such constructs comprise: (a) a coding sequence not expressed endogenously and not having any known vertebrate target (e.g. Sec-miR 5'-AAAUGUA-CUGCGCGUGGAGAC-3', SEQ ID NO: 6); (b) miR backbone sequences providing processing of pre-miRNA to mature miRNA flanking the coding sequence (e.g. miR-155 or miR-130 backbone sequences); and (c) an EXOmotif enhancing loading into exosomes (e.g. GGAG). Such miRNA constructs may be expressed in e.g. the 3'-UTR of a gene encoding a reporter polypeptide, or from the 3'-UTR of a gene encoding a suitably non-toxic protein (e.g. an endogenous structural protein such as actin or tubulin, or a highly expressed protein such as ubiquitin). In some embodiments, multiple copies (e.g. at least 2, at least 4) of the engineered miRNA may be provided in tandem.

In some cases, the second polypeptide or the first polypeptide may be detectable by a non-invasive imaging method performed on the subject. Such non-invasive imagine methods include MRI imaging, PET imaging, SPECT imaging, photoacoustic imaging, and bioluminescent imaging. Synthetic biomarkers detectable by MRI imaging include polypeptide contrast agents, such as ferritin (or mutants thereof, such as *Pyrococcus furiousus* ferritin mutants L55P, F57S, or F123S), or lanthanide-binding proteins (or engineered fusions thereof, such as the LBT-ubiquitin fusions described in Daughtry et al. ChemBioChem 2012, 13, 2567-2574). Synthetic biomarkers detectable by PET or SPECT imaging include the human sodium iodide symporter (e.g. in conjunction with administration of PET-active iodine/iodide isotopes, see e.g. Penheiter et al. Curr Gene Ther. 2012 February; 12(1): 33-47), HSV-tk or mutants thereof such as HSV-sr39tk (e.g. in conjunction with administration of positron-labeled acycloguanosine or pyrimidine analog PET reporters such as [18F]FHBG, see Yaghoubi S S et al. Nat Protoc. 2006; 1(6):3069-75), and the dopamine D2 receptor or mutants thereof such as D2R80A or D2R194A (e.g. in conjunction with administration of positron-labeled D2 binders such as 3-(2'-[18F]-fluoroethyl)-spiperone). Synthetic biomarkers detectable by photoacoustic imaging include the pigment-producing enzymes such as 0-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). Synthetic biomarkers detectable by bioluminescent imaging include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396(2010): 290-297). In some embodiments, the synthetic biomarker may be a contrast agent, an enzyme producing a detectable molecule, or a transporter driving accumulation of a detectable molecule. The synthetic biomarker may be measured in situ within subject's body.

In some cases, the present disclosure provides for a method of detecting diseased cells in a subject, comprising administering a composition to the subject, wherein the composition comprises a first nucleic acid sequence encoding a first polypeptide or nucleic acid biomarker and a second nucleic acid sequence encoding a second polypeptide or second nucleic acid biomarker, wherein the composition is configured such that when the composition is in a cell: the second polypeptide or the second nucleic acid biomarker is expressed in an amount that reflects delivery of at least the first and the second nucleic acids to the cell, and the first polypeptide or nucleic acid biomarker is expressed differentially in a diseased cell versus a non-diseased cell. In some cases, (i) the cell induces expression of the first nucleic acid sequence in a diseased cell preferentially over expression of the first nucleic acid sequence in non-diseased cells, wherein the first polypeptide is a detectable biomarker or a therapeutic agent; and (ii) the cell induces expression of the second nucleic acid sequence equally in diseased and in non-diseased cells and the second nucleic acid sequence yields the second polypeptide that is not the detectable biomarker or the therapeutic agent, such that a level of expression of the second polypeptide provides a control for assessing the relative level of the nucleic acid sequences in the cell. In some cases, the first nucleic acid sequence encoding the first polypeptide and the second nucleic acid sequence encoding the second polypeptide may be on independent genetic constructs. In some cases, in the composition the sequences comprising the first nucleic acid sequence encoding the first polypeptide and the second nucleic acid sequence encoding the second polypeptide may be on independent genetic constructs. In some cases, the vector comprises: (a) a first promoter operably linked to the first nucleic acid sequence, wherein the promoter induces expression of the first nucleic acid sequence in a diseased cell preferentially over expression of the first nucleic acid sequence in non-diseased cells; and (b) a second promoter sequence that induces expression equally in diseased and in non-diseased cells and is operably linked to the second nucleic acid. In some cases, the method may comprise detecting the first polypeptide or nucleic acid biomarker and/or the second polypeptide or nucleic acid biomarker. In some cases, such method is a non-invasive imaging method performed on the subject. Such non-invasive imagine methods include MRI imaging, PET imaging, SPECT imaging, photoacoustic imaging, and bioluminescent imaging.

In instances where the synthetic biomarker is a polypeptide biomarker detectable by a non-invasive imaging method, the method may further comprise localizing the diseased cell in the body of the subject. The localizing may be associated with a particular resolution, for example 10 mm to 10 cm, at least 10 mm, or at most 10 cm. The localizing may be associated with a particular minimum detectable tumor size, for example a tumor size between 3 mm$^3$ and 10 cm$^3$. In some cases, the particular minimum range may be may be 1 cm$^3$ to 10 cm$^3$, or 900 mm$^3$ to 1 cm$^3$, or 800 mm$^3$ to 900 mm$^3$, or 700 mm$^3$ to 800 mm$^3$, or 600 mm$^3$ to 700 mm$^3$, or 500 mm$^3$ to 600 mm$^3$, or 400 mm$^3$ to 500 mm$^3$, or 300 mm$^3$ to 400 mm$^3$, or 200 mm$^3$ to 300 mm$^3$, or 100 mm$^3$ to 200 mm$^3$, or 50 mm$^3$ to 100 mm$^3$, or 10 mm$^3$ to 50 mm$^3$, or 3 mm$^3$ to 10 mm$^3$ in size. In some cases, the localization occurs in a non-invasive imaging scan (e.g. PET, MRI, SPECT, etc). In some cases, the localization occurs during surgical intervention in situ, for example by the use of visual inspection (in the case of visual-range absorbing reporters) or by the use of visual inspection combined with fluorescent excitation.

In some cases, the additional localization step above may be followed by a surgical step to eliminate the detected and/or localized diseased cell. The surgical step may be performed by the same or different party to that which administers the biomarker-encoding composition and/or localizes the diseased cell. The surgical step may be surgical excision of the diseased cell or a tumor associated with the diseased cell. The surgical or nonsurgical elimination step may involve a minimally-invasive killing technique, such as a radiosurgery (including but not limited to Gamma Knife, Reflexion, CyberKnife, and related techniques using targeted ionizing radiation to kill diseased cells).

In some cases, the non-invasive imaging method may be performed a certain period of time after administration of the composition inducing expression of the synthetic biomarker. The non-invasive imaging method may be performed at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, at least about 6 months, or at least about 1 year after administration of the composition comprising the first and second nucleic acid. The non-invasive imaging method may be performed at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, at most about 6 months, or at most about 1 year after administration of the composition comprising the first and second nucleic acid. In some embodiments, the non-invasive imaging method may be performed multiple times after administration of the composition comprising the first and second nucleic acid (e.g. to monitor synthetic biomarker levels over time). The non-invasive imaging method may be performed at least about 1, 2, 3, 4, 5, 6, 7, 8, 9, 10, 15, 20, or 25 times after administration of the composition comprising the first and second nucleic acid. The non-invasive imaging method may be performed weekly or monthly following after administration of the composition comprising the first and second nucleic acid.

In some cases, the first polypeptide or nucleic acid biomarker and/or the second polypeptide or nucleic acid biomarker may be detected in a biological sample from the subject. The biological sample may be a sample collected by a non-invasive method from the subject. Exemplary non-invasive samples include, but are not limited to, saliva, sputum, sweat, urine, stool, semen, cervicovaginal secretions, breast milk, rheum, tears, and cheek epithelial swabs. The biological sample may be a sample collected by a minimally-invasive method from the subject. Exemplary minimally-invasive samples include but are not limited to blood samples (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy). In some cases, the biological sample may be obtained a certain period of time after administration of the composition inducing expression of the synthetic biomarker. The biological sample may be obtained at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, or at least about 6 months after administration of the composition comprising the first and second nucleic acid. The biological sample may be obtained at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, or at most about 6 months after administration of the composition comprising the first and second nucleic acid. In some embodiments, the biological sample may be obtained, and any biomarker detection protocols performed multiple times post after administration of the composition comprising the first and second nucleic acid (e.g. to monitor synthetic biomarker levels over time). The biological sample may be obtained at least about 1, 2, 3, 4, 5, 6, 7, 8, 9, 10, 15, 20, or 25 times after administration of the composition comprising the first and second nucleic acid. The biological sample may be obtained weekly or monthly following after administration of the composition comprising the first and second nucleic acid.

In some cases, the method may comprise detecting the first or the second nucleic acid biomarker by a specific nucleic acid detection method. The first or the second nucleic acid biomarker may be detected by sequencing. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, and primer walking.

In some cases, the first or the second nucleic acid biomarker may be detected by "real time amplification" methods also known as quantitative PCR (qPCR) or Taqman (see, e.g., U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye. The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified.

In some embodiments, for qPCR or Taqman detection, an RT-PCR step may first be performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In some embodiments, qPCR or Taqman may be used immediately following a reverse-transcriptase reaction performed on isolated cellular mRNA; this variety serves to quantitate the levels of individual mRNAs during qPCR.

In some embodiments, for qPCR or Taqman detection or RNA sequencing, a "pre-amplification" step may be first performed on cDNA transcribed from cellular RNA. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof. The pre-amplification may be either general or targeted in the same way as the reverse-transcription reaction described above.

RNA levels may also be measured without amplification by hybridization to a probe, for example, using a branched nucleic acid probe, such as a QuantiGene® Reagent System from Pommies.

Heterodimer-based Synthetic Biomarker Design

In some aspects, the present disclosure provides for a composition comprising a first nucleic acid sequence encoding a first polypeptide and a second nucleic acid sequence encoding a second polypeptide, wherein the composition is configured such that when the composition is in a cell: (i) the cell expresses the first nucleic acid sequence to yield the first polypeptide; (ii) the cell expresses the second nucleic acid sequence to yield the second polypeptide; and (iii) the first polypeptide and the second polypeptide expressed by the cell are configured to combine to form a heterodimer protein. In some cases, the first polypeptide and the second polypeptide may be on independent genetic constructs. In some cases, the first polypeptide and the second polypeptide may be on independent genetic constructs.

In some cases, the heterodimer protein may be a derivative of a naturally occurring heterodimer or a natural enzyme or autofluorescent protein split into two complementing polypeptide halves. Examples of such systems include, but are not limited to, an FRB/FKBP12 heterodimer, a split luciferase protein, or a split GFP protein.

In some cases when the heterodimer protein may be a derivative of a naturally occurring heterodimer (e.g. the FRB/FKBP12 pair) each half of the heterodimer protein are linked to complementary halves of an enzyme or detection pair, such that dimerization of the heterodimer activates the enzyme or allows detection of the detection pair. In some cases, each half of the heterodimer protein may be linked to a split recombinase, such as a Cre recombinase, that may activate expression of an additional element (e.g. a synthetic biomarker or a therapeutic molecule) when its activity is reconstituted by dimerization of the heterodimer. In some cases, each half of the heterodimer protein may be linked to one of two autofluorescent proteins forming a FRET pair, such that FRET may be detected when the heterodimer is formed.

In some cases, the first nucleic acid sequence and the second nucleic acid sequence may be operably linked to a first genetic element and a second genetic element, wherein both the first genetic element and the second genetic element may be selectively activated to express the first and the second polypeptide in a same diseased cell type. The first or second genetic element may be a promoter, an enhancer, or a miRNA binding site. Exemplary promoters include, but are not limited to, Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-GlcNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof. Exemplary miRNAs binding sites include, but are not limited to, at least one miR-15, miR-16, let-7, miR-122 or miR-34 binding sequence.

In some cases, the genetic constructs the first and the second polypeptide are encoded on may be a vector. Exemplary vectors include any of the vectors described herein.

In some aspects, the present disclosure provides for a method of detecting or treating a diseased cell, comprising administering a composition, wherein the composition comprises: a first nucleic acid sequence encoding a first polypeptide and a second nucleic acid sequence encoding a second polypeptide, wherein the composition is configured such that when the composition is in a cell: (i) the cell expresses the first nucleic acid sequence to yield the first polypeptide; (ii) the cell expresses the second nucleic acid sequence to yield the second polypeptide; and (iii) the first polypeptide and the second polypeptide expressed by the cell are configured to combine to form a heterodimer protein. In some cases, the composition is administered intravenously, subcutaneously, intraventricularly, intrathecally, intracerebroventricularly, transdermally, intramuscularly, orally, inhalation, nasally, rectally, intratumorally, or proxi-tumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g. Rojas-Solano et al. J Bronchology Intery Pulmonol. 2018 July; 25(3): 168-175). In some embodiments, the composition is administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region. In some cases, the method may further comprise detecting the heterodimer protein.

In some cases, the detecting comprises a non-invasive detection method performed on the subject. Exemplary non-invasive detection methods (e.g. for autofluorescent or luminescent protein) include, but are not limited to, SPECT imaging and bioluminescent imaging. The imaging method may be performed at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, at least about 6 months, or at least about 1 year after administration of the composition encoding the heterodimer protein. The imaging method may be performed at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, at most about 6 months, or at most about 1 year after administration of the composition encoding the heterodimer protein. In some embodiments, the imaging method may be performed multiple times post after administration of the composition encoding the heterodimer protein (e.g. to monitor synthetic biomarker levels over time). The imaging method may be performed at least about 1, 2, 3, 4, 5, 6, 7, 8, 9, 10, 15, 20, or 25 times after administration of the composition encoding the heterodimer protein. The imaging method may be performed weekly or monthly following after administration of the composition encoding the heterodimer protein.

In some cases, the detecting may comprise detecting the heterodimer protein from a biological sample from the subject. The biological sample may be a sample collected by a non-invasive method from the subject. Exemplary non-invasive samples include, but are not limited to, saliva, sputum, sweat, urine, stool, semen, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy).

In some cases, the biological sample may be obtained a certain period of time after administration of the composition inducing expression of the synthetic biomarker. The biological sample may be obtained at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, or at least about 6 months after administration of the composition encoding the heterodimer protein. The biological sample may be obtained at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, or at most about 6 months after administration of the composition encoding the heterodimer protein. In some embodiments, the biological sample may be obtained, and any biomarker detection protocols performed multiple times after administration of the composition encoding the heterodimer protein. The biological sample may be obtained at least about 1, 2, 3, 4, 5, 6, 7, 8, 9, 10, 15, 20, or 25 times after administration of the composition encoding the heterodimer protein. The biological sample may be obtained weekly or monthly following after administration of the composition encoding the heterodimer protein. The heterodimer protein in the biological sample may be detected by fluorescence assay, FRET assay, TR-FRET assay, or luminescent assay.

Alternatively or additionally, the heterodimer protein may be detected in a heterodimer-specific immunodetection assay. Several methods and devices are well known for determining levels of proteins including immunoassays such as described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. These assays include various sandwich, competitive, or non-competitive assay formats, to generate a signal that is related to the presence or amount of a protein analyte of interest. Any suitable immunoassay may be utilized, for example, lateral flow, enzyme-linked immunoassays (ELISA), radioimmunoassays (RIAs), competitive binding assays, or any combination thereof.

Ex-Vivo Constructs and Methods for Synthetic Biomarkers to Use in Disease Detection, Monitoring, or Diagnosis In some aspects, the present disclosure provides for a composition comprising a non-naturally occurring recombinant genetic construct comprising a sequence encoding a polypeptide or nucleic acid sequence, wherein the sequence comprises a first promoter that selectively drives expression of the polypeptide or nucleic acid biomarker sequence in a plurality of different types of diseased cells isolated from a subject when transduced into the cells ex vivo.

In some cases, the composition may comprise the cells transduced with the recombinant genetic construct. In some cases, the plurality of different types of cells are diseased or disordered cells. In some cases, the cells are blood cells, lymphocytes, leukocytes, epithelial cells, gastrointestinal cells, placental cells, amniotic cells, lung epithelial cells, urinary epithelial cells, or kidney cells.

In some cases, the diseased or disordered cells may be cancerous cell, cells indicative of an autoimmune disease (e.g. T-cells or lymphocytes with self-directed activity, or normal cells damaged by autoimmunity), TACs, or cells indicative of a neurodegenerative disease (e.g. cells bearing a toxic amyloid or proximal to a toxic amyloid). Exemplary cancers, autoimmune, and neurodegenerative diseases include any of the diseases described herein. In some cases, the diseased or disordered cells may be virally-infected cells. Exemplary viral infections include, but are not limited to, those caused by HIV, hepatitis C virus, hepatitis B virus, hepatitis D virus, herpesviruses, Epstein-Barr virus, cytomegalovirus, and human T-lymphotropic virus type III.

In some cases, the first promoter may be a promoter activated in the cells when the cells are in a diseased state. The first promoter may be a pan-tumor specific promoter. In some cases, the first promoter is a cancer-specific promoter. In some cases, the first promoter is a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-GlcNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCA5) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

In some cases, the recombinant genetic construct for detection ex vivo may comprise retroviral, lentiviral, or adenoviral packaging elements or long terminal repeats. The recombinant genetic construct may be a CELiD vector. The recombinant genetic construct may be a vector derived from a bacteriophage or plant, invertebrate, or animal (including human) virus such as an adeno-associated viral vector (e.g. AAV1, AAV2, AAV4, AAV5, AAV6, AAV7, AAV8, AAV9, or pseudotyped combination thereof such as AAV2/5, AAV2/2, AAV-DJ, or AAV-DJ8), a retroviral vector (e.g. MLV or self-inactivating or SIN versions thereof, or pseudotyped versions thereof), herpesvirus (e.g. HSV- or EBV-based), a lentivirus vector (e.g. HIV-, FIV-, or EIAV-based, or pseudotyped versions thereof), or an adenoviral vector (e.g. Ad5-based, including replication-deficient, replication-competent, or helper-dependent versions thereof). The recombinant genetic construct may also be a packaging vector compatible with any of these viral systems.

The vector may be a non-viral vector. The non-viral vector may be a minicircle vector. The minicircle may be a self-replicating minicircle. The self-replicating minicircle may comprise an S/MAR element. The non-viral vector may be a nanoplasmid or mini-intronic plasmid (MIP). MIP places the bacterial replication origin and any selectable marker as an intron in the transgene expression cassette. Further, MIP may keep the juxtaposition of the 5' and 3'; ends of transgene expression cassette as in minicircle (see e.g. Lu et al., a mini-intronic plasmid (MIP): a novel robust transgene expression vector in vivo and in vitro, mol. Ther. 2013 May; 21(5): 954-963)

In some cases, the polypeptide or nucleic acid sequence selectively expressed when transduced into ex vivo may be selected from the group consisting of a photoacoustic reporter, a bioluminescent reporter, an autofluorescent reporter, a chemiluminescent reporter, a luminescent reporter, a colorimetric reporter, a quantifiable nucleic acid, and any combination thereof. Autofluorescent reporters include GFP, mCherry, or derivatives thereof. Colorimetric reporters include pigment-producing enzymes such as (3-galactosidase (e.g. in combination with administration of X-gal), and tyrosinase. Bioluminescent, chemiluminescent or luminescent reporters include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396(2010): 290-297). Reporters detectable by photoacoustic imaging include the pigment-producing enzymes such as (3-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photo-switchable proteins (e.g. Dronpa, Dronpa-M159T, and BphP1 or variants thereof). The quantifiable nucleic acid may be a ribozyme, a self-splicing intron, an RNA hairpin, a microRNA, or barcoded versions thereof, or other types of quantifiable RNA. The quantifiable nucleic acid may comprise a unique sequence detectable by quantitative PCR or hybridization-based techniques. When the polypeptide or nucleic acid is a polypeptide, the polypeptide may comprise an N-terminal secretion signal sequence (e.g. the N-terminal signal peptide from CD33 or CD8a).

In some cases, the composition may have a certain diagnostic efficiency, wherein the diagnostic efficiency is measured in a diseased cell preferentially over expression of said biomarker in non-diseased cells in said subject such that a relative ratio of said biomarker expressed in said diseased cell over said non-diseased cells is greater than 1.0; (b) detecting said biomarker; and (c) using said biomarker detected in (b) to determine that said subject has said diseased cell at an accuracy of at least 90%.

In some cases, the composition administered to the cells ex vivo may comprise a second polypeptide or nucleic acid that modulates the proliferation of diseased or disordered cells. The second polypeptide may be under the control of a second promoter that selectively drives expression of the second polypeptide or nucleic acid in the diseased or disordered cell. The second promoter may be a pan-cancer specific promoter. The second promoter may be a cancer-specific promoter. The promoter may be any of the specific promoters described herein. The second polypeptide may comprise a transforming agent or a growth factor. The transforming agent may comprise telomerase or SV40 large T antigen. The growth factor may be e.g. EGF, PDGF, FGF, HGH, or IGF-1.

In some aspects, the present disclosure provides for a method for detecting a diseased or disordered cell ex-vivo, comprising delivering ex vivo a non-naturally occurring recombinant genetic construct to a population of cells isolated from a subject, wherein the non-naturally occurring recombinant genetic construct comprises: a sequence encoding a polypeptide or nucleic acid sequence, wherein the sequence comprises a first promoter that selectively drives expression of the polypeptide or nucleic acid sequence in a plurality of different types of cells isolated from a subject when transduced into the cells.

In some aspects, the present disclosure provides for a method for detecting a subject's disease or absence thereof, comprising contacting one or more cells of said subject with a genetic construct ex-vivo, wherein said genetic construct comprises a disease-activated promoter operably linked to a barcode molecule and said disease-activated promoter drives expression of said barcode molecule in a cell affected by said disease; quantifying an expression level of said barcode molecule; and detecting said disease or absence thereof based on said expression level.

In some cases, the method for detecting a diseased or disordered cell ex-vivo may be capable of detecting a particular number of diseased cells in a background of normal cells. In some embodiments, the method may be capable of detecting about at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, at least about 200, at least about 300, at least about 400, or at least about 500 diseased cells per 5 million normal cells. In some embodiments, the normal cells are blood cells (e.g. PBMCs).

In some cases, the method may comprise isolating a biological sample comprising the cells from the subject. The biological sample may be a sample collected by a non-invasive method from the subject. Exemplary non-invasive samples include, but are not limited to, samples comprised of naturally shed bodily substances or non-destructive scraping of externally accessible tissues, such as saliva, sputum, sweat, urine, stool, semen, mucus, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples or fractions thereof (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy).

In some cases, the method may comprise culturing the population of cells for a certain period of time after the recombinant genetic construct is delivered to the cells. The population of cells may be cultured for least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, or at least about 1 month after delivery of the genetic construct to the cells. The population of cells may be cultured for most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, or at most about 1 month after delivery of the genetic construct to the cells.

In some cases, the method may comprise detecting the polypeptide or nucleic acid sequence. The detecting may occur before or after culturing the population of cells. The detecting may comprise a photoacoustic, a bioluminescent, fluorescent reporter, chemiluminescent, luminescent, colorimetric, or nucleic acid assay. The detecting may also comprise an immunoassay. Immunoassays include those described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. Immunoassays include various sandwich, competitive, or non-competitive assay formats, which generate a signal that is related to the presence or amount of a protein analyte of interest. Any suitable immunoassay may be utilized, for example, lateral flow, enzyme-linked immunoassays (ELISA), radioimmunoassays (RIAs), competitive binding assays, and the like.

The method of detection may comprise sequencing. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, and primer walking.

The detection may comprise a "real time amplification" method also known as quantitative PCR (qPCR) or Taqman (see, e.g., U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye. The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified.

In some embodiments, for qPCR or Taqman detection, an RT-PCR step may first be performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In some embodiments, qPCR or Taqman may be used immediately following a reverse-transcriptase reaction performed on isolated cellular mRNA; this variety serves to quantitate the levels of individual mRNAs during qPCR.

In some embodiments, for qPCR or Taqman detection or RNA sequencing, a "pre-amplification" step may be first performed on cDNA transcribed from cellular RNA. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof. The pre-amplification may be either general or targeted in the same way as the reverse-transcription reaction described above.

Improved Biomarkers, Construct Design, and Methods for Disease Stage Indication

In some aspects, the present disclosure provides for a composition comprising a vector, wherein the vector comprises a plurality of different promoters operably linked to a plurality of different nucleic acid sequences, wherein each the promoter drives expression of the plurality of nucleic acid sequences in a cell to yield a plurality of polypeptides or nucleic acid biomarker sequences, wherein levels of individual polypeptides or nucleic acid biomarkers of the plurality of nucleic acid sequences are indicative of a stage of a disease of the cell. In some cases, the stage of the disease of the cell is diseased, non-diseased or an intermediate state. In some cases, the plurality of different promoters may be included on a plurality of independent genetic constructs or vectors that are administered simultaneously or separately. In some embodiments, the plurality of independent genetic constructs administered separately are administered within 8, 16, 24, 36, 48, 60, or 72 hours of one another. In some embodiments, disease stage may be assessed by dissemination of cancer cells away from their tissue of origin via metastasis to distal tissues. In cases such as this, the plurality of different promoters may comprise at least a promoter with high cancer specificity in the initial tissue site (e.g. breast, when breast cancer is being staged) and a promoter active with high specificity at a common metastatic site (e.g. lung, spleen, liver) different from the initial site. In some cases, the plurality of different promoters may comprise at least a promoter with high cancer specificity in the initial tissue site (e.g. breast, when breast cancer is being staged) and multiple promoters active with high specificity at multiple distinct metastatic sites (e.g. lung, spleen, liver). Thus, such systems may provide activation of more distinct promoters (which can be read out by their operably linked biomarkers downstream) as the cancer metastasizes from its home site to metastatic sites, providing an assessment of how widely the tumor has metastasized. In some embodiments, one of the promoter active with high specificity at a common metastatic site is MMP-2, which provides high expression at all stages at lung cancer but is not overexpressed in breast cancer.

In some cases, the disease may be cancer, an autoimmune disease (e.g. a T-cell or lymphocyte with self-directed activity, or a normal cell damaged by autoimmunity), or a neurodegenerative disease (e.g. a cell bearing a toxic amyloid or proximal to a toxic amyloid). Exemplary cancers include, but are not limited to, carcinomas, sarcomas, lymphomas, leukemias, and adenomas. Carcinomas may arise from cells that cover internal and external parts of the body such as the lung, breast, and colon. Sarcomas may arise from cells that are located in bone, cartilage, fat, connective tissue, muscle, and other supportive tissues. Lymphomas may arise in the lymph nodes and immune system tissues. Leukemias may arise in the bone marrow and accumulate in the bloodstream. Adenomas may arise in the thyroid, the pituitary gland, the adrenal gland, and other glandular tissues. Specific exemplary examples of cancer types include suitable for detection with the methods according to the disclosure include acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

In some cases, the disease may be a viral infection cell. Exemplary viral infections include, but are not limited to, those caused by HIV, hepatitis C virus, hepatitis B virus, hepatitis D virus, herpesviruses, Epstein-Barr virus, cytomegalovirus, and human T-lymphotropic virus type III.

In some cases, when the disease is cancer, the plurality of different promoters may comprise a first promoter activated in an early stage of cancer. In some cases, the plurality of different promoters may comprise a second promoter activated in an intermediate stage of cancer. In some cases, the plurality of different promoters comprises a third promoter activated in a late stage of cancer.

In some cases, the disease may be an autoimmune disease. Exemplary autoimmune diseases include, but are not limited to, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

In some cases, the disease may a neurodegenerative disease. Neurodegenerative diseases include, but are not limited to, Multiple sclerosis (MS), Alzheimer's disease (AD), Parkinson's disease (PD), and Amyotrophic lateral sclerosis (ALS), or neurodegeneration due to infection by viruses of families Herpesviridae, Polyomaviridae, Bornaviridae, Orthomyxoviridae, Paramyxoviridae, Rhabdoviridae, Flaviviridae, Picornaviridae, or Retroviridae (see Zhou et al. Virol J. 2013; 10: 172).

In some cases, the nucleic acid biomarker may be e.g. a natural or engineered miRNA, an RNA hairpin, RNA aptamers or barcoded versions thereof.

In some cases, the vector provided in the composition to detect the stage of disease may be any of the vectors described herein.

In some cases, at least one of the plurality of polypeptides may comprise a polypeptide detectable by non-invasive imaging. Such non-invasive imagine methods include MRI imaging, PET imaging, SPECT imaging, photoacoustic imaging, and bioluminescent imaging. Synthetic biomarkers detectable by MRI imaging include, but are not limited to, polypeptide contrast agents, such as ferritin (or mutants thereof, such as *Pyrococcus* furiousus ferritin mutants L55P, F57S, or F123S), or lanthanide-binding proteins (or engineered fusions thereof, such as the LBT-ubiquitin fusions described in Daughtry et al. ChemBioChem 2012, 13, 2567-2574). Synthetic biomarkers detectable by PET or SPECT imaging include the human sodium iodide symporter (e.g. in conjunction with administration of PET-active iodine/iodide isotopes, see e.g. Penheiter et al. Curr Gene Ther. 2012 February; 12(1): 33-47), HSV-tk or mutants thereof such as HSV-sr39tk (e.g. in conjunction with administration of positron-labeled acycloguanosine or pyrimidine analog PET reporters such as [18F]FHBG, see Yaghoubi S S et al. Nat Protoc. 2006; 1(6):3069-75), and the dopamine D2 receptor or mutants thereof such as D2R80A or D2R194A (e.g. in conjunction with administration of positron-labeled D2 binders such as 3-(2'-[18F]-fluoroethyl)-spiperone). Synthetic biomarkers detectable by photoacoustic imaging include the pigment-producing enzymes such as 0-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). Synthetic biomarkers detectable by bioluminescent imaging include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396 (2010): 290-297). In some embodiments, the synthetic biomarker may be a contrast agent, an enzyme producing a detectable molecule, or a transporter driving accumulation of a detectable molecule. The synthetic biomarker may be measured in situ within subject's body.

In some cases, the barcode molecules may be polypeptides or nucleic acids detectable in a biological sample from the subject. When the barcode molecule is a polypeptide, the polypeptide may comprise an N-terminal secretion signal sequence (e.g. the N-terminal signal peptide from CD33 or CD8a). Exemplary polypeptide biomarkers include, but are not limited to, photoacoustic reporters, bioluminescent reporters, autofluorescent reporters, chemiluminescent reporters, luminescent reporters, colorimetric reporters, and any combination thereof. Autofluorescent reporters include GFP, mCherry, or derivatives thereof. Colorimetric reporters include pigment-producing enzymes such as 0-galactosidase (e.g. in combination with administration of X-gal), and tyrosinase. Bioluminescent, chemiluminescent or luminescent reporters include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396 (2010): 290-297). Reporters detectable by photoacoustic imaging include the pigment-producing enzymes such as 0-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photo-switchable proteins (e.g. Dronpa, Dronpa-M159T, and BphP1 or variants thereof). When the barcode molecule is a nucleic acid sequence, the detectable nucleic acid sequence may comprise, but not be limited to, a ribozyme, a self-splicing intron, an RNA hairpin, a microRNA, or barcoded versions thereof, or other types of quantifiable RNA. The quantifiable nucleic acid sequence may comprise a unique sequence detectable by quantitative PCR or hybridization-based techniques.

By ascribing an exclusive label to a unique member within a larger group, barcodes afford the opportunity to identify and quantify that member (e.g. expression of a reporter under the control of a particular cancer specific promoter) within the context of a larger and more complex mixture of many members (e.g. multiple promoter-reporter constructs expressed within the same cell), as well as offering the opportunity to isolate a single member from the complex mixture. For instance, in the case of barcodes based on nucleic acids, hybridization of barcodes based on base pairing complementarity may be used to capture and isolate or otherwise reduce the complexity of a mixture by said capture event. For barcodes based on peptides, unique features including immunocapture or interactions of ligands and receptors may be used to capture and isolate or otherwise reduce the complexity of a mixture by said capture event.

In some aspects, the present disclosure provides for a method for detecting a stage of disease, comprising administering to a subject a composition comprising a vector, wherein the vector comprises: a plurality of different promoters operably linked to a plurality of different nucleic acid sequences, wherein each the promoter drives expression of the plurality of nucleic acid sequences in a cell to yield a plurality of polypeptides or synthetic nucleic acid sequences, wherein levels of individual polypeptides of the plurality of nucleic acid sequences are indicative of a stage of a disease of the cell. In some cases, the stage of the disease of the cell may be diseased, non-diseased or an intermediate state. In some aspects, the present disclosure provides for a method for detecting different types of cancers, comprising administering to a subject a composition comprising a vector, wherein the vector comprises, a plurality to different promoters operably linked to a plurality of different nucleic acid sequences in a cell to yield a plurality of polypeptides or synthetic nucleic acid sequences, wherein levels of individual polypeptides of the plurality of nucleic acid sequences are indicative of a different type of cancer within the body. In some cases, the cancer detected within the body may be derived, but not limited to, tissues of the breast, liver, colon, brain, lung, kidney, pancreas, testis, ovaries, blood or components of the blood, bone, stomach, eye, endocrine or neuroendocrine tissues, head and neck, gastrointestinal, musculoskeletal, skin, respiratory, neurologic, or genitourinary, or cancers derived from other parts of the body.

In some cases, the composition is administered intravenously, subcutaneously, intraventricularly, intrathecally, intracerebroventricularly, transdermally, intramuscularly, orally, inhalation, nasally, rectally,intratumorally, or proxi-tumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g. Rojas-Solano et al. J Bronchology Intery Pulmonol. 2018 July; 25(3): 168-175). In some embodiments, the composition is administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region.

In some cases, when the disease is cancer, the plurality of different promoters may comprise a first promoter activated in an early stage of cancer. In some cases, the plurality of different promoters may comprise a second promoter activated in an intermediate stage of cancer. In some cases, the plurality of different promoters comprises a third promoter activated in a late stage of cancer. In some cases, the method may identify masses of tissue or lesions in the subject as pre-cancerous, benign, dysplastic, or metastatic in nature.

In some cases, the method may comprise isolating a biological sample from the subject. The biological sample may be a sample collected by a non-invasive method from the subject. Exemplary non-invasive samples include, but are not limited to, samples comprised of naturally shed bodily substances or non-destructive scraping of externally accessible tissues, such as saliva, sputum, sweat, urine, stool, semen, mucus, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples or fractions thereof (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy). In some cases, the biological sample may be collected period of time after the composition is administered to the subject.

The population of cells may be cultured for least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, or at least about 1 month after delivery of the genetic construct to the cells. The population of cells may be cultured for most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, or at most about 1 month after delivery of the genetic construct to the cells.

In some cases, the method may comprise detecting the polypeptide or nucleic acid sequence. The detecting may occur before or after culturing the population of cells. The detecting may comprise a photoacoustic, a bioluminescent, fluorescent reporter, chemiluminescent, luminescent, colorimetric, or nucleic acid assay. The detecting may also comprise an immunoassay. Immunoassays include those described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. Immunoassays include various sandwich, competitive, or non-competitive assay formats, which generate a signal that is related to the presence or amount of a protein analyte of interest. Any suitable immunoassay may be utilized, for example, lateral flow, enzyme-linked immunoassays (ELISA), radioimmunoassays (RIAs), competitive binding assays, and the like.

The method of detection may comprise sequencing. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, and primer walking.

The detection may comprise a "real time amplification" method also known as quantitative PCR (qPCR) or Taqman (see, e.g., U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye. The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified.

In some embodiments, for qPCR or Taqman detection, an RT-PCR step may first be performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In some embodiments, qPCR or Taqman may be used immediately following a reverse-transcriptase reaction performed on isolated cellular mRNA; this variety serves to quantitate the levels of individual mRNAs during qPCR.

In some embodiments, for qPCR or Taqman detection or RNA sequencing, a "pre-amplification" step may first be performed on cDNA transcribed from cellular RNA. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof. The pre-amplification may be either general or targeted in the same way as the reverse-transcription reaction described above.

Improved Synthetic Biomarker Design and Method for Expression Leakiness Reduction In some aspects, the present disclosure provides for a composition comprising an engineered nucleic acid encoding an expressible reporter gene that exhibits about 10% or less expression in normal cells versus diseased cells when compared to a recombinant nucleic acid comprising a reporter gene comprising a nucleic acid sequence of SEQ ID NO: 1 or SEQ ID NO: 2.

In some cases, the engineered nucleic acid may comprise a pan-tumor specific promoter operably linked to the expressible reporter gene. In some cases, the pan-tumor specific promoter may comprise a transcriptional response element. The transcriptional response element may comprise a modified p53 response element. A modification within the modified p53 response element may result in decreased promoter activity in normal cells relative to diseased cells. A modification within the modified p53 response element may result in increased promoter activity in diseased cells relative to normal cells.

In some cases, the engineered nucleic acid encoding the expressible reporter gene may be any of the vectors described herein.

In some cases, the reporter gene may encode a detectable polypeptide or a detectable nucleic acid. The detectable nucleic acid biomarker may be a ribozyme, a self-splicing intron, an RNA hairpin, a microRNA, RNA aptamers or barcoded versions thereof, or other types of quantifiable RNA. The quantifiable nucleic acid may comprise a unique sequence detectable by quantitative PCR or hybridization-based techniques.

The reporter gene may encode a photoacoustic reporter, a bioluminescent reporter, an autofluorescent reporter, a chemiluminescent reporter, a luminescent reporter, a colorimetric reporter, or any combination thereof. Autofluorescent reporters include GFP, mCherry, or derivatives thereof. Colorimetric reporters include pigment-producing enzymes such as 0-galactosidase (e.g. in combination with administration of X-gal), and tyrosinase. Bioluminescent, chemiluminescent or luminescent reporters include luciferases (e.g. in combination with administration of coelenterazines described herein), including Gaussia luciferases, Renilla luciferases, and Photinus luciferases (e.g. including the engineered Ppy RE8 and RE9 versions described in Branchini et al. Anal. Biochem. 396(2010): 290-297). Reporters detectable by photoacoustic imaging include the pigment-producing enzymes such as (3-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). The detectable nucleic acid biomarker may be a ribozyme, a self-splicing intron, an RNA hairpin, a microRNA, or barcoded versions thereof, or other types of quantifiable RNA. The quantifiable nucleic acid may comprise a unique sequence detectable by quantitative PCR or hybridization-based techniques. The reporter gene may encode a polypeptide detectable by a non-invasive imaging method. Such non-invasive imagine methods include MRI imaging, PET imaging, SPECT imaging, photoacoustic imaging, and bioluminescent imaging. Polypeptides detectable by MRI imaging include polypeptide contrast agents, such as ferritin (or mutants thereof, such as Pyrococcus furiousus ferritin mutants L55P, F57S, or F123S), or lanthanide-binding proteins (or engineered fusions thereof, such as the LBT-ubiquitin fusions described in Daughtry et al. ChemBioChem 2012, 13, 2567-2574). Polypeptides detectable by PET or SPECT imaging include the human sodium iodide symporter (e.g. in conjunction with administration of PET-active iodine/iodide isotopes, see e.g. Penheiter et al. Curr Gene Ther. 2012 February; 12(1): 33-47), HSV-tk or mutants thereof such as HSV-sr39tk (e.g. in conjunction with administration of positron-labeled acycloguanosine or pyrimidine analog PET reporters such as [18F]FHBG, see Yaghoubi S S et al. Nat Protoc. 2006; 1(6):3069-75), and the dopamine D2 receptor or mutants thereof such as D2R80A or D2R194A (e.g. in conjunction with administration of positron-labeled D2 binders such as 3-(2'-[18F]-fluoro-ethyl)-spiperone). Polypeptides detectable by photoacoustic imaging include the pigment-producing enzymes such as 0-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). Polypeptides detectable by bioluminescent imaging include luciferases (e.g. in combination with administration of coelenterazines described herein), including Gaussia luciferases, Renilla luciferases, and Photinus luciferases (e.g. including the engineered Ppy RE8 and RE9 versions described in Branchini et al. Anal. Biochem. 396 (2010): 290-297). In some embodiments, the Polypeptides may be a contrast agent, an enzyme producing a detectable molecule, or a transporter driving accumulation of a detectable molecule.

In some cases, the disease affecting the diseased cells may be cancer. Exemplary cancers include, but are not limited to, carcinomas, sarcomas, lymphomas, leukemias, and adenomas. Carcinomas may arise from cells that cover internal and external parts of the body such as the lung, breast, and colon. Sarcomas may arise from cells that are located in bone, cartilage, fat, connective tissue, muscle, and other supportive tissues. Lymphomas may arise in the lymph nodes and immune system tissues. Leukemias may arise in the bone marrow and accumulate in the bloodstream. Adenomas may arise in the thyroid, the pituitary gland, the adrenal gland, and other glandular tissues. Specific exemplary examples of cancer types include suitable for detection with the methods according to the disclosure include acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

In some aspects, the present disclosure provides for a method of detecting a disease in a subject comprising an engineered nucleic acid encoding an expressible reporter gene that exhibits about 10% or less expression in normal cells versus cells affected by the disease from the subject when compared to a recombinant nucleic acid comprising a reporter gene comprising a nucleic acid sequence of SEQ ID NO: 1 or SEQ ID NO: 2. The subject may be suspected of having cancer. The disease may be cancer or any of the subtypes mentioned herein.

In some cases, the engineered nucleic acid may be administered intravenously, subcutaneously, intraventricularly, intrathecally, intracerebroventricularly, transdermally, intramuscularly, orally, inhalation, nasally, rectally,intratumorally, or proxi-tumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g. Rojas-Solano et al. J Bronchology Intery Pulmonol. 2018 July; 25(3): 168-175). In some embodiments, the engineered nucleic acid may be administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region.

In some cases, the method may comprise isolating a biological sample from the subject. The biological sample may be a sample collected by a non-invasive method from the subject. Exemplary non-invasive samples include, but are not limited to, samples comprised of naturally shed bodily substances or non-destructive scraping of externally accessible tissues, such as saliva, sputum, sweat, urine, stool, semen, mucus, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples or fractions thereof (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy). In some cases, the biological sample may be collected period of time after the composition is administered to the subject.

The population of cells may be cultured for least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, or at least about 1 month after delivery of the genetic construct to the cells. The population of cells may be cultured for most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, or at most about 1 month after delivery of the genetic construct to the cells.

In some cases, the method may comprise detecting the polypeptide or nucleic acid sequence. The detecting may comprise a photoacoustic, a bioluminescent, fluorescent reporter, chemiluminescent, luminescent, colorimetric or nucleic acid assay. The detecting may also comprise an immunoassay. Immunoassays include those described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. Immunoassays include various sandwich, competitive, or non-competitive assay formats, which generate a signal that is related to the presence or amount of a protein analyte of interest. Any suitable immunoassay may be utilized, for example, lateral flow, enzyme-linked immunoassays (ELISA), radioimmunoassays (RIAs), competitive binding assays, and the like.

The method of detection may comprise sequencing. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, and primer walking.

The detection may comprise a "real time amplification" method also known as quantitative PCR (qPCR) or Taqman (see, e.g., U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye. The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified.

In some embodiments, for qPCR or Taqman detection, an RT-PCR step may be first performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In some embodiments, qPCR or Taqman may be used immediately following a reverse-transcriptase reaction performed on isolated cellular mRNA; this variety serves to quantitate the levels of individual mRNAs during qPCR.

In some embodiments, for qPCR or Taqman detection or RNA sequencing, a "pre-amplification" step may be first performed on cDNA transcribed from cellular RNA. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof. The pre-amplification may be either general or targeted in the same way as the reverse-transcription reaction described above.

Synthetic Biomarker Design and Method Utilizing miRNA Binding Sites Used To Modulate Marker Expression In some aspects, the present disclosure provides for a composition that exhibits about 10% or less expression in normal cells versus diseased cells and comprises a recombinant nucleic acid comprising a nucleic acid sequence encoding a reporter gene that includes one or more miRNA binding sequences in a 3' untranslated region of the reporter gene.

In some cases, binding or lack of binding of a miRNA expressed in the diseased cells to at least one of the one or more miRNA binding sequences may result in differential translation or half-life of an mRNA encoding the reporter gene. In some cases, binding of a miRNA expressed in the diseased cells to at least one of the one or more miRNA binding sequences may result in reduced translation of the reporter gene or reduction of a half-life of an mRNA encoding the reporter gene. In some cases, the reporter gene exhibits increased expression in the cancer cell due to downregulation of at least one miRNA expressed in the cancer cell.

In some cases, the diseased cell may be a cancerous cell, a cell indicative of an autoimmune disease (e.g. a T-cell or lymphocyte with self-directed activity, or a normal cell damaged by autoimmunity), or a cell indicative of a neurodegenerative disease (e.g. a cell bearing a toxic amyloid or proximal to a toxic amyloid). Cancers, neurodegenerative diseases, and autoimmune diseases include any of the diseases described herein. In some cases, the diseased cell may be a virally-infected cell. Exemplary viruses include, but are not limited to, HIV, hepatitis C virus, hepatitis B virus, hepatitis D virus, herpesviruses, Epstein-Barr virus, cytomegalovirus, and human T-lymphotropic virus type III.

In some cases, the composition may comprise more than one miRNA binding sequences in the 3' untranslated region of the reporter gene. The composition may comprise at least two miRNA binding sequences in the 3' untranslated region of the reporter gene, wherein two miRNA binding sequences have a substantially identical nucleotide sequence capable of binding to a same miRNA. The composition may comprise at least two miRNA binding sequences in the 3' untranslated region of the reporter gene, wherein the at least two miRNA binding sequences have different nucleotide sequences, each of the different nucleotide sequences capable of binding to different miRNAs. The composition may comprise at least 3, at least 4, at least 5, at least 6, at least 7, at least 8, at least 9, or at least 10 miRNA binding sequences capable of binding the same miRNA or a combination of miRNAs.

In some cases, the recombinant nucleic acid may comprise DNA. When the recombinant nucleic acid comprises DNA, the recombinant nucleic acid may be part of any of the vectors described herein.

The recombinant nucleic acid may be a synthetic or in vitro-transcribed mRNA.

The one or more miRNA binding sequences may comprise at least one miR-15, miR-16, let-7, miR-122 or miR-34 binding sequence.

In some cases, the reporter gene may encode a detectable polypeptide or a detectable nucleic acid. The detectable nucleic acid may be a ribozyme, a self-splicing intron, an RNA hairpin, a microRNA, RNA aptamers or barcoded versions thereof, or other types of quantifiable RNA. The quantifiable nucleic acid may comprise a unique sequence detectable by quantitative PCR or hybridization-based techniques.

The reporter gene may encode a photoacoustic reporter, a bioluminescent reporter, an autofluorescent reporter, a chemiluminescent reporter, a luminescent reporter, a colorimetric reporter, or any combination thereof. Autofluorescent reporters include GFP, mCherry, or derivatives thereof. Colorimetric reporters include pigment-producing enzymes such as 0-galactosidase (e.g. in combination with administration of X-gal), and tyrosinase. Bioluminescent, chemiluminescent or luminescent reporters include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396(2010): 290-297). Reporters detectable by photoacoustic imaging include the pigment-producing enzymes such as (3-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). The detectable nucleic acid may be a ribozyme, a self-splicing intron, an RNA hairpin, a microRNA, or barcoded versions thereof, or other types of quantifiable RNA. The quantifiable nucleic acid may comprise a unique sequence detectable by quantitative PCR or hybridization-based techniques.

The reporter gene may encode a polypeptide detectable by a non-invasive imaging method. Such non-invasive imagine methods include MRI imaging, PET imaging, SPECT imaging, photoacoustic imaging, and bioluminescent imaging. Polypeptides detectable by MRI imaging include polypeptide contrast agents, such as ferritin (or mutants thereof, such as *Pyrococcus furiousus* ferritin mutants L55P, F57S, or F123S), or lanthanide-binding proteins (or engineered fusions thereof, such as the LBT-ubiquitin fusions described in Daughtry et al. ChemBioChem 2012, 13, 2567-2574). Polypeptides detectable by PET or SPECT imaging include the human sodium iodide symporter (e.g. in conjunction with administration of PET-active iodine/iodide isotopes, see e.g. Penheiter et al. Curr Gene Ther. 2012 February; 12(1): 33-47), HSV-tk or mutants thereof such as HSV-sr39tk (e.g. in conjunction with administration of positron-labeled acycloguanosine or pyrimidine analog PET reporters such as [18F]FHBG, see Yaghoubi S S et al. Nat Protoc. 2006; 1(6):3069-75), and the dopamine D2 receptor or mutants thereof such as D2R80A or D2R194A (e.g. in conjunction with administration of positron-labeled D2 binders such as 3-(2'-[18F]-fluoroethyl)-spiperone). Polypeptides detectable by photoacoustic imaging include the pigment-producing enzymes such as 0-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). Polypeptides detectable by bioluminescent imaging include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396(2010): 290-297). In some embodiments, the polypeptide may be a contrast agent, an enzyme producing a detectable molecule, or a transporter driving accumulation of a detectable molecule.

In some aspects, the present disclosure provides for a method of detecting diseased cells, comprising administering to a subject a composition that exhibits about 10% or less expression in normal cells versus diseased cells and comprises a recombinant nucleic acid comprising a nucleic acid sequence encoding a reporter gene that includes one or more miRNA binding sequences in a 3' untranslated region of the reporter gene.

In instances where the reporter gene is a polypeptide biomarker detectable by a non-invasive imaging method, the method involving administering to a subject a composition inducing expression of a synthetic biomarker in a diseased cell may further comprise localizing the diseased cell in the body of the subject. The localizing may be associated with a particular resolution, for example 10 mm to 10 cm, at least 10 mm, or at most 10 cm. The localizing may be associated with a particular minimum detectable tumor size, for example a tumor size between 3 $mm^3$ and 10 cm3. In some cases, the particular minimum range may be may be 1 $cm^3$ to 10 $cm^3$, or 900 $mm^3$ to 1 $cm^3$, or 800 $mm^3$ to 900 $mm^3$, or 700 $mm^3$ to 800 $mm^3$, or 600 $mm^3$ to 700 $mm^3$, or 500 $mm^3$ to 600 $mm^3$, or 400 $mm^3$ to 500 $mm^3$, or 300 $mm^3$ to 400 $mm^3$, or 200 $mm^3$ to 300 $mm^3$, or 100 $mm^3$ to 200 $mm^3$, or 50 $mm^3$ to 100 $mm^3$, or 10 $mm^3$ to 50 $mm^3$, or 3 $mm^3$ to 10 $mm^3$ in size. In some cases, the localization occurs in a non-invasive imaging scan (e.g. PET, MRI, SPECT, etc). In some cases, the localization occurs during surgical intervention in situ, for example by the use of visual inspection (in the case of visual-range absorbing reporters) or by the use of visual inspection combined with fluorescent excitation.

In some cases, the additional localization step above may be followed by a surgical step to eliminate the detected and/or localized diseased cell. The surgical step may be performed by the same or different party to that which administers the biomarker-encoding composition and/or localizes the diseased cell. The surgical step may be surgical excision of the diseased cell or a tumor associated with the diseased cell. The surgical or nonsurgical elimination step may involve a minimally-invasive killing technique, such as a radiosurgery (including but not limited to Gamma Knife, Reflexion, CyberKnife, and related techniques using targeted ionizing radiation to kill diseased cells).

In some cases, the engineered nucleic acid may be administered intravenously, subcutaneously, intraventricularly, intrathecally, intracerebroventricularly, transdermally, intramuscularly, orally, by inhalation, nasally, rectally, intratumorally, or proxi-tumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g. Rojas-Solano et al. J Bronchology Intery Pulmonol. 2018 July; 25(3): 168-175). In some embodiments, the engineered nucleic acid may be administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region.

In some cases, the method may comprise isolating a biological sample from the subject. The biological sample may be a sample collected by a non-invasive method from the subject. Exemplary non-invasive samples include, but are not limited to, samples comprised of naturally shed bodily substances or non-destructive scraping of externally accessible tissues, such as saliva, sputum, sweat, urine, stool, semen, mucus, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples or fractions thereof (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy). In some cases, the biological sample may be collected period of time after the composition is administered to the subject.

The population of cells may be cultured for least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, or at least about 1 month after delivery of the genetic construct to the cells. The population of cells may be cultured for most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, or at most about 1 month after delivery of the genetic construct to the cells.

In some cases, the method may comprise detecting the polypeptide or nucleic acid sequence. The detecting may comprise a photoacoustic, a bioluminescent, fluorescent reporter, chemiluminescent, luminescent, colorimetric or nucleic acid assay. The detecting may also comprise an immunoassay. Immunoassays include those described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. Immunoassays include various sandwich, competitive, or non-competitive assay formats, which generate a signal that is related to the presence or amount of a protein analyte of interest. Any suitable immunoassay may be utilized, for example, lateral flow, enzyme-linked immunoassays (ELISA), radioimmunoassays (RIAs), competitive binding assays, and the like.

The method of detection may comprise sequencing. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, and primer walking.

The detection may comprise a "real time amplification" method also known as quantitative PCR (qPCR) or Taqman (see, e.g., U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye. The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified.

In some embodiments, for qPCR or Taqman detection, an RT-PCR step may be first performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In some embodiments, qPCR or Taqman may be used immediately following a reverse-transcriptase reaction performed on isolated cellular mRNA; this variety serves to quantitate the levels of individual mRNAs during qPCR.

In some embodiments, for qPCR or Taqman detection or RNA sequencing, a "pre-amplification" step may be first performed on cDNA transcribed from cellular RNA. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with polyA specific primers, and any combination thereof. The pre-amplification may be either general or targeted in the same way as the reverse-transcription reaction described above.

CELiD-based Design and Method for Improved Safety and Persistent Synthetic Biomarker Expression In some aspects, the present disclosure provides for a composition exhibiting significantly longer expression of synthetic biomarker versus plasmid DNA or minicircle DNA comprising a linear vector comprising a double-stranded nucleic acid comprising a promoter operatively linked to a DNA sequence encoding a synthetic biomarker, wherein a forward and a reverse strand of the double-stranded nucleic acid are covalently linked on each of their terminal ends, wherein the promoter induces expression of the synthetic biomarker in a diseased cell preferentially over expression of the synthetic biomarker in a non-diseased cell such that a relative concentration of the synthetic biomarker expressed in the diseased cell over the non-diseased cell is greater than 1.0.

In some cases, the disease may be cancer, an autoimmune disease (e.g. a T-cell or lymphocyte with self-directed activity, or a normal cell damaged by autoimmunity), or a neurodegenerative disease (e.g. a cell bearing a toxic amyloid or proximal to a toxic amyloid). Exemplary cancers, autoimmune diseases, and neurodegenerative diseases include any of those described herein. In some cases, the disease may be a viral infection. Exemplary viral infections include, but are not limited to, those caused by HIV, hepatitis C virus, hepatitis B virus, hepatitis D virus, herpesviruses, Epstein-Barr virus, cytomegalovirus, and human T-lymphotropic virus type III.

In some cases, the linear vector may comprise inverted terminal repeats (ITRs) flanking the promoter operatively linked to the DNA sequence encoding the synthetic biomarker, wherein the ITRs are derived from an Adeno-Associated Virus (AAV). In some cases, the AAV may be AAV2. In some cases, the promoter may drive expression of the synthetic biomarker selectively in a plurality of diseased cells in a subject.

In some cases, the promoter may have a cell-type specificity. In some cases, the promoter is a pan-cancer specific promoter. In some cases, the promoter may be a cancer-specific promoter. In some cases, the promoter may be any of the specific promoters mentioned herein.

In some cases, the synthetic biomarker may comprise an MRI reporter, a PET reporter, a SPECT reporter, a photoacoustic reporter, a bioluminescent reporter, a fluorescent reporter, chemiluminescent reporter, a luminescent reporter, colorimetric reporter, a quantifiable nucleic acid biomarker and combinations thereof and any combination thereof. The detectable nucleic biomarker acid may be a ribozyme, a self-splicing intron, an RNA hairpin, a microRNA, or barcoded versions thereof, or other types of quantifiable RNA. The quantifiable nucleic acid biomarker may comprise a unique sequence detectable by quantitative PCR or hybridization-based techniques.

In some aspects, the present disclosure provides for a method of identifying a diseased cell, comprising: (a) administering to a subject a composition, wherein the composition exhibits significantly longer expression of synthetic biomarker versus plasmid DNA or minicircle DNA comprising a linear vector comprising a double-stranded nucleic acid comprising a promoter operatively linked to a DNA sequence encoding a synthetic biomarker, wherein a forward and a reverse strand of the double-stranded nucleic acid are covalently linked on each of their terminal ends; and (b) detecting the synthetic biomarker, wherein the synthetic biomarker is expressed in a diseased cell preferentially over expression of the synthetic biomarker in non-diseased cells in the subject such that a relative concentration of the synthetic biomarker expressed in the diseased cell over the non-diseased cells is greater than 1.0.

In instances where the synthetic biomarker is a polypeptide biomarker detectable by a non-invasive imaging method, the method involving administering to a subject a composition inducing expression of a synthetic biomarker in a diseased cell may further comprise (d) localizing the diseased cell in the body of the subject. The localizing may be associated with a particular resolution, for example 10 mm to 10 cm, at least 10 mm, or at most 10 cm. The localizing may be associated with a particular minimum detectable tumor size, for example a tumor size between 3 $mm^3$ and 10 $cm^3$. In some cases, the particular minimum range may be may be 1 $cm^3$ to 10 $cm^3$, or 900 $mm^3$ to 1 $cm^3$, or 800 $mm^3$ to 900 $mm^3$, or 700 $mm^3$ to 800 $mm^3$, or 600 $mm^3$ to 700 $mm^3$, or 500 $mm^3$ to 600 $mm^3$, or 400 $mm^3$ to 500 $mm^3$, or 300 $mm^3$ to 400 $mm^3$, or 200 $mm^3$ to 300 $mm^3$, or 100 $mm^3$ to 200 $mm^3$, or 50 $mm^3$ to 100 $mm^3$, or 10 $mm^3$ to 50 $mm^3$, or 3 $mm^3$ to 10 $mm^3$ in size. In some cases, the localization occurs in a non-invasive imaging scan (e.g. PET, MRI, SPECT, etc). In some cases, the localization occurs during surgical intervention in situ, for example by the use of visual inspection (in the case of visual-range absorbing reporters) or by the use of visual inspection combined with fluorescent excitation.

In some cases, the additional localization step above may be followed by a surgical step to eliminate the detected and/or localized diseased cell. The surgical step may be performed by the same or different party to that which administers the biomarker-encoding composition and/or localizes the diseased cell. The surgical step may be surgical excision of the diseased cell or a tumor associated with the diseased cell. The surgical or nonsurgical elimination step may involve a minimally-invasive killing technique, such as a radiosurgery (including but not limited to Gamma Knife, Reflexion, CyberKnife, and related techniques using targeted ionizing radiation to kill diseased cells).

In some cases, the composition is administered intravenously, subcutaneously, intraventricularly, intrathecally, intracerebroventricularly, transdermally, intramuscularly, orally, by inhalation, nasally, rectally, intratumorally, or proxi-tumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g.

Rojas-Solano et al. J Bronchology Intery Pulmonol. 2018 July; 25(3): 168-175). In some embodiments, the composition is administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region.

In some cases, the detection of the diseased cell may have an accuracy at least about 50%, at least about 53%, at least about 55%, at least about 57%, at least about 60%, at least about 63%, at least about 65%, at least about 67%, at least about 70%, at least about 72%, at least about 75%, at least about 77%, at least about 78%, at least about 79%, at least about 80%, at least about 81%, at least about 82%, 83%, at least about 84%, 85%, at least about 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values. In some cases the detection of the diseased cell may have an accuracy of at most about 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

In some cases, the detection of the diseased cell may have a sensitivity of at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values. In some cases, the detection of the diseased cell may have a sensitivity of at most about 81%, 82%, 83%, 84%, 85%, 86%, 87%, 88%, 89%, 90%, 91%, 92%, 93%, 94%, 95%, 96%, 97%, 98%, or 99%, or any range in between these values.

In some cases, the detection of the diseased cell may have a specificity of at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values. In some cases, the detection of the diseased cell may have a specificity of at most about 81%, 82%, 83%, 84%, 85%, 86%, 87%, 88%, 89%, 90%, 91%, 92%, 93%, 94%, 95%, 96%, 97%, 98%, or 99%, or any range in between these values In some cases, the detection of the diseased cell may have a negative predictive value (NPV) of at least about 80%, 81%, 82%, 83%, 84%, 85%, 86%, 87%, 88%, 89%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. In some cases, the detection of the diseased cell may have a NPV of at least about 81%, 82%, 83%, 84%, 85%, 86%, 87%, 88%, 89%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values.

In some cases, the detection of the diseased cell may have a positive predictive value (PPV) of at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any range between these values. In some cases, the detection of the diseased cell may have a PPV of at most about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any range between these values.

In some cases, detection of the diseased cell may involve using a non-invasive imaging method performed on the subject. The non-invasive imaging method may be photoacoustic, MRI, SPECT, or PET imaging. The imaging method may be performed at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, at least about 6 months, or at least about 1 year after administration of the composition to the subject. The imaging method may be performed at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, at most about 6 months, or at most about 1 year after administration of the composition to the subject. In some embodiments, the imaging method may be performed multiple times after administration of the composition to the subject (e.g. to monitor synthetic biomarker levels over time). The imaging method may be performed at least about 1, 2, 3, 4, 5, 6, 7, 8, 9, 10, 15, 20, or 25 times after administration of the composition to the subject. The imaging method may be performed weekly or monthly following after administration of the composition to the subject.

In some cases, detection of the diseased cell may involve detection from a biological sample from the subject. In some cases, the method may comprise isolating a biological sample from the subject. The biological sample may be a sample collected by a non-invasive method from the subject. Exemplary non-invasive samples include, but are not limited to, samples comprised of naturally shed bodily substances or non-destructive scraping of externally accessible tissues, such as saliva, sputum, sweat, urine, stool, semen, mucus, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples or fractions thereof (e.g.

obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy).

In some cases, detection may be performed a period of time after the composition is administered to the subject. The period of time may be at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, or at least about 6 months after the composition is administered to the subject. The period of time may be at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, or at most about 6 months after the composition is administered to the subject. In some embodiments, the biological sample may be obtained, and any biomarker detection protocols performed multiple times after the composition is administered to the subject (e.g. to monitor synthetic biomarker levels over time). Detection from the biological sample may occur at least about 1, 2, 3, 4, 5, 6, 7, 8, 9, 10, 15, 20, or 25 times after the composition is administered to the subject. Detection from the biological sample may occur weekly or monthly after the composition is administered to the subject.

Design and Method for Reduction of Background Biomarker Expression from Normal Organ Tissues In some aspects, the present disclosure provides for a composition comprising a vector expressing a synthetic biomarker, wherein the synthetic biomarker exhibits about 10% or less expression in normal organ cells versus diseased cells. In some cases, the organ may be liver, kidney, spleen, or a combination thereof. In some cases, the vector may comprise a recombinant nucleic acid encoding a promoter operably linked to a synthetic biomarker.

Promoters may include pan-cancer specific promoters, cancer-specific promoters, or any of the specific promoters described herein.

Synthetic biomarkers may include MRI reporters, PET reporters, SPECT reporters, photoacoustic reporters, bioluminescent reporters, autofluorescent reporters, chemiluminescent reporters, luminescence reporters, colorimetric reporters, quantifiable nucleic acids and any combination thereof. Detectable nucleic acids may be ribozymes, self-splicing introns, RNA hairpins, microRNAs, or barcoded versions thereof, or other types of quantifiable RNA. The quantifiable nucleic acids may comprise a unique sequence detectable by quantitative PCR or hybridization-based techniques.

The vector may comprise regulatory elements that silence or attenuate transcription or mRNA half-life of the nucleic acid sequence in normal liver, spleen, or kidney cells. The regulatory elements may comprise one or more miRNA target sequences in a transcribed, but an untranslated region, of the recombinant nucleic acid. Presence of the one or more miRNA target sequences may inhibit expression from the recombinant nucleic acid sequence. One or more miRNA target sequences may comprise at least one miRNA target sequence for at least one tissue specific miRNA. At least one tissue specific miRNA may comprise at least one miRNA enriched in normal hepatic, renal, or splenic tissues. At least one miRNA enriched in normal hepatic tissues may comprise, but not be limited to, miR-122, miR-33, miR-33*, miR-223, miR-30c, miR-144, miR-148a, miR-24, miR-29, or any combination thereof.

The composition may comprise a transfection agent as described herein.

Synthetic or Engineered Cell Design/Method for Use With Synthetic Biomarkers

In some aspects, the present disclosure provides for an engineered particle that mimics one or many functions of a biological cell or macrophage including inducing the expression of a biomarker in a diseased cell preferentially over expression of the biomarker in non-diseased cells such that the relative concentration ratio of the biomarker expressed in the diseased cell over the non-diseased cells is greater than 1.0.

The engineered particle may be an artificial cell, a minimal cell, or a lipid-enclosed synthetic particle. Production of artificial cells is described in e.g. Bastiaan et al. Acc. Chem. Res., 2017, 50 (4), pp 769-777, which is incorporated by reference herein. The engineered particle may comprise biological membranes, polymeric membranes, simple polymers, crosslinked proteins, lipid membranes or polymer-lipid complexes formed in vitro or in vivo with purified components into nanoparticles, liposomes, polymersomes, exosomes, microvesicles, apoptotic blebs, transport vesicles, synaptic vesicles, secretory vesicles, or microcapsules. The engineered particle may comprise a transmembrane chimeric protein or a naturally occurring protein comprising an extraparticle specific binding domain operably linked to an intraparticle signaling domain, wherein the intraparticle signaling domain is capable of activating at least one enzymatic reaction within the engineered particle. The engineered particle may comprise a nucleic acid sequence encoding a synthetic biomarker, wherein the at least one enzymatic reaction results in the production of the synthetic biomarker within the engineered particle. Exemplary synthetic biomarkers include any reporters described herein. The extraparticle specific binding domain may comprise an scFv or a Fab fragment. The engineered particle may comprise cytoplasm and other components isolated from intact cells. The engineered particle may comprise purified recombinant macromolecular components or macromolecular components such as, but not limited to, cellular proteins, DNA, synthetic gene circuits, organelles, ATP, enzymes, NADP, transcription factors, nucleotides, or cell-free transcription-translation extracts.

Synthetic Biomarker Design and Method Using Multiplex Combinatorial Biomarkers for Disease Detection and/or Generating a Profile of a Subject's Disease In some aspects, the present disclosure provides for at least one vector, wherein the at least one vector comprises: a plurality of different promoters operably linked to a plurality of different nucleic acid sequences, wherein the promoters drive expression of the plurality of nucleic acid sequences in a cell to yield a plurality of polypeptides or nucleic acid biomarker sequences, wherein the promoters induce expression of the plurality of polypeptides or nucleic acid biomarker sequences in a diseased cell preferentially over expression of the plurality of polypeptides or nucleic acid biomarker sequences in non-diseased cells in a subject such that a relative ratio of the plurality of polypeptides or nucleic acid biomarker sequences expressed in the diseased cell over the non-diseased cells is greater than 1.0. In some embodiments, each of said promoters may induce expression of said plurality of polypeptides or nucleic acid biomarker sequences in a diseased cell preferentially over expression of said plurality of polypeptides or nucleic acid biomarker sequences in non-diseased cells in said subject such that a relative ratio of said plurality of polypeptides or nucleic acid biomarker sequences expressed in said diseased cell over said non-diseased cells is greater than 1.0.

In some aspects, the present disclosure provides methods for generating a profile of a subject's disease. The methods comprise contacting one or more cells of said subject with a plurality of genetic constructions, wherein the plurality of genetic constructs comprises a plurality of disease-activated promoters respectively operably linked to a plurality of barcode molecules and the disease-activated promoter drives expression of the corresponding barcode molecule in a cell affected by the disease. Further, the methods comprise quantifying expression levels of the plurality of barcode molecules to generate the profile. In some embodiments, the methods further comprise detecting a disease based on the generated profile, which comprises expression levels of the barcode molecules corresponding to the plurality of disease-activated promoters using a classifier (machine learning or classifier algorithm) to detect the disease or the absence thereof.

By ascribing an exclusive label to a unique member within a larger group, barcodes afford the opportunity to identify and quantify that member (e.g. expression of a reporter under the control of a particular cancer specific promoter) within the context of a larger and more complex mixture of many members (e.g. multiple promoter-reporter constructs expressed within the same cell), as well as offering the opportunity to isolate a single member from the complex mixture. For instance, in the case of barcodes based on nucleic acids, hybridization of barcodes based on base pairing complementarity may be used to capture and isolate or otherwise reduce the complexity of a mixture by said capture event. For barcodes based on peptides, unique features including immunocapture or interactions of ligands and receptors may be used to capture and isolate or otherwise reduce the complexity of a mixture by said capture event.

The methods further comprise detecting said disease or absence thereof with an AUC (area under the curve) value of at least 55%, 60%, 65%, 70%, 75%, 80%, 85%, 90%, 95%, 96%, 97%, 98%, 99% or more. The methods further comprise detecting said disease or absence thereof with a specificity of at least 55%, 60%, 65%, 70%, 75%, 80%, 85%, 90%, 95%, 96%, 97%, 98%, 99% or more. The methods further comprise detecting said disease or absence thereof with a sensitivity of at least 55%, 60%, 65%, 70%, 75%, 80%, 85%, 90%, 95%, 96%, 97%, 98%, 99% or more.

After quantifying the barcode molecule levels in a first-round screening and determining a particular disease, for example a particular cancer (i.e., breast cancer), or a cancer within a particular tissue origin, a plurality of genetic constructs comprising the particular cancer (i.e., breast cancer)-activated promoters may be used ex-vivo or in vivo to transfect one or more cells of the same subject that has gone through the first round of screening. The following rounds (e.g., more than two, three, four, five, six, seven, eight, nine, ten or more) may serve to increase the accuracy of disease identification (including tissue origin identification).

In some embodiments, the methods of contacting one or more cells can be performed ex-vivo. In some embodiments, the methods of contacting one or more cells can be performed in-vivo.

In some embodiments, the at least one vector may be a single vector containing all the elements above. In some embodiments, the at least one vector may be a plurality of vectors each comprising a distinct promoter. In some embodiments, each of the plurality of vectors each comprising a distinct promoter also comprise a distinct polypeptide or nucleic acid biomarker sequence. When the at least one vector is a plurality of vectors each comprising a distinct promoter, the vectors may be administered within at least 8, at least 12, at least 16, at least 24, at least 32, at least 48, at least 56, or at least 72 hours of each other. When the at most one vector is a plurality of vectors each comprising a distinct promoter, the vectors may be administered within at most 8, at most 12, at most 16, at most 24, at most 32, at most 48, at most 56, or at most 72 hours of each other.

In some embodiments, the distinct promoter is a disease-activated promoter. In some embodiments, the disease-activated promoter is a cancer-activated promoter as disclosed herein. In some embodiments, the plurality of cancer-activated promoters comprises promoters activated in a plurality of cancers within different tissue origins. For example, the plurality of cancer-activated promoters comprises a first promoter activated in a lung cancer within lung tissue, a second promoter activated in liver cancer within liver tissue, a third promoter activated in breast cancer within breast tissue, a fourth promoter activated in pancreatic cancer within pancreas tissue, etc. In some embodiments, the plurality of cancer-specific promoters are activated in a plurality (e.g. two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-five or more, or thirty or more) of different tissue origins.

In some embodiments, the plurality of cancer-specific promoters comprises a first promoter that produces a strong signal in detection after being activated in one or more different types of cancers. For example, promoter MMP11 produces strong signals in detection after being activated in cancers, such as BLCA, BRCA, CESE, CHOL, COAD, ESCA, HNSC, LUAD, LUSC, PAAD, OV, READ, STAD, SARC, etc. In some embodiments, the plurality of cancer-specific promoters comprises a second promoter that produces a low background signal. For example, promoter MMP13 produces almost non-existing signal in detection in cancer types that MMP13 is not activated. In some embodiments, the plurality of cancer-specific promoters comprises a third promoter that has a high signal-to-background signal ratio. For example, promoter MMP12 produces a sufficient amount of signal in detection after being activated in particular cancer types that MMP12 can be activated, and at the same time, produces low signal in detection in particular cancer types that MMP12 are not designed to be activated. In certain embodiments, the plurality of cancer-specific promoters comprise all three types of promoter as disclosed herein. In certain embodiments, the plurality of cancer-specific promoters comprises one or more promoters with high signals in detection and one or more promoters with low background signals in detection. In certain embodiments, plurality of cancer-specific promoters comprises one or more promoters with high signals in detection and one or more promoters with high signal-to-background signal ratio. In certain embodiments, the plurality of cancer-specific promoters comprises one or more promoters with low background signals in detection and one or more promoters with high signal-to-background signal ratio.

In certain embodiments, the plurality of disease-activated promoters comprises a plurality of cancer-activated promoters that are selective for and activated in a selected group of tissue origin. For example, the plurality of disease-activated promoters comprises one or more promoters that are selective for and activated in multiple tissues, such as breast, lung, liver, etc. In some embodiments, the plurality of disease-activated promoters comprises a plurality of cancer-activated promoters that are selective for and activated in the same tissue origin. For instances, the plurality of disease-activated promoters comprises several different promoters and each of them is selective for and activated in the same tissue, such as breast tissue.

In certain embodiments, the plurality of disease-activated promoters comprises a plurality of cancer-activated promoters activated in a plurality of different molecular subtypes of a cancer respectively within the same tissue origin. For example, the plurality of disease-activated promoters comprises a plurality of disease-specific promoters activated in luminal A breast cancer, luminal B breast cancer, triple-negative/basal-like breast cancer, HER2-enriched breast cancer, and/or normal-like breast cancer. The plurality of disease-activated promoters comprises a plurality of disease-specific promoters activated in CMS1, CMS2, CMS3, and/or CMS4 colorectal cancer. In certain embodiments, the plurality of disease-activated promoters comprises a plurality of cancer-activated promoters activated in one molecular subtype of a cancer within a tissue origin. For example, the plurality of disease-activated promoters comprises more than one different promoters that are activated in luminal A breast cancer. In certain embodiments, the plurality of disease-activated promoters comprises two or more different cancer-activated promoters activated in one stage of a cancer within a tissue origin. In certain embodiments, the plurality of disease-activated promoters comprises disease-specific promoters that are activated in different stages of a cancer with a molecular subtype within a tissue origin.

In some cases, the disease is cancer, an autoimmune disease (e.g. a T-cell or lymphocyte with self-directed activity, or a normal cell damaged by autoimmunity), or a neurodegenerative disease (e.g. a cell bearing a toxic amyloid or proximal to a toxic amyloid). Exemplary cancers include, but are not limited to, carcinomas, sarcomas, lymphomas, leukemias, and adenomas. Carcinomas may arise from cells that cover internal and external parts of the body such as the lung, breast, and colon. Sarcomas may arise from cells that are located in bone, cartilage, fat, connective tissue, muscle, and other supportive tissues. Lymphomas may arise in the lymph nodes and immune system tissues. Leukemias may arise in the bone marrow and accumulate in the bloodstream. Adenomas may arise in the thyroid, the pituitary gland, the adrenal gland, and other glandular tissues. Specific exemplary examples of cancer types include suitable for detection with the methods according to the disclosure include acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, Wilms tumor, Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, Uveal Melanoma, lip melanoma, spindle cell carcinoma, liposarcoma, nasal sarcoma, mammary adenocarcinoma, insulinoma, osteosarcoma, mast cell tumors, hemangiosarcoma, non-small cell lung carcinoma (NSCLC), marginal lymphoma, malignant melanoma, or chronic lymphocytic leukemia.

In some cases, the disease may be a viral infection. Exemplary viral infections include, but are not limited to, those caused by HIV, hepatitis C virus, hepatitis B virus, hepatitis D virus, herpesviruses, Epstein-Barr virus, cytomegalovirus, and human T-lymphotropic virus type III.

In some cases, the disease may be an autoimmune disease. Exemplary autoimmune diseases include, but are not limited to, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

In some cases, the disease may be a neurodegenerative disease. Neurodegenerative diseases include, but are not limited to, Multiple sclerosis (MS), Alzheimer's disease (AD), Parkinson's disease (PD), and Amyotrophic lateral sclerosis (ALS), or neurodegeneration due to infection by viruses of families Herpesviridae, Polyomaviridae, Bornaviridae, Orthomyxoviridae, Paramyxoviridae, Rhabdoviridae, Flaviviridae, Picornaviridae, or Retroviridae (see Zhou et al. Virol J. 2013; 10: 172).

In some cases, the disease may be a viral infection. Exemplary viral infections include, but are not limited to, those caused by HIV, hepatitis C virus, hepatitis B virus, hepatitis D virus, herpesviruses, Epstein-Barr virus, cytomegalovirus, and human T-lymphotropic virus type III.

In some cases, at least one of the plurality of polypeptides or nucleic acid biomarker sequences may comprise a sequence of a polypeptide detectable by non-invasive imaging. Such non-invasive imagine methods include MRI imaging, PET imaging, SPECT imaging, photoacoustic imaging, and bioluminescent imaging. Synthetic biomarker polypeptides detectable by MRI imaging include polypeptide contrast agents, such as ferritin (or mutants thereof, such as *Pyrococcus* furiousus ferritin mutants L55P, F57S, or F123S), or lanthanide-binding proteins (or engineered fusions thereof, such as the LBT-ubiquitin fusions described in Daughtry et al. ChemBioChem 2012, 13, 2567-2574). Synthetic biomarkers detectable by PET or SPECT imaging include the human sodium iodide symporter (e.g. in conjunction with administration of PET-active iodine/iodide isotopes, see e.g. Penheiter et al. Curr Gene Ther. 2012 February; 12(1): 33-47), HSV-tk or mutants thereof such as HSV-sr39tk (e.g. in conjunction with administration of positron-labeled acycloguanosine or pyrimidine analog PET reporters such as [18F]FHBG, see Yaghoubi S S et al. Nat Protoc. 2006; 1(6):3069-75), and the dopamine D2 receptor or mutants thereof such as D2R80A or D2R194A (e.g. in conjunction with administration of positron-labeled D2 binders such as 3-(2'[18F]-fluoroethyl)-spiperone). Synthetic biomarkers detectable by photoacoustic imaging include the pigment-producing enzymes such as 0-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). Synthetic biomarkers detectable by bioluminescent imaging include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396 (2010): 290-297). In some embodiments, the synthetic biomarker may be a contrast agent, an enzyme producing a detectable molecule, or a transporter driving accumulation of a detectable molecule. The synthetic biomarker may be measured in situ within subject's body. The synthetic biomarker may be selected from the group consisting of a photoacoustic reporter, a bioluminescent reporter, an autofluorescent reporter, a chemiluminescent reporter, a luminescent reporter, or a colorimetric reporter, or any combination thereof.

In some cases, at least one of the plurality of polypeptides or nucleic acid biomarker sequences may encode polypeptides or nucleic acids detectable in a biological sample from the subject. When the biomarker is a polypeptide, the polypeptide may comprise an N-terminal secretion signal sequence (e.g. the N-terminal signal peptide from CD33 or CD8a). Exemplary polypeptide biomarkers include, but are not limited to, photoacoustic reporters, bioluminescent reporters, autofluorescent reporters, chemiluminescent reporters, luminescent reporters, colorimetric reporters, and any combination thereof. Autofluorescent reporters include GFP, mCherry, or derivatives thereof. Colorimetric reporters include pigment-producing enzymes such as 0-galactosidase (e.g. in combination with administration of X-gal), and tyrosinase. Bioluminescent, chemiluminescent or luminescent reporters include luciferases (e.g. in combination with administration of coelenterazines described herein), including *Gaussia* luciferases, *Renilla* luciferases, and Photinus luciferases (e.g. including the engineered Ppy RE8 and RE9 versions described in Branchini et al. Anal. Biochem. 396 (2010): 290-297). Reporters detectable by photoacoustic imaging include the pigment-producing enzymes such as (3-galactosidase (e.g. in combination with administration of X-gal) and tyrosinase, autofluorescent proteins (e.g. GFP, mCherry, or derivatives thereof), non-fluorescent GFP-like chromoproteins (e.g. aeCP597 and cjBlue and derivatives thereof), bacteriophytochrome-based near-infrared fluorescent proteins (e.g. IFP1.4, Wi-Phy, IFP1.4rev, IFP2.0, iRFP713, iRFP720, iRFP713/V256C, iRFP682, iRFP702, iRFP670, mIFP, iBlueberry, GAF-FP, BphP1-FP/C20S, or AphB variants), and reversibly photoswitchable proteins (e.g. Dronpa, Dronpa-M159T, and BphP1 or variants thereof). The synthetic biomarker may be measured in situ within subject's body. The synthetic biomarker may be selected from the group consisting of a photoacoustic reporter, a bioluminescent reporter, an autofluorescent reporter, a chemiluminescent reporter, a luminescent reporter, or a colorimetric reporter, or any combination thereof.

In some cases, the nucleic acid biomarker is e.g. a natural or engineered miRNA, an RNA hairpin, RNA aptamers or barcoded versions thereof. The detectable nucleic acid biomarker may be a ribozyme, a self-splicing intron, an RNA hairpin, a microRNA, or barcoded versions thereof, or other types of quantifiable RNA. The quantifiable nucleic acid may comprise a unique sequence detectable by quantitative PCR or hybridization-based techniques. When the nucleic acid is an miRNA, the miRNA may be detected e.g. by standard library generation techniques such as degenerate primer-based annealing and ligation, poly(A) polymerase labeling followed by RT or ligation, or sequential adapter ligation coupled to q-PCR, sequencing, or an electrophoretic detection method. When the biomarker is a polypeptide, the polypeptide may comprise an N-terminal secretion signal sequence (e.g. the N-terminal signal peptide from CD33 or CD8a).

When the nucleic acid is an engineered miRNA, the nucleic acid may be the Sec-miR or miR-neg constructs described in Ronald et al. (Ronald et al. PLoS ONE 11(7): e0159369.) Such constructs comprise: (a) a coding sequence not expressed endogenously and not having any known vertebrate target (e.g. Sec-miR 5'-AAAUGUA-CUGCGCGUGGAGAC-3', SEQ ID NO: 6); (b) miR backbone sequences providing processing of pre-miRNA to mature miRNA flanking the coding sequence (e.g. miR-155 or miR-130 backbone sequences); and (c) an EXOmotif enhancing loading into exosomes (e.g. GGAG). Such miRNA constructs may be expressed in e.g. the 3'-UTR of a gene encoding a reporter polypeptide, or from the 3'-UTR of a gene encoding a suitably non-toxic protein (e.g. an endogenous structural protein such as actin or tubulin, or a highly expressed protein such as ubiquitin). In some embodiments, multiple copies (e.g. at least 2, at least 4) of the engineered miRNA may be provided in tandem.

In certain embodiments, the barcode molecule may uniquely identify a disease-specific promoter of said genetic construct. The barcode molecule may comprise a nucleotide sequence or a peptide sequence. In certain embodiments, the barcode molecule may comprise a unique DNA or RNA. When the barcode molecule comprises RNA, the RNA is a barcode processed from a miRNA scaffold. In certain embodiments, the miRNA scaffold comprises 5', 3', and loop regions derived said miRNA scaffold, and stem regions comprising said barcode. In certain embodiments, the miRNA may be an engineered miRNA as described herein. When the barcode comprises a peptide sequence, the barcode comprises an enzyme reporter. The peptide sequences may comprise an N-terminal secretion signal sequence as described herein. Further, the peptide sequences may be detectable by non-invasive imaging as described herein.

In some cases, the at least one vector may be any of the vectors described herein. In some embodiments, the genetic construct comprises a non-viral vector. In some embodiments, the non-viral vector is a nanoplasmid. In some embodiments, the genetic construct comprises a replication-incompetent recombinant virion or an isolated inverted terminal repeat (ITRs) derived therefrom. In some embodiments, the virion may be a lentiviral, adeno-associated viral, adenoviral, or gamma-retroviral virion. In some embodiments, the virion is derived from a virus with primarily episomal genome maintenance within infected cells. In some embodiments, the replication-incompetent virion is a recombinant adenovirus vector. In some embodiments, the AAV is serotype 1, 2, 3, 4, 5, 6, 8, 9, AdS, Ad-RGD, or Ad-19a164, or a pseudotyped variant thereof.

In some cases, the plurality of different promoters operably linked to a plurality of different nucleic acid sequences may comprise at least one promoter. The plurality of different promoters operably linked to a plurality of different nucleic acid sequences may comprise at least 2, at least 3, at least 4, at least 5, at least 6, at least 7, at least 8, at least 9, at least 10, at least 11, at least 12, at least 13, at least 14, or at least 15 promoters. The plurality of different promoters operably linked to a plurality of different nucleic acid sequences may comprise at most 2, at most 3, at most 4, at most 5, at most 6, at most 7, at most 8, at most 9, at most 10, at most 11, at most 12, at most 13, at most 14, or at most 15 promoters.

In some cases, the plurality of different promoters operably linked to a plurality of different nucleic acid sequences may comprise at least one promoter from Table 2. The plurality of different promoters operably linked to a plurality of different nucleic acid sequences may comprise at least 2, at least 3, at least 4, at least 5, at least 6, at least 7, at least 8, at least 9, at least 10, at least 11, at least 12, at least 13, at least 14, or at least 15 promoters from Table 2. The plurality of different promoters operably linked to a plurality of different nucleic acid sequences may comprise at most 2, at most 3, at most 4, at most 5, at most 6, at most 7, at most 8, at most 9, at most 10, at most 11, at most 12, at most 13, at most 14, or at most 15 promoters from Table 2.

In some aspects, the present disclosure provides for a method for detecting a disease in a subject, comprising: (a) administering to a subject a composition comprising the at least one vector above (e.g. comprising a plurality of different promoters operably linked to a plurality of different nucleic acid sequences, wherein the promoters drive expression of the plurality of nucleic acid sequences in a cell to yield a plurality of polypeptides or nucleic acid biomarker sequences, wherein the promoters induce expression of the plurality of polypeptides or nucleic acid biomarker sequences in a diseased cell preferentially over expression of the plurality of polypeptides or nucleic acid biomarker sequences in non-diseased cells in a subject such that a relative ratio of the plurality of polypeptides or nucleic acid biomarker sequences expressed in the diseased cell over the non-diseased cells is greater than 1.0); (b) detecting said plurality of polypeptides or nucleic acid biomarker sequences to obtain an expression profile; and (c) detecting said diseased cell based said expression profile, thereby detecting said disease.

In some cases, the method for detecting the disease in the subject comprises detecting said plurality of polypeptides or nucleic acid biomarker sequences from a sample from the subject. In some cases, the method may comprise isolating a biological sample from the subject. The biological sample may be a sample collected by a non-invasive method from the subject. Exemplary non-invasive samples include, but are not limited to, samples comprised of naturally shed bodily substances or non-destructive scraping of externally accessible tissues, such as saliva, sputum, sweat, urine, stool, semen, mucus, cervicovaginal secretions, breast milk, rheum, tears, and cheek epithelial swabs. The biological sample may be a sample collected by a minimally-invasive method from the subject. Exemplary minimally-invasive samples include, but are not limited to, blood samples or fractions thereof (e.g. obtained by venipuncture or capillary tube), pleural fluid samples (e.g. obtained by thoracentesis), amniotic fluid samples (e.g. obtained by amniocentesis), and gastric fluid samples (e.g. obtained by gastric lavage). The biological sample may be a sample obtained by biopsy, such as a skin biopsy sample (e.g. obtained by punch, shave, saucerization, wedge, incisional, or excisional biopsy), a bone marrow sample (e.g. obtained by aspiration biopsy), a lymph node or breast biopsy (e.g. obtained by fine-needle aspiration, core needle biopsy, vacuum assisted biopsy, or image-guided biopsy), a surgical biopsy sample (e.g. of an internal organ obtained by excisional or incisional biopsy), or a mouth, GI-tract, lung, bladder, or urinary tract biopsy (e.g. obtained by endoscopy).

In some cases, the biological sample may be obtained a certain period of time after administration of the composition comprising the at least one vector. The biological sample may be obtained at least about 15 minutes, at least about 30 minutes, at least about 1 hour, at least about 2 hours, at least about 4 hours, at least about 8 hours, at least about 16 hours, at least about 24 hours, at least about 36 hours, at least about 48 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 1 month, at least about 2 months, at least about 3 months, at least about 4 months, at least about 5 months, or at least about 6 months after administration of the composition comprising the at least one vector. The biological sample may be obtained at most about 15 minutes, at most about 30 minutes, at most about 1 hour, at most about 2 hours, at most about 4 hours, at most about 8 hours, at most about 16 hours, at most about 24 hours, at most about 36 hours, at most about 48 hours, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 1 month, at most about 2 months, at most about 3 months, at most about 4 months, at most about 5 months, or at most about 6 months after administration of the composition comprising the at least one vector. In some embodiments, the biological sample may be obtained, and any biomarker detection protocols performed multiple times after administration of the composition comprising the at least one vector (e.g. to monitor synthetic biomarker levels over time). The biological sample may be obtained at least about 1, 2, 3, 4, 5, 6, 7, 8, 9, 10, 15, 20, or 25 times after administration of the composition comprising the at least one vector. The biological sample may be obtained weekly or monthly after administration of the composition comprising the at least one vector.

In some cases, the composition comprising the at least one vector may be administered intravenously, subcutaneously, intraventricularly, intrathecally, intracerebroventricularly, transdermally, intramuscularly, orally, by inhalation, nasally, rectally, intratumorally, or proxi-tumorally to the subject. Proxi-tumorally may denote administration to the tissue within proximity of a tumor, or administration into a region that would be predicted to be accessible to the tumor via the lymphatic system (e.g. an adjoining lymph node). Intratumoral or proxi-tumoral approaches may involve the use of additional imaging techniques such as e.g. endoscopic ultrasonography (see e.g. Shirley et al. Gastroenterol Res Pract. 2013; 2013: 207129) or via a brochioscope (see e.g. Rojas-Solano et al. J Bronchology Intery Pulmonol. 2018 July; 25(3): 168-175). In some embodiments, the composition comprising the at least one vector may be administered into at least one of the cervical, epitrochlear, supraclavicular, cervical, axillary, mediastinal, supratrochlear, mesenteric, inguinal, femoral, or popliteal lymph nodes. In some cases, lymph-node based administration may serve as a method of centralized local delivery to a tissue region.

In some cases, the composition comprising the at least one vector may comprise a transfection agent as described herein.

In some cases, the composition comprising the at least one vector may comprise a pharmaceutically acceptable carrier, as described herein.

In some cases, the method for detecting the disease in the subject may comprise applying a machine learning or classifier algorithm to said expression profile, wherein the machine learning or classifier algorithm is configured to distinguish between an expression profile indicative of a diseased cell from an expression profile indicative of a non-diseased cell.

Machine learning or classifier algorithms refer generally to supervised learning and classification approaches executed by a computer system. In supervised learning approaches, a group of samples from two or more groups (e.g. diseased and non-diseased) are analyzed with a statistical classification method. Biomarker presence/absence/level data can be used as a classifier that differentiates between the two or more groups. A new sample can then be analyzed so that the classifier can associate the new sample with one of the two or more groups. Commonly used supervised classifiers/classifier algorithms include without limitation the neural network (multi-layer perceptron), support vector machines, k-nearest neighbors, Gaussian mixture model, Gaussian, naive Bayes, decision tree and radial basis function (RBF) classifiers. Linear classification methods include Fisher's linear discriminant, logistic regression, naive Bayes classifier, perceptron, and support vector machines (SVMs). Other classifiers/classifier algorithms for use with the invention include quadratic classifiers, k-nearest neighbor, boosting, decision trees, random forests, neural networks, pattern recognition, Bayesian networks and Hidden Markov models.

Classification using supervised methods is generally performed by the following methodology:

In order to solve a given problem of supervised learning (e.g. learning to recognize handwriting) one has to consider various steps:

1. Gather a training set. These can include, for example, samples that are from a food or environment contaminated or not contaminated with a particular microbe, samples that are contaminated with different serotypes of the same microbe, samples that are or are not contaminated with a combination of different species and serotypes of microbes, etc. The training samples are used to "train" the classifier.

2. Determine the input "feature" representation of the learned function. The accuracy of the learned function depends on how the input object is represented. Typically, the input object is transformed into a feature vector, which contains a number of features that are descriptive of the object. The number of features should not be too large, because of the curse of dimensionality; but should be large enough to accurately predict the output. The features might include a set of bacterial species or serotypes present in a food or environmental sample derived as described herein.

3. Determine the structure of the learned function and corresponding learning algorithm. A learning algorithm is chosen, e.g., artificial neural networks, decision trees, Bayes classifiers or support vector machines. The learning algorithm is used to build the classifier.

4. Build the classifier (e.g. classification model). The learning algorithm is run on the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set.

Once the machine learning classifier (e.g. classification model) is determined as described above, it can be used to classify a sample, e.g., a sample from a subject that has received the composition comprising the at least one vector above.

In some cases, the relative pattern of biomarker or barcode molecule expression from the plurality of vectors provides a "unique fingerprint" corresponding to one or more different types of cancers In some cases, a method by which artificial intelligence and machine learning can be applied to the patterns of biomarker expression in order to develop a predictive series of plurality of vectors for accurate cancer detection.

In some cases, the method comprises detecting the polypeptide or nucleic acid sequence encoded by the at least one vector. The detecting may also comprise an immunoassay. Immunoassays include those described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. Immunoassays include various sandwich, competitive, or non-competitive assay formats, which generate a signal that is related to the presence or amount of a protein analyte of interest. Any suitable immunoassay may be utilized, for example, lateral flow, enzyme-linked immunoassays (ELISA), radioimmunoassays (RIAs), competitive binding assays, and the like. When the polypeptide is a reporter polypeptide, the detecting may comprise a photoacoustic assay, a bioluminescence assay, a fluorescence assay, a chemiluminescent assay, a colorimetric assay, or any combination thereof.

The method of detection may comprise sequencing. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, and primer walking.

The detection may comprise a "real time amplification" method also known as quantitative PCR (qPCR) or Taqman (see, e.g., U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye. The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified.

In some embodiments, for qPCR or Taqman detection, an RT-PCR step may be first performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In some embodiments, qPCR or Taqman may be used immediately following a reverse-transcriptase reaction performed on isolated cellular mRNA; this variety serves to quantitate the levels of individual mRNAs during qPCR.

In some embodiments, for qPCR or Taqman detection or RNA sequencing, a "pre-amplification" step may be first performed on cDNA transcribed from cellular RNA. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof. The pre-amplification may be either general or targeted in the same way as the reverse-transcription reaction described above.

Methods of Detecting and/or Treating Disease using Activatable Molecules

In some aspects, the present disclosure provides for a method of detecting a condition in a subject comprising administering a genetic construct comprising a promoter operably linked to a sequence encoding an activatable molecule, wherein the disease-activated prompter drives expression of the activatable molecule in a cell affected by the disease.

Genetic constructs can include any of the constructs described herein, including RNA, single-stranded DNA, double-stranded DNA, or any of the vectors described herein. In some embodiments, the genetic construct comprises a non-viral vector. In some embodiments, the non-viral vector is a nanoplasmid. In some embodiments, the genetic construct comprises a replication-incompetent recombinant virion or an isolated inverted terminal repeat (ITRs) derived therefrom. In some embodiments, the virion may be a lentiviral, adeno-associated viral, adenoviral, or gamma-retroviral virion. In some embodiments, the virion is derived from a virus with primarily episomal genome maintenance within infected cells. In some embodiments, the replication-incompetent virion is a recombinant adenovirus vector. In some embodiments, the AAV is serotype 1, 2, 3, 4, 5, 6, 8, 9, AdS, Ad-RGD, or Ad-19a/64, or a pseudotyped variant thereof.

In some embodiments the promoter used as part of the method for detecting a condition in a subject is a disease-activated promoter. Suitable promoters include natural pan-tumor specific promoters, natural tissue specific promoters, natural disease-specific/disease-activated promoters, natural constitutive promoters, and any composites thereof. The promoter may be a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-GlcNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1

(SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member Cl (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

In some embodiments, when the promoter (e.g. disease-activated promoter) is activated, the expressed activatable molecule is converted into a derivative barcode molecule by an enzyme endogenous to the cell affected by the disease. Accordingly, the activatable molecule can comprise a molecule (e.g. polynucleotide, polypeptide, small molecule, or combination thereof) which is converted to an active (or detectable) barcode form by the action of an enzyme present in the cell affected by the disease. In some embodiments, the enzyme present in the cell affected by the disease is a protease expressed by the cell. In some embodiments, the enzyme is an enzyme naturally present in the genome of the cell. In some embodiments, the enzyme is an enzyme exogenous to the genome of the cell. In some embodiments, the enzyme is an enzyme introduced to the genome of a cell. In some embodiments, the enzyme introduced to the genome of the cell is a viral enzyme or protease (e.g. in the case of viral diseases or viral-induced cancers).

In some embodiments, the activatable molecule comprises a masking moiety fused to a detectable moiety (or barcode) by a release segment cleavable by a protease. In some embodiments, the activatable molecule is oriented from N- to C-terminus in the order (MM)-(CM)-(DM). In some embodiments, the activatable molecule is oriented from N- to C-terminus in the order (DM)-(CM)-(MM).

The cleavable moiety (CM) of the activatable molecule may include an amino acid sequence that can serve as a substrate for a protease. Optionally, the CM comprises a cysteine-cysteine pair capable of forming a disulfide bond, which can be cleaved by action of a reducing agent. The CM is positioned in the activatable molecule such that when the CM is cleaved by a cleaving agent (e.g., a protease substrate of a CM is cleaved by the protease and/or the cysteine-cysteine disulfide bond is disrupted via reduction by exposure to a reducing agent), resulting in a cleaved state, the detectable moiety or barcode is detectable or activated. It should be noted that the amino acid sequence of the CM may overlap with or be included within the MM, such that all or a portion of the CM facilitates "masking" of the detectable moiety or barcode when the activatable molecule is in the uncleaved conformation. The CM may be selected based on a protease that is localized in cells to be detected as characteristic of a disease. A variety of different conditions are known in which are identifiable by a protease presence in a cell. For example, the disease can be cancer, particularly a solid tumor. There are many reports in the literature of increased levels of proteases having known substrates in a number of cancers, e.g., solid tumors. See, e.g., La Rocca et al, (2004) British J. of Cancer 90(7): 1414-1421. As such, where a cancerous target is to be detected, a suitable CM will be one which comprises a peptide substrate that is cleavable by a protease that is present at the cancerous site, particularly that is present at elevated levels at the cancerous site as compared to non-cancerous tissues. In some embodiments, the cellular protease that cleaves the cleavable moiety is an extracellular protease. In some embodiments, the cellular protease that cleaves the cleavable moiety is an intracellular protease. In some cases, an intracellular protease is a cancer-associated intracellular protease. Cancer-associated intracellular proteases can include cathepsins (e.g. cathepsin B, cathepsin C, or any combination thereof), caspases (e.g. caspase-2, caspase-8, caspase-9, caspase-10, or any combination thereof), or serpin. In some cases, an extracellular protease is a cancer-associated extracellular protease. Cancer-associated extracellular proteases include urokinase plasminogen activator (uPA), matrix metalloproteinases (e.g. MMP1, MMP2, MMP3, MMP7, MMP8, MMP8, MMP10, MMP11, MMP12, MMP13, MMP14, MMP15, MMP16, MMP17, MMP19, MMP20, MMP24, MMP25, MMP28, or any combination thereof), or an ADAM (A disintegrin and metalloproteases) protein (e.g. ADAM2, ADAM7, ADAMS, ADAMS, ADAM10, ADAM11, ADAM12, ADAM15, ADAM17, ADAM18, ADAM19, ADAM22, ADAM23, ADAM28, ADAM33, or any combination thereof). Example cleavable moieties capable of being cleaved by proteases described herein can be found e.g. in US20190211089A1, US20180303952A1, or US20190211089A1, which are incorporated for that purpose herein. In some cases, the disease is a viral disease. Example proteases serving as markers of viral diseases that can cleave cleavable moieties according to the disclosure are described e.g. in Pethe et al. Proc Natl Acad Sci USA. 2019 Jan. 2; 116(1):168-176, which is incorporated by reference herein. Example proteases serving as markers of neurological diseases that can cleave cleavable moieties according to the disclosure are described e.g. Gervais et al. Cell. 1999 Apr. 30; 97(3):395-406, which is incorporated by reference herein.

The detectable moiety (or barcode) can comprise any of the detectable moieties or barcodes described herein. In some embodiments, the detectable moiety is an antibody or an antigen-binding fragment thereof. The antibody or antigen-binding fragment thereof can comprise previously-described binding elements against well-established targets (e.g. HER2, HER3, FGFR2, EPHB2, EGFR). Alternatively or additionally, the antibody or antigen-binding fragment thereof can comprise anti-epitope tag binding elements such as anti-V5, anti-c-myc, anti-HA, anti-HIS, anti-FLAG, anti-AU1, anti-AU5, anti-Myc, anti-OLLAS, anti-T7, anti-VSV-G, anti E-Tag, anti-S-Tag, anti-Avi, anti-HSV, anti-KT3, anti-TK15, anti-strep-tag-II, anti-MBP, anti-GFP, or any combination thereof.

The masking moiety (MM) of an activatable molecule generally refers to an amino acid sequence positioned in the activatable such that in an uncleaved state, the MM interferes with activity or detection of the detectable moiety or barcode. In some embodiments, a masking moiety is a mimotope cognate of a detectable antibody or an inhibitory antibody. For example, the detectable moiety or barcode may comprise an anti-epitope tag antibody and the masking moiety may comprise an epitope tag, such that the binding site of the antibody is blocked by the tag as long as the cleavable moiety is intact. Alternatively or additionally, the masking moiety may be a peptide sequence corresponding to an epitope of an anti-target antibody, wherein the detectable moiety is the anti-target antibody. Alternatively or additionally, the masking moiety may be a synthetic mimotope peptide sequence with greater or lesser affinity than a natural polypeptide sequence of an anti-target antibody, wherein the detectable moiety is the anti-target antibody.

In some embodiments, the method of detecting a condition in a subject further comprises assaying the barcode molecule or detectable moiety thereby detecting the disease. Suitable assays for detecting detectable moieties or barcodes include any of the assay methodologies described herein, including but not limited to ELISA, sandwich-ELISA, laminar flow assay, immunohistochemical assay, or immunofluorescent assay.

In some aspects, the present disclosure provides for a method for identifying a location of a diseased tissue in a subject, comprising: delivering a genetic construct comprising a ubiquitous promoter operably linked to a sequence encoding an activatable molecule to a subject; wherein the activatable molecule is configured to be converted to a barcode molecule by an enzyme expressed by the diseased tissue.

A ubiquitous promoter may comprise any promoter described as promoting exogenous gene expression in a variety of tissues. In some embodiments, a ubiquitous promoter comprises a cytomegalovirus (CMV) immediate-early enhancer, a chicken beta-actin (CAG) promoter, an elongation factor 1α (EF1α) promoter, a Ubiquitin C (UbC) promoter, or a CMV promoter.

A genetic construct can comprise any of the genetic constructs or vectors described herein.

Activatable molecules can include any of the activatable molecules described herein (e.g. comprising detectable, cleavable, and/or masking moieties as described herein).

Diseases and corresponding tissues can include any of the diseases and tissues described herein.

In some aspects, the present disclosure provides for a method for treating a subject having a disease or at risk of having the disease, comprising: administering a genetic construct comprising an activatable molecule operably linked to a disease-activated promoter to the subject; wherein the activatable molecule is configured to be convert to a therapeutic molecule by an enzyme expressed by a tissue associated with the disease.

In some embodiments, the genetic construct comprises any of the genetic constructs described herein and is administered systemically (e.g. parenteral administration such as injection, infusion, or implantation). In some embodiments, the genetic construct comprises any of the genetic constructs described herein and is administered in a tissue-specific manner (e.g. topically, intrathecally, intramuscularly)

Activatable molecules can include any of the activatable molecules described herein (e.g. comprising detectable, cleavable, and/or masking moieties as described herein). Therapeutic molecules may comprise a suitable antibody or antigen-binding fragment thereof against a cancer-associated cell marker (e.g. HER2, HER3, CD20, CD52, EGFR, VEGF, EPCAM, CTLA-4, CD30, or a combination thereof), a protein toxin (e.g. anthrax toxin as described in e.g. Weidle et al. Cancer Genomics Proteomics. March-April 2014; 11(2):67-79, which is incorporated by reference herein) or a small-molecule toxin (see e.g. Giang et al. AAPS J. 2014 September; 16(5): 899-913, which is incorporated by reference herein).

Diseases and corresponding tissues can include any of the diseases and tissues described herein.

In some aspects, the present disclosure provides for a method for preventing a disease in a subject in need thereof, comprising administering a genetic construct comprising a disease-activated promoter operably linked to a sequence encoding an activatable therapeutic molecule to the subject, wherein the disease-activated promoter drives expression of the activatable molecule in a tissue affected by the disease; wherein the activatable therapeutic molecule is converted to a therapeutic molecule by an enzyme endogenous to a cell affected by the disease upon disease onset.

A genetic construct can comprise any of the genetic constructs or vectors described herein.

In some embodiments, the genetic construct is administered at varying times with respect to knowledge about the disease. In some embodiments, the genetic construct is administered prior to onset of symptoms of the disease. In some embodiments, the genetic construct is administered after performing a diagnostic test identifying risk for onset of the disease. Of particular interest are diseases for which high-accuracy tests for risk are known but for which the exact onset is difficult to predict. In some embodiments, the disease that is prevented is wet age-related macular degeneration (wet AMD), cancer, breast cancer, or ovarian cancer. In some embodiments, the diagnostic test to identify the disease that is prevented is a genotyping test to identify a germline apolipoprotein E (APOE) E2 allele, a germline BRCA1 mutation, or a germline BRCA2 mutation. Alternatively or additionally, the genetic construct is administered after a risk factor for a later disease, such as chemotherapy or radiation treatment. In some embodiments, the subject has been treated for cancer, breast cancer, or ovarian cancer prior to administration of the genetic construct.

Activatable molecules can include any of the activatable molecules described herein (e.g. comprising detectable, cleavable, and/or masking moieties as described herein). Therapeutic molecules may include antibodies or antigen-binding fragments thereof known to treat the disease that is to be prevented, for example anti-VEGF in the case of wet AMD or anti-HER2 in the case of breast or ovarian cancer or germline BRCA1/2 mutation.

TABLE 1

Example Sequences Useful with Methods and Compositions According to the Disclosure

| SEQ ID NO: | NAME | SEQUENCE |
| --- | --- | --- |
| 1 | MC-pSurv-SEAP-WPRE-pA Minicircle | CCCCAACTGGGGTAACCTTTGGGCTCCCCGGGCGCGACTAGT AATAAAATATCTTTATTTTCATTACATCTGTGTGTTGGTTTT TTGTGTGAATCGATAGTACTAACATACGCTCTCCATCAAAAC AAAACGAAACAAAACAAACTAGCAAAATAGGCTGTCCCCAGT GCAAGTGCAGGTGCCAGAACATTTCTCTACTAGTGCCATAGA ACCAGAGAAGTGAGTGGATGTGATGCCCAGCTCCAGAAGTGA CTCCAGAACACCCTGTTCCAAAGCAGAGGACACACTGATTTT TTTTTTAATAGGCTGCAGGACTTACTGTTGGTGGGACGCCCT GCTTTGCGAAGGGAAAGGAGGAGTTTGCCCTGAGCACAGGCC CCCACCCTCCACTGGGCTTTCCCCAGCTCCCTTGTCTTCTTA TCACGGTAGTGGCCCAGTCCCTGGCCCCTGACTCCAGAAGGT GGCCCTCCTGGAAACCCAGGTCGTGCAGTCAACGATGTACTC GCCGGGACAGCGATGTCTGCTGCACTCCATCCCTCCCCTGTT CATTTGTCCTTCATGCCCGTCTGGAGTAGATGCTTTTTGCAG AGGTGGCACCCTGTAAAGCTCTCCTGTCTGACTTTTTTTTTT TTTTTAGACTGAGTTTTGCTCTTGTTGCCTAGGCTGGAGTGC AATGGCACAATCTCAGCTCACTGCACCCTCTGCCTCCCGGGT TCAAGCGATTCTCCTGCCTCAGCCTCCCGAGTAGTTGGGATT ACAGGCATGCACCACCACGCCCAGCTAATTTTTGTATTTTTA GTAGAGACAAGGTTTCACCGTGATGGCCAGGCTGGTCTTGAA CTCCAGGACTCAAGTGATGCTCCTGCCTAGGCCTCTCAAAGT GTTGGGATTACAGGCGTGAGCCACTGCACCCGGCCTGCACGC GTTCTTTGAAAGCAGTCGAGGGGGCGCTAGGTGTGGGCAGGG ACGAGCTGGCGCGGCGTCGCTGGGTGCACCGCGACCACGGGC AGAGCCACGCGGCGGGAGGACTACAACTCCCGGCACACCCCG CGCCGCCCCGCCTCTACTCCCAGAAGGCCGCGGGGGGTGGAC CGCCTAAGAGGGCGTGCGCTCCCGACATGCCCCGCGGCGCGC CATTAACCGCCAGATTTGAATCGCGGGACCCGTTGGCAGAGG TGGGAATTCACCGGTCACCATGGTTCTGGGGCCCTGCATGCT GCTGCTGCTGCTGCTGGGCCTGAGGCTACAGCTCTCCCT GGGCATCATCCCAGTTGAGGAGGAGAACCCGGACTTCTGGAA CCGCGAGGCAGCCGAGGCCCTGGGTGCCGCCAAGAAGCTGCA GCCTGCACAGACAGCCGCCAAGAACCTCATCATCTTCCTGGG CGATGGGATGGGGGTGTCTACGGTGACAGCTGCCAGGATCCT AAAAGGGCAGAAGAAGGACAAACTGGGGCCTGAGATACCCCT GGCTATGGACCGCTTCCCATATGTGGCTCTGTCCAAGACATA CAATGTAGACAAACATGTGCCAGACAGTGGAGCCACAGCCAC GGCCTACCTGTGCGGGGTCAAGGGCAACTTCCAGACCATTGG CTTGAGTGCAGCCGCCCGCTTTAACCAGTGCAACACGACACG CGGCAACGAGGTCATCTCCGTGATGAATCGGGCCAAGAAAGC AGGGAAGTCAGTGGGAGTGGTAACCACCACGAGTGCAGCA CGCCTCGCCAGCCGGCACCTACGCCCACACGGTGAACCGCAA CTGGTACTCGGACGCCGACGTGCCTGCCTCGGCCCCGCCAGGA GGGGTGCCAGGACATCGCTACGCAGCTCATCTCCAACATGGA CATTGATGTGATCCTGGGTGGAGGCCGAAAGTACATGTTTCG CATGGGAACCCCAGACCCTGAGTACCCAGATGACTACAGCCA AGGTGGGACCAGGCTGGACGGGAAGAATCTGGTGCAGGAATG GCTGGCGAAGCGCCAGGGTGCCCGGTATGTGTGGAACCGCAC TGAGCTCATGCAGGCTTCCCTGGACCCGTCTGTGACCCATCT CATGGGTCTCTTTGAGCCTGGAGACATGAAATACGAGATCCA CCGAGACTCCACACTGGACCCCTCCCTGATGGAGATGACAGA GGCTGCCCTGCGCCTGCTGAGCAGGAACCCCCGCGGCTTCTT CCTCTTCGTGGAGGGTGGTCGCATCGACCACGGTCATCACGA AAGCAGGGCTTACCGGGCACTGACTGAGACGATCATGTTCGA CGACGCCATTGAGAGGGCGGGCCAGCTCACCAGCGAGGAGGA CACGCTGAGCCTCGTCACTGCCGACCACTCCCACGTCTTCTC CTTCGGAGGCTACCCCCTGCGAGGGAGCTCCATCTTCGGGCT GGCCCCTGGCAAGGCCCGGGACAGGAAGGCCTACACGGTCCT CCTATACGGAAACGGTCCAGGCTATGTGCTCAAGGACGGCGC CCGGCCGGATGTTACCGAGAGCGAGAGCGGGAGCCCCGAGTA TCGGCAGCAGTCAGCAGTGCCCCTGGACGAAGAGACCCACGC AGGCGAGGACGTGGCGGTGTTCGCGCGCGGCCCGCAGGCGCA CCTGGTTCACGGCGTGCAGGAGCAGACCTTCATAGCGCACGT CATGGCCTTCGCCGCCTGCCTGGAGCCCTACACCGCCTGCGA CCTGGCGCCCCCGCCGGCACCACCGACGCCGCGCACCCGGG GCGGTCCCGGTCCAAGCGTCTGGATTGAGCTAGCTTCGAATT TAAATCGGATCCCTGCAGGAGCTCGTCGACAATCAACCTCTG GATTACAAAATTTGTGAAAGATTGACTGGTATTCTTAACTAT GTTGCTCCTTTTACGCTATGTGGATACGCTGCTTTAATGCCT TTGTATCATGCTATTGCTTCCCGTATGGCTTTCATTTTCTCC TCCTTGTATAAATCCTGGTTGCTGTCTCTTTATGAGGAGTTG TGGCCCGTTGTCAGGCAACGTGGCGTGGTGTGCACTGTGTTT GCTGACGCAACCCCCACTGGTTGGGGCATTGCCACCACCTGT |

TABLE 1-continued

Example Sequences Useful with Methods and Compositions According to the Disclosure

| SEQ ID NO: | NAME | SEQUENCE |
|---|---|---|
| | | CAGCTCCTTTCCGGGACTTTCGCTTTCCCCCTCCCTATTGCC<br>ACGGCGGAACTCATCGCCGCCTGCCTTGCCCGCTGCTGGACA<br>GGGGCTCGGCTGTTGGGCACTGACAATTCCGTGGTGTTGTCG<br>GGGAAATCATCGTCCTTTCCTTGGCTGCTCGCCTGTGTTGCC<br>ACCTGGATTCTGCGCGGGACGTCCTTCTGCTACGTCCCTTCG<br>GCCCTCAATCCAGCGGACCTTCCTTCCCGCGGCCTGCTGCCG<br>GCTCTGCGGCCTCTTCCGCGTCTTCGCCTTCGCCCTCAGACG<br>AGTCGGATCTCCCTTTGGGCCGCCTCCCCGCCTGGTACCTTT<br>AAGACCAATGACTTACAAGGCAGCTGTAGATCTTAGCCACTT<br>TTTAAAAGAAAAGGGGGGACTGGAAGGGCTAATTCACTCCCA<br>ACGAAAATAAGATCTGCTTTTTGCTTGTACTGGGTCTCTCTG<br>GTTAGACCAGATCTGAGCCTGGGAGCTCTCTGGCTAACTAGG<br>GAACCCACTGCTTAAGCCTCAATAAAGCTTGCCTTGAGTGCT<br>TCAAGTAGTGTGTGCCCGTCTGTTGTGTGACTCTGGTAACTA<br>GAGATCCCTCAGACCCTTTTAGTCAGTGTGGAAAATCTCTAG<br>CAGTAGTAGTTCATGTCATCTTATTATTCAGTATTTATAACT<br>TGCAAAGAAATGAATATCAGAGAGTGAGAGGAACTTGTTTAT<br>TGCAGCTTATAATGGTTACAAATAAAGCAATAGCATCACAAA<br>TTTCACAAATAAAGCATTTTTTTCACTGCATTCTAGTTGTGG<br>TTTGTCCAAACTCATCAATGTATCTTATCATGTCTGGCTCTA<br>GCTATCCCGCCCCTAACTCCGCCCAGTTCCGCCCATTCTCCG<br>CCCCTCCCGCCCCTAACTCCGCCCAATGGCTGACTAATTTTT<br>TTTATTTATGCAGAGGCCGAGGCCGCCTCGGCCTCTGAGCTA<br>TTCCAGAAGTAGTGAGGAGGCTTTTTTGGAGGCCTAGACTTT<br>TGCAGATCGACCCATGGGGGCCCG |
| 2 | MC-pSurv-Luc2-WPRE-pA | CCCCAACTGGGGTAACCTTTGGGCTCCCCGGGCGCGACTAGT<br>AATAAAATATCTTTATTTTCATTACATCTGTGTGTTGGTTTT<br>TTGTGTGAATCGATAGTACTAACATACGCTCTCCATCAAAC<br>AAAACGAAACAAAACAAACTAGCAAAATAGGCTGTCCCCAGT<br>GCAAGTGCAGGTGCCAGAACATTTCTCTACTAGTGAATTGAT<br>GCCATAGAACCAGAGAAGTGAGTGGATGTGATGCCCAGCTCC<br>AGAAGTGACTCCAGAACACCCTGTTCCAAAGCAGAGGACACA<br>CTGATTTTTTTTTAATAGGCTGCAGGACTTACTGTTGGTGG<br>GACGCCCTGCTTTGCGAAGGGAAAGGAGGAGTTTGCCCTGAG<br>CACAGGCCCCCACCCTCCACTGGGCTTTCCCCAGCTCCCTTG<br>TCTTCTTATCACGGTAGTGGCCCAGTCCCTGGCCCCTGACTC<br>CAGAAGGTGGCCCTCCTGGAAACCCAGGTCGTGCAGTCAACG<br>ATGTACTCGCCGGGACAGCGATGTCTGCTGCACTCCATCCCT<br>CCCCTGTTCATTTGTCCTTCATGCCCGTCTGGAGTAGATGCT<br>TTTTGCAGAGGTGGCACCCTGTAAAGCTCTCCTGTCTGACTT<br>TTTTTTTTTTTTAGACTGAGTTTTGCTCTTGTTGCCTAGGC<br>TGGAGTGCAATGGCACAATCTCAGCTCACTGCACCCTCTGCC<br>TCCCGGGTTCAAGCGATTCTCCTGCCTCAGCCTCCCGAGTAG<br>TTGGGATTACAGGCATGCACCACCACGCCCAGCTAATTTTTG<br>TATTTTTAGTAGAGACAAGGTTTCACCGTGATGGCCAGGCTG<br>GTCTTGAACTCCAGGACTCAAGTGATGCTCCTGCCTAGGCCT<br>CTCAAAGTGTTGGGATTACAGGCGTGAGCCACTGCACCCGGC<br>CTGCACGCGTTCTTTGAAAGCAGTCGAGGGGGCGCTAGGTGT<br>GGGCAGGGACGAGCTGGCGCGGCGTCGCTGGGTGCACCGCGA<br>CCACGGGCAGAGCCACGCGGCGGGAGGACTACAACTCCCGGC<br>ACACCCCGCGCCGCCCCGCCTCTACTCCCAGAAGGCCGCGGG<br>GGGTGGACCGCCTAAGAGGGCGTGCGCTCCCGACATGCCCCG<br>CGGCGCGCCATTAACCGCCAGATTTGAATCGCGGGACCCGTT<br>GGCAGAGGTGGAAGCTTGGCAATCCGGTACTGTTGGTAAAGC<br>CACCATGGAAGATGCCAAAAACATTAAGAAGGGCCCAGCGCC<br>ATTCTACCCACTCGAAGACGGGACCGCCGGCGAGCAGCTGCA<br>CAAAGCCATGAAGCGCTACGCCCTGGTGCCCGGCACCATCGC<br>CTTTACCGACGCACATATCGAGGTGGACATTACCTACGCCGA<br>GTACTTCGAGATGAGCGTTCGGCTGGCAGAAGCTATGAAGCG<br>CTATGGGCTGAATACAAACCATCGGATCGTGGTGTGCAGCGA<br>GAATAGCTTGCAGTTCTTCATGCCCGTGTTGGGTGCCCTGTT<br>CATCGGTGTGGCTGTGGCCCCAGCTAACGACATCTACAACGA<br>GCGCGAGCTGCTGAACAGCATGGGCATCAGCCAGCCCACCGT<br>CGTATTCGTGAGCAAGAAAGGGCTGCAAAAGATCCTCAACGT<br>GCAAAAGAAGCTACCGATCATACAAAAGATCATCATCATGGA<br>TAGCAAGACCGACTACCAGGGCTTCCAAAGCATGTACACCTT<br>CGTGACTTCCCATTTGCCACCCGGCTTCAACGAGTACGACTT<br>CGTGCCCGAGAGCTTCGACCGGGACAAAACCATCGCCCTGAT<br>CATGAACAGTAGTGGCAGTACCGGATTGCCCAAGGGCGTAGC<br>CCTACCGCACCGCACCGCTTGTGTCCGATTCAGTCATGCCCG<br>CGACCCCATCTTCGGCAACCAGATCATCCCCGACACCGCTAT<br>CCTCAGCGTGGTGCCATTTCACCACGGCTTCGGCATGTTCAC |

TABLE 1-continued

Example Sequences Useful with Methods and Compositions According to the Disclosure

| SEQ ID NO: | NAME | SEQUENCE |
|---|---|---|
| | | CACGCTGGGCTACTTGATCTGCGGCTTTCGGGTCGTGCTCAT
GTACCGCTTCGAGGAGGAGCTATTCTTGCGCAGCTTGCAAGA
CTATAAGATTCAATCTGCCCTGCTGGTGCCCACACTATTTAG
CTTCTTCGCTAAGAGCACTCTCATCGACAAGTACGACCTAAG
CAACTTGCACGAGATCGCCAGCGGCGGGGCGCCGCTCAGCAA
GGAGGTAGGTGAGGCCGTGGCCAAACGCTTCCACCTACCAGG
CATCCGCCAGGGCTACGGCCTGACAGAAACAACCAGCGCCAT
TCTGATCACCCCCGAAGGGGACGACAAGCCTGGCGCAGTAGG
CAAGGTGGTGCCCTTCTTCGAGGCTAAGGTGGTGGACTTGGA
CACCGGTAAGACACTGGGTGTGAACCAGCGCGGCGAGCTGTG
CGTCCGTGGCCCCATGATCATGAGCGGCTACGTTAACAACCC
CGAGGCTACAAACGCTCTCATCGACAAGGACGGCTGGCTGCA
CAGCGGCGACATCGCCTACTGGGACGAGGACGAGCACTTCTT
CATCGTGGACCGGCTGAAGAGCCTGATCAAATACAAGGGCTA
CCAGGTAGCCCCAGCCGAACTGGAGAGCATCCTGCTGCAACA
CCCCAACATCTTCGACGCCGGGGTCGCCGGCCTGCCCGACGA
CGATGCCGGCGAGCTGCCCGCCGCAGTCGTCGTGCTGGAACA
CGGTAAAACCATGACCGAGAAGGAGATCGTGGACTATGTGGC
CAGCCAGGTTACAACCGCCAAGAAGCTGCGCGGTGGTGTTGT
GTTCGTGGACGAGGTGCCTAAAGGACTGACCGGCAAGTTGGA
CGCCCGCAAGATCCGCGAGATTCTCATTAAGGCCAAGAAGGG
CGGCAAGATCGCCGTGTAATCTAGAGCTAGCGAATTCAGATC
TGATATCTCTAGAGTCGAGCTAGCTTCGAATTTAAATCGGAT
CCCTGCAGGAGCTCGTCGACAATCAACCTCTGGATTACAAAA
TTTGTGAAAGATTGACTGGTATTCTTAACTATGTTGCTCCTT
TTACGCTATGTGGATACGCTGCTTTAATGCCTTTGTATCATG
CTATTGCTTCCCGTATGGCTTTCATTTTCTCCTCCTTGTATA
AATCCTGGTTGCTGTCTCTTTATGAGGAGTTGTGGCCCGTTG
TCAGGCAACGTGGCGTGGTGTGCACTGTGTTTGCTGACGCAA
CCCCCACTGGTTGGGGCATTGCCACCACCTGTCAGCTCCTTT
CCGGGACTTTCGCTTTCCCCCTCCCTATTGCCACGGCGGAAC
TCATCGCCGCCTGCCTTGCCCGCTGCTGGACAGGGGCTCGGC
TGTTGGGCACTGACAATTCCGTGGTGTTGTCGGGGAAATCAT
CGTCCTTTCCTTGGCTGCTCGCCTGTGTTGCCACCTGGATTC
TGCGCGGGACGTCCTTCTGCTACGTCCCTTCGGCCCTCAATC
CAGCGGACCTTCCTTCCCGCGGCCTGCTGCCGGCTCTGCGGC
CTCTTCCGCGTCTTCGCCTTCGCCCTCAGACGAGTCGGATCT
CCCCTTTGGGCCGCCTCCCCGCCTGGTACCTTTAAGACCAATG
ACTTACAAGGCAGCTGTAGATCTTAGCCACTTTTTAAAAGAA
AAGGGGGGACTGGAAGGGCTAATTCACTCCCAACGAAAATAA
GATCTGCTTTTTGCTTGTACTGGGTCTCTCTGGTTAGACCAG
ATCTGAGCCTGGGAGCTCTCTGGCTAACTAGGGAACCCACTG
CTTAAGCCTCAATAAAGCTTGCCTTGAGTGCTTCAAGTAGTG
TGTGCCCGTCTGTTGTGTGACTCTGGTAACTAGAGATCCCTC
AGACCCTTTTAGTCAGTGTGGAAAATCTCTAGCAGTAGTAGT
TCATGTCATCTTATTATTCAGTATTTATAACTTGCAAAGAAA
TGAATATCAGAGAGTGAGAGGAACTTGTTTATTGCAGCTTAT
AATGGTTACAAATAAAGCAATAGCATCACAAATTTCACAAAT
AAAGCATTTTTTCACTGCATTCTAGTTGTGGTTTGTCCAAA
CTCATCAATGTATCTTATCATGTCTGGCTCTAGCTATCCCGC
CCCTAACTCCGCCCAGTTCCGCCCATTCTCCGCCCCTCCCGC
CCCTAACTCCGCCCAATGGCTGACTAATTTTTTTTATTTATG
CAGAGGCCGAGGCCGCCTCGGCCTCTGAGCTATTCCAGAAGT
AGTGAGGAGGCTTTTTTGGAGGCCTAGACTTTTGCAGATCGA
CCCATGGGGCCCG |
| 3 | Mini R6K origin (mini-ori)#1 | GGCTTGTTGTCCACAACCGTTAAACCTTAAAAGCTTTAAAAG
CCTTATATATTCTTTTTTTCTTATAAAACTTAAAACCTTAG
AGGCTATTTAAGTTGCTGATTTATATTAATTTTATTGTTCAA
ACATGAGAGCTTAGTACGTGAAACATGAGAGCTTAGTACGTT
AGCCATGAGAGCTTAGTACGTTAGCCATGAGGGTTTAGTTCG
TTAAACATGAGAGCTTAGTACGTTAAACATGAGAGCTTAGTA
CGTACTATCAACAGGTTGAACTGCTGATC |
| 4 | RNA-OUT SELECTABLE MARKER #1 | GTAGAATTGGTAAAGAGAGTCGTGTAAAATATCGAGTTCGCA
CATCTTGTTGTCTGATTATTGATTTTTGGCGAAACCATTTGA
TCATATGACAAGATGTGTATCTACCTTAACTTAATGATTTTG
ATAAAAATCATTA |
| 5 | Example nanoplasmid with SEAP insert, WPRE element, | GCCATAGAACCAGAGAAGTGAGTGGATGTGATGCCCAGCTCC
AGAAGTGACTCCAGAACACCCTGTTCCAAAGCAGAGGACACA
CTGATTTTTTTTTTTAATAGGCTGCAGGACTTACTGTTGGTG
GGACGCCCTGCTTTGCGAAGGGAAAGGAGGAGTTTGCCCTGA |

TABLE 1-continued

Example Sequences Useful with Methods and Compositions According to the Disclosure

| SEQ ID NO: | NAME | SEQUENCE |
|---|---|---|
| | survivin promoter, R6K origin, RNA-out selectable marker | GCACAGGCCCCCACCCTCCACTGGGCTTTCCCCAGCTCCCTT
GTCTTCTTATCACGGTAGTGGCCCAGTCCCTGGCCCCTGACT
CCAGAAGGTGGCCCTCCTGGAAACCCAGGTCGTGCAGTCAAC
GATGTACTCGCCGGGACAGCGATGTCTGCTGCACTCCATCCC
TCCCCTGTTCATTTGTCCTTCATGCCCGTCTGGAGTAGATGC
TTTTTGCAGAGGTGGCACCCTGTAAAGCTCTCCTGTCTGACT
TTTTTTTTTTTTTTAGACTGAGTTTTGCTCTTGTTGCCTAGG
CTGGAGTGCAATGGCACAATCTCAGCTCACTGCACCCTCTGC
CTCCCGGGTTCAAGCGATTCTCCTGCCTCAGCCTCCCGAGTA
GTTGGGATTACAGGCATGCACCACCACGCCCAGCTAATTTTT
GTATTTTTAGTAGAGACAAGGTTTCACCGTGATGGCCAGGCT
GGTCTTGAACTCCAGGACTCAAGTGATGCTCCTGCCTAGGCC
TCTCAAAGTGTTGGGATTACAGGCGTGAGCCACTGCACCCGG
CCTGCACGCGTTCTTTGAAAGCAGTCGAGGGGGCGCTAGGTG
TGGGCAGGGACGAGCTGGCGCGGCGTCGCTGGGTGCACCGCG
ACCACGGGCAGAGCCACGCGGCGGGAGGACTACAACTCCCGG
CACACCCCGCGCCGCCCCGCCTCTACTCCCAGAAGGCCGCGG
GGGGTGGACCGCCTAAGAGGGCGTGCGCTCCCGACATGCCCC
GCGGCGCGCCATTAACCGCCAGATTTGAGTCGCGGGACCCGT
TGGCAGAGGTGGGAATTCACCGGTCACCATGGTTCTGGGGCC
CTGCATGCTGCTGCTGCTGCTGCTGGGCCTGAGGCTACA
GCTCTCCCTGGGCATCATCCCAGTTGAGGAAGAGAACCCGGA
CTTCTGGAACCGCGAGGCAGCCGAGGCCCTGGGTGCCGCCAA
GAAGCTGCAGCCTGCACAGACAGCCGCCAAGAACCTCATCAT
CTTCCTGGGCGATGGGATGGGGGTGTCTACGGTGACAGCTGC
CAGGATCCTAAAAGGGCAGAAGAAGGACAAACTGGGGCCTGA
GATACCCCTGGCTATGGACCGCTTCCCATATGTGGCTCTGTC
CAAGACATACAATGTAGACAAACATGTGCCAGACAGTGGAGC
CACAGCCACGGCCTACCTGTGCGGGGTCAAGGGCAACTTCCA
GACCATTGGCTTGAGTGCAGCCGCCCGCTTTAACCAGTGCAA
CACGACACGCGGCAACGAGGTCATCTCCGTGATGAATCGGGC
CAAGAAAGCAGGGAAGTCAGTGGGAGTGGTAACCACCACACG
AGTGCAGCACGCCTCGCCAGCCGGCACCTACGCCCACACGGT
GAACCGCAACTGGTACTCGGACGCCGACGTGCCTGCCTCGGC
CCGCCAGGAGGGGTGCCAGGACATCGCTACGCAGCTCATCTC
CAACATGGACATTGATGTGATCCTGGGTGGAGGCCGAAAGTA
CATGTTTCGCATGGGAACCCCAGACCCTGAGTACCCAGATGA
CTACAGCCAAGGTGGGACCAGGCTGGACGGGAAGAATCTGGT
GCAGGAATGGCTGGCGAAGCGCCAGGGTGCCCGGTATGTGTG
GAACCGCACTGAGCTCATGCAGGCTTCCCTGGACCCGTCTGT
GACCCATCTCATGGGTCTCTTTGAGCCTGGAGACATGAAATA
CGAGATCCACCGAGACTCCACACTGGACCCCTCCCTGATGGA
GATGACAGAGGCTGCCCTGCGCCTGCTGAGCAGGAACCCCCG
CGGCTTCTTCCTCTTCGTGGAGGGTGGTCGCATCGACCACGG
TCATCACGAAAGCAGGGCTTACCGGGCACTGACTGAGACGAT
CATGTTCGACGACGCCATTGAGAGGGGGCCAGCTCACCAG
CGAGGAGGACACGCTGAGCCTCGTCACTGCCGACCACTCCCA
CGTCTTCTCCTTCGGAGGCTACCCCCGCGAGGGAGCTCCAT
CTTCGGGCTGGCCCCTGGCAAGGCCCGGGACAGGAAGGCCTA
CACGGTCCTCCTATACGGAAACGGTCCAGGCTATGTGCTCAA
GGACGGCGCCCGGCCGGATGTTACCGAGAGCGAGAGCGGGAG
CCCCGAGTATCGGCAGCAGTCAGCAGTGCCCCTGGACGAAGA
GACCCACGCAGGCGAGGACGTGGCGGTGTTCGCGCGCGGCCC
GCAGGCGCACCTGGTTCACGGCGTGCAGGAGCAGACCTTCAT
AGCGCACGTCATGGCCTTCGCCGCCTGCCTGGAGCCCTACAC
CGCCTGCGACCTGGCGCCCCCCGCCGGCACCACCGACGCCGC
GCACCCGGGGCGGTCCCGGTCCAAGCGTCTGGATTGAGCTAG
CTTCGAATTTAAATCGGATCCCTGCAGGAGCTCGTCGACAAT
CAACCTCTGGATTACAAAATTTGTGAAAGATTGACTGGTATT
CTTAACTATGTTGCTCCTTTTACGCTATGTGGATACGCTGCT
TTAATGCCTTTGTATCATGCTATTGCTTCCCGTATGGCTTTC
ATTTTCTCCTCCTTGTATAAATCCTGGTTGCTGTCTCTTTAT
GAGGAGTTGTGGCCCGTTGTCAGGCAACGTGGCGTGGTGTGC
ACTGTGTTTGCTGACGCAACCCCCACTGGTTGGGCATTGCC
ACCACCTGTCAGCTCCTTTCCGGGACTTTCGCTTTCCCCCTC
CCTATTGCCACGGCGGAACTCATCGCCGCCTGCCTTGCCCGC
TGCTGGACAGGGGCTCGGCTGTTGGGCACTGACAATTCCGTG
GTGTTGTCGGGGAAATCATCGTCCTTTCCTTGGCTGCTCGCC
TGTGTTGCCACCTGGATTCTGCGCGGGACGTCCTTCTGCTAC
GTCCCTTCGGCCCTCAATCCAGCGGACCTTCCTTCCCGCGGC
CTGCTGCCGGCTCTGCGGCCTCTTCCGCGTCTTCGCCTTCGC
CCTCAGACGAGTCGGATCTCCCTTTGGGCCGCCTCCCCGCCT
GGTACAAGTAACCGCGAATTCCTGTGCCTTCTAGTTGCCAGC |

TABLE 1-continued

Example Sequences Useful with Methods and Compositions According to the Disclosure

| SEQ ID NO: | NAME | SEQUENCE |
|---|---|---|
| | | CATCTGTTGTTTGCCCCTCCCCCGTGCCTTCCTTGACCCTGG AAGGTGCCACTCCCACTGTCCTTTCCTAATAAAATGAGGAAA TTGCATCGCATTGTCTGAGTAGGTGTCATTCTATTCTGGGGG GTGGGGTGGGGCAGGACAGCAAGGGGGAGGATTGGGAAGACA ATAGCAGGCATGCTGGGGATGCGGTGGGCTCTATGGCCCGGG ACGGCCGCTAGCCCGCCTAATGAGCGGGCTTTTTTTTGGCTT GTTGTCCACAACCGTTAAACCTTAAAAGCTTTAAAAGCCTTA TATATTCTTTTTTTTCTTATAAAACTTAAAACCTTAGAGGCT ATTTAAGTTGCTGATTTATATTAATTTTATTGTTCAAACATG AGAGCTTAGTACGTGAAACATGAGAGCTTAGTACGTTAGCCA TGAGAGCTTAGTACGTTAGCCATGAGGGTTTAGTTCGTTAAA CATGAGAGCTTAGTACGTTAAACATGAGAGCTTAGTACGTAC TATCAACAGGTTGAACTGCTGATCCACGTTGTGGTAGAATTG GTAAAGAGAGTCGTGTAAAATATCGAGTTCGCACATCTTGTT GTCTGATTATTGATTTTTGGCGAAACCATTTGATCATATGAC AAGATGTGTATCTACCTTAACTTAATGATTTTGATAAAAATC ATTAGGTACGGCCGCGGTGCCAGGGCGTGCCCTTGGGCTCCC CGGGCGCGACTAGT |

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1.—Plasmid and Minicircle Construction

Figure 2A:
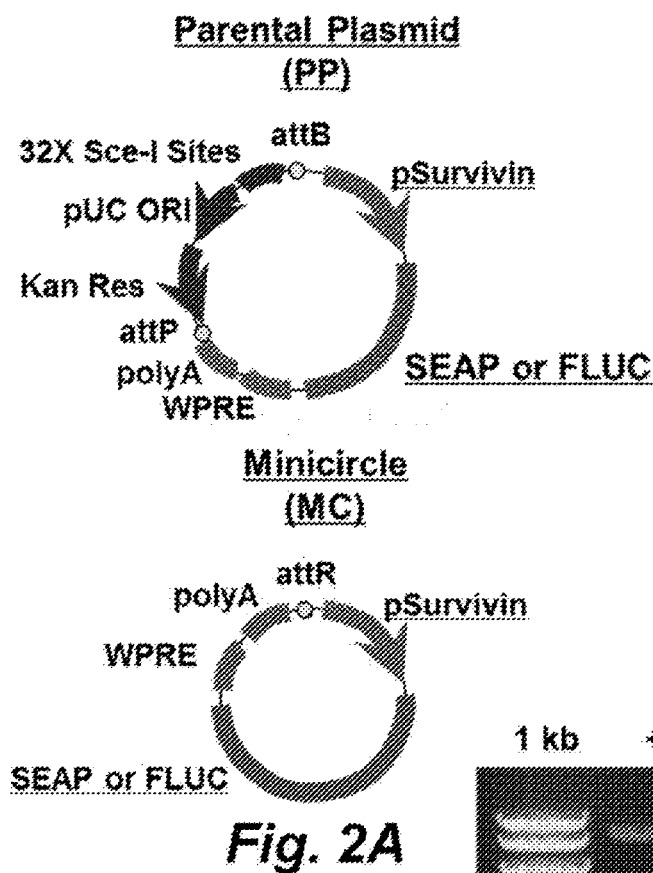
FIGS. 2A-2B illustrate the design and construction of tumor-activatable vectors.
Figure 2B:
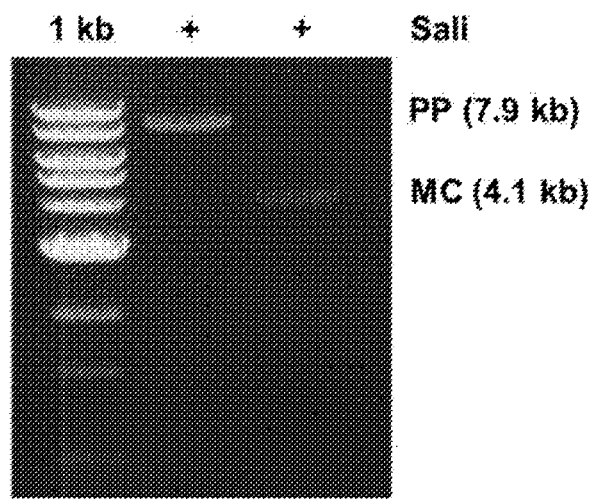

All plasmids were constructed using standard PCR and cloning technology and sequenced by Sequetech (Mountain View, Calif.). To generate both parental plasmids (PP) and MCs the system described by Kay et al., (2010) Nat. Biotechnol. 28: 1287-1289, incorporated herein by reference in its entirety was used (System Biosciences, Mountain View, Calif). The 977 base-pair (bp) Survivin promoter was sub-cloned from pSurv-FL (Ray S, et al. (2008) Molecular therapy: J. Am. Soc. Gene Therapy 16:1848-1856) into the MN-100 PP backbone (System Biosciences, Mountain View, Calif.) containing a SV40 polyA and Woodchuck Hepatitis virus posttranscriptional element (WPRE) to generate PP-pSurv-WPRE. Next, the SEAP transgene from pSELECT-zeo-SEAP (Invivogen, San Diego, Calif.) was subcloned into PP-pSurv-WPRE to generate PP-pSurv-SEAP-WPRE (FIG. 2A-top). Both PP-pSurv-SEAP-WPRE (PP) and MC-pSurv-SEAP-WPRE (MC) (FIG. 2A-bottom) were amplified and purified according to the protocol outlined in Kay et al., (2010) Nat. Biotechnol. 28: 1287-1289) and the supplier's instructions (System Biosciences, Mountain View, Calif.).

ZYCY10P3S2T E. coli were transformed with the PP, colonies were picked, and E. coli were grown overnight in TB broth. To generate MCs, site-specific recombination via expression of phiC31 integrase was initiated by addition of equal volume of LB broth containing 0.001% L-arabinose and 16 mL NaOH, and cultures were grown for an additional 5.5 h at 30° C. For the PP, the cells were grown in the same media without L-arabinose supplementation. Endotoxin-free mega kits (Qiagen, Valencia, Calif.) were used to purify both PP and MC.

Example 2.—Cell Culture and Transfection

MDA-MB-231 (ATCC, Manassas, Va.), MeWo (ATCC, Manassas, Va.) and SK-MEL-28 human melanoma cell lines were maintained on MEM and DMEM (Gibco, Carlsbad, Calif), respectively. Media was supplemented with 10% Fetal Bovine Serum (FBS) and 1×Antibiotic-Antimycotic solution (Life Technologies) and cells were maintained in 5% CO2 incubator at 37° C.

Cell lines were plated ($1.25 \times 10^5$ cells per well) in 24-well plates 1 day prior to transfection. Cells were transfected with equal mass of PP or MC (1 μg) and 2111 of a linear polyethylenimine transfection agent (jetPEI, Polyplus transfection, Illkirch, France) according to the manufacturer's instructions. Medium was collected daily, centrifuged at 1200 rpm for 3 minutes and the supernatant was stored at −20° C. until SEAP concentrations were measured. Following medium collection, each well was washed with PBS and fresh medium was added; therefore, SEAP measurements reflect protein production over a 24-hour period.

Example 3.—Subcutaneous Tumor Model and Intratumoral Administration of Minicircles $2 \times 10^6$ MeWo cells were implanted into the right flank of female nude mice (Nu/Nu; Charles River) and tumors developed over a period of 3 weeks (n=4). MCs (20 μg) were complexed with a linear polyethylenimine transfection agent (in vivo-jetPEI, Polyplus transfection, Illkirch, France) at an N/P ratio of 6 (N/P is the number of nitrogen residues in in vivo jetPEI per nucleic acid phosphate) and resuspended in 504, 5% glucose.

Intratumoral (I. T.) injections were performed over approximately 2 min by injecting DNA-transfection agent complexes at multiple loci within each tumor. Two cohorts of control mice received either an intramuscular (I.M.) injection of MC at the same dose (n=3) or an I.T. injection of 5% glucose only (n=3).

Example 4.—Experimental Melanoma Metastases Model, BLI, and Systemic Administration of Minicircles To evaluate the ability to detect tumors after systemic administration of MCs, an experimental metastases model described previously (Bhang et al., (2011) Nat. Med. 17:123-129) was used. $5 \times 10^6$ MeWo cells stably expressing a BRET fusion protein (RLuc8.6-TurboFP-BRET6) (Dragulescu-Andrasi et al., (2011) Proc. Nat. Acad. Sci. U.S.A. 108:12060-12065) were injected into irradiated (5 Gy) female nude mice (Nu/Nu; Charles River) via the tail-vein (200 µL of PBS total volume). At weekly intervals following cell injection, tumor development was monitored with BLI immediately following intravenous administration of the substrate coelenterazine (35 µg/mouse; diluted in 150 µl of PBS) using an IVIS-200 imaging system (PerkinElmer). Using the software package Living Image 4.1, region of interests (ROIs) were drawn over the lungs in each image to quantitate tumor burden. BLI data is expressed as lung average radiance in photons/second/cm2/steradian.

Tumor-bearing mice (n=7) or irradiated control mice (n=7) were administered 40 µg of MC complexed with a linear polyethylenimine transfection agent (N/P ratio of 8; in vivo-jetPEI, Polyplus transfection, Illkirch, France) and resuspended in 400 µl of 5% glucose. Mice were then injected via the tail-vein with two 200 µl injections and a gap of 5 minutes between the first and second injection. An additional control group (n=5) of irradiated mice were administered 400 µl of 5% glucose alone.

Example 5.—Plasma Collection

Blood samples were collected via the submandibular vein at least 1 day prior to MC injection and for up to 2 weeks following injection. Blood (approximately 75-100 ml) was collected in lithium heparin-coated microtubes (BD), kept on ice before processing, and then centrifuged at 10,000×g for 5 minutes at 4° C. Plasma was collected and stored at −80° C. prior to SEAP measurements.

Example 6.—SEAP Assay

To measure SEAP concentration in both medium and plasma the Great EscAPe SEAP Chemiluminescence Assay kit 2.0 according the manufacturer's instructions (Clontech) was used. Briefly, 25 µl of medium or plasma was added to 1× dilution buffer, and endogenous alkaline phosphatase was heat-inactivated at 65° C. for 30 minutes. Samples were put on ice for 3 minutes and then allowed to recover to room temperature. 100 µl of SEAP substrate was added, incubated for 30 minutes at room temperature, and luminescence (relative light units; RLU) was measured over 10 seconds using a TD 20/20 luminometer (Turner Designs, Sunnyvale, Calif.).

Example 7.—Tumor-Activatable Minicircles are Advantageous Over Plasmids Across Multiple Melanoma Cell Lines The transcriptional activity of two tumor-specific promoters, pSury and the progression elevated gene-3 promoter (pPEG) (Bhang et al., (2011) Nat. Med. 17: 123-129) were compared to assess which promoter would give the lowest background in healthy tissues. Plasmids expressing a codon-optimized firefly luciferase (Luc2) driven by either pSury or pPEG were constructed and delivered systemically into healthy female Nu/Nu mice. After two days, pSury-driven plasmids showed significantly lower background Luc2 expression than pPEG driven constructs, particularly in the heart and lung (FIGS. 18A-18D). The tumor-specific promoter activity in both primary human fibroblasts and two human tumor cell lines was also compared. Again, pSury had lower background activity in human fibroblasts and equivalent or higher expression in tumor cell lines (FIGS. 19A-19C).

Figure 15:
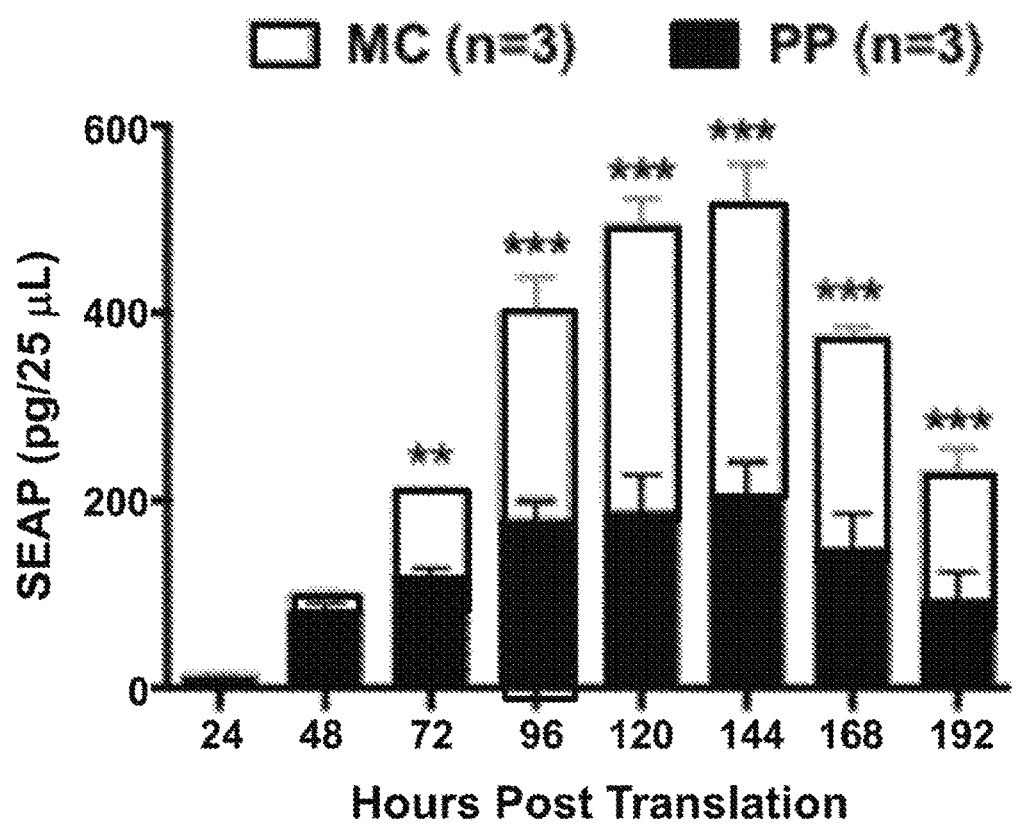
FIG. 15 is a graph illustrating a comparison of the transfections of the constructs of the disclosure in cultured cancer cells. Transfection of equal mass of MC (n=3) and PP (n=3) using equal volumes of transfection agent into MeWo human melanoma cells lead to significantly higher SEAP concentration in medium with MCs from day 3 to day 8 ($p<0.01$; *$p<0.001$). Data is expressed as mean±SD.
Figure 20:
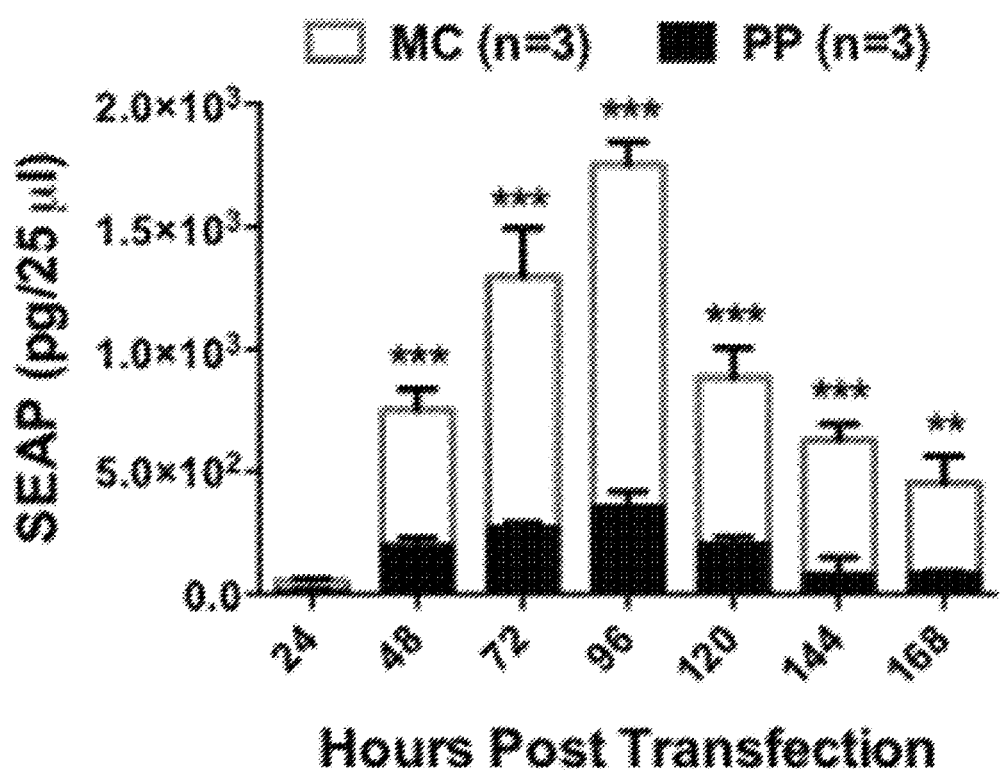
FIG. 20 illustrates a comparison of tumor-activatable PPs and MCs in cultured SK-MEL-28 melanoma cells. SK-MEL-28 human melanoma cells were transfected with equal masses of tumor-activatable MC (n=3) and PP (n=3) and equal volumes of transfection agent PEI. Significantly higher SEAP activity was observed in medium of cells transfected with MCs from 10 day 2 to day 7 ($p<0.01$; $*p<0.001$). Data is expressed as mean±SD.
Figure 21A:
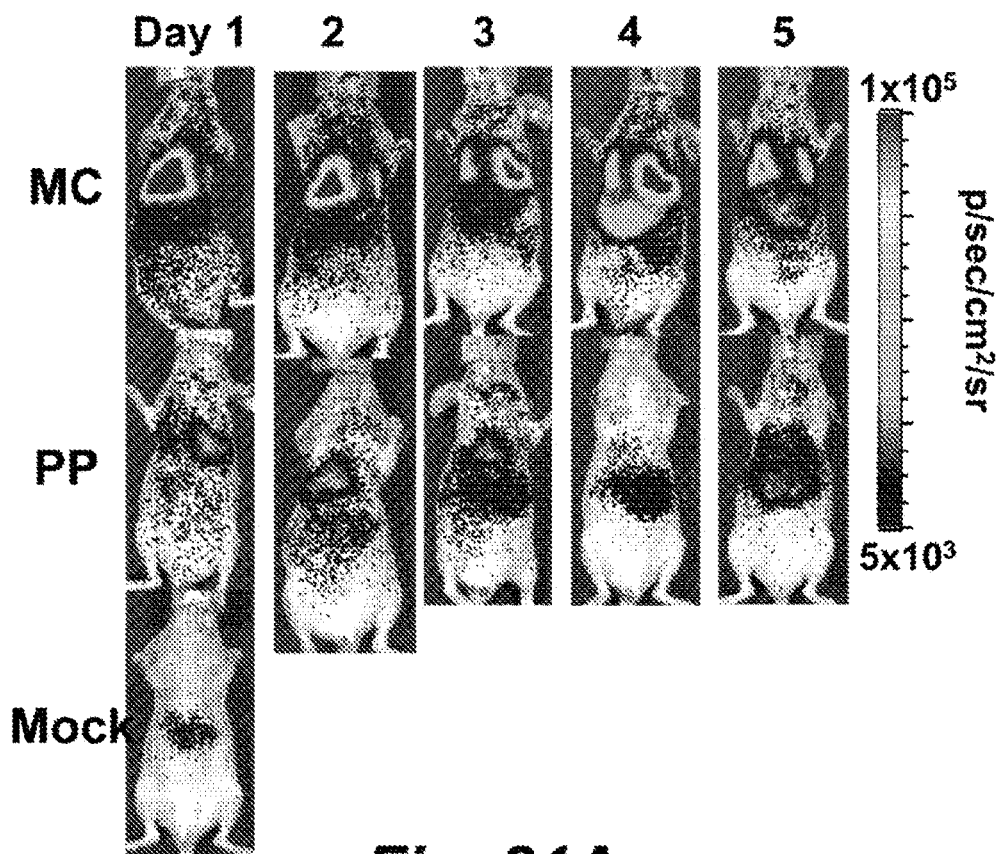
FIGS. 21A and 21B illustrate a comparison of trans-gene expression between MCs and PPs driven by a strong constitutive promoter in healthy (tumor-free) mice.
Figure 21B:
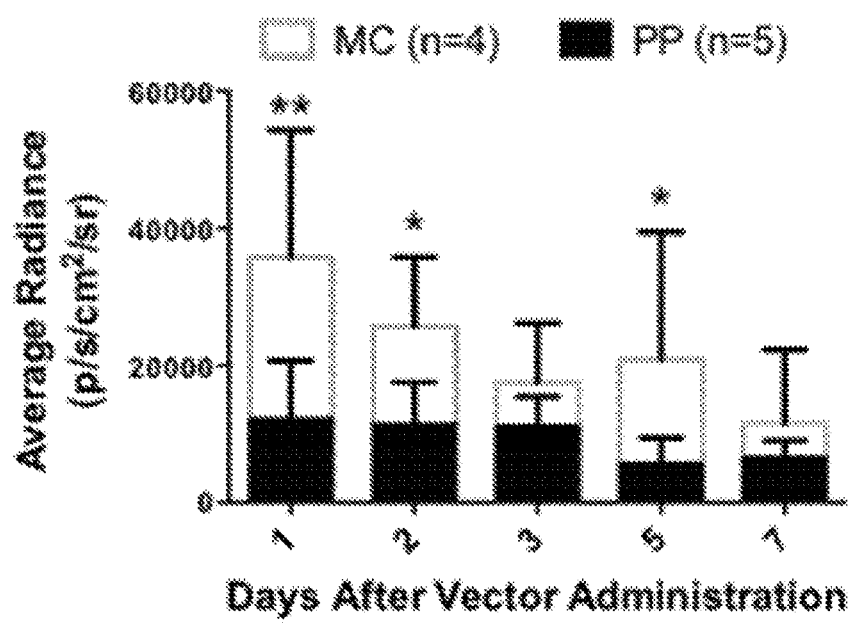

Tumor-activatable parental plasmids (PP; approximately 7.9 kb) and minicircles (MC; approximately 4.1 kb) with pSury driving SEAP expression (FIGS. 2A-4) were developed. To compare SEAP concentration attainable with these two constructs, two human melanoma cell lines (MeWo, FIG. 15; and SK-MEL-28, FIG. 20) were transfected with equal mass of PP and MC and equal volume of a linear polyethylenimine (PEI) transfection agent. Equal mass was compared since the main advantage of MC usage is their smaller size and the main dose limitation of non-viral DNA vectors in vivo is typically the amount of transfection agent, not the amount of DNA. Following transfection, SEAP concentration was measured in the culture medium each day for up to 8 days. Each data point reflected the SEAP accumulation within the previous 24-hour period not the cumulative SEAP concentration across multiple days. By day 3 in MeWo cells, MCs had significantly higher SEAP concentration in the medium compared to PPs and these differences were maintained until the last day (day 8) of the experiment (FIG. 15). Similar results were obtained for SK-MEL-28 cells. The only significant differences were noted at day 2 (FIG. 20). Therefore, MCs driven by the tumor-activatable pSury have improved transgene expression profiles in melanoma cancer cells compared to their parental plasmid counterparts. To ensure that MCs provide an advantage over PPs in vivo, the transgene expression levels achieved by PPs and MCs driven by the strong constitutive elongation factor-1 alpha promoter (pEF1) after systemic administration in mice (n=5 for PP and n=4 for MC) were compared and found significantly higher (p<0.05) lung expression with MCs at multiple time points post-delivery (FIGS. 21A and 21B).

Figure 7:
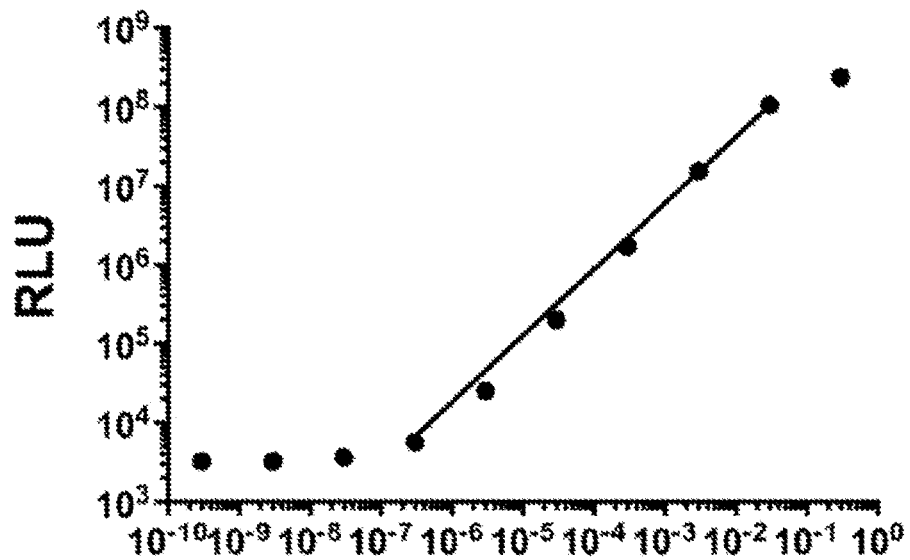
FIG. 7 is a SEAP assay standard curve for blood-based cancer detection after systemic administration of tumor-specific SEAP Minicircles. Standard curve analysis of the SEAP assay revealed that RLU values above approximately $10^4$ were within the linear region of detectable SEAP levels in plasma.
Figure 8:
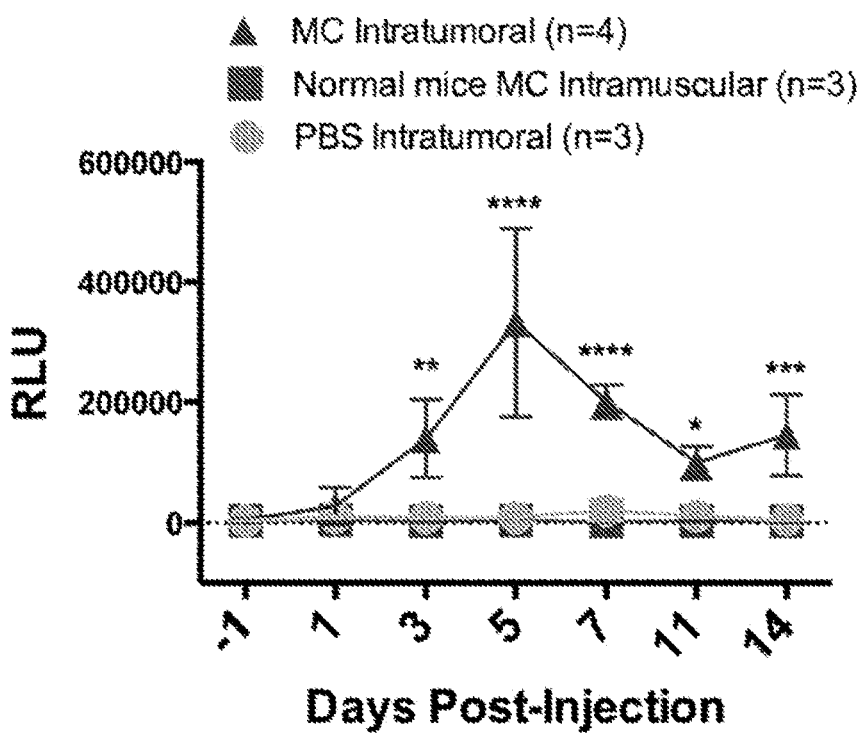
FIG. 8 is a graph illustrating that intratumoral administration of tumor-activatable MCs leads to detectable blood reporter activity. Nude mice bearing subcutaneous human melanoma xenografts were intratumorally (I.T.) administered tumor-activatable MCs expressing SEAP (n=4; MC I.T.) or 5% glucose (n=3; Mock). A group of control mice also received intramuscular (I.M.) injections of MCs (n=3; MC I.M.). Plasma SEAP measurements before and for up to 2 weeks following MC administration revealed that only MC I.T. mice had elevated SEAP levels from days 3 to 14 (*$p<0.05$; $p<0.01$; *$p<0.001$). Data is expressed as mean±SD.
Figure 10:
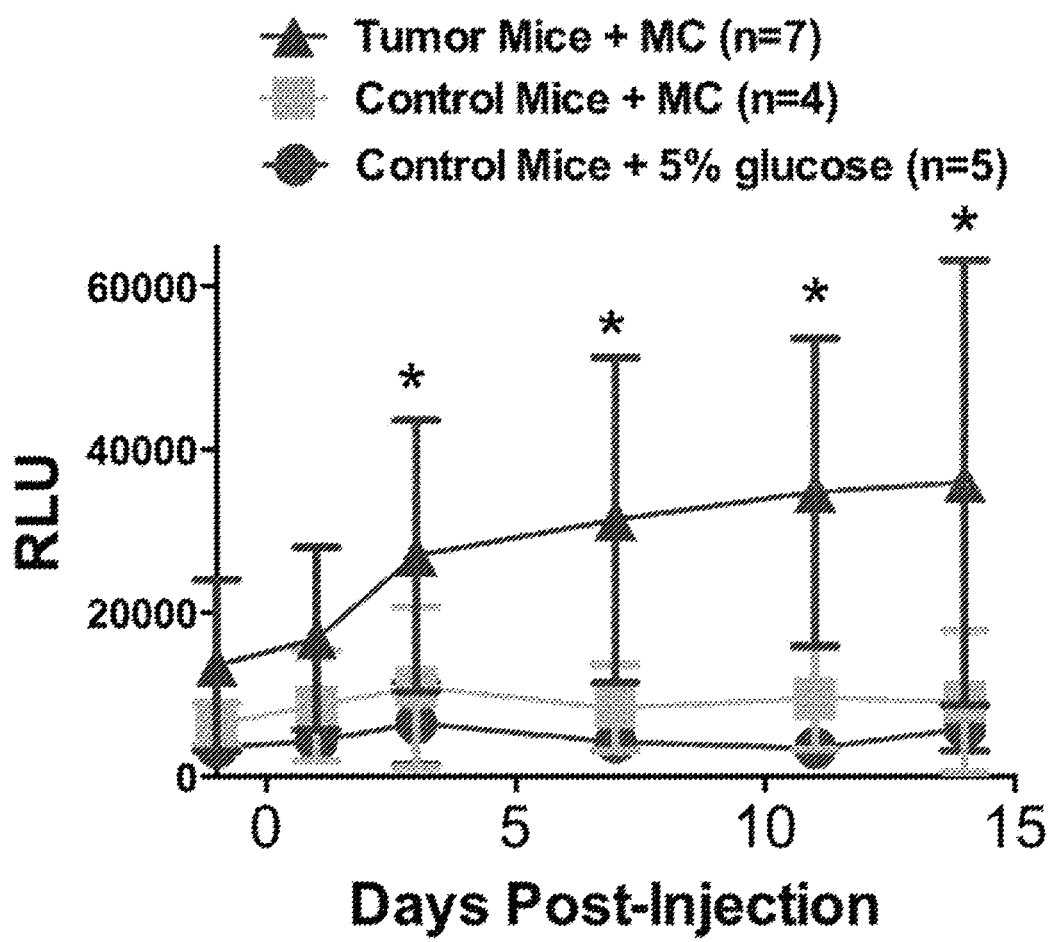
FIG. 10 is a graph illustrating blood-based cancer detection after systemic administration of tumor-specific SEAP minicircles. Significantly higher SEAP activity was detected in blood samples from tumor-bearing mice than control mice from days 3 to 14 post-injection of pSurvivin-SEAP MCs ($p<0.05$). No significant differences were noted between control mice receiving MC or 5% glucose. Error bars represent SD.
Figure 11:
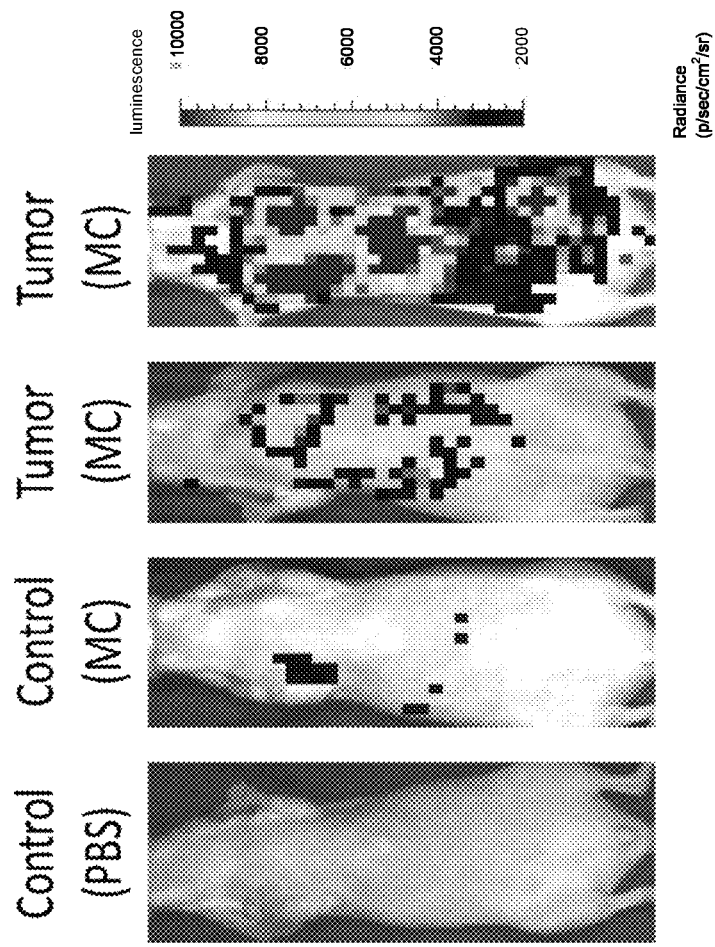
FIG. 11 is a series of digital images illustrating molecular-genetic imaging cancer detection 3 days after systemic administration of tumor-specific FLUC minicircles.
Figure 12:
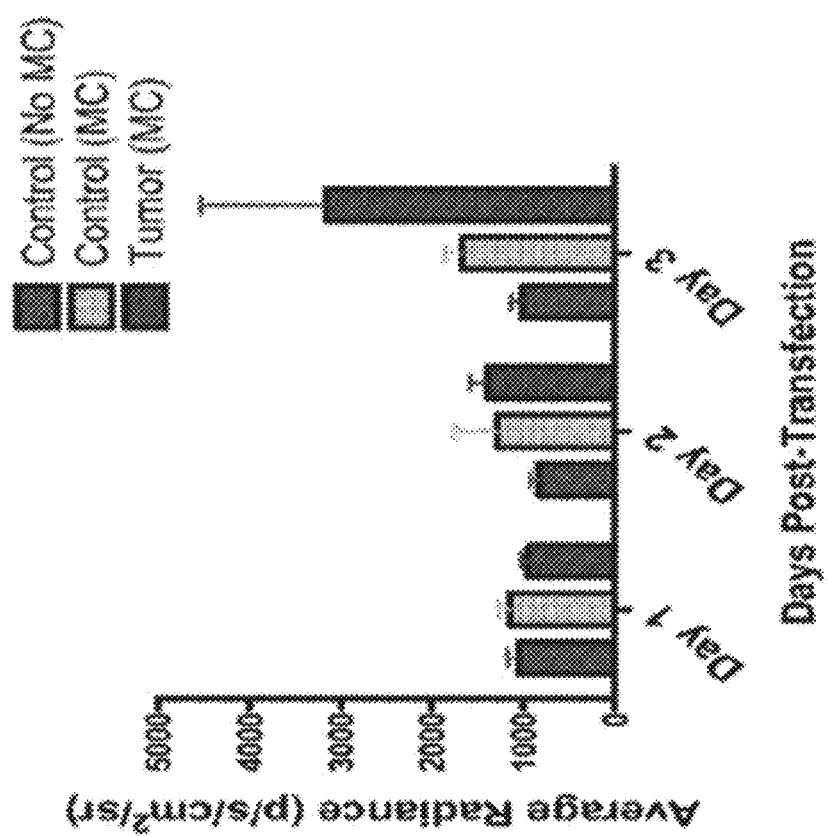
FIG. 12 is a graph illustrating molecular-genetic imaging cancer detection after systemic administration of tumor-specific FLUC minicircles.
Figures 22A, 22B:
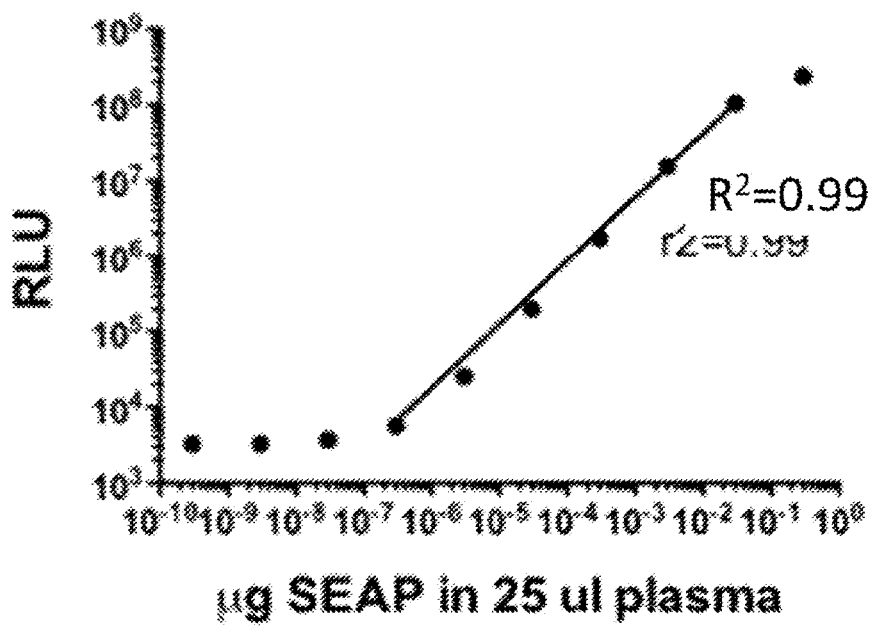
FIG. 22A illustrates a standard curve analysis of plasma SEAP assay. Triplicate samples were measured at 10-fold dilutions of SEAP in 25 IA of plasma. SEAP activity was linear over 5 orders of magnitude and showed a detection limit of approximately $3\times10^{-7}$ µg (0.3 µg) in 25 µl of plasma.
FIG. 22B illustrates SEAP measures over the entire linear range that were reproducible with coefficient of variance (% CV) measures less than 4%.

Example 8.—Intratumoral Injection of Tumor-Activatable MCs Leads to Detectable Plasma SEAP Concentration Since pSury transcriptional activity is relatively low compared to strong promoters such as pCMV (FIGS. 18A-18D), it was determined whether direct intratumoral (I.T.) administration of tumor-activatable MCs would lead to a detectable SEAP signal in the blood. Mice bearing subcutaneous MeWo xenografts (approximately 50-80 mm$^3$) were I.T. administered 20 lag of MCs complexed with PEI (n=4) or PBS only (n=3) and SEAP concentration was measured before and at 1, 3, 5, 7, 11 and 14 days after injection (FIG. 7). Standard curve analysis showed that SEAP measurements in plasma were reproducible over 5 orders of magnitude and a SEAP concentration as low as 0.3 ng in 25 µl of plasma was detectable (FIGS. 22A and 22B). By day 3, significantly (p<0.01) increased plasma SEAP concentration was detected in mice receiving MC compared to control mice (FIGS. 15A-15D; p<0.01). Furthermore, significant differences between these two groups were noted for up to 2 weeks post-administration. The tumor specificity of expression was also examined by performing intramuscular (I.M.) MC injections on a group of mice (n=3). No significant differences were noted between tumor-bearing mice receiving I.T. 5% glucose (Mock) injections or I.M. MC-injected mice. Hence, when adequate transfection efficiency is achieved, pSurv-driven tumor-activatable MCs produce SEAP within tumors at levels sufficient enough to be detectable in the blood at multiple time points following administration.

Figure 23:
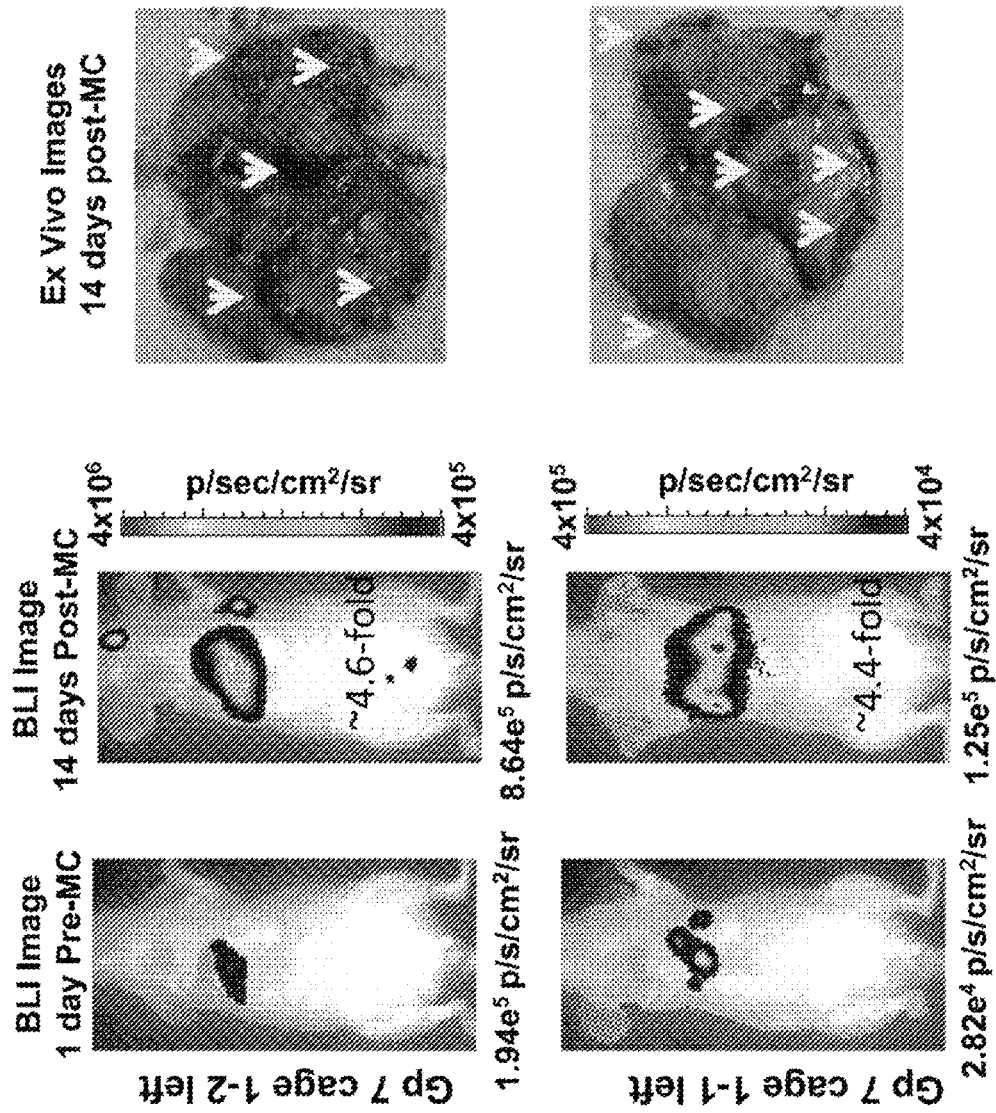
FIG. 23 illustrates tumor burden before and after MC Administration. Bioluminescence (BLI) images (left) of two representative mice (top and bottom) prior to and two weeks following MC administration and corresponding ex vivo images (right) of lungs at time of sacrifice (2 weeks after MC administration). Values below each BLI image represent average radiance in regions of interest drawn over the lungs. There is a difference in image scales for the two mice. Indicating continual tumor growth, both mice showed an approximate 4.5-fold increase in BLI signal over the 2-week period following MC administration. At sacrifice, tumors within the lungs were melanotic and multiple tumor foci throughout the lungs were observed in both mice (white arrows). Based on BLI signal changes, total tumor burden at the time of MC administration (two weeks prior to sacrifice) would have been approximately 4.5-fold less than that seen in the ex vivo images presented here.

Example 9.—Systemic Injection of Tumor-Activatable MCs can Identify Tumor-Bearing Subjects and Assess Tumor Burden The ability of a measurement of plasma SEAP concentration following systemic administration of tumor-activatable MCs to distinguish tumor-bearing from healthy subjects was tested. MeWo melanoma cells stably expressing a bioluminescence resonance energy transfer (BRET) fusion reporter were administered via the tail vein into irradiated nude mice (n=7) and tumor development was monitored over time with bioluminescence imaging (BLI) (FIGS. 15A-15C) and assessed qualitatively at sacrifice (FIG. 23). Although a wide range of tumor burden was observed qualitatively 3 days prior to MC administration, all tumors were primarily localized within the lungs (FIGS. 15A-15C). Following sacrifice, as expected, multiple melanotic tumor foci were noted throughout the lungs (FIG. 23). Based on changes in BLI signal, tumors would have been approximately 4.5-fold smaller at the time of MC administration (2 weeks prior).

Figure 16A:
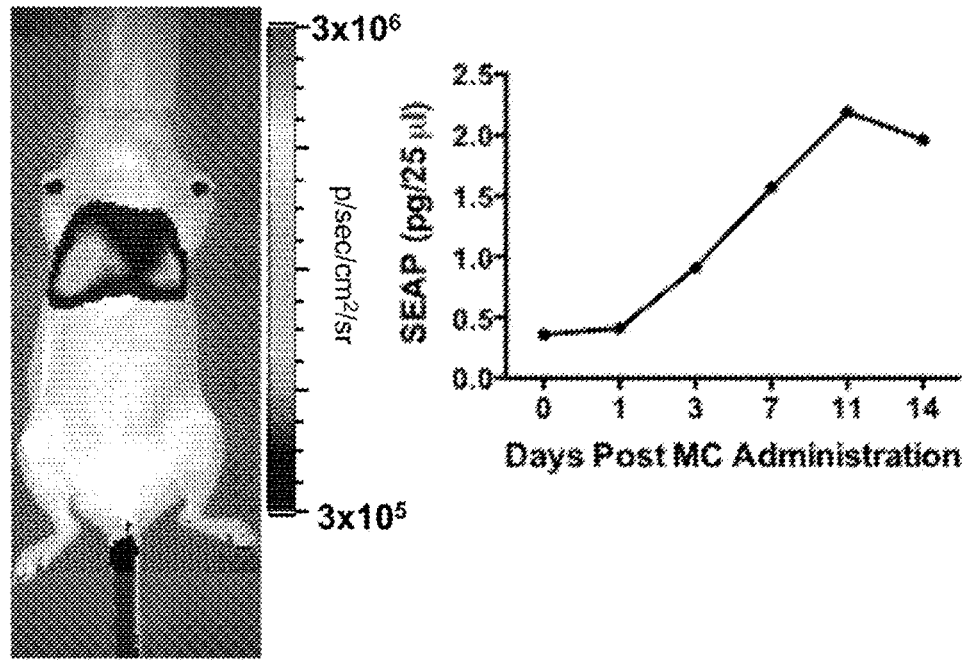
FIGS. 16A-16D illustrate the systemic delivery of tumor-activatable MCs allowing identification of tumor-bearing subjects.
Figure 16B:
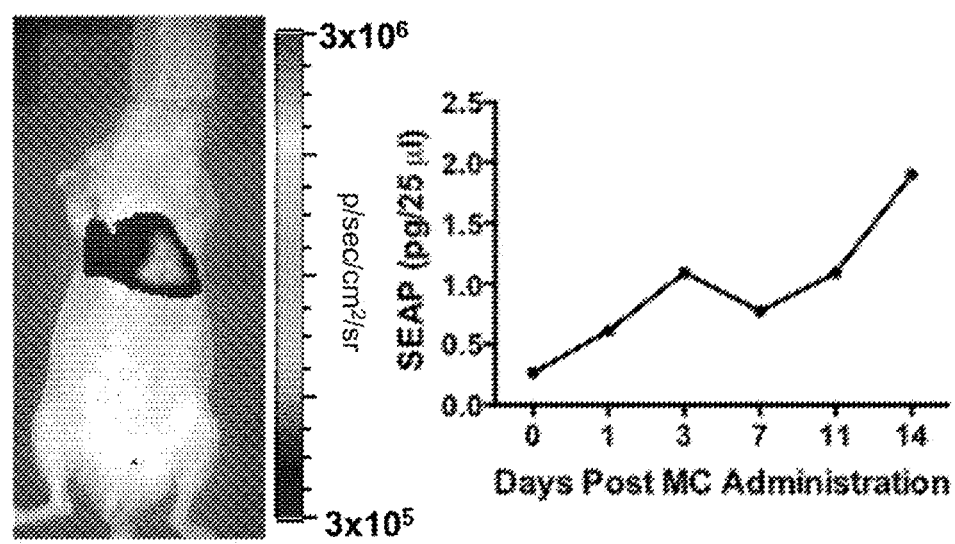
Figure 16C:
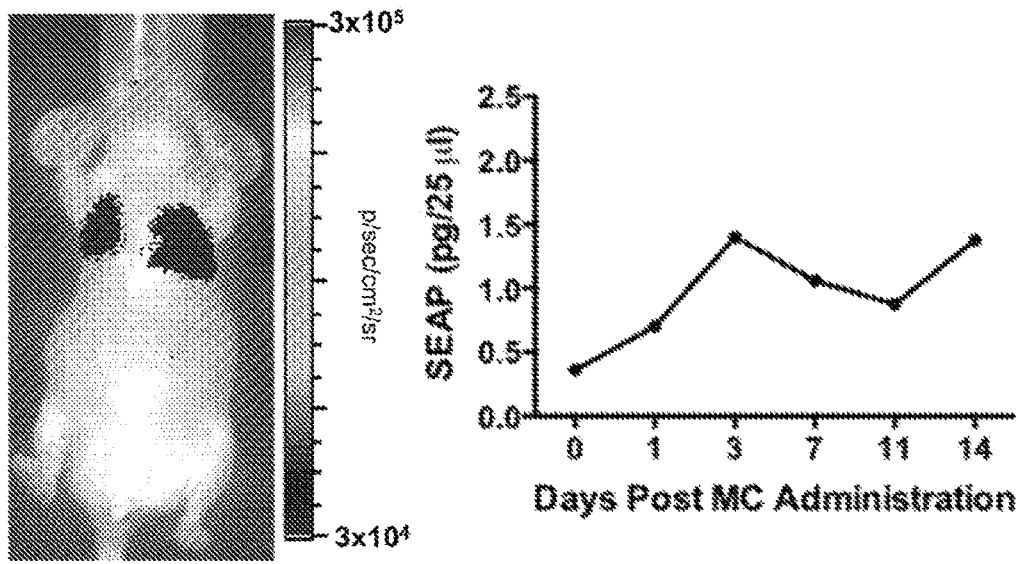
Figure 16D:
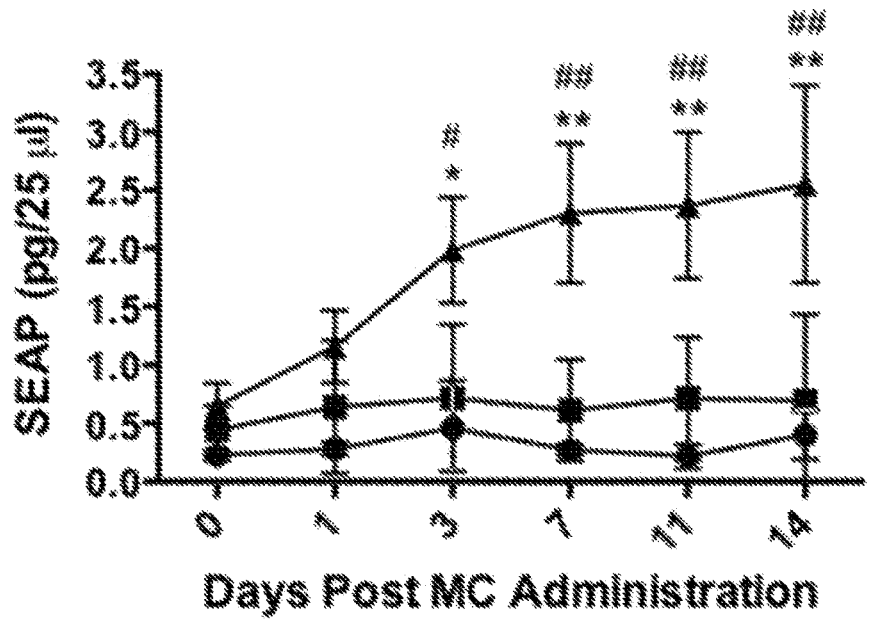

For each mouse, plasma SEAP concentration was measured before (0 days) and at 1, 3, 7, 11 and 14 days after tail-vein administration of 40 μg of MC (Tumor+MC). As control groups, healthy (tumor-free) mice also received either MC (Control+MC; n=6) or 5% glucose (Control MC; n=5). As seen in FIGS. 16A-16C, for individual tumor-bearing mice plasma SEAP concentration was elevated post-MC injection. Regardless of tumor burden, the tumor-bearing mice showed significantly (p<0.05) higher plasma SEAP concentration profiles between days 3-14 post-administration compared to both control groups (FIG. 15). Some healthy mice receiving MC showed a slightly positive SEAP signal (most likely reflecting promoter leakiness, as also noted with pSury in FIG. 18A-18D), overall no significant differences were noted between the two control mice groups (FIG. 16D). Therefore, measurement of plasma SEAP levels following systemic administration of tumor-activatable MCs could differentiate between tumor-bearing and healthy subjects and a wide window of opportunity (>1 week) was available to identify tumor-bearing subjects.

Since SEAP levels were elevated at multiple time points following MC administration, the cumulative shedding of SEAP into plasma was evaluated by calculating the plasma SEAP concentration area under the curve (AUC) for each mouse. Comparison of this single metric across all mice revealed no differences between the two control groups (Control+/−MC), but significantly (p<0.05) elevated values between tumor-bearing mice and both control groups (FIG. 17A).

Figure 17A:
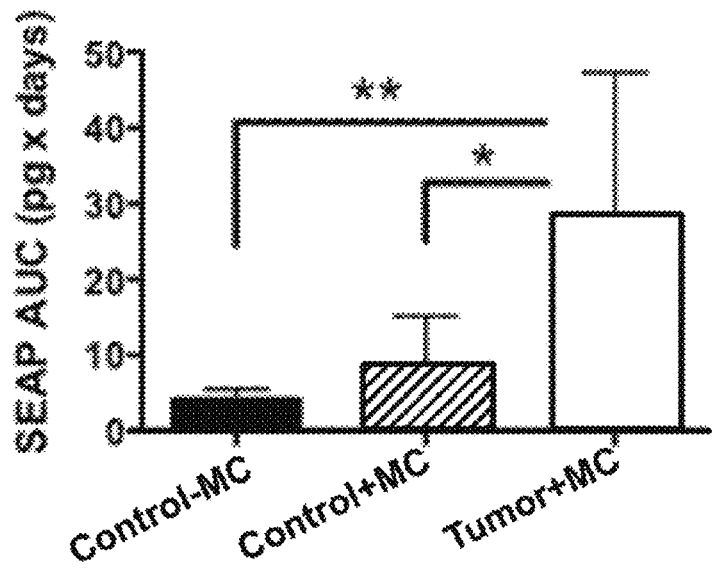
FIGS. 17A-17C illustrate that tumor-activatable MCs can robustly identify tumor-bearing subjects and measure tumor burden.
Figure 17B:
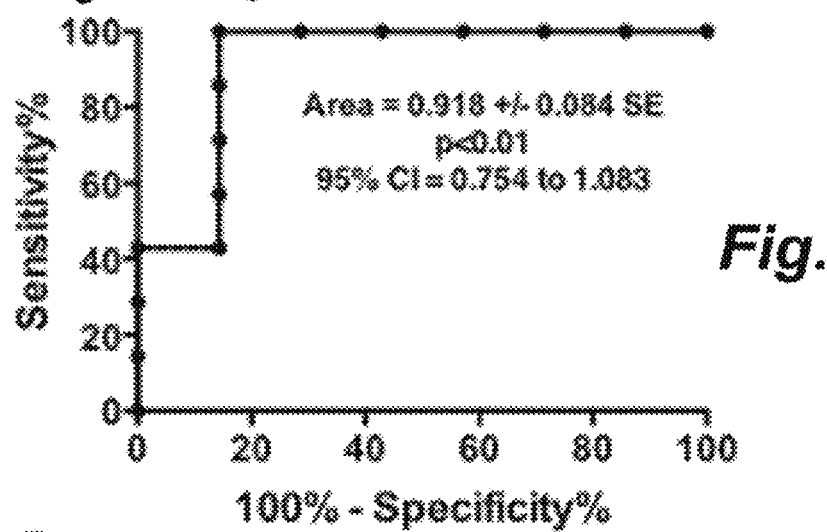

The ability of the assay to distinguish between tumor-bearing and healthy subjects by performing receiver operator-characteristic curve (ROC) analysis was evaluated, as shown in FIG. 17B. This revealed a significant (p<0.05) area of 0.918 (±0.084 SE) and a 95% confidence interval of 0.754 to 1.083. Hence, with this first-generation vector used at the MC doses described, the assay was reliable in identifying tumor-bearing subjects.

Figure 17C:
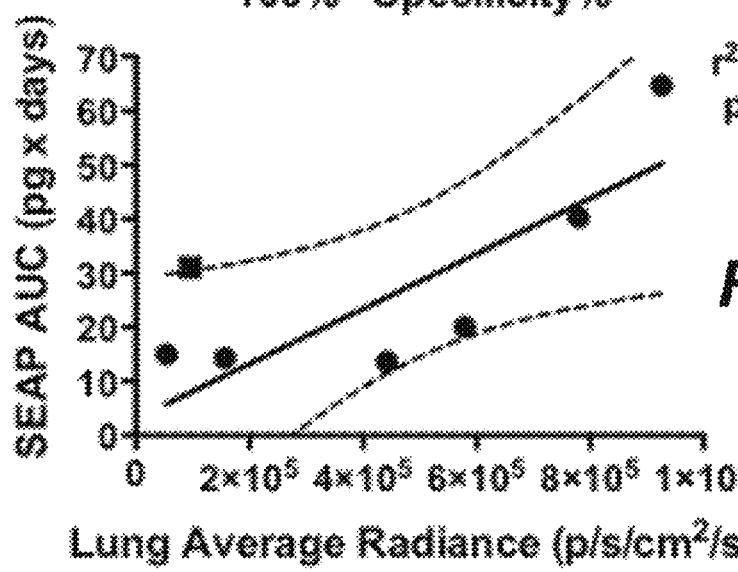
Figure 18A:
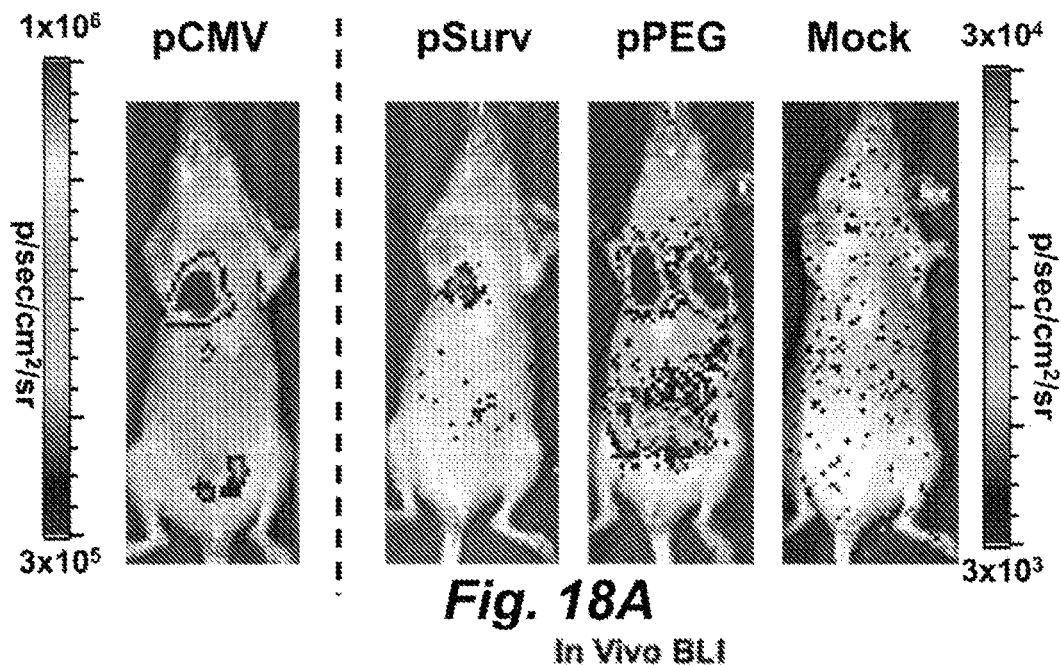
FIGS. 18A-18D illustrate comparison of promoter activities in vivo in healthy (tumor-free) mice. Mice were systemically administered plasmids (30 µg; PGL4.2 back-bone; complexed with PEI (N/P=6)) expressing the bioluminescence imaging (BLI) reporter gene codon-optimized firefly luciferase (Luc2) driven by pCMV (n=3), pSury (n=5), or pPEG (n=3). Mock-injected mice received 5% glucose (n=3). Each mouse was also co-injected with a plasmid expressing the BLI reporter gene humanized Renilla luciferase (hRluc) driven by pCMV to assess transfection efficiency (3 µg; 10-fold less than Luc2 plasmid mass).
Figure 18B:
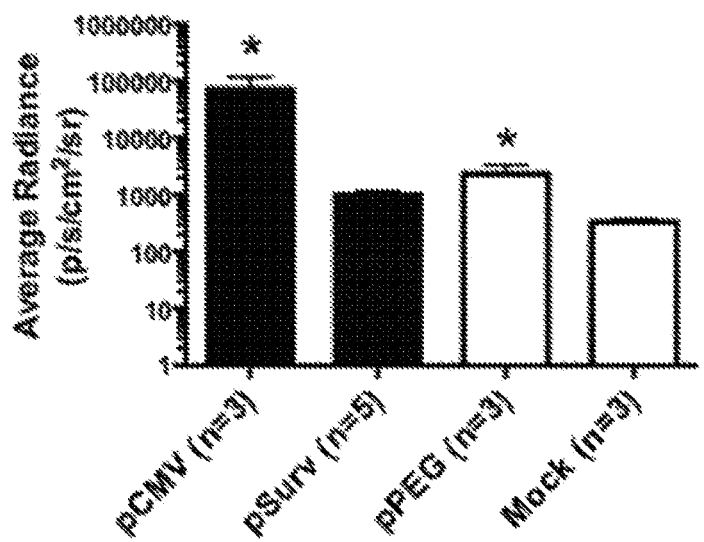
Figure 18C:
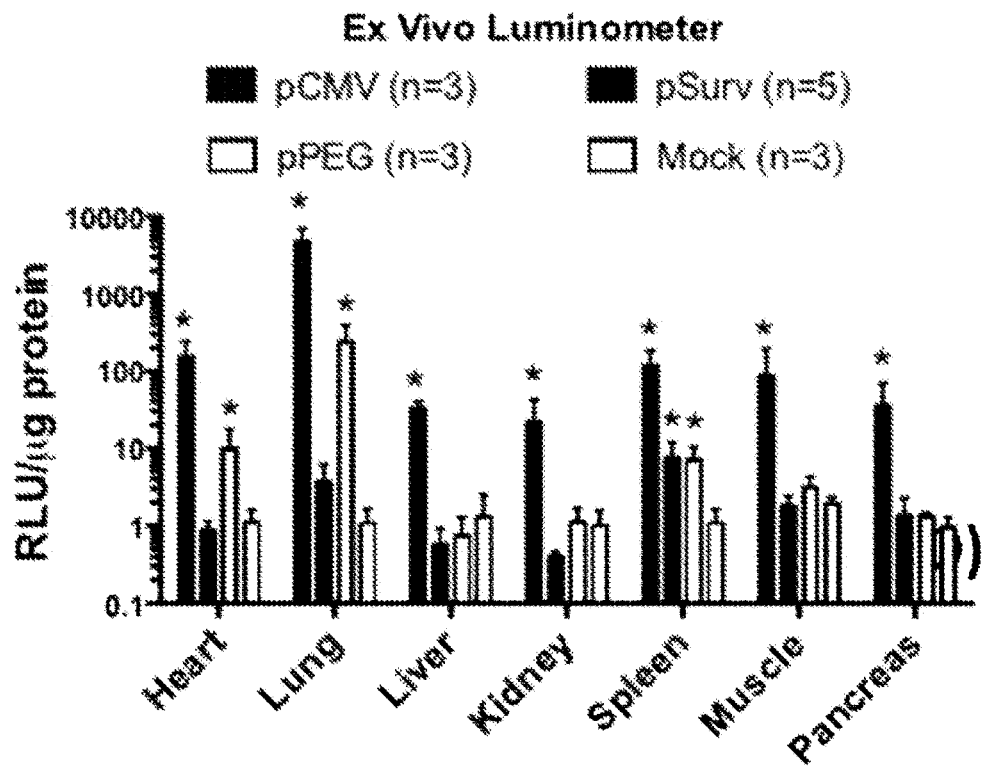
Figure 18D:
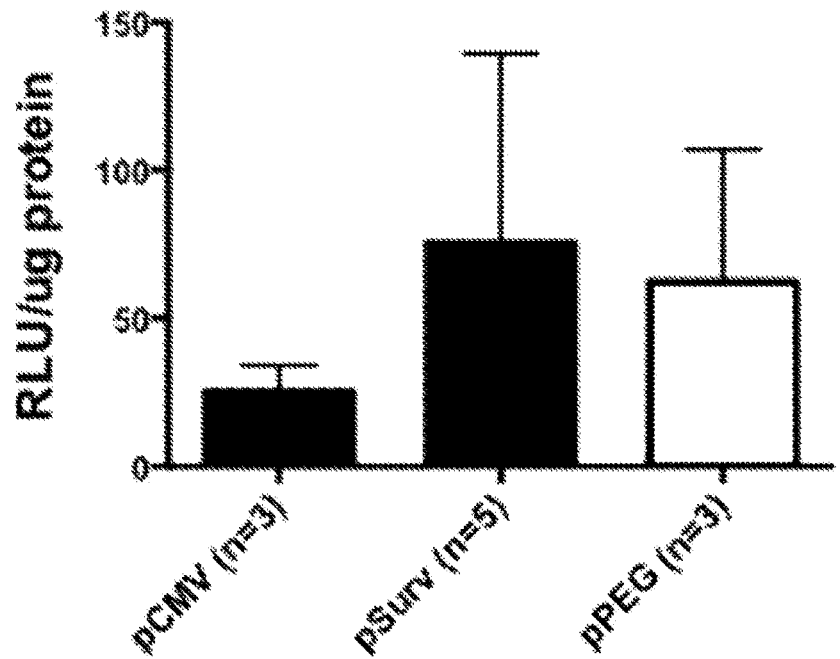

Some tumor-bearing subjects had AUC values that were only slightly above the mean of the control mice receiving MC FIG. 17A. Moreover, as shown in FIG. 16A-16C, the change of plasma SEAP concentration appeared to qualitatively correspond to the degree of tumor burden. Based on these two observations, it was hypothesized that SEAP AUCs would correlate with lung tumor burden (as assessed by BLI within 3 days prior to MC administration). Since tumors were primarily located within the lungs, and the optical BLI signal is tissue-depth dependent, the evaluation was restricted to mice with only lung tumors (n=6). One mouse with multiple metastatic foci outside the lung was excluded, although inclusion of this mouse showed an $r^2$ of 0.056 and a p-value of close to significance (p=0.0541). As expected, ROI analysis of the lung BLI signal prior to MC administration revealed a wide range of lung tumor sizes (FIG. 17). Importantly, lung tumor burden was significantly correlated with SEAP AUC values ($r^2$=0.714; p<0.05) (FIG. 16C). Therefore, our tumor-activatable MC system not only shows a robust ability to identify tumor-bearing subjects but provided tumor burden is restricted to one organ can also be used to evaluate disease extent.

Example 10.—Statistical Analysis

All statistical analysis was performed using Prism 6.0 software (Graphpad software). Comparison of SEAP measurements from cell culture medium was performed using two-way analysis of variance (ANOVA) followed by Sidak's multiple comparisons test. Longitudinal plasma SEAP measurements from mice were compared using two-way repeated measures ANOVA followed by Tukey's multiple comparisons test. Comparison of SEAP AUC measurements across mice cohorts was performed using a one-way ANOVA followed by Tukey's multiple comparisons test. ROC analysis was performed between SEAP AUC data from tumor-bearing and healthy mice receiving MC. Finally, Pearson correlation analysis of SEAP AUC and lung tumor burden measurements was performed. For all tests a nominal p-value less than 0.05 was considered to be significant.

Example 11.—Discovery of New Promoters for Tumor Detection

Publicly-available databases were mined to discover new endogenous genes (and hence promoters) that may serve as part of synthetic biomarker constructs alternative to or in addition to Survivin/BIRC5. Two sources of data were utilized: tumor sample expression from The Cancer Genome Atlas (TCGA), which has curated over 20,000 primary cancer samples from 33 types of cancer against pair matched normal tissues; and the Genotype-Tissue Expression (GTEx) database, which contains diverse information on expression data in normal tissues. An algorithm was applied to the combined data set that ranked target genes by the number of distinct tumor types in which the lowest quartile of that target's gene expression was significantly higher than the highest quartile of gene expression across all corresponding normal tissues (e.g. to find genes that are expressed in several tumor types at levels above 'background' level in all normal tissues). Normal tissue expression data from GTEx was selected as a better indicator of healthy normal tissue than matching normal tissues from cancer patients in the TCGA database. The algorithm was run versus expression data from all 19,000 genes in the human genome and the algorithm revealed overexpression of genes across a substantial number of tumor types over all normal tissues. Many of these genes are presented in Table 2 below.

TABLE 2

Genes for which tumor expression is significantly higher than all normal tissues

| Gene Symbol | Rank | Name |
|---|---|---|
| UBE2T | 12 | ubiquitin conjugating enzyme E2 T [Source:HGNC Symbol; Acc:HGNC:25009] |
| CHEK1 | 10 | checkpoint kinase 1 [Source:HGNC Symbol; Acc:HGNC:1925] |
| ECT2 | 10 | epithelial cell transforming 2 [Source:HGNC Symbol; Acc:HGNC:3155] |
| BCL2L12 | 9 | BCL2 like 12 [Source:HGNC Symbol; Acc:HGNC:13787] |
| CENPI | 9 | centromere protein I [Source:HGNC Symbol; Acc:HGNC:3968] |
| E2F1 | 9 | E2F transcription factor 1 [Source:HGNC Symbol; Acc:HGNC:3113] |
| FLAD1 | 9 | flavin adenine dinucleotide synthetase 1 [Source:HGNC Symbol; Acc:HGNC:24671] |
| PPM1G | 9 | protein phosphatase, Mg2+/Mn2+ dependent 1G [Source:HGNC Symbol; Acc:HGNC:9278] |
| UBE2S | 9 | ubiquitin conjugating enzyme E2 S [Source:HGNC Symbol; Acc:HGNC:17895] |
| AUNIP | 8 | aurora kinase A and ninein interacting protein [Source:HGNC Symbol; Acc:HGNC:28363] |
| CDC6 | 8 | cell division cycle 6 [Source:HGNC Symbol; Acc:HGNC:1744] |
| CENPL | 8 | centromere protein L [Source:HGNC Symbol; Acc:HGNC:17879] |
| DNA2 | 8 | DNA replication helicase/nuclease 2 [Source:HGNC Symbol; Acc:HGNC:2939] |
| DSN1 | 8 | DSN1 homolog, MIS12 kinetochore complex component [Source:HGNC Symbol; Acc:HGNC:16165] |
| DTYMK | 8 | deoxythymidylate kinase [Source:HGNC Symbol; Acc:HGNC:3061] |
| GPRIN1 | 8 | G protein regulated inducer of neurite outgrowth 1 [Source:HGNC Symbol; Acc:HGNC:24835] |
| MTFR2 | 8 | mitochondrial fission regulator 2 [Source:HGNC Symbol; Acc:HGNC:21115] |
| RAD51AP1 | 8 | RAD51 associated protein 1 [Source:HGNC Symbol; Acc:HGNC:16956] |
| SNRPA1 | 8 | small nuclear ribonucleoprotein polypeptide A' [Source:HGNC Symbol; Acc:HGNC:11152] |
| ATAD2 | 7 | ATPase family, AAA domain containing 2 [Source:HGNC Symbol; Acc:HGNC:30123] |
| BUB1 | 7 | BUB1 mitotic checkpoint serine/threonine kinase [Source:HGNC Symbol; Acc:HGNC:1148] |
| CACYBP | 7 | calcyclin binding protein [Source:HGNC Symbol; Acc:HGNC:30423] |
| CDCA3 | 7 | cell division cycle associated 3 [Source:HGNC Symbol; Acc:HGNC:14624] |
| CENPO | 7 | centromere protein O [Source:HGNC Symbol; Acc:HGNC:28152] |
| FEN1 | 7 | flap structure-specific endonuclease 1 [Source:HGNC Symbol; Acc:HGNC:3650] |
| FOXM1 | 7 | forkhead box M1 [Source:HGNC Symbol; Acc:HGNC:3818] |
| KIAA1524 | 7 | |
| KIF2C | 7 | kinesin family member 2C [Source:HGNC Symbol; Acc:HGNC:6393] |
| KPNA2 | 7 | karyopherin subunit alpha 2 [Source:HGNC Symbol; Acc:HGNC:6395] |
| MYBL2 | 7 | MYB proto-oncogene like 2 [Source:HGNC Symbol; Acc:HGNC:7548] |
| NEK2 | 7 | NIMA related kinase 2 [Source:HGNC Symbol; Acc:HGNC:7745] |
| RANBP1 | 7 | RAN binding protein 1 [Source:HGNC Symbol; Acc:HGNC:9847] |
| SNRPB | 7 | small nuclear ribonucleoprotein polypeptides B and B1 [Source:HGNC Symbol; Acc:HGNC:11153] |
| SPC24 | 7 | SPC24, NDC80 kinetochore complex component [Source:HGNC Symbol; Acc:HGNC:26913] |
| TACC3 | 7 | transforming acidic coiled-coil containing protein 3 [Source:HGNC Symbol; Acc:HGNC:11524] |
| TBC1D31 | 7 | TBC1 domain family member 31 [Source:HGNC Symbol; Acc:HGNC:30888] |
| TK1 | 7 | thymidine kinase 1 [Source:HGNC Symbol; Acc:HGNC:11830] |
| ZNF695 | 7 | zinc finger protein 695 [Source:HGNC Symbol; Acc:HGNC:30954] |
| AURKA | 6 | aurora kinase A [Source:HGNC Symbol; Acc:HGNC:11393] |
| BIRC5 | 6 | baculoviral IAP repeat containing 5 [Source:HGNC Symbol; Acc:HGNC:593] |
| BLM | 6 | BLM RecQ like helicase [Source:HGNC Symbol; Acc:HGNC:1058] |
| C17orf53 | 6 | chromosome 17 open reading frame 53 [Source:HGNC Symbol; Acc:HGNC:28460] |
| CBX3 | 6 | chromobox 3 [Source:HGNC Symbol; Acc:HGNC:1553] |
| CCNB1 | 6 | cyclin B1 [Source:HGNC Symbol; Acc:HGNC:1579] |
| CCNE1 | 6 | cyclin E1 [Source:HGNC Symbol; Acc:HGNC:1589] |
| CCNF | 6 | cyclin F [Source:HGNC Symbol; Acc:HGNC:1591] |
| CDC20 | 6 | cell division cycle 20 [Source:HGNC Symbol; Acc:HGNC:1723] |
| CDC45 | 6 | cell division cycle 45 [Source:HGNC Symbol; Acc:HGNC:1739] |
| CDCA5 | 6 | cell division cycle associated 5 [Source:HGNC Symbol; Acc:HGNC:14626] |
| CDKN3 | 6 | cyclin dependent kinase inhibitor 3 [Source:HGNC Symbol; Acc:HGNC:1791] |
| CELSR3 | 6 | cadherin EGF LAG seven-pass G-type receptor 3 [Source:HGNC Symbol; Acc:HGNC:3230] |
| CENPA | 6 | centromere protein A [Source:HGNC Symbol; Acc:HGNC:1851] |
| CEP72 | 6 | centrosomal protein 72 [Source:HGNC Symbol; Acc:HGNC:25547] |
| CKS2 | 6 | CDC28 protein kinase regulatory subunit 2 [Source:HGNC Symbol; Acc:HGNC:2000] |
| COL10A1 | 6 | collagen type X alpha 1 chain [Source:HGNC Symbol; Acc:HGNC:2185] |
| CSE1L | 6 | chromosome segregation 1 like [Source:HGNC Symbol; Acc:HGNC:2431] |
| DBF4 | 6 | DBF4 zinc finger [Source:HGNC Symbol; Acc:HGNC:17364] |
| GINS1 | 6 | GINS complex subunit 1 [Source:HGNC Symbol; Acc:HGNC:28980] |
| GPR19 | 6 | G protein-coupled receptor 19 [Source:HGNC Symbol; Acc:HGNC:4473] |
| KIF18A | 6 | kinesin family member 18A [Source:HGNC Symbol; Acc:HGNC:29441] |
| KIF4A | 6 | kinesin family member 4A [Source:HGNC Symbol; Acc:HGNC:13339] |
| KIFC1 | 6 | kinesin family member C1 [Source:HGNC Symbol; Acc:HGNC:6389] |
| MCM10 | 6 | minichromosome maintenance 10 replication initiation factor [Source:HGNC Symbol; Acc:HGNC:18043] |
| MCM2 | 6 | minichromosome maintenance complex component 2 [Source:HGNC Symbol; Acc:HGNC:6944] |
| MCM7 | 6 | minichromosome maintenance complex component 7 [Source:HGNC Symbol; Acc:HGNC:6950] |
| MRGBP | 6 | MRG domain binding protein [Source:HGNC Symbol; Acc:HGNC:15866] |
| MTHFD2 | 6 | methylenetetrahydrofolate dehydrogenase (NADP+ dependent) 2, methenyltetrahydrofolate cyclohydrolase [Source:HGNC Symbol; Acc:HGNC:7434] |

TABLE 2-continued

Genes for which tumor expression is significantly higher than all normal tissues

| Gene Symbol | Rank | Name |
|---|---|---|
| NCAPH | 6 | non-SMC condensin I complex subunit H [Source:HGNC Symbol; Acc:HGNC:1112] |
| NDC80 | 6 | NDC80, kinetochore complex component [Source:HGNC Symbol; Acc:HGNC:16909] |
| NUDT1 | 6 | nudix hydrolase 1 [Source:HGNC Symbol; Acc:HGNC:8048] |
| RNASEH2A | 6 | ribonuclease H2 subunit A [Source:HGNC Symbol; Acc:HGNC:18518] |
| RUVBL1 | 6 | RuvB like AAA ATPase 1 [Source:HGNC Symbol; Acc:HGNC:10474] |
| SGOL1 | 6 | |
| SHCBP1 | 6 | SHC binding and spindle associated 1 [Source:HGNC Symbol; Acc:HGNC:29547] |
| SNRPG | 6 | small nuclear ribonucleoprotein polypeptide G [Source:HGNC Symbol; Acc:HGNC:11163] |
| TIMELESS | 6 | timeless circadian regulator [Source:HGNC Symbol; Acc:HGNC:11813] |
| TRIP13 | 6 | thyroid hormone receptor interactor 13 [Source:HGNC Symbol; Acc:HGNC:12307] |
| TROAP | 6 | trophinin associated protein [Source:HGNC Symbol; Acc:HGNC:12327] |
| UBE2C | 6 | ubiquitin conjugating enzyme E2 C [Source:HGNC Symbol; Acc:HGNC:15937] |
| WDHD1 | 6 | WD repeat and HMG-box DNA binding protein 1 [Source:HGNC Symbol; Acc:HGNC:23170] |
| AFP1 | 6 | Alpha fetoprotein [Source:HGNC symbol;AccHGNC:317] |

Genes are shown above with their name according to the HUGO Gene Nomenclature committee at genenames.org; "Acc HGNC" refers to the HGNG accession number on genenames.org A more detailed analysis was performed for breast cancer, where individual genes in the list of 120 above were screened to see which genes met a profile wherein: (i) expression was elevated in cancer relative to matched normal tissues; and (ii) background expression across all normal tissues sampled is low (e.g. to find "high confidence" markers that work especially well for breast cancer). This subanalysis identified 4 candidates, of which 2, ubiquitin conjugating enzyme E2 C (UBE2C) and collagen type X alpha 1 chain (COL10A1) show a significant amount of expression in breast invasive carcinomas in TCGA relative to normal tissues and low background expression.

When this analysis was completed individually for each tumor type besides breast, it revealed two additional genes, cadherin 6 (CDH6) and ATP binding cassette subfamily C member 4 (ABCC4) which show specifically elevated expression in kidney (kidney renal cell carcinoma and kidney renal clear cell carcinoma) and prostate (prostate adenocarcinoma), respectively.

Example 11A.—Analysis of Sensitivity of Detection for Ex-Vivo Promoter Approaches To determine a limit of sensitivity for ex-vivo promoter approaches, where cells are isolated from a patient via e.g. a blood draw, the cells are transfected with a synthetic biomarker, and expression of the biomarker is assessed to determine the presence of diseased cells, an experiment was performed dosing FLuc-bearing-lentivirus-transduced naive H1299 cells doped into a background of normal human PBMCs. Various numbers of transduced cells were doped into 5 million isolated human PBMCs (half the approximate number of cells obtained from an 8 ml blood draw), and the samples were processed and analyzed for luciferase expression. The results are presented in FIG. 24 (FIG. 24), which estimates that the limit of detection using FLuc as a synthetic biomarker using this approach is 3-10 "diseased" reporter-active cells per 5 million normal cells.

Example 12.—Cancer-Activated DNA Constructs Differentiate Tumor-Bearing and Healthy Mice The survivin-SEAP nanoplasmid (nDNA-Survivin-SEAP) was formulated with in vivo JetPEI, a linear polyethylenimine derivative that was also used in PoC experiments (FIGS. 16A-16D). DNA nanoplasmids, like DNA minicircles, eliminate bacterial backbones and the need for antibiotic resistant genes as a transformation selected marker using a growth restrictive non-coding, antisense RNA sequence. Sharing similar properties of enhanced expression, DNA nanoplasmids are produced without using a complex recombination event, thus, DNA nanoplasmids can achieve robust expression and can be manufactured at scale equivalent to regular DNA plasmids. Significant efforts were used to optimize and characterize the formulations prior to in vivo application. Thus, the nanoplasmid/JetPEI polyplexes, and any ternary transfection complexes used at Earli, are characterized by size, charge and polydispersity. The optimization process also took into consideration the properties of encapsidation efficiency, serum stability and the ability to protect the payload against nucleases. Collectively, these optimizations provide a system with enhanced sensitivity and transfection capabilities.

Figures 26A, 26B, 26C, 26D, 26E, 26F:
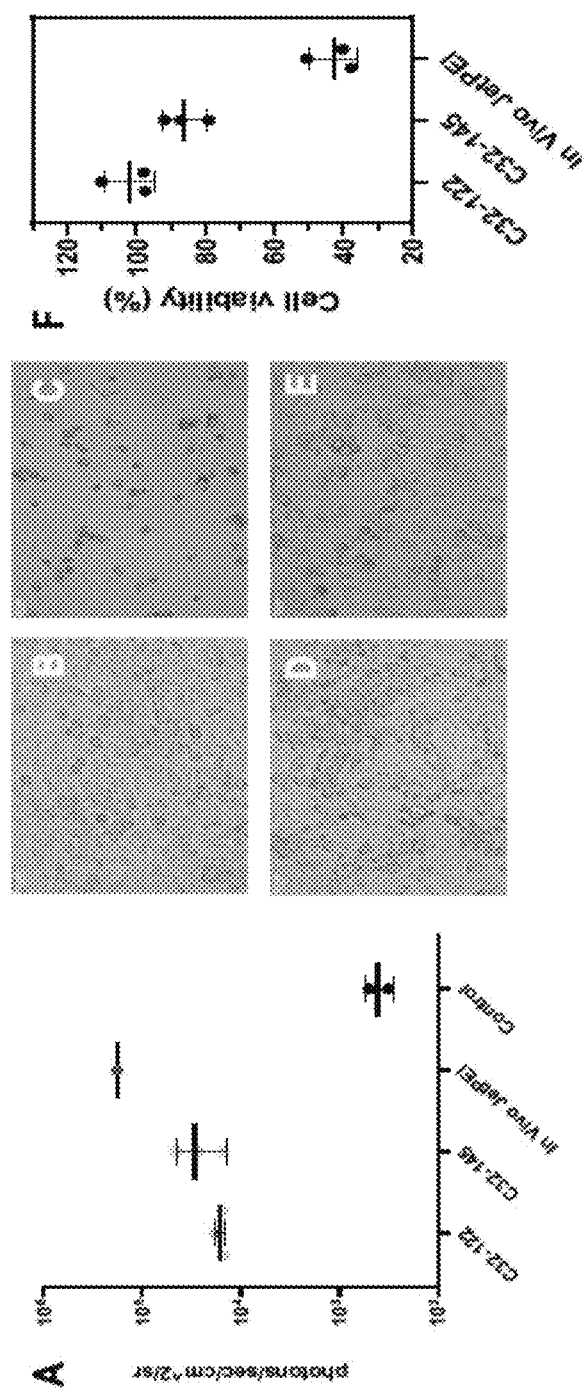
FIGS. 26A-26F illustrate in vivo efficacy and in vitro cytotoxicity of polymer/DNA complex.

A formulation of 15 μg of nDNA-Survivin-SEAP with JetPEI was generated, characterized and was injected intravenously into animals with modest tumor burden. The results indicate that at the highest differential point on Day 4 there was a 36-fold increase in SEAP levels over non-tumor-bearing animals that were dosed with identical levels of the formulated nanoplasmids (FIG. 26, see JetPEI delivery). The sensitivity was dramatically increased and the overall level of specificity, as assessed in the difference in signal to noise ratio was increased over ten-fold. The decline of cancer-activated expression of SEAP in the latter portion of the current study is likely due to cell division and a loss of the DNA templates from the nucleus. Because multiple timepoints showed an elevation of SEAP levels, an AUC analysis was performed for each mouse. The AUC across all days provided 19-fold differential than non-tumorigenic animals dosed with the nanoplasmids. Given the tightness of intragroup data for each cohort and the clear differentiation in SEAP levels, it was not surprising that the ROC analysis yielded 100% sensitivity and 100% specificity. DNA delivery using related poly((β-amino ester)s C32-122 and C32-145 (see e.g., Mol Ther. 2007 July; 15(7):1306-1312. for structures) was also shown; such delivery agents had somewhat less efficient delivery than JetPEI (FIG. 26A) but somewhat lower toxicity (FIG. 26F).

Example 13.—Assess Cancer-Activated DNA Constructs in Different Tumor Models

To avoid complexities associated with assessment of tumor size using bioluminescent-based techniques, tumor models in which disease burden can be determined via caliper measurements including subcutaneous tumors or models in which disease burden presents near the external surface of the animals are used. At least two orthotopic models are studied where the tissues are accessible to physical measurements with calipers. Characterization of each of the cell line used in the patient derived xenograft (CDX) is performed prior to the establishment of each model. Additional validation is performed by in vitro transfection to confirm SEAP expression form the cancer-activated DNA constructs. When possible, tumorigenic models with intact immune systems are used.

Figure 25:
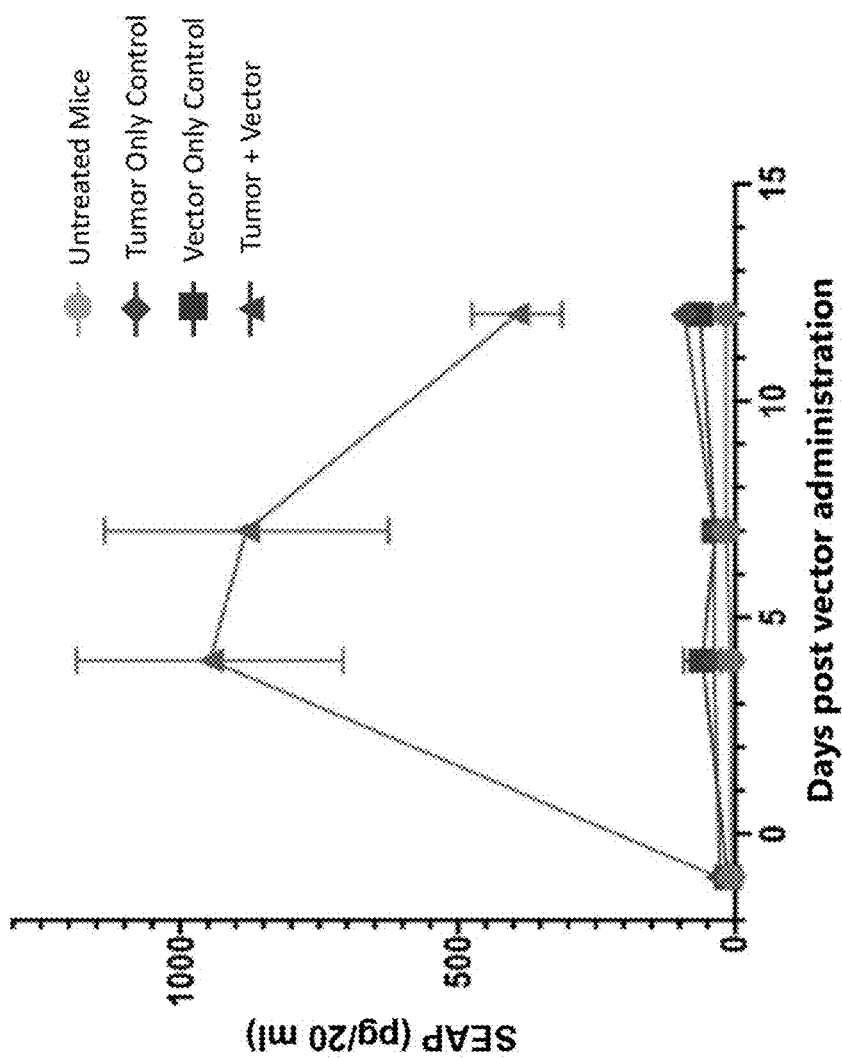
FIG. 25 illustrates the results of the experiment of Example 12, cancer-activated DNA constructs differentiate tumor-bearing and healthy mice: following intravenous administration of surviving-SEAP DNA nanoplasmids, whole blood was collected by submandibular bleeds and processed into plasma. SEAP assays were performed on 20 µl aliquots. Cohort size are n=5.

The activity of biomarker expression from nDNA-Survivin-SEAP using a syngeneic mammary tumor model established by injecting $1\times10^6$ 4T1 cells into the mammary fat pad of Balb/c nude mice is initially characterized. The formulated vector is administered by intravenous injection into cohorts of tumor-bearing animals when the tumors attain sizes of either 20 mm³, 50 mm³, 100 mm³ or 200 mm³. Plasma is collected from animals by submandibular bleeds at day −2 (pre-injection) as well as day 2, 6, 9, 13 post-injection and will be processed for SEAP quantification and AUC and ROC analyses from all in vivo studies. Based on the precision of the data in FIG. 25, each cohort is comprised of five animals. The number of animals per cohort is increased to 10 or more to account for the potential loss in precision and differentiation of SEAP signal.

At terminal necropsy, tissues with high levels of the vector but low levels of transcript are subjected to bisulfate sequencing in order to determine methylation status of the nanoplasmid DNA in those tissues. In addition, any organ that shows high levels of vector DNA or SEAP transcript will be collected in repeat experiments in order to determine if gross histologic changes are present, via an external third-party histology (Histowiz, Brooklyn, NY). Collectively, these data inform IND-enabling GLP toxicology and biodistribution studies.

Example 14.—Develop New DNA Delivery Agents for In Vitro Transfection

The challenges of systemic gene delivery provide the guiding principles for the development of new formulations. Nucleic acids need to be efficiently encapsulated into nanoparticles to protect the cargo from nuclease degradation. Once administered, the DNA nanoparticles may avoid detection and destruction by innate or adaptive immunosurveillance in the bloodstream. By a process known as extravasation, the nanoparticles are taken up by tissues, including the cancer cells, where the DNA template get released from delivery materials and be transported into the nucleus to act as a transcriptional template. Finally, the components of the nanoparticle shell are metabolized and eliminated from the cells without causing systemic toxicity. While these challenges have long confounded efforts to successfully develop non-viral DNA delivery technologies, there have been significant advances in the cytosolic delivery of RNA. This has been enabled by a new generation of ionizable cationic materials—both polymeric and lipid-based—that have superior cell uptake and endosomal escape profiles and have culminated in the regulatory approval and commercialization of the first RNAi drug (Alnylam's Patisiran). The development strategy is to leverage improvements in nucleic acid complexation, particle surface engineering, and endosomal escape, while conferring additional functionalities to improve nuclear transport, to achieve non-viral DNA delivery at diagnostically relevant concentrations for cancer detection.

For the development of new carriers for DNA nanoparticles, a two-pronged approach is taken. The first is based on making modifications to lipid nanoparticle (LNPs) formulations that have been developed using ionizable cationic lipids that have been used for the delivery of nucleic acids in gene therapy applications. LNPs are very efficient at condensing anionic DNA and show high encapsulation efficiency and have most often been applied to a wide variety of cargos for the transfection of hepatic tissues. However, ionizable lipid structure and degradation profiles can be engineered for distribution to other tissues. Because the inherent properties of size and charge are suitable for extravasation into the liver, the surface of these particles are modified with polymers to prolong circulation.

The second prong uses of novel polymer compositions with unique biodegradable properties. Designed with hydrolysable bonds, polymers called poly (β-amino esters (PBAEs) have demonstrated an efficient ability to transfect a wide variety of cells and are easily eliminated from the cell and body once their cargo has been delivered. DNA formulated in PBAE complexes coated with polyglutamic acid were able to efficiently target and transduce T cells in vivo. PBAE/DNA polyplexes using the new polymer subunits were prepared. These new PBAEs demonstrated significantly less toxicity than JetPEI (FIGS. 26B-F). Other classes of degradable cationic polymers are studied such as charge altering reversible transporters.

Clearance from the bloodstream by innate immunity through toll-like receptor activation, liver clearance, macrophage uptake or eliciting an adaptive immune response through neutralizing antibodies is a challenge to in vivo delivery. As a result, strategies which shield the surface charge of formulated particles to increase the persistence and the ability of complexes to be broadly distributed are investigated. Coating the nanoparticles with various ratios of covalently attached polyethylene glycol (PEG) is a strategy that is utilized. Methods to absorb polyglutamic acid (PGA) onto the surface of nanoparticles through electrostatic interactions are also developed. Yet, these coatings can substantially increase the particle size as well as reduce cell uptake, which can both compromise transfection efficiency. As a result, modifications are being considered to the subunits which may degrade the stealth coating over time or may make de-shielding on the nanoparticles in response to properties of the tumor microenvironment including low pH, hypoxia or local proteases.

Figure 27:
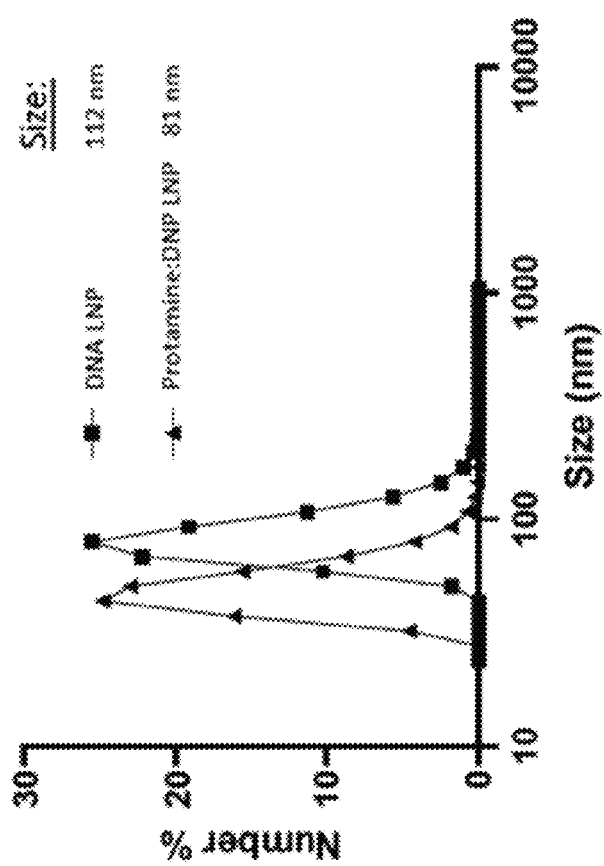
FIG. 27 illustrates that protamine condenses DNA polyplex size. 62.5 µg of DNA was condensed by thoroughly mixing with 130 µg of protamine at 1:1 v/v in 50 mM Sodium acetate buffer (pH=5.0). The DNA/protamine complex was then diluted to 1.5 mL with 50 mM Sodium acetate buffer (pH=5.0). The Protamine: DNA LNP was assembled on a NanoAssemblr (Precision NanoSystems) with a total flow rate of 12 mL/min. The as-prepared particles were dialyzed against 1×PBS for at least 18 h, after which the size was determined by a Zetasizer.

The DNA-delivering capability is increased of LNPs and polymeric nanoparticles by including specific nuclear-targeting moieties that can retain DNA compaction and enhance nuclear localization by passive diffusion or directed transport. One such potential nuclear delivery agent is protamine, which is comprised of arginine rich sequences that bind DNA in a non-specific manner and is believed to act as a histone substitute for stabilization of DNA during sperm head condensation. The addition of protamine may generate delivery complexes that are significantly more compact. As can be seen in FIG. 27, the pre-incubation of DNA with protamine, resulted in the production of modestly smaller lipid nanoparticle complexes. It remains to be determined if the relatively smaller particles have enhanced transduction properties. Incorporating a microtubule-associated sequences (MTAS) and nuclear localization signals (NLS) into the formulations disclosed here may also be used to enhance nuclear transport.

A rigorous set of in vivo physical characterization methods are employed, including understanding the encapsulation efficiency, size, charge and heterogeneity of the formulations, and stability in serum containing physiological buffer, in order to assess the quality of our formulations prior to testing biodistribution and efficacy in animal models. The parameters for the polyplexes may include: (1) sizes ranging from 75 nm-150 nm (2) a net neutral charge or slightly negative surface charge (3) possess a polydispersity index of less than 0.15 (4) have an efficiency of encapsulation of greater than 85% and (5) serum stability greater than 30 minutes.

Figure 28:
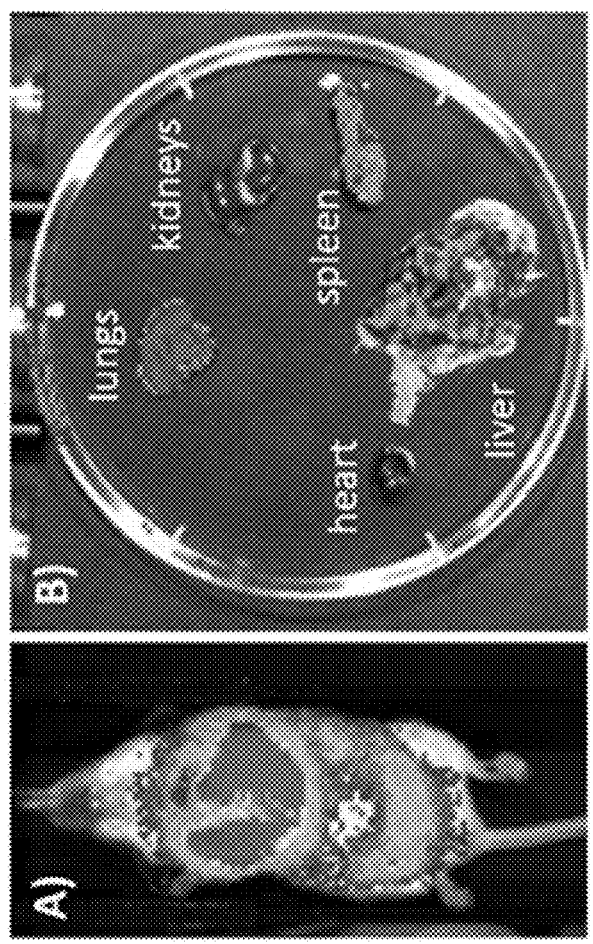
FIG. 28 illustrates an example of using luciferase to determine biodistribution of delivery formulations. A) In vivo bioluminescence imaging (BLI) of a mouse administered a tail vein injection with 40 mg of a CMV luciferase vector that had been formulated in JetPEI. Four days post administration, the mouse was anesthetized, administered D-luciferin substrate and imaged now on an AMI-HT (Spectral Instruments Imaging). B) After in vivo imaging, the mouse was sacrificed, and organs harvested for ex vivo BLI.

Initial in vivo testing for biodistribution and transfection strength is performed with formulated complexes of DNA nanoplasmids which utilize the strong constitutive CMV promoter to drive the expression of firefly luciferase (FIG. 28). Batches of approximately 20 different formulations are tested per experiment. Cohorts of Balb/c mice (n=3 per cohort) are injected with formulated complexes containing 25 µg of the DNA nanoplasmid. Blood samples taken at intermediate timepoints are used for comprehensive clinical chemistry, whereas terminal bleeds are used for hematology as well as cytokine analysis to define the toxicity profile of the nanoparticle formulations that produce high levels of luminescence in vivo or ex vivo. Further, animals with higher levels of luminescence have additional organs collected for a more extensive biodistribution analyses by QPCR for estimation of DNA vector copy numbers. Additional tissues to be collected include brain, gonads, injection site and bone marrow.

Formulations with broad distribution and luminescence equivalent to or superseding the levels provided by the control JetPEI group are moved into efficacy studies. As with biodistribution and safety studies, the new polyplexes may demonstrate efficacy that is similar or is better than the same nanoplasmid formulated with JetPEI. The use of the new formulations may also result in low background levels of SEAP in non-tumor bearing animals.

Example 15.—Scaling the Cancer-Activated Nanoplasmid Platform into Larger Animal Models While many oncology-based drugs have been tested and validated with the context to explore tumor xenografts established in murine models, these systems have inherent limitations including a combination of one or more of the following: a lack of genetic diversity and a suitable tumor microenvironment, a heterogeneity between tumor types regarding enhanced permeability and retention (EPR) as well as the propensity of many, but not all, of these models to be established in animals with severely compromised immune systems or completely lacking an immune system. Moving the platform into naturally occurring cancers in larger animal models obviates many of these limitations. Likewise, one challenge with the use of murine xenograft models is trying to comprehend the scaling of safe and efficacious dosing, particularly when considering the enormous difference in scale between a young murine species that weighs 20-35 grams and the average weight of a human adult in North America exceeds 65 kilograms. In translating our platform into canine models, a wide variety of naturally occurring types of tumors are evaluated in a diverse range of animal sizes, depending upon the breed of dog.

Figures 29A, 29B:
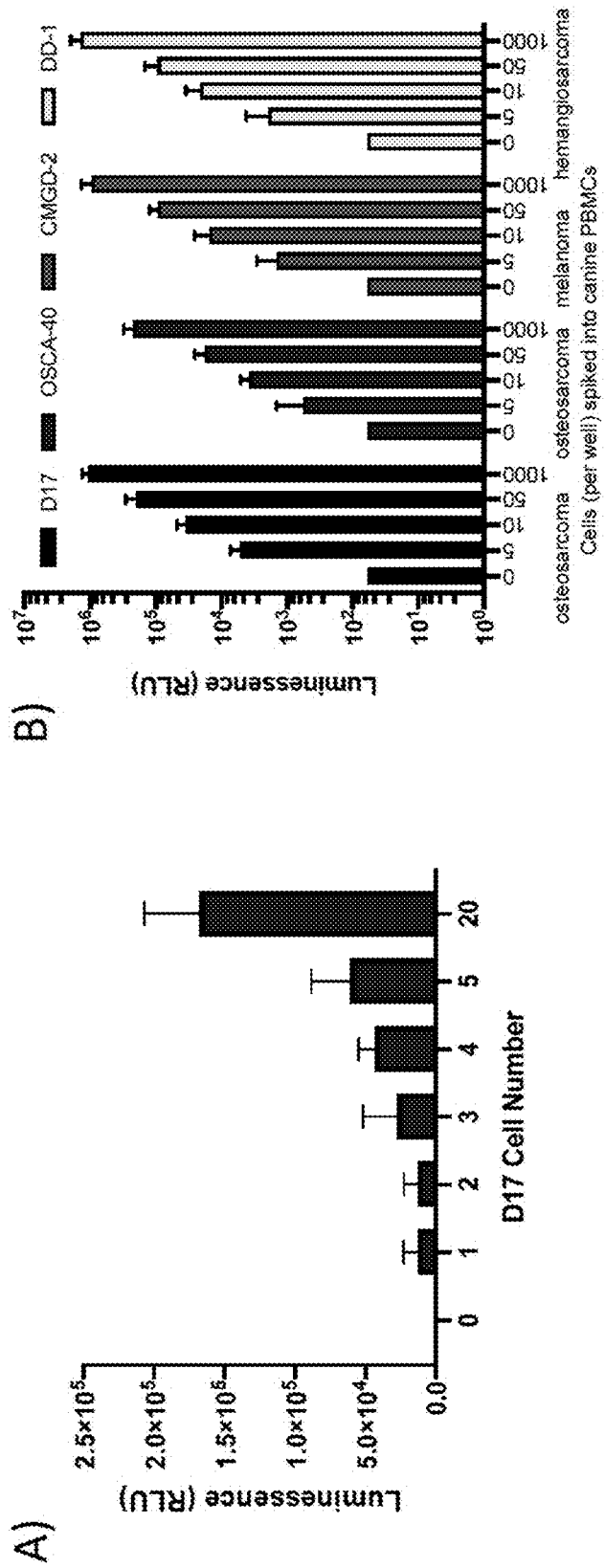
FIGS. 29A and 29B illustrates sensitivity and specificity of Ad-Survivin-FLuc in an ex vivo assay in canine PBMCs and cells derived from canine tumors. Naïve, untransduced cells derived from various subtypes of canine malignancies including osteosarcoma, melanoma and hemangiosarcoma were spiked into 5e5 canine PBMCs and then transduced with 0.3 MOI of Ad-Survivin-FLuc. A) Analysis demonstrates single cell detection of A17 osteosarcoma cells or B) robustness of detection across cells derived from multiple tumor types.

As to the nature of the test article, the initial studies are performed with a construct comprised of the human survivin promoter driving the expression of the human SEAP protein. The degree of identity between the sequences in the human and canine survivin promoter is conserved. Transient transfection of the nDNA-Survivin-SEAP construct into cells derived from canine cancers indicate that the promoter is functional in a wide variety of canine cells (FIGS. 29A and 29B).

For the in vivo efficacy studies, only dogs with malignant tumors will be enrolled. Information are collected on the dogs age, size, weight, breed as well as current treatments (if any). If available, the clinics are also providing additional information on current treatments, tumor staging, concomitant radiological data. For the initial studies, animals that have high existing burden of disease and are treatment naïve are enrolled, though a desire for expeditious treatment may require us to relax requirements on the latter. Three dosing groups with n=3 dogs per cohort are injected with a formulated cancer-activated nanoplasmid via an intravenous route of administration. Three additional dogs that may be terminally ill from non-cancerous diseases may be used as controls if they can be enrolled, though it may prove difficult to ascertain that the animals are truly cancer-free. A blood draw covering clinical chemistry and hematology will be taken just prior to dosing as well as 1, 2, 4, and 6 hours post dosing for PK data. Additional blood samples will be collected 3, 6, 9, 12 and 15 days after dosing to monitor for clinical chemistry as well as detect the presence of the human SEAP in plasma. Additional blood parameters may be collected based on the results of the acute toxicity studies. When possible, clinicians collect samples from a subsequent biopsy or surgical resection of the tumor after the administration of the disclosed test article and pass along the materials. Following nucleic acid isolation, the samples for the presence of nanoplasmid DNA QPCR and for the presence of the SEAP transcript by RT-QPCR are interrogated. RT-QPCR are used to assess the relative levels of survivin transcript within the tumors.

Example 16.—an Ex Vivo Approach for the Use of Cancer-Activated Synthetic Biomarker Constructs As a general tool for large-scale detection of early cancers, the development costs could be significantly reduced, and timelines appreciably shortened if we had the capability of employing the cancer-activated synthetic biomarker expression system in an ex vivo setting. A number of recent reports have been published indicating that live circulating tumor cells (CTCs) could be isolated and expanded ex vivo, maintaining biological function unique to those cells thus making it possible to apply the disclosed cancer-activated synthetic biomarker platform to these cells. The number of these cells that are shed into the blood might be small.

Ex vivo application of the cancer-activated synthetic biomarker platform may not be limited to trying to take advantage of dysregulated expression in CTCs. A number of groups have identified blood-based biomarkers of cancer by comparing the gene expression profiles from PBMCs isolated from breast cancer patients versus expression profiles from healthy volunteer blood or from whole blood of lung cancer patients. In addition, a cell-based in vivo sensor for activated M2 macrophages that had been engineered with a tumor-activatable synthetic biomarker expression system has been reported. Collectively, at least at a transient level, non-tumorigenic cells in the same milieu as cancer cells may have transiently altered transcriptional profiles that may be exploited in an ex vivo approach using the disclosed cancer-activated biosynthetic marker platform. Collectively, any cell population, including CTCs, that may have an altered gene expression profile as a result of cancer can be referred to as a "Transcriptionally Altered Cell" or TAC for short.

The cellular portion of whole blood, i.e. the PBMCs and other cells present, can be interrogated with the disclosed cancer-activated biomarker constructs by using recombinant adenoviruses or lentiviruses with broad tropism for efficient delivery. Many different cell types are amenable high efficiency gene transfer with recombinant viruses resulting in the ability to introduce dozens or even hundreds of copies of each transcriptional unit on a per cell basis. Each of those transcriptional units may drive the expression of analytes, such as luciferase, with high sensitivity levels that can be easily quantified.

In addition to highly sensitive reporters, the ability to efficiently transduce a wide range of cell types should confer enhanced sensitivity, as measured by increased signal output, since efficient transduction eliminates the need to enrich specific subtypes of cells or rare populations such as EpCAM-positive CTCs.

Figure 24:
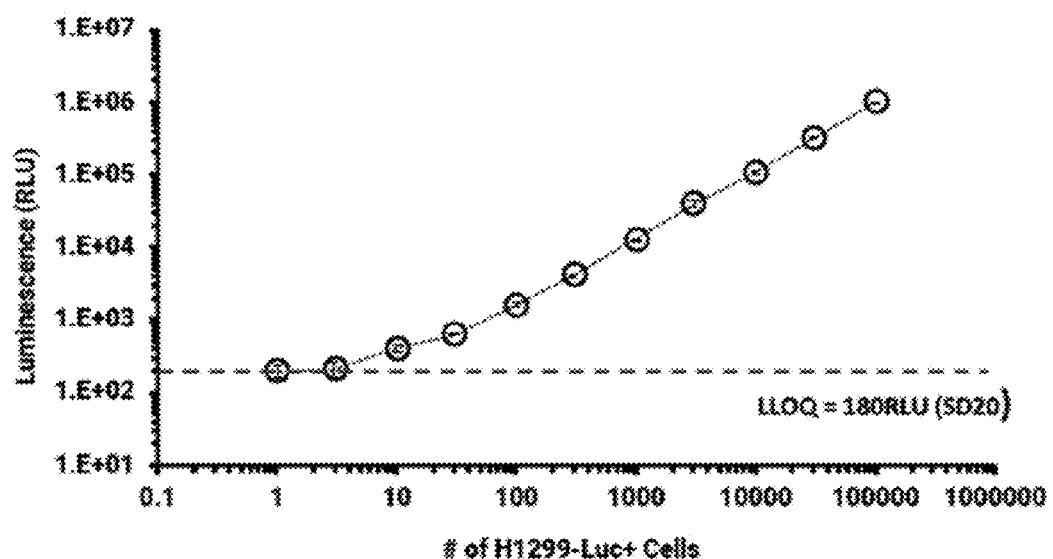
FIG. 24 illustrates the results of the experiment of Example 11, doping FLuc expressing cells into normal PBMCs, demonstrating that the limit of detection for such a detection method is at least 3-10 diseased cells per 5 million normal PBMCs.

To ascertain the theoretical sensitivity of an ex vivo assay, H1299 cells that were engineered to constitutively express the firefly luciferase (FLuc) protein, were spiked into 5e6 PBMCs from healthy volunteers, the approximate number of cells from a standard 8 mL blood draw. Following processing, a linear relationship of luciferase expression to spiked H1299s was noted with a detection limit between 3-10 cells (FIG. 24). In order to understand if our viral vectors could transduce cancer cells in a complex mixture of human PBMCs, a recombinant adenovirus containing the human survivin promoter to drive expression of firefly luciferase (Ad-Survivin-FLuc) was used to transduce a mixture increasing number of naïve (unmanipulated) H1299 cells in the context of 5e6 PBMCs from healthy volunteers. Derived from a human non-small cell lung carcinoma cell line, H1299 cells have demonstrated high levels of survivin expression and thus should provide robust luciferase expression if transduced with our vector. Following a 2-day incubation period, luciferase activity analyses demonstrated that the sensitivity of the ex vivo assay can detect as few as 2 of the naïve cells spiked into 5e6 human PBMCs (FIGS. 30A and 30B) indicating the ability to transduce and detect cancerous cells with this platform in complex mixtures. In order to ascertain specificity, samples containing only PBMCs were transduced with Ad-CMV-FLuc (FIG. 30C, blue column) resulting in robust luciferase expression and demonstrating that cells within the PBMC fraction are capable of being transduced by adenovirus. The lack of measurable luciferase activity from PBMCs transduced with Ad-Survivin-FLuc (FIG. 30C, red column) versus non-transduced PBMCs (FIG. 30C, gray column) indicates that the vector only produces a robust signal in the presence of the cells with dysregulated survivin expression, such as the H1299 cells spiked into the PBMCs in FIG. 31B.

Figure 31:
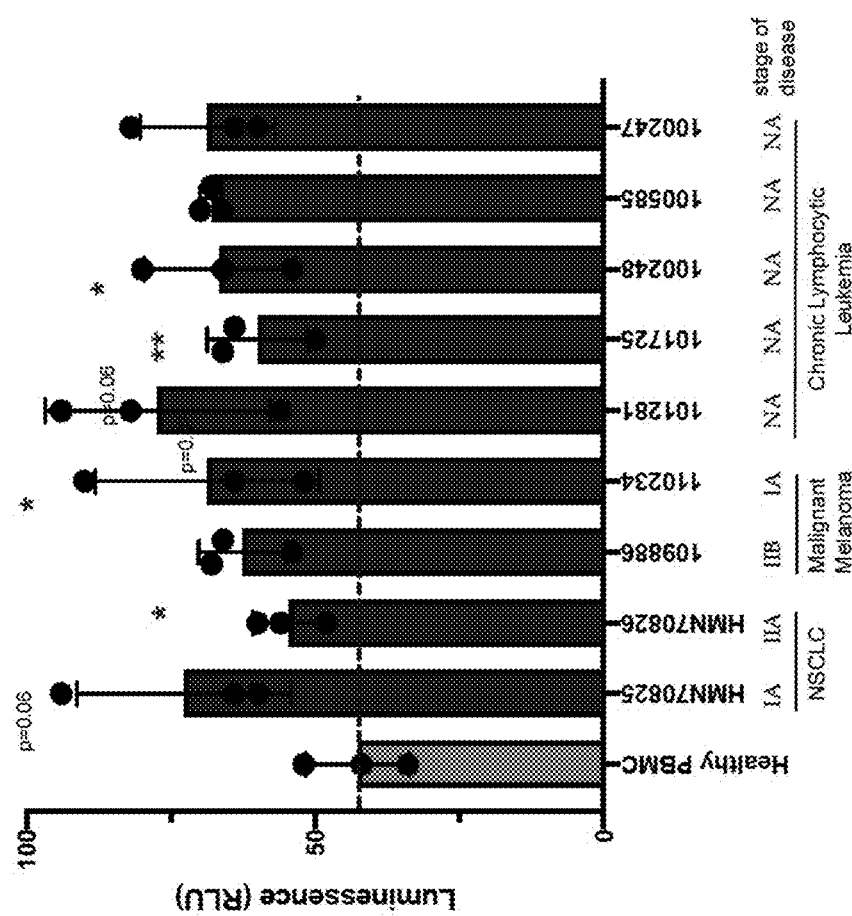
FIG. 31 shows that Ad-survivin-FLuc distinguishes cancer vs normal in an ex vivo assay on human PBMCs. Commercially available samples of human PBMCs from normal healthy volunteers and cancer patients were enumerated, and then equivalent numbers of cells were transduced at consistent MOI with Ad-survivin-Fluc and then the samples split into triplicate. Following incubation for three days, the cells were lysed and analyzed for luciferase activity. Data is calculated as the average and Std Dev of the triplicate sample measurements. P-values were calculated by Students T-test relative to normal PBMCs.

Similar experiments were performed in which the same Ad-Survivin-Fluc vector was used to transduce samples containing $5 \times 10^5$ canine PBMCs that had been spiked with naïve canine cancer cells derived from dog tumors. High levels of canine survivin expression have also been previously reported in canine tumors including osteosarcoma. Although the survivin promoter used in the vector was of human origin, the similarity between the promoter sequences from the two species resulted in robust production of the luciferase reporter. Sensitivity for detection of canine tumor cells was down to the single cell level (FIG. 29A) and detected cells derived from multiple canine tumor types (FIG. 29B). Finally, an initial set of human PBMCs derived from normal healthy volunteers as well as from cancer patients were procured from commercial sources. Following transduction with the Ad-Survivin-Fluc construct, the samples were incubated over 72 hours, lysed and assay for luciferase activity (FIG. 31). Normal PBMCs healthy human volunteers set the baseline, while the individual cancer-derived patient samples had elevated luciferase levels. Surprisingly several of the samples with statistically significant data were collected from patients with Stage 1 and Stage 2. The results with this experiment were obtained as a proof of concept study and there are parameters that must be optimized, such as using an alternative promoter or combinations of promoters to impact the specificity and rate of detection.

Figure 32A:
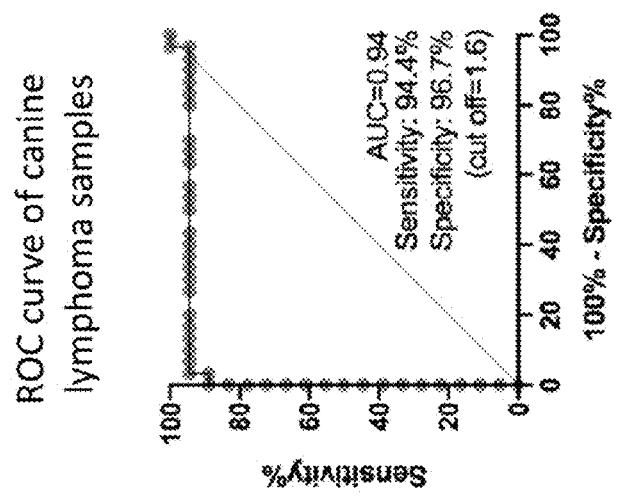
FIGS. 32A and 32B show a diagnostic performance of survivin-activated luciferase expression in discerning healthy canine individuals and canine lymphoma cancer patients. (A) Comparison of the fold-change in luminescence expression of healthy canine individuals (n=31) and canine lymphoma cancer patients (n=17). (B) Diagnosis predictive capacity of survivin-activated luciferase activity to distinguish canine lymphoma cancer subjects and healthy canine subjects.
Figure 32B:
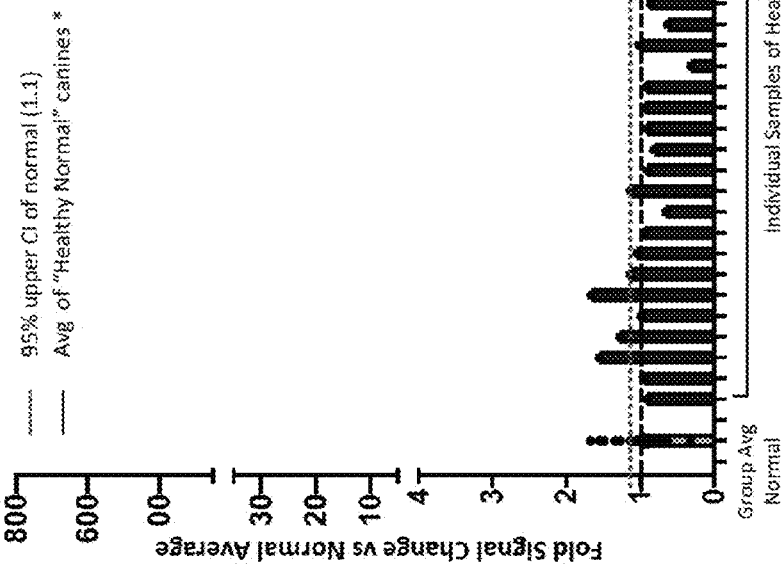

Example 17.—Canine Studies Using the First-Generation Ex Vivo Assay Demonstrates 89% Detection Rate of Lymphoma Peripheral blood mononuclear cells (PBMCs) were separated from canine whole blood using a BD Vacutainer® CPT™ mononuclear cell preparation tube (BD Biosciences, 362753). Separated PBMCs were resuspended in RPMI medium (ATCC, 302001) supplemented with heat-inactivated fetal bovine serum (VWR, 89510-184), penicillin-streptomycin antibiotic (Gibco, catalog 15140-122), and L-glutamine (ThermoFisher, 25030081). Cell viability was determined by trypan blue dye exclusion (Gibco, T10282). The ex vivo bioassay was performed in the following manner: $3 \times 10^6$ PBMCs were seeded into a single well of a 96-well plate (VWR, 10861) in a final volume of 200 microliters. Cells were then transduced at a MOI of 0.3 with an adenoviral vector engineered to contain the firefly luciferase reporter gene driven by the BIRC5/Survivin promoter. Transduced cells were allowed to incubate at 37° C. (5% CO2) for 72 hrs. Afterwards, medium was removed, and cells were lysed in the well with 20 microliters of passive lysis buffer (Promega, E1910). The lysate was then transferred into a single well of a 96-well white solid assay plate (Corning, CLS3912), followed by the addition of 100 microliters of luciferase substrate buffer (Promega, E4550). Luminescence was measured at 0.3 second integration time using a Promega GloMax Navigator microplate reader. All data were collected and analyzed with Graphpad Prism. FIG. 32A shows a comparison of the fold-change in luminescence expression of healthy canine individuals (n=31) and canine lymphoma cancer patients (n=17). FIG. 32B shows a diagnosis predictive capacity of survivin-activated luciferase activity to distinguish canine lymphoma cancer subjects and healthy canine subjects.

Example 18.—Development of Combinatorial Cancer Detection Approach Using Combinatorial Detection of Cancer-Activated Promoters The cascades of regulatory sequences that drive the expression of those dysregulated genes can be coupled into the cancer-activated biosynthetic marker platform to drive the specificity and sensitivity required for improved cancer detection rates with a high degree of accuracy beyond simply looking for the gene product alone.

New promoters were identified by applying a bioinformatics approach to compliment previously published literature on dysregulated gene expression in malignancies. For the former, an analysis of TCGA is initiated, which has curated over 20,000 primary cancer samples, from 33 types of cancer against pair matched normal tissues. A wide variety of other databases, such as the ICGC and the Clinical Proteome Tumor Analyses Consortium (CPTAC), may also be used.

The workflow permits using a series filters, including a slider bar to select custom levels and threshold of signal to noise ratios across specific tumor types and matched normal controls. The ability to filter on tumor staging is critical since dysregulated gene expression patterns that occur in early stage cancers is studied first. Lastly, a biodistribution filter may help predict the relative contribution of leaky promoters within the context of the different types of transfection agent formulations disclosed herein.

The validity and rationale of many of the steps were tested by applying the filters independently against the TCGA database and assessing the target output versus published literature. In preliminary data, threshold filters of signal-to-noise ratios in cancer vs matched normal tissues were applied and the stringency progressively increased. For normal tissue expression data, Genotype-Tissue Expression (GTEx) database data was selected as an indicator of healthy tissue than the matched normal tissue data in the TCGA. Results from this step revealed overexpression of 88 genes across a substantial number of tumor types versus normal tissues. For validation of cancer-activated promoter activity, the regulatory sequences from each of newly identified promoter targets were: (a) subcloned into a nanoplasmid expression construct in such a way that they are operably linked to a reporter open reading frame (e.g. a luciferase gene) to produce a promoter-reporter construct; and (b) transfected into various cancer cell lines. Specifically, several of the individual promoter sequences were subcloned upstream of the cloning sequences of the firefly (Photinus) luciferase reporter gene and firefly luciferase biomarker expression was analyzed after each vector was transfected into a cancer-derived tissue culture cell line. A separate expression plasmid utilizing the CMV promoter (a strong constitutive promoter) to drive expression of the orthogonal Renilla luciferase was added into the transfection mixture at a concentration 50-fold less than the test plasmid as an internal control (assessment of the level of Renilla luciferase produced from the co-transfected plasmid permitted normalization of transfection efficiency between different cell lines).

The cell lines utilized for transfection comprised: (a) immortalized cell lines selected with the guidance of expression data from the Cancer Cell Line Encyclopedia (CCLE); (b) primary patient human cell lines established from tumors of different origin (e.g. lung, breast and pancreatic tissues); and (c) canine cell lines isolated from various types of dog/canine cancers. In vitro transfections of each cell line were performed using Lipofectamine 3000 as a transfection agent (although the disclosed cassettes are also readily transferrable into recombinant expression constructs for packaging into recombinant viral vectors such as adenovirus). The relative levels of each gene were confirmed by assessment of firefly (Photinus) luciferase activity, after normalization for transfection using the Renilla luciferase signal. The activity of each of the reporter constructs in cell lines derived from cancers of the liver, ovaries and pancreas is shown in FIGS. 33A, 33B and 33C respectively, wherein the relative intensity of expression of each reporter-promoter construct in each cell line is depicted via color density (particular values are shown with reference to the density legend to the right of each graph). Likewise, the activity of the reporter-promoter constructs in cell lines derived from breast and lung is shown in FIGS. 33D and 33E respectively. The same data was generated by transfection of the promoter-reporter construct into untransformed cell lines derived from normal lung tissues; the corresponding low levels activity of the same promoters in these untransformed cells (FIG. 33F) demonstrates that many of these cancer-activated promoters may be useful in differentiating tumors from non-tumor bearing tissues (see e.g., MMP12, CEP55, COL10A1, KIF20A, FAM111B, CST1, AFP, BIRC5, UBE2C, MCM10) Finally, the activity of the constructs were tested in cell lines derived from canine cancers (FIG. 34). Despite the promoter sequences having been derived from human sequences, many of the constructs yielded robust activity in the canine cell line (see e.g., BIRC5, BIRC5-501, CXCR4, UBE2C, TRIP13, CDKN3, MCM10, CDC20, TROAP, CEP55, KIF20A, and cBIRC5).

Example 19.—Development of a Multiplex Nucleic Acid/Protein Barcode Approach Combining Cancer-Activated Promoters to Improve Cancer Detection Rates The use of easily quantifiable synthetic barcodes as surrogate reporter markers of activity can simplify analyses where multiple outputs are to be analyzed (e.g., simultaneous analysis of the activity of multiple promoters in a cell line). In order to assess if the simultaneous use of multiple unique promoters (i.e. multiplexing) would be amenable to the use of nucleic acid or protein barcodes, a series of individual promoters were first cloned upstream a of secreted luciferase molecule. The secretory domain/signal peptide from the IL-6 protein was included at the termini of the protein, resulting in the conversion of luciferase (normally restricted to intracellular localization) into an enzyme that is secreted from the cells. Subsequently, multiple DNA constructs were generated in which a series of unique nucleic acid barcodes were introduced in between the sequences encoding for the signal peptide and the luciferase (FIG. 35A, see colored inserts between signal peptide and luciferase). In this case, barcodes of 6 nucleotides were used (which can provide up to 4096 unique sequences for detection) though longer stretches of nucleotides (e.g. at least 6, at least 7, at least 9, at least 10, at least 11, at least 12, at least 13, at least 14, at least 15, at least 16, at least 17, at least 18, at least 19, or at least 20 or more) are envisioned and provide for a larger set of combinations. Because each of the different promoters is assigned to a corresponding unique barcode due to inclusion in the expressed protein construct, one should be able to quantify the levels of barcode as a surrogate marker for reporter expression. These signal peptide-barcode-luciferase constructs were then subcloned into nanoplasmid constructs under the control of several candidate reporters such as ABCC4, BIRC5 (aka survivin), UBE2C, COL10A1, E2F, FOXA1 and MCM10 and were transfected into cell lines for expression analysis (see e.g., FIG. 36).

Each of the barcoded, cancer-activated luciferase reporter constructs was tested individually by transfecting parallel plates of H1299 cells. A DNA construct that contained a CMV-driven Renilla luciferase expression cassette was included into each transfection mixture to control for variances in transfection efficiency. Following incubation for an additional 24 hours post transfection, the cells were lysed and assayed for luminescence activity. FIG. 35B demonstrates that, when tested individually, each of the promoters produces discernable levels of luciferase activity within the H1299 cells. Furthermore, the differences in relative strength of each of the promoters results in a unique pattern. In a parallel set of plates, H1299 cells were transfected with a mixture of the barcoded constructs containing equimolar ratios of each of the cancer-activated reporter constructs. Following a 24-hour incubation of the transfected cells, RNA was purified from the cells and analyzed by next generation sequencing to quantify the relative levels of barcoded sequences present within the cellular transcripts. FIG. 35C demonstrates that transfection of the H1299 cells with the multiplexed mixture resulted in a nearly identical pattern of relative expression pattern as the individually transfected cells as assessed by the quantities of the nucleic acid barcode. The results from these combined experiments provide evidence that these unique cancer-activated expression patterns from the promoters, or fingerprints, may have utility in identifying molecular characteristics associated with the specific cells that are being tested. Furthermore, barcoding can provide a useful surrogate for assessing the relative activity levels in a multiplex format.

Example 20.—Use of an Antibody Capture Format to Detect Activation of Promoter-Reporter Constructs in Cells The types of barcodes used to identify unique promoter/reporter combinations may exist as nucleic acid sequences (FIG. 35A). Alternatively, barcodes may take other forms including, but not limited to, the use of small proteins or peptide fragments. In this current example, the peptide barcode fragment that is fused onto the termini of the luciferase reporter protein allows the secreted luciferase to be captured in an enzyme-linked immunosorbent assay (ELISA) based assay in which the each of the individual wells of the 96-well plate used to perform the assay are first coated with a specific antibody with affinity to one of the unique protein tags. In this way, each well in the plate can be used to pan and surveil the complex mixture of secreted media for the presence of individual peptide tags. To demonstrate the utility of this approach, an engineered secreted form of a luciferase protein was generated by fusion of the secretory domain/signal peptide from IL-6 to the N-terminus of luciferase. Additionally, a series of peptide epitope-based barcodes were introduced in between the sequences encoding for the signal peptide and the luciferase (FIG. 36A). Epitope tags included for the initial proof of concept experiments included FLAG (DYKDDDDK), HA (a fragment of the influenza hemagglutinin protein), V5 (a peptide domain present on the V and P proteins from the paramyxovirus known as simian virus 5) and HSV (a fragment of a protein expressed by the herpes simplex virus). Using the same CMV promoter, the four constructs with unique protein barcodes were individually transfected into cells (see e.g., FIG. 36A). After an additional 24 hours of incubation, aliquots of media were collected from each transfection condition and panned in a 96-well plate in which each of the individual wells were coated with a unique capture antibody against each of the unique epitopes (FIG. 36B). Following a series of buffer washes to eliminate non-specific binding, each of the wells was developed for luciferase activity. The data, shown in FIG. 36C, demonstrates that H1299 cells transfected with a construct harboring a specific protein epitope could be captured in wells coated with the corresponding antibodies—as demonstrated by the large increase in luciferase activity. Conversely, that same lysate does not result in an increase in luminescence in non-antibody coated control wells (blocked for non-specific binding) or in wells coated with antibodies against other epitopes. Taken together, these data demonstrate that the barcodes can provide a physical method of separation in addition to providing a surrogate measure of relative promoter activity.

Figures 37A, 37B, 37C:
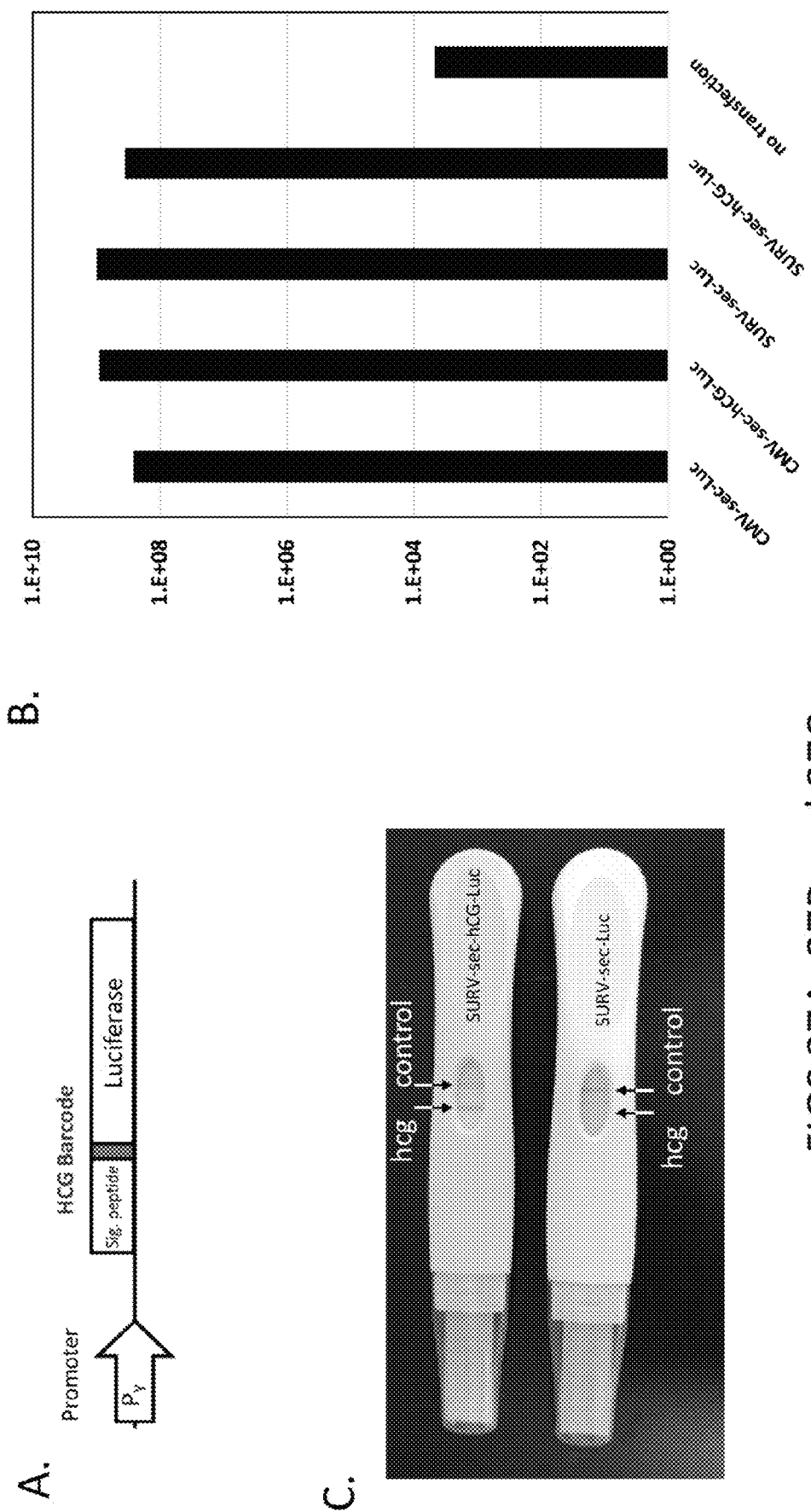
FIGS. 37A, 37B, and 37C show a design of a reporter-promoter construct designed to use an off-the-shelf lateral flow assay (e.g. a pregnancy hCG lateral flow immunoassay)
Figure 38:
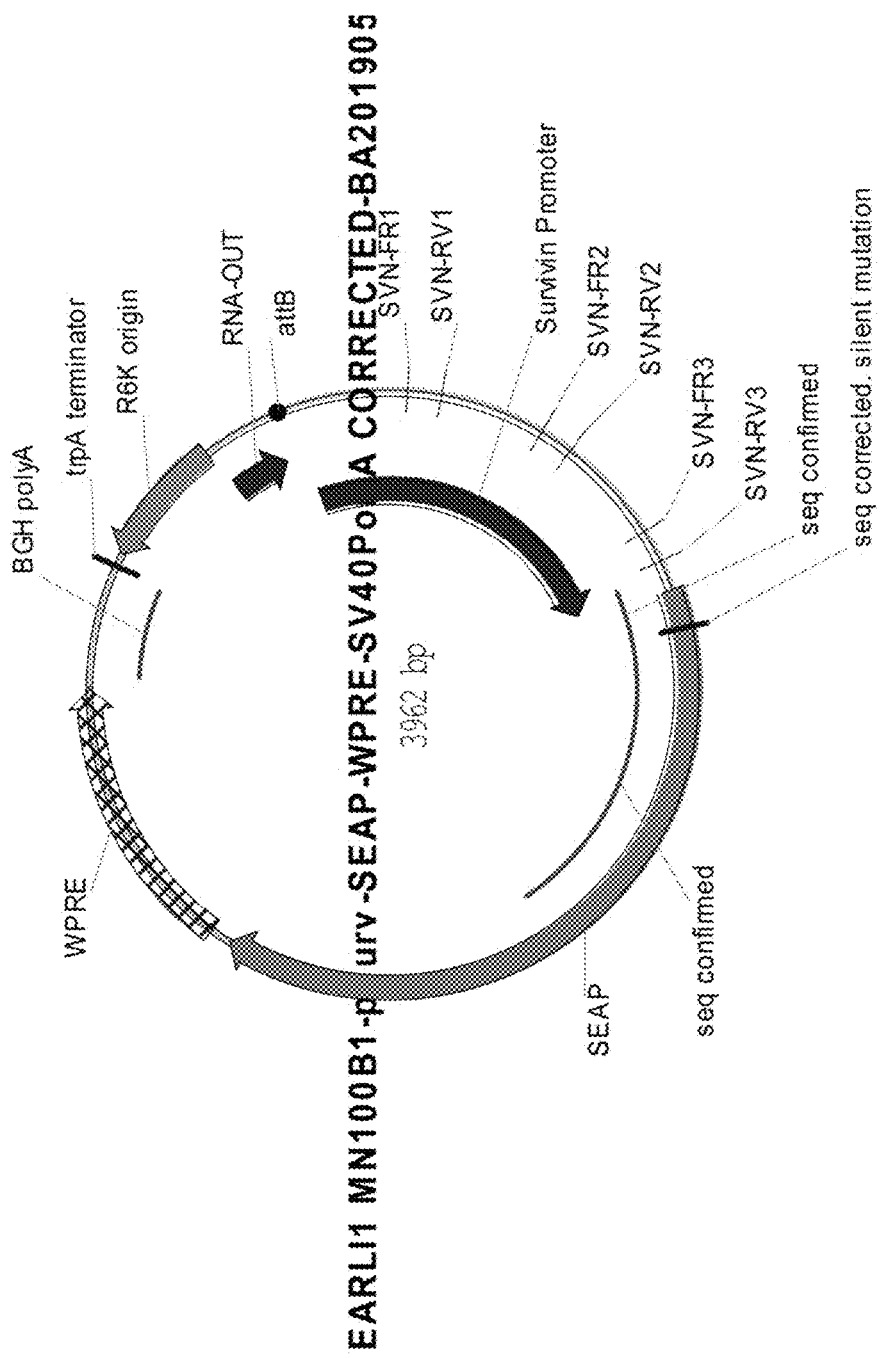
FIG. 38 shows an example nanoplasmid-based promoter construct as described herein. The sequence of this construct is outlined in SEQ ID NO: 5, and involves a mini-R6K origin, an RNA-out selectable marker, a survivin promoter, SEAP as a reporter, and a WPRE element.

The peptide fragment used as a barcode can be designed for alternative screening and panning methodologies other than an ELISA format. Alternative assay formats may be useful to provide fast, high quality and inexpensive solutions for the detection of specific analytes. As one example, a rapid test using lateral flow chromatography with patient urine has been commonly employed for the detection of human pregnancy. In order to test the ability of alternative assay formats for the detection of cancer-activated markers, the nucleic acid barcodes inserted into our secreted variant of luciferase was replaced with the beta subunit from the human chorionic gonadotropin (hCG) protein. The chimeric protein was cloned downstream of either the cancer-activated human survivin promoter or from the CMV promoter (FIG. 37A). In order to ensure that the hCG barcode did not alter the activity of the constructs, parallel sets of plates of H1299 cells were transfected with recombinant DNA constructs. Identical DNA constructs lacking the hCG barcode served as controls. A DNA construct that contained a CMV-driven *Renilla* luciferase expression cassette was included into each transfection mixture to control for variances in transfection efficiency. Following incubation for an additional 24 hours post transfection, the cells were lysed, and aliquots of the media were assayed for luminescence activity. As seen in FIG. 37B, the presence of the hCG bar code did not substantially alter the expression of the luciferase reporter protein. Finally, 700 µl of the supernatant of the same was loaded into a commercial pregnancy test kit, bought at a local pharmacy. Seen in FIG. 37, the pregnancy test kit can clearly differentiate between cells which had been transfected with a non-barcoded variant of the reporter versus the hCG barcoded variant.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Embodiments

The following are intended to be example embodiments and not limiting in any way.
1. A method comprising:
   (a) administering to a subject a composition, wherein said composition induces expression of a biomarker in a diseased cell preferentially over expression of said biomarker in non-diseased cells in said subject such that a relative ratio of said biomarker expressed in said diseased cell over said non-diseased cells is greater than 1.0;
   (b) detecting said biomarker; and
   (c) using said biomarker detected in (b) to determine that said subject has said diseased cell at an accuracy of at least 70%.
2. The method of embodiment 1, wherein said relative ratio is a concentration ratio.
3. The method of embodiment 1 or 2, wherein said biomarker is detected in biological sample from said subject.

4. The method of embodiment 3, wherein said biological sample is a bodily fluid from said subject.
5. The method of embodiment 4, wherein said biological sample is a blood or blood-based sample from said subject.
6. The method of embodiment 3, wherein said biological sample is a gaseous sample from said subject.
7. The method of embodiment 6, wherein said gaseous sample is the breath from said subject.
8. The method of any one of embodiments 1-7, wherein said subject is a mammal.
9. The method of embodiment 8, wherein said subject is human.
10. The method of embodiment 8, wherein said subject is an animal.
11. The method of embodiment 3, wherein said biological sample is measured in situ within the human or animal body.
12. The method of any one of embodiments 1-11, wherein said composition comprises a nucleic acid vector.
13. The method of embodiment 12, wherein said vector is selected from the group consisting of nanoplasmids, plasmids, minicircles, recombinant viral vectors, or CELiDs.
14. The method of embodiment 13, wherein said composition comprises a minicircle, wherein said minicircle is a self-replicating minicircle.
15. The method of embodiment 14, wherein said self-replicating minicircle comprises an S/MAR element.
16. The method of any one of embodiments 1-15, wherein said composition comprises a promoter operably linked to a nucleotide sequence encoding the biomarker.
17. The method of embodiment 16, wherein said promoter drives expression in a plurality of different types of diseased cells in said subject.
18. The method of any one of embodiments 1-17, wherein said promoter drives expression of said biomarker in said diseased plurality of different types of diseased cells preferentially over expression of said biomarker in said non-diseased cells in said subject.
19. The method of embodiment 17, wherein promoter is selected from the group consisting of a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-GlcNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

20. The method of any one of embodiments 1-19, wherein said biomarker is selected from the group consisting of MRI reporter, a PET reporter, a SPECT reporter, a photoacoustic reporter, a bioluminescent reporter, a fluorescent reporter, chemiluminescent reporter, luminescence reporter, colorimetric reporter, a quantifiable nucleic acid biomarker, and any combination thereof.

21. The method of embodiment 20, wherein the quantifiable nucleic acid biomarker is an engineered miRNA.

22. The method of embodiment 20 or 21, wherein detection of said biomarker determines a location of the diseased cell.

23. The method of any one of embodiments 1-22, wherein said biomarker is detectable in a bodily sample of said subject, by non-invasive imaging or combinations thereof.

24. The method of embodiment 23, wherein said biomarker is detected using a blood-based assay.

25. The method of any one of embodiments 1-24, wherein said composition further comprises a transfection agent.

26. The method of embodiment 25, wherein said transfection agent is a linear or branched polyethylenimine, nanoparticle, lipophilic particle, solid nanoparticle, peptide, micelle, dendrimer, polymeric composition, hydrogel, synthetic or naturally derived exosome, virus-like particles, or any combination thereof.

27. The method of any one of embodiments 1-26, wherein said composition further comprises a pharmaceutically acceptable carrier.

28. The method of embodiment 27, wherein said pharmaceutically acceptable carrier is selected from the group consisting of water, peanut oil, soybean oil, mineral oil, sesame oil, saline, gum acacia, gelatin, starch paste, talc, keratin, colloidal silica, urea, aqueous dextrose, glycerol solution, glucose, lactose, sucrose, glycerol monostearate, sodium chloride solution, propylene, glycol, cocoa butter, or ethanol.

29. A method for treating a subject having or suspected of having a disease, comprising administering to said subject a composition that induces expression of a therapeutically effective agent by a diseased cell associated with said disease preferentially over expression of said therapeutically effective agent by non-diseased cells in said subject such that a relative concentration of said therapeutically effective agent expressed by said diseased cell over said non-diseased cells is greater than 1.0, which therapeutically effective agent treats said subject at a therapeutic efficacy of at least 10% as determined by a decrease in a cell population of said diseased cell.

30. The method of embodiment 29, wherein said composition comprises a vector.

31. The method of embodiment 29 or 30, wherein said composition comprises a promoter operably linked to a nucleotide sequence encoding a therapeutically effective agent.

32. The method of embodiment 31, wherein said therapeutically effective agent is selected from the group consisting of a therapeutically effective polypeptide, small activating RNA (saRNA), microRNA (miRNA), small interfering RNA (siRNA) or combinations of polypeptide and said nucleic acids.

33. The method of embodiment 32, wherein said therapeutically effective agent is selected from the group consisting of HSVtk, cytosine deaminase, DT diaphorase, nitroreductase, guanine phosphoribosyl transferase, purine nucleoside phosphorylase, thymidine phorphorylase, carboxylesterase, folylpolyglutamyl synthetase, carboxypeptidase A1, carboxypeptidase G2, cytochrome P-450.

34. A composition comprising a first nucleic acid sequence encoding a first polypeptide or nucleic acid biomarker and a second nucleic acid sequence encoding a second polypeptide or second nucleic acid biomarker, wherein said composition is configured such that when said composition is in a cell: said second polypeptide or nucleic acid biomarker is expressed in an amount that reflects delivery of said first and said second nucleic acids to said cell, and said first polypeptide or nucleic acid biomarker is expressed differentially in a diseased cell versus a non-diseased cell.

35. The composition of embodiment 34, wherein:
(i) said cell induces expression of said first nucleic acid sequence in a diseased cell preferentially over expression of said first nucleic acid sequence in non-diseased cells, wherein said expressed first polypeptide or nucleic acid is a detectable biomarker or a therapeutic agent; and
(ii) said cell induces expression of said second nucleic acid sequence equally in diseased and in non-diseased cells and said second nucleic acid sequence yields said second polypeptide or nucleic acid biomarker that is not said detectable biomarker or said therapeutic agent, such that a level of expression of said second polypeptide or nucleic acid biomarker provides a control for assessing the relative level of said nucleic acid sequences in said cell.

36. The composition of embodiment 34 or 35, wherein in said composition said sequences comprising said first nucleic acid sequence encoding said first polypeptide and said second nucleic acid sequence encoding said second polypeptide are on independent genetic constructs.

37. The composition of any one of embodiments 34-36, wherein said first polypeptide is said detectable biomarker and said therapeutic agent.

38. The composition of any one of embodiments 34-37, wherein said cell is a diseased cell.

39. The composition of any one of embodiments 34-38, wherein said composition further comprises a vector comprising said first and said second nucleic acid.

40. The composition of embodiment 39, wherein said vector comprises:
   (a) a first promoter operably linked to said first nucleic acid sequence, wherein said promoter induces expression of said first nucleic acid sequence in a diseased cell preferentially over expression of said first nucleic acid sequence in non-diseased cells; and
   (b) a second promoter sequence that induces expression equally in diseased and in non-diseased cells and is operably linked to said second nucleic acid.

41. The composition of embodiment 39 or embodiment 40, wherein said vector is a non-viral vector.

42. The composition of embodiment 41, wherein said non-viral vector is a minicircle vector.

43. The composition of embodiment 39 or embodiment 40, wherein said vector is a nanoplasmid vector.

44. The composition of any one of embodiments 34-42, wherein said first and second polypeptides or nucleic acid biomarkers are detectable in a bodily sample of said subject, by non-invasive imaging or combinations thereof.

45. A method of detecting diseased cells in a subject, comprising administering a composition to said subject, wherein said composition comprises:
   a first nucleic acid sequence encoding a first polypeptide or nucleic acid biomarker and a second nucleic acid sequence encoding a second polypeptide or second nucleic acid biomarker,
      wherein said composition is configured such that when said composition is in a cell:
   (i) said cell induces expression of said first nucleic acid sequence in a diseased cell preferentially over expression of said first nucleic acid sequence in non-diseased cells, wherein said first polypeptide is a detectable biomarker or a therapeutic agent; and
   (ii) said cell induces equivalent expression of said second nucleic acid sequence equally in diseased and in non-diseased cells and said second nucleic acid sequence yields said second polypeptide that is not said detectable biomarker or said therapeutic agent, such that a level of expression of said second polypeptide provides a control for assessing the relative level of said nucleic acid sequences in said cell.

46. The method of embodiment 45, wherein in said composition said sequences comprising said first nucleic acid sequence encoding said first polypeptide or nucleic acid biomarker and said second nucleic acid sequence encoding said second polypeptide or nucleic acid biomarker are on independent constructs.

47. The method of embodiment 45 or embodiment 46, wherein said first polypeptide is said detectable biomarker and said therapeutic agent.

48. The method of any one of embodiments 45-47, wherein said cell is a diseased cell.

49. The method of any one of embodiments 45-48, wherein said composition further comprises a vector comprising said first and said second nucleic acid.

50. The method of embodiments 49, wherein said vector comprises:
   (a) a first promoter operably linked to said first nucleic acid sequence, wherein said promoter induces expression of said first nucleic acid sequence in a diseased cell preferentially over expression of said first nucleic acid sequence in non-diseased cells; and
   (b) a second promoter sequence that induces equivalent expression equally in diseased and in non-diseased cells and is operably linked to said second nucleic acid.

51. The method of embodiment 49 or embodiment 50, wherein said vector is a non-viral vector.

52. The method of embodiment 51, wherein said non-viral vector is a minicircle vector.

53. The method embodiment 49 or embodiment 50, wherein said vector is a nanoplasmid vector.

54. The method of any one of embodiments 45-52, wherein said first and second polypeptides are detectable in a bodily sample of said subject, by non-invasive imaging or combinations thereof.

55. A composition comprising
   a first nucleic acid sequence encoding a first polypeptide and
   a second nucleic acid sequence encoding a second polypeptide,
      wherein said composition is configured such that when said composition is in a cell: (i) said cell expresses said first nucleic acid sequence to yield said first polypeptide;
      (ii) said cell expresses said second nucleic acid sequence to yield said second polypeptide; and
      (iii) said first polypeptide and said second polypeptide expressed by said cell are configured to combine to form a heterodimer protein.

56. The composition of embodiment 55, wherein said first nucleic acid sequence and said second nucleic acid sequence are operably linked to a first genetic element and a second genetic element, wherein both said first genetic element and said second genetic element are selectively activated to express said first and said second polypeptide in a same diseased cell type.

57. The composition of embodiment 56, wherein said first or said second generic element is a promoter, an enhancer, or a miRNA-binding site.

58. The composition of any one of embodiments 55-57, wherein said heterodimer protein is an FRB/FKBP12 heterodimer, a split luciferase protein, or a split GFP protein.

59. The composition of embodiment 58, wherein said FRB/FKBP12 heterodimer linked to first and second halves of a Cre recombinase.

60. The composition of any one of embodiments 55-59, wherein said first and said second polypeptide are linked to a first and a second autofluorescent protein, wherein said first and said second autofluorescent protein form a FRET pair.

61. The composition of any one of embodiments 55-60, wherein said heterodimer protein is configured to modulate the activity of a diseased cell.

62. The composition of any one of embodiments 55-61, wherein said first polypeptide and said second polypeptide are on independent genetic constructs.

63. A method of detecting or treating a diseased cell, comprising administering a composition to a subject according to any one of embodiments 55-62, wherein said first and said second polypeptide are selectively transcribed or translated in said diseased cell.

64. The method of embodiment 63, comprising detecting said heterodimer protein.

65. A composition comprising a non-naturally occurring recombinant genetic construct comprising a sequence encoding a polypeptide or nucleic acid sequence, and wherein said sequence comprises a first promoter that selectively drives expression of said polypeptide or nucleic acid biomarker sequence in a plurality of different types of cells isolated from a subject when transduced into said cells ex vivo.

66. The composition of embodiment 65, comprising said cells.

67. The composition of embodiment 65 or 66, wherein said cells comprise cells found in blood or blood fractions, saliva, urine, stool, cerebrospinal fluid, semen, vaginal secretions, sputum, sweat, breast milk, synovial fluid, mucus (including rheum), tears, bile, gastric fluid, interstitial fluid, biopsies of tissues or epithelial cells that are naturally shed or specifically collected from the body (such as cheek cell scrapings), aqueous humor, amniotic fluid, pleural fluid or breath exhalation.

68. The composition of any one of embodiments 65-67, wherein said plurality of different types of cells are diseased or disordered cells.

69. The composition of embodiment 68, wherein said diseased or disordered cells are a plurality of different types of tumor cells.

70. The composition of any one of embodiments 65-69, wherein said first promoter is a pan-tumor specific promoter.

71. The composition of any one of embodiments 65-70, wherein said first promoter is a cancer-specific promoter.

72. The composition of any one of embodiments 65-71, wherein said first promoter is an endogenous promoter from said cells activated when the cell is in the diseased state.

73. The composition of any one of embodiments 65-72, wherein said recombinant genetic construct comprises retroviral, lentiviral, or adenoviral packaging elements or long terminal repeats.

74. The composition of any one of embodiments 65-73, wherein said recombinant genetic construct is a non-viral vector.

75. The composition of embodiment 74, wherein said non-viral vector is a minicircle vector.

76. The composition of any one of embodiments 65-75, wherein the composition has a certain diagnostic efficiency, wherein the diagnostic efficiency is measured in a diseased cell preferentially over expression of said biomarker in non-diseased cells in said subject such that a relative ratio of said biomarker expressed in said diseased cell over said non-diseased cells is greater than 1.0;
(b) detecting said biomarker; and (c) using said biomarker detected in (b) to determine that said subject has said diseased cell at an accuracy of at least 90%.

77. The composition of any one of embodiments 65-76, wherein said polypeptide or nucleic acid sequence is a reporter polypeptide and is selected from the group consisting of a photoacoustic reporter, a bioluminescent reporter, an autofluorescent reporter, a chemiluminescent reporter, a luminescent reporter, or a colorimetric reporter, a quantifiable nucleic acid biomarker, or any combination thereof.

78. The composition of embodiment 77, wherein said reporter polypeptide is a luminescent reporter, and said luminescent reporter is luciferase.

79. The method of any one of embodiments 65-78, wherein said polypeptide or nucleic acid sequence is a nucleic acid sequence, and is a ribozyme, a self-splicing intron, a microRNA, a RNA aptamer, or another type of quantifiable RNA biomarker.

80. The composition of embodiment 79, wherein said nucleic acid sequence biomarker is detectable by quantitative PCR, sequencing, or hybridization-based techniques.

81. The composition of any one of embodiments 65-80, wherein said cell is a diseased or disordered cell, wherein said genetic construct further encodes a second polypeptide that modulates the proliferation the diseased or disordered cell diseased cell under the control of a second promoter that selectively drives expression of said second polypeptide in said diseased or disordered cell.

82. A method for detecting a diseased or disordered cell ex-vivo, comprising delivering ex vivo a non-naturally occurring recombinant genetic construct to a population of cells isolated from a subject, wherein the non-naturally occurring recombinant genetic construct comprises:
a sequence encoding a polypeptide or nucleic acid biomarker sequence,
wherein said sequence comprises a first promoter that selectively drives expression of said polypeptide or nucleic acid biomarker sequence in a plurality of different types of cells isolated from a subject when transduced into said cells.

83. The method of embodiment 82, comprising isolating said population of cells.

84. The method of embodiment 83, comprising isolating said cells via a non-invasive method.

85. The method of embodiment 84, comprising obtaining the cells by saliva, sputum, sweat, urine, stool, semen, cervicovaginal secretions, breast milk, rheum, tears, or cheek epithelium.

86. The method of embodiment 85, comprising isolating cells via a minimally-invasive method.

87. The method of embodiment 86, comprising obtaining the cells by venipuncture, thoracentesis, amniocentesis, or gastric lavage.

88. The method of embodiment 87, comprising isolating said cells by biopsy.

89. The method of any one of embodiments 82-88, wherein said cells comprise cells found in blood or blood fractions, saliva, urine, stool, cerebrospinal fluid, semen, vaginal secretions, sputum, sweat, breast milk, synovial fluid, mucus (including rheum), tears, bile, gastric fluid, interstitial fluid, biopsies of tissues or epithelial cells that are naturally shed or specifically collected from the body (such as cheek cell scrapings), aqueous humor, amniotic fluid, pleural fluid or breath exhalation.

90. The method of any one of embodiments 82-89, comprising detecting said polypeptide or nucleic acid sequence.

91. The method of any one of embodiments 82-90, wherein said disease is cancer, an autoimmune disease, or a neurodegenerative disease.

92. The method of any one of embodiments 82-91, wherein said promoter is a pan-cancer specific promoter.

93. A composition comprising a vector, wherein said vector comprises a plurality of different promoters operably linked to a plurality of barcode molecules, wherein each said promoter drives expression of said plurality of barcode molecules in a cell, and wherein levels of said plurality of barcode molecules are indicative of a stage of a disease of said cell.

94. The composition of embodiment 93, wherein said stage of said disease of said cell is diseased, non-diseased or an intermediate state.

95. The composition of any one of embodiments 93-94, wherein said disease is cancer, wherein said plurality of different promoters comprises a first promoter activated in an early stage of cancer.

96. The composition of any one of embodiments 93-95, wherein said disease is cancer, wherein said plurality of different promoters comprises a second promoter activated in an intermediate stage of cancer.

97. The composition of any one of embodiments 93-96, wherein said disease is cancer, wherein said plurality of different promoters comprises a third promoter activated in a late stage of cancer.

98. The composition of any one of embodiments 93-97, wherein said vector is a non-viral vector.

99. The composition of any one of embodiments 93-98, wherein said non-viral vector is a minicircle vector.

100. The composition of any one of embodiments 93-97, wherein said vector is a nanoplasmid vector.

101. The composition of any one of embodiments 93-99, wherein when said plurality of barcode molecule comprises a plurality of polypeptide, each of said polypeptides is detectable by non-invasive imaging.

102. The composition of embodiment 101, wherein non-invasive imaging comprises photoacoustic, MRI, or PET imaging.

103. The composition of any one of embodiments 101, wherein each of said polypeptides is detectable in a bodily sample.

104. The composition of embodiment 103, wherein said bodily sample is blood or blood fractions, saliva, urine, stool, cerebrospinal fluid, semen, vaginal secretions, sputum, sweat, breast milk, synovial fluid, mucus (including rheum), tears, bile, gastric fluid, interstitial fluid, biopsies of tissues or epithelial cells that are naturally shed or specifically collected from the body (such as cheek cell scrapings), aqueous humor, amniotic fluid, pleural fluid or breath exhalation..

105. A method for detecting a stage of disease, comprising administering to a subject a composition comprising a vector, wherein said vector comprises:
   a plurality of different promoters operably linked to a plurality of different barcode molecules, wherein each said promoter drives expression of said plurality of barcode molecules in a cell,
   wherein levels of individual barcode molecule are indicative of a stage of a disease of said cell.

106. The method of embodiment 105, wherein said stage of said disease of said cell is diseased, non-diseased or an intermediate state.

107. The method of embodiment 105 or 106, said method determines nodules, masses of tissue or lesions in said subject as pre-cancerous, benign, dysplastic, or metastatic in nature.

108. The method of any one of embodiments 105-107, wherein said disease is cancer, wherein said plurality of different promoters comprises a first promoter activated in activated in an early stage of cancer.

109. The method of any one of embodiments 105-108, wherein said disease is cancer, wherein said plurality of different promoters comprises a second promoter activated in an intermediate stage of cancer.

110. The method of any one of embodiments 105-109, wherein said disease is cancer, wherein said plurality of different promoters comprises a third promoter activated in a late stage of cancer.

111. The method of any one of embodiments 105-110, wherein said vector is a non-viral vector.

112. The method of any one of embodiments 105-111, wherein said non-viral vector is a minicircle vector.

113. The method of any one of embodiments 105-110, wherein said vector is a nanoplasmid vector.

114. The method of any one of embodiments 105-112, wherein when said plurality of barcode molecules comprises a plurality of polypeptides, the method further comprises detecting at least one of said plurality of polypeptides by non-invasive imaging.

115. The method of embodiment 114, wherein non-invasive imaging comprises photoacoustic, MRI, SPECT, or PET imaging.

116. The method of any one of embodiments 105-115, comprising at detecting at least one of said plurality of barcode molecules in a bodily sample.

117. The method of embodiment 116, wherein said bodily sample is found in blood or blood fractions, saliva, urine, stool, cerebrospinal fluid, semen, vaginal secretions, sputum, sweat, breast milk, synovial fluid, mucus (including rheum), tears, bile, gastric fluid, interstitial fluid, biopsies of tissues or epithelial cells that are naturally shed or specifically collected from the body (such as cheek cell scrapings), aqueous humor, amniotic fluid, pleural fluid or breath exhalation.

118. The method of any one of embodiments 105-117, wherein said composition is administered intravenously, subcutaneously, intraventricularly, intrathecally, intracerebroventricularly, transdermally, intramuscularly, orally, by inhalation, nasally, rectally, intratumorally, proxi-tumorally, or into a lymph node in said subject.

119. A composition comprising an engineered nucleic acid encoding an expressible reporter gene that exhibits about 10% or less expression in normal cells versus diseased cells when compared to a recombinant nucleic acid comprising a reporter gene comprising a nucleic acid sequence of SEQ ID NO: 1 or SEQ ID NO: 2.

120. The composition of embodiment 119, wherein said engineered nucleic acid comprises a pan-tumor specific promoter.

121. The composition of embodiment 120, wherein said pan-tumor specific promoter comprises a transcriptional response element.

122. The composition of embodiment 121, wherein said transcriptional response element comprises a modified p53 response element.

123. The composition of embodiment 122, wherein a modification within said modified p53 response element results in decreased promoter activity in normal cells relative to diseased cells.

124. The composition of embodiment 122 or 123, wherein a modification within said modified p53 response element results in increased promoter activity in diseased cells relative to normal cells.

125. The composition of any one of embodiments 119-124, wherein said disease is cancer.

126. A method comprising administering to a subject a composition according to any one of embodiments 119-125.

127. The method of embodiment 126, wherein said subject is suspected of having cancer.

128. The method of embodiment 125 or 126, wherein said composition is administered intravenously, subcutaneously, intraventricularly, intrathecally, intracerebroventricularly, transdermally, intramuscularly, orally, by inhalation, nasally, rectally, intratumorally, proxi-tumorally, or into a lymph node in said subject.

129. A composition that exhibits about 10% or less expression in normal cells versus diseased cells and comprises a recombinant nucleic acid comprising a nucleic acid sequence encoding a reporter gene that includes one or more miRNA binding sequences in a 3' untranslated region of said reporter gene.

130. The composition of embodiment 129, wherein binding of an miRNA expressed in said diseased cells to at least one of the one or more miRNA binding sequences results in reduced translation of said reporter gene or reduction of a half-life of an mRNA encoding said reporter gene.

131. The composition of embodiment 129 or 130, wherein said diseased cell is a cancer cell.

132. The composition of embodiment 131, wherein said reporter gene exhibits increased expression in said cancer cell due to downregulation of at least one miRNA expressed in said cancer cell.

133. The composition of any one of embodiments 129-132, wherein said composition comprises at least two miRNA binding sequences in said 3' untranslated region of said reporter gene, wherein two miRNA binding sequences have a substantially identical nucleotide sequence capable of binding to a same miRNA.

134. The composition of any one of embodiments 129-133, wherein said composition comprises at least two miRNA binding sequences in said 3' untranslated region of said reporter gene, wherein said at least two miRNA binding sequences have different nucleotide sequences, each of said different nucleotide sequences capable of binding to different miRNAs.

135. The composition of any one of embodiments 129-134, wherein said recombinant nucleic acid comprises DNA.

136. The composition of any one of embodiments 129-135, wherein said recombinant nucleic acid is a synthetic or in vitro-transcribed mRNA.

137. The composition of any one of embodiments 129-136, wherein said one or more miRNA binding sequences comprise at least one miR-15, miR-16, let-7, miR-122 or miR-34 binding sequence.

138. A method of detecting a diseased cell, comprising administering to a subject a composition according to any one of embodiments 129-137.

139. The method of embodiment 138, comprising detecting said reporter gene.

140. The method of embodiment 138, wherein said subject is suspected of having cancer.

141. The method of any one of embodiments 138-140, wherein said composition is administered intravenously, subcutaneously, intraventricularly, intrathecally, intracerebroventricularly, transdermally, intramuscularly, orally by inhalation, nasally, rectally, intratumorally, proxi-tumorally, or into a lymph node in said subject.

142. A composition exhibiting significantly longer expression of synthetic biomarker versus plasmid DNA, minicircle DNA, or nanoplasmid DNA comprising a linear vector comprising a double-stranded nucleic acid comprising a promoter operatively linked to a DNA sequence encoding a synthetic biomarker, wherein a forward and a reverse strand of said double-stranded nucleic acid are covalently linked on each of their terminal ends, wherein said promoter induces expression of said synthetic biomarker in a diseased cell preferentially over expression of said synthetic biomarker in a non-diseased cell such that a relative concentration of said synthetic biomarker expressed in said diseased cell over said non-diseased cell is greater than 1.0.

143. The composition of embodiment 142, wherein said linear vector comprises inverted terminal repeats (ITRs) flanking said promoter operatively linked to said DNA sequence encoding said synthetic biomarker, wherein said ITRs are derived from an Adeno-Associated Virus (AAV).

144. The composition of embodiment 143, wherein said AAV is AAV2.

145. The composition of any one of embodiments 142-144, wherein said promoter drives expression of said synthetic biomarker selectively in a plurality of diseased cells in a subject.

146. The composition of embodiment 145, wherein said promoter is a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyl-transferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCA5) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

147. The composition of any one of embodiments 142-146, wherein said an MRI reporter, a PET reporter, a SPECT reporter, a photoacoustic reporter, a bioluminescent reporter, a fluorescent reporter, chemiluminescent reporter, luminescence reporter, colorimetric reporter, a quantifiable nucleic acid biomarker and combinations thereof and any combination thereof.

148. The composition of embodiment 147, wherein detection for said biomarker determines a location of the diseased cell.

149. A method of identifying a diseased cell, comprising administering to a subject a composition according to any one of embodiments 142-148, and detecting said synthetic biomarker, wherein said synthetic biomarker is expressed in a diseased cell preferentially over expression of said synthetic biomarker in non-diseased cells in said subject such that a relative concentration of said synthetic biomarker expressed in said diseased cell over said non-diseased cells is greater than 1.0.

150. The method of embodiment 149, wherein said diseased cell is a cancer cell.

151. The method of any one of embodiments 149-150, wherein detecting said synthetic biomarker identifies said diseased cell with an accuracy of at least 90%.

152. The method of any one of embodiments 149-151, comprising detecting said synthetic biomarker using a non-invasive imaging method performed on said subject.

153. The method of any one of embodiments, wherein non-invasive imaging comprises photoacoustic, MRI, SPECT, or PET imaging.

154. The method of any one of embodiments 149-153, comprising detecting said synthetic biomarker in a bodily sample from said subject.

155. The method of embodiment 154, wherein said bodily sample is found in blood or blood fractions, saliva, urine, stool, cerebrospinal fluid, semen, vaginal secretions, sputum, sweat, breast milk, synovial fluid, mucus (including rheum), tears, bile, gastric fluid, interstitial fluid, biopsies of tissues or epithelial cells that are naturally shed or specifically collected from the body (such as cheek cell scrapings), aqueous humor, amniotic fluid, pleural fluid or breath exhalation.

156. The method of embodiment 154, wherein the sample is a biopsy sample.

157. The method of embodiment 152 or 153, wherein detection of said biomarker determines a location of the diseased cell.

158. The method of any one of embodiments 149-157, wherein said subject is suspected of having cancer.

159. The method of any one of embodiments 149-158, wherein said composition is administered intravenously, subcutaneously, intraventricularly, intrathecally, intracerebroventricularly, transdermally, intramuscularly, orally, by inhalation, nasally, rectally, intratumorally, proxi-tumorally, or into a lymph node in said subject.

160. A composition exhibiting significantly longer expression of synthetic biomarker versus plasmid DNA or minicircle DNA comprising a linear vector comprising a double-stranded nucleic acid comprising a promoter operatively linked to a DNA sequence encoding a therapeutically effective agent, wherein a forward and a reverse strand of said double-stranded nucleic acid are covalently linked on each of their terminal ends, wherein said promoter induces expression of said therapeutically effective agent in a diseased cell preferentially over expression of said synthetic biomarker in a non-diseased cell such that a relative concentration of said therapeutically effective agent expressed in said diseased cell over said non-diseased cell is greater than 1.0.

161. The composition of embodiment 160, wherein said linear vector comprises inverted terminal repeats (ITRs) flanking said promoter operatively linked to said DNA sequence encoding said therapeutically effective agent, wherein said ITRs are derived from an Adeno-Associated Virus (AAV).

162. The composition of embodiment 160 or 161, wherein said AAV is AAV2.

163. The composition of any one of embodiments 160-162, wherein said promoter drives expression of said therapeutically effective agent selectively in a plurality of diseased cells in a subject.

164. The composition of embodiment 163, wherein said promoter is a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-G1cNAc:betaGal beta-1,3-N-acetylglucosaminyl-transferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695 (ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory subunit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member C1 (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof 165. The composition of any one of embodiments 160-164, wherein said therapeutically effective agent is selected from the group consisting of a therapeutically effective polypeptide, small activating RNA (saRNA), microRNA (miRNA), small interfering RNA (siRNA) or combinations of said therapeutically effective polypeptide and said nucleic acids. 166. The composition of embodiment 165, wherein said therapeutically effective agent is selected from the group consisting of HSVtk, cytosine deaminase, DT diaphorase, nitroreductase, guanine phosphoribosyl transferase, purine nucleoside phosphorylase, thymidine phorphorylase, carboxylesterase, folylpolyglutamyl synthetase, carboxypeptidase A1, carboxypeptidase G2, cytochrome P-450.

167. A method of treating a diseased cell, comprising administering to a subject a composition according to any one of embodiments 160-166, and detecting said synthetic biomarker, wherein said synthetic biomarker is expressed in a diseased cell preferentially over expression of said synthetic biomarker in non-diseased cells in said subject such that a relative concentration of said synthetic biomarker expressed in said diseased cell over said non-diseased cells is greater than 1.0.

168. The method of embodiment 167, wherein said diseased cell is a cancer cell.

169. The method of any one of embodiments 167-168, wherein said subject is suspected of having cancer.

170. The method of any one of embodiments 167-169 wherein said composition is administered intravenously, subcutaneously, intraventricularly, intrathecally, intracerebroventricularly, transdermally, intramuscularly, orally, by inhalation, nasally, rectally, intratumorally, proxi-tumorally, or into a lymph node in said subject.

171. A composition comprising a non-viral vector expressing a synthetic biomarker, wherein said synthetic biomarker exhibits about 10% or less expression in normal organ cells versus diseased cells.

172. The composition of embodiment 171, wherein said organ is liver, kidney, spleen, or a combination thereof.

173. The composition of embodiment 171, wherein said non-viral vector comprises a recombinant nucleic acid encoding a promoter operably linked to a synthetic biomarker.

174. The composition of embodiment 173, wherein said promoter is a Survivin promoter (BIRC5), a CXCR4 promoter, an ATP binding cassette subfamily C member 4 (ABCC4) promoter, an anterior gradient 2, protein disulphide isomerase family member (AGR2) promoter, activation induced cytidine deaminase (AICDA) promoter, an UDP-GlcNAc:betaGal beta-1,3-N-acetylglucosaminyltransferase 3 (B3GNT3) promoter, a cadherin 3 (CDH3) promoter, a CEA cell adhesion molecule 5 (CEACAM5) promoter, a centromere protein F (CENPF) promoter, a centrosomal protein 55 (CEP55) promoter, a claudin 3 (CLDN3) promoter, a claudin 4 (CLDN4) promoter, a collagen type XI alpha 1 chain (COL11A1) promoter, a collagen type I alpha 1 chain (COL1A1) promoter, a cystatin SN (CST1) promoter, a denticleless E3 ubiquitin protein ligase homolog (DTL) promoter, a family with sequence similarity 111 member B (FAM111B) promoter, a forkhead box A1 (FOXA1) promoter, a kinesin family member 20A (KIF20A), a laminin subunit gamma 2 (LAMC2) promoter, a mitotic spindle positioning (MISP) promoter, a matrix metallopeptidase 1 (MMP1) promoter, a matrix metallopeptidase 12 (MMP12) promoter, a matrix metallopeptidase 13 (MMP13) promoter, a mesothelin (MSLN) promoter, a cell surface associated mucin 1 (MUC1) promoter, a phospholipase A2 group IID (PLA2G2D) promoter, a regulator of G protein signaling 13 (RGS13) promoter, a secretoglobin family 2A member 1 (SCGB2A1) promoter, topoisomerase II alpha (TOP2A) promoter, a ubiquitin D (UBD) promoter, a ubiquitin conjugating enzyme E2 C (UBE2C), a USH1 protein network component harmonin (USH1C), a V-set domain containing T cell activation inhibitor 1 (VTCN1) promoter, a Hexokinase type II promoter, a TRPM4 promoter, a stromelysin 3 promoter, a surfactant protein A promoter, a secretory leukoprotease inhibitor promoter, a tyrosinase promoter, a stress-inducible grp78/BiP promoter, an interleukin-10 promoter, an α-B-crystallin/heat shock protein 27 promoter, an epidermal growth factor receptor promoter, a mucin-like glycoprotein promoter, an mts1 promoter, an NSE promoter, a somatostatin receptor promoter, a c-erbB-3 promoter, a c-erbB-2 promoter, a c-erbB4 promoter, a thyroglobulin promoter, an α-fetoprotein promoter, a villin promoter, an albumin promoter, a glycoprotein A33 promoter, the B cell-specific Moloney leukemia virus insertion site 1 promoter, a cyclooxygenase-2 promoter, a fibroblast growth factor promoter; a human epidermal growth factor receptor 2, a human telomerase reverse transcriptase promoter; a kinase domain insert containing receptor promoter; a rad51 recombinase promoter; TTF-1, an urokinase-type plasminogen activator receptor promoter, a ubiquitin conjugating enzyme E2 T (UBE2T) promoter, a checkpoint kinase 1 (CHEK1) promoter, an epithelial cell transforming 2 promoter (ECT2), a BCL2-like 12 (BCL2L12) promoter, a centromere protein I (CENPI) promoter, an E2F transcription factor 1 (E2F1) promoter, a flavin adenine dinucleotide synthetase 1 (FLAD1) promoter, a protein phosphatase, Mg2+/Mn2+ dependent 1G (PPM1G) promoter, an ubiquitin conjugating enzyme E2 S (UBE2S) promoter, an aurora kinase A and ninein interacting protein (AUNIP) promoter, a cell division cycle 6 (CDC6) promoter, a centromere protein L (CENPL) promoter, a DNA replication helicase/nuclease 2 (DNA2) promoter, a DSN1 homolog, MIS12 kinetochore complex component (DSN1) promoter, a deoxythymidylate kinase (DTYMK) promoter, a G protein regulated inducer of neurite outgrowth 1 (GPRIN1) promoter, a mitochondrial fission regulator 2 (MTFR2) promoter, a RAD51 associated protein 1 (RAD51AP1) promoter, a small nuclear ribonucleoprotein polypeptide A' (SNRPA1) promoter, an ATPase family, AAA domain containing 2 (ATAD2) promoter, a BUB1 mitotic checkpoint serine/threonine kinase (BUB1) promoter, a calcyclin binding protein (CACYBP) promoter, a cell division cycle associated 3 (CDCA3) promoter, a centromere protein 0 (CENPO) promoter, a flap structure-specific endonuclease 1 (FEN1) promoter, a forkhead box M1 (FOXM1) promoter, a cell proliferation regulating inhibitor of protein phosphatase 2A (KIAA1524) promoter, a kinesin family member 2C (KIF2C) promoter, a karyopherin subunit alpha 2 (KPNA2) promoter, a MYB proto-oncogene like 2 (MYBL2) promoter, a NIMA related kinase 2 (NEK2) promoter, a RAN binding protein 1 (RANBP1) promoter, a small nuclear ribonucleoprotein polypeptides B and B1 (SNRPB) promoter, a SPC24/NDC80 kinetochore complex component (SPC24) promoter, a transforming acidic coiled-coil containing protein 3 (TACC3) promoter, a TBC1 domain family member 31 (TBC1D31) promoter, a thymidine kinase 1 (TK1) promoter, a zinc finger protein 695

(ZNF695) promoter, an aurora kinase A (AURKA) promoter, a BLM RecQ like helicase (BLM) promoter, a chromosome 17 open reading frame 53 (C17orf53) promoter, a chromobox 3 (CBX30) promoter, a cyclin B1 (CCNB1) promoter, a cyclin E1 (CCNE1) promoter, a cyclin F (CCNF), a cell division cycle 20 (CDC20) promoter, a cell division cycle 45 (CDC45) promoter, a cell division cycle associated 5 (CDCAS) promoter, a cyclin dependent kinase inhibitor 3 (CDKN3) promoter, a cadherin EGF LAG seven-pass G-type receptor 3 (CELSR3) promoter, a centromere protein A (CENPA) promoter, a centrosomal protein 72 (CEP72) promoter, a CDC28 protein kinase regulatory sub-unit 2 (CKS2) promoter, a collagen type X alpha 1 chain (COL10A1) promoter, a chromosome segregation 1 like (CSE1L) promoter, a DBF4 zinc finger promoter, a GINS complex subunit 1 (GINS1) promoter, a G protein-coupled receptor 19 (GPR19) promoter, a kinesin family member 18A (KIF18A) promoter, a kinesin family member 4A (KIF4A) promoter, a kinesin family member Cl (KIFC1) promoter, a minichromosome maintenance 10 replication initiation factor (MCM10) promoter, a minichromosome maintenance complex component 2 (MCM2) promoter, a minichromosome maintenance complex component 7 (MCMI) promoter, a MRG domain binding protein (MRGBP) promoter, a methylenetetrahydrofolate dehydrogenase (NADP+ dependent) 2, methenyltetrahydrofolate cyclohydrolase (MTHFD2) promoter, a non-SMC condensin I complex subunit H (NCAPH) promoter, a NDC80, kinetochore complex component (NDC80) promoter, a nudix hydrolase 1 (NUDT1) promoter, a ribonuclease H2 subunit A (RNASEH2A) promoter, a RuvB like AAA ATPase 1 (RUVBL1) promoter, a serologically defined breast cancer antigen NY-BR-85 (SGOL1) promoter, a SHC binding and spindle associated 1 (SHCBP1) promoter, a small nuclear ribonucleoprotein polypeptide G (SNRPG) promoter, a timeless circadian regulator promoter, a thyroid hormone receptor interactor 13 (TRIP13) promoter, a trophinin associated protein (TROAP) promoter, a ubiquitin conjugating enzyme E2 C (UBE2C) promoter, a WD repeat and HMG-box DNA binding protein 1 (WDHD1) promoter, an alpha fetoprotein (AFP) promoter, a fragment thereof, or any combination thereof.

175. The composition of embodiment 173 or 174, wherein said recombinant nucleic acid comprises regulatory elements that silence or attenuate transcription or mRNA half-life of said nucleic acid sequence in normal liver cells.

176. The composition of embodiment 175, wherein said regulatory elements comprise one or more miRNA target sequences in a transcribed, but an untranslated region, of said recombinant nucleic acid.

177. The composition of embodiment 176, wherein the presence of the one or more miRNA target sequences inhibits expression from said recombinant nucleic acid sequence.

178. The composition of any one of embodiments 176-177, wherein said one or more miRNA target sequences comprise at least one miRNA target sequence for at least one tissue specific miRNA.

179. The composition of embodiment 178, wherein said at least one tissue specific miRNA comprises at least one miRNA enriched in normal hepatic tissues.

180. The composition of embodiment 179, wherein said at least one miRNA enriched in normal hepatic tissues comprises miR-122, miR-33, miR-33*, miR-223, miR-30c, miR-144, miR-148a, miR-24, miR-29, or any combination thereof.

181. The composition of any one of embodiments 170-180, wherein said composition further comprises a transfection agent.

182. The composition of embodiment 181, wherein said transfection agent is a linear or branched polyethylenimine, nanoparticle, lipophilic particle, solid nanoparticle, peptides, micelles, dendrimers, polymeric compositions, hydrogels, synthetic or naturally derived nanocell, exosomes, a virus-like particle, or any combination thereof.

183. An engineered particle that mimics one or many functions of a biological cell or macrophage including inducing the expression of a biomarker in a diseased cell preferentially over expression of said biomarker in non-diseased cells such that said relative concentration ratio of said biomarker expressed in said diseased cell over said non-diseased cells is greater than 1.0.

184. The engineered particle of embodiment 183, wherein said engineered particle is an artificial cell, a minimal cell, or a lipid-enclosed synthetic particle.

185. The engineered particle of embodiment 183 or 184, wherein said engineered particle comprises biological membranes, polymeric membranes, simple polymers, crosslinked proteins, lipid membranes or polymer-lipid complexes formed in vitro or in vivo with purified components into nanoparticles, liposomes, polymersomes, exosomes, microvesicles, apoptotic blebs, transport vesicles, synaptic vesicles, secretory vesicles, or microcapsules.

186. The engineered particle of any one of embodiments 183-185, wherein said engineered particle comprises a transmembrane chimeric protein or a naturally occurring protein comprising an extraparticle specific binding domain operably linked to an intraparticle signaling domain, wherein said intraparticle signaling domain is capable of activating at least one enzymatic reaction within said engineered particle.

187. The engineered particle of embodiment 186, wherein said engineered particle comprises a nucleic acid sequence encoding a synthetic biomarker, wherein said at least one enzymatic reaction results in the production of said synthetic biomarker within said engineered particle.

188. The engineered particle of embodiment 186 or 187, wherein said extraparticle specific binding domain comprises an scFv or a Fab fragment.

189. The engineered particle of any one of embodiments 183-188, wherein said engineered particle comprises cytoplasm and other components isolated from intact cells 190. The engineered particle of any one of embodiments 183-173, wherein said engineered particle comprises purified recombinant macromolecular components or macromolecular components such as, but not limited to, cellular proteins, DNA, synthetic gene circuits, organelles, ATP, enzymes, NADP, transcription factors, nucleotides, or cell-free transcription-translation extracts.

191. At least one vector, wherein said at least one vector comprises:
    a plurality of different promoters operably linked to a plurality of different nucleic acid sequences, wherein said promoters drive expression of said plurality of nucleic acid sequences in a cell to yield a plurality of polypeptides or nucleic acid biomarker sequences,
    wherein said promoters induce expression of said plurality of polypeptides or nucleic acid biomarker sequences in a diseased cell preferentially over expression of said plurality of polypeptides or nucleic acid biomarker sequences in non-diseased cells in a subject such that a relative ratio of said plurality of polypeptides or nucleic acid biomarker sequences expressed in said diseased cell over said non-diseased cells is greater than 1.0.

192. The vector of embodiment 191, wherein each of said promoters induce expression of said plurality of polypeptides or nucleic acid biomarker sequences in a diseased cell preferentially over expression of said plurality of polypeptides or nucleic acid biomarker sequences in non-diseased cells in said subject such that a relative ratio of said plurality of polypeptides or nucleic acid biomarker sequences expressed in said diseased cell over said non-diseased cells is greater than 1.0.

193. The vector of embodiment 191 or 192, wherein said plurality of different promoters comprises at least 2, at least 3, at least 4, or at least 5 promoters.

194. The vector of any one of embodiments 191-193, wherein said plurality of different promoters comprises at most 12, at most 13, at most 14, or at most 15 promoters.

195. The vector of any one of embodiments 191-194, wherein at least two of said plurality of different promoters are selected from Table 1.

196. The vector of any one of embodiments 191-195, wherein said vector is a plasmid, nanoplasmid, minicircle, recombinant viral vector, or CELiD.

197. The vector of embodiment 196, wherein said minicircle is a self-replicating minicircle.

198. The vector of embodiment 197, wherein said self-replicating minicircle comprises an S/MAR element.

199. The vector of any one of embodiments 191-198, wherein said plurality of polypeptides or nucleic acid biomarker sequences comprises at least one reporter polypeptide selected from the group consisting of a photoacoustic reporter, a bioluminescent reporter, an autofluorescent reporter, a chemiluminescent reporter, a luminescent reporter, or a colorimetric reporter, or any combination thereof.

200. The vector of any one of embodiments 191-199, wherein said plurality of polypeptides or nucleic acid biomarker sequences comprises at least one polypeptide with an N-terminal secretion signal sequence.

201. The vector of any one of embodiments 191-200, wherein said plurality of polypeptides or nucleic acid biomarker sequences comprises at least one nucleic acid biomarker sequence selected from the group consisting of a ribozyme, a self-splicing intron, a microRNA, a RNA aptamer, or another type of quantifiable RNA biomarker.

202. The vector of any one of embodiments 191-201, wherein said disease is cancer, an autoimmune disease, or a neurodegenerative disease.

203. A method for detecting a disease in a subject, comprising:
administering to a subject a composition comprising the vector according to any one of embodiments 191-201;
detecting said plurality of polypeptides or nucleic acid biomarker sequences to obtain an expression profile; and
detecting said diseased cell based said expression profile, thereby detecting said disease.

204. The method of embodiment 203, wherein (b) comprises detecting said plurality of polypeptides or nucleic acid biomarker sequences from a sample from said subject.

205. The method of embodiment 204, wherein said sample is a bodily fluid from said subject.

206. The method of embodiment 205, wherein said biological sample is a blood or blood-based sample from said subject.

207. The method of any one of embodiments 203-206, wherein said plurality of polypeptides or nucleic acid biomarker sequences comprises at least one nucleic acid biomarker sequence, wherein (b) comprises detecting said at least one nucleic acid biomarker sequence by quantitative PCR, sequencing, or a hybridization-based technique.

208. The method of any one of embodiments 203-207, wherein said plurality of polypeptides or nucleic acid biomarker sequences comprises at least one reporter polypeptide, comprising detecting said at least one reporter polypeptide by photoacoustic assay, bioluminescence assay, fluorescence assay, chemiluminescent assay, colorimetric assay, or any combination thereof.

209. The method of any one of embodiments 203-208, wherein (c) comprises applying a machine learning or classifier algorithm to said expression profile, wherein said machine learning or classifier algorithm is configured to distinguish between an expression profile indicative of a diseased cell from an expression profile indicative of a non-diseased cell.

210. The method of any one of embodiments 203-209, wherein said composition is administered intravenously, subcutaneously, intraventricularly, intrathecally, intracerebroventricularly, transdermally, intramuscularly, orally, by inhalation, nasally, rectally, intratumorally, proxi-tumorally, or into a lymph node in said subject.

211. The method of any one of embodiments 203-210, wherein said composition further comprises a pharmaceutically acceptable carrier.

212. The method of any one of embodiments 203-211, wherein said composition further comprises a transfection agent.

213. A method for detecting a subject's disease or absence thereof, comprising:
(a) contacting one or more cells of said subject with a genetic construct ex-vivo, wherein: said genetic construct comprises a disease-activated promoter operably linked to a barcode molecule and said disease-activated promoter drives expression of said barcode molecule in a cell affected by said disease;
(b) quantifying an expression level of said barcode molecule; and
(c) detecting said disease or absence thereof based on said expression level.

214. A method for generating a profile of a subject's disease, comprising:
(a) contacting one or more cells of said subject with a plurality of genetic constructs, wherein:
said plurality of genetic constructs comprises a plurality of disease-activated promoters respectively operably linked to a plurality of barcode molecules and said disease-activated promoter drives expression of said corresponding barcode molecule in a cell affected by said disease; and
(b) quantifying expression levels of said plurality of barcode molecules to generate said profile.

215. The method of embodiment 214, wherein said contacting is ex-vivo.

216. The method of embodiment 214, wherein said contacting is in vivo.

217. The method of embodiment 213 or embodiment 214, further comprising isolating said one or more cells from said subject.

218. The method of embodiment 213 or embodiment 214, wherein said disease-activated promoter comprises a cancer-activated promoter or said plurality of disease-activated promoters comprise a plurality of cancer-specific promoters.

219. The method of embodiment 218, wherein the cancer-activated promoter or plurality of cancer-activated promoters are activated in Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, Uveal Melanoma, lip melanoma, spindle cell carcinoma, liposarcoma, nasal sarcoma, mammary adenocarcinoma, insulinoma, osteosarcoma, mast cell tumors, hemangiosarcoma, non-small cell lung carcinoma (NSCLC), marginal lymphoma, malignant melanoma, or chronic lymphocytic leukemia.

220. The method of any one of embodiments 218-219, comprising a plurality of cancer-activated promoters, wherein said plurality of cancer-activated promoters comprises promoters activated in a plurality of cancers within different tissue origins.

221. The method of any one of embodiments 220, wherein said plurality of cancer-specific promoters are activated in a plurality (e.g. two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-five or more, or thirty or more) of different tissue origins.

222. The method of any one of embodiments 220-221, wherein said plurality of cancer-specific promoters comprise a first promoter that produces a strong signal, a second promoter that produces a low background signal, a third promoter that has a high signal-to-background signal ratio, or any combinations thereof.

223. The method of embodiment 222, wherein said plurality of cancer-specific promoters comprises at least one said first promoter, at least one said second promoter, and at least one said third promoter.

224. The method of embodiment 214, wherein said plurality of disease-activated promoters comprise a plurality of cancer-activated promoters that are selective for and activated in a selected group of tissue origin.

225. The method of embodiment 214, wherein said plurality of disease-activated promoters comprises a plurality of cancer-activated promoters that are selective for and activated in the same tissue origin.

226. The method of embodiment 214, wherein said plurality of disease-activated promoters comprises a plurality of cancer-activated promoters activated in a plurality of different molecular subtypes of a cancer respectively within the same tissue origin.

227. The method of embodiment 214, wherein said plurality of disease-specific promoters comprise a plurality of cancer-activated promoters activated in one molecular subtype of a cancer within a tissue origin.

228. The method of embodiment 214, wherein said plurality of genetic constructs comprises two or more different cancer-activated promoters activated in one stage of a cancer within a tissue origin.

229. The method of any of embodiments 213-228, comprising contacting at least one cell with said plurality of genetic constructs or said genetic construct.

230. The method of any of embodiments 213-229, wherein said genetic construct or said plurality of genetic constructs comprises a non-viral vector.

231. The method of embodiment 230, wherein said non-viral vector is a nanoplasmid.

232. The method of any of embodiments 213-229, wherein said genetic construct or said plurality of genetic constructs comprises a replication-incompetent recombinant virion or an isolated inverted terminal repeat (ITRs) derived therefrom.

233. The method of embodiment 232, wherein said virion is a lentiviral, adeno-associated viral, adenoviral, or gamma-retroviral virion.

234. The method of embodiment 232, wherein said virion is derived from a virus with primarily episomal genome maintenance within infected cells.

235. The method of embodiment 233, wherein said replication-incompetent virion is a recombinant adenovirus vector.

236. The method of embodiment 235, wherein said AAV is serotype 1, 2, 3, 4, 5, 6, 8, 9, AdS, Ad-RGD, or Ad-19a/64, or a pseudotyped variant thereof.

237. The method of any one of embodiments 232-236, wherein said replication-incompetent recombinant virion is combined with said cells from said subject at a multiplicity of infection (MOI) of 0.001-10.

238. The method of any one of embodiments 213-237, wherein said subject is human or canine.

239. The method of any one of embodiments 213-238, wherein said subject has previously received surgical, chemotherapeutic, radiological or immunotherapeutic treatment for cancer.

240. The method of any one of embodiments 213-239, wherein said subject has at least one risk factor for cancer such as, having Li-Fraumeni syndrome, lynch syndrome, familial adenomatous polyposis, lung nodules, Von Hippel-Lindau disease, aplastic anemia, myelodysplastic syndrome, Cowden syndrome, hereditary breast and ovarian cancer syndrome (HBOC), or BRCA mutations; being a current smoker, ex-smoker or exposed to heavy doses of second hand smoke; exposure to carcinogens, excessive sunlight, immunosuppressive agents, infectious agents such as hepatitis B or C as well as human papilloma virus; or being obese.

241. The method of any one of embodiments 213-239, wherein said subject has at least one symptom of cancer, such as a positive signal on a mammogram or from a cancer screening diagnostic test, disproportionate blood cell distribution, weight loss, swollen lumps or glands, night sweats, blood in urine, blood in stool, unexpected bleeding or discharge from body including nipples, dizziness, blurred vision or loss of balance, diarrhea, acute pain, low grade fever, constipation, loss of appetite, nagging cough or hoarseness, or jaundice.

242. The method of any of embodiments 214-241, further comprising (c) detecting said disease based on said profile.

243. The method of embodiment 242, further comprising processing said profile comprising expression levels of said barcode molecules corresponding to said plurality of disease-activated promoters using a classifier to detect said disease or absence thereof.

244. The method of embodiment 243, wherein detecting said disease or absence thereof further comprises determining a tissue origin.

245. The method of embodiment 213, comprising detecting said disease or absence thereof with an AUC of at least 65%, 70%, 75%, 80%, 85%, 90%, or 95%.

246. The method of embodiment 213, comprising detecting said disease or absence thereof with a sensitivity of at least 65%, 70%, 75%, 80%, 85%, 90%, or 95%.

247. The method of embodiment 213, comprising detecting said disease or absence thereof with a specificity of at least 65%, 70%, 75%, 80%, 85%, 90%, or 95%.

248. The method of embodiment 242, further comprising, subsequent to (c), (d) using one or more disease-activated promoters corresponding to a disease detected in (c) to repeat (a) and (b) to confirm said disease detected in (c) and/or detect a subtype of said disease detected in (c).

249. The method of embodiment 248, further comprising repeating (d) to confirm said disease detected in (c) and/or detect a subtype of said disease detected in (c).

250. The method of any one of embodiments 213-249, wherein a barcode molecule uniquely identifies a disease-specific promoter of said genetic construct.

251. The method of any one of embodiments 213-249, wherein said barcode molecule comprises a nucleotide sequence or a peptide sequence.

252. The method of embodiment 251, wherein said barcode molecule comprises a nucleotide sequence, wherein said nucleotide sequence comprises a unique DNA or RNA.

253. The method of embodiment 252, wherein said barcode molecule comprises RNA, wherein said RNA is a barcode processed from a miRNA scaffold.

254. The method of embodiment 253, wherein said miRNA scaffold comprises 5', 3', and loop regions derived said miRNA scaffold, and stem regions comprising said barcode.

255. The method of embodiment 251, wherein said barcode molecule comprises a peptide sequence, wherein said peptide sequence comprises an enzyme reporter.

256. The method of embodiment 251, wherein said enzyme reporter is a luciferase, an EGFP, a GFP, an RFP, horseradish peroxidase (HRP), an alkaline phosphatase (AP), glucose oxidase (GO), or beta galactosidase (BGAL), or any combination thereof.

257. The method of any one of embodiments 213-256, wherein said barcode molecule is secretable or sheddable from said cells.

258. The method of embodiment 257, comprising quantifying an expression level of said barcode or expression levels of said barcodes in extracellular fluid in contact with said cells.

259. The method of embodiment 258, wherein said contact with said cells is in vivo and said extracellular fluid comprises blood or blood fractions, saliva, urine, stool, cerebrospinal fluid, semen, vaginal secretions, sputum, sweat, breast milk, synovial fluid, mucus (including rheum), tears, bile, gastric fluid, interstitial fluid, aqueous humor, amniotic fluid, or pleural fluid.

260. The method of embodiment 257 or embodiment 258, comprising quantifying an expression level of said barcode or expression levels of said barcodes in extracellular fluid at least 8 hours, at least 12 hours, at least 24 hours, at least 36 hours, at least 48 hours, at least 72 hours following said contact with said cells.

261. The method of any one of embodiments 252-254, wherein said quantifying comprises sequencing said barcode molecule or plurality of barcode molecules.

262. The method of any one of embodiments 255-257, wherein said quantifying comprises measuring an activity of said enzyme reporter or reporters.

263. The method of embodiment 262, wherein said activity of said enzyme reporter or reporters is measure by an immunochemistry reaction, lateral flow electrophoresis, or mass spectrophotometer.

264. The method of any of embodiments 214-265, further comprising transmitting said profile on an intranet or the internet.

265. The method of any of embodiments 213-264, further comprising providing a therapeutic treatment based on said detecting said disease or absence thereof or said profile.

---

What is claimed is:

1. A method, comprising:
   (a) introducing a plurality of DNA molecules to a subject suspected of having a cancer via intravenous administration, wherein:
      said plurality of DNA molecules comprises a plurality of different promoters or their functional fragments thereof from genes overexpressed in a tumor cell operably linked to genes encoding reporter proteins, wherein said plurality of DNA molecules is in nanoplasmids or linear vectors comprising double-stranded DNA molecules, wherein said plurality of different promoters or their functional fragments thereof from said genes overexpressed in said tumor cell drive expression of said reporter proteins in a cell transfected by said nanoplasmids or said linear vectors, wherein said plurality of different promoters from said genes overexpressed in said tumor cell are selected from the group consisting of a BIRC5 promoter, AGR2 promoter, CST1 promoter, FAMl11B promoter, CEP55 promoter, CEACAM5 promoter, KIF20A promoter and their functional fragments thereof; wherein said tumor cell is a liver, ovarian, pancreatic, breast, lung, smooth muscle, bladder, kidney, skin, prostate, or bone tumor cell; wherein said reporter proteins comprise human sodium iodide symporter, herpes simplex virus thymidine kinase (HSV-tk) or its functional mutants thereof, dopamine D2 receptor or its functional mutants thereof, or a peptide epitope tag; and
   (b) after step (a), intravenous administrating positron emission tomography (PET)-active iodine or iodide isotopes to said subject suspected of having a cancer when said reporter proteins comprise said human sodium iodide symporter or intravenous administrating labeled-pyrimidine reporters which can detected by PET or labeled-pyrimidine-analog PET reporters which can detected by PET to said subject suspected of having a cancer when said reporter proteins comprise said HSV-tk or its functional mutants thereof or intravenous administrating labeled dopamine D2 receptor binders which can detected by PET to said subject suspected of having a cancer when the reporter proteins comprise said dopamine D2 receptor or its functional mutants thereof, or intravenous administrating a labeled binding element that recognizes the peptide epitope tag and can detected by PET to said subject suspected of having a cancer when said reporter proteins comprise said peptide epitope tag; and
      detecting a visual image of said reporter proteins in a tissue or tissues of said subject suspected of having a cancer via a PET imaging method.

2. The method of claim 1, wherein said plurality of different promoters of said genes overexpressed in said tumor cell comprises three promoters.

3. The method of claim 1, wherein said plurality of different promoters of said genes overexpressed in said tumor cell comprises a plurality of promoters which can be activated in a plurality of different molecular subtypes of a cancer from the same tissue origin if the plurality of promoters is present in the cancer.

4. The method of claim 1, wherein said plurality of DNA molecules is in said nanoplasmids, wherein said nanoplasmids further comprise: (i) a minimized bacterial ColE1 or R6K origin of replication; and (ii) a bacterial RNA-based selectable marker.

5. The method of claim 1, wherein said subject is a human or canine.

6. The method of claim 1, wherein said subject has at least one symptom of cancer.

7. The method of claim 1, wherein step (b) is performed at least 8 hours, at least 12 hours, at least 24 hours, at least 36 hours, at least 48 hours, or at least 72 hours after step (a).

8. The method of claim 1, wherein said plurality of DNA molecules is introduced to said subject suspected of having a cancer via intravenous administration as a composition, wherein said composition comprises said plurality of DNA molecules and a linear or branched polyethylenimine.

9. The method of claim 1, wherein said plurality of DNA molecules is introduced to said subject suspected of having a cancer via intravenous administration as a composition, wherein said composition comprises said plurality of DNA molecules and lipophilic nanoparticles.

10. The method of claim 1, wherein said plurality of DNA molecules is introduced to said subject suspected of having a cancer via intravenous administration as a composition, wherein said composition comprises said plurality of DNA molecules and poly(β-amino ester)s C32-122, or poly(β-amino ester)s C32-145.

11. The method of claim 1, wherein said plurality of different promoters of said genes overexpressed in said tumor cell comprises: (i) BIRC5 promoter, (ii) CST1 promoter or CEP55 promoter, and (iii) FAM111B promoter or CEACAM5 promoter, or its functional fragments thereof.

12. The method of claim 1, wherein a forward and a reverse strand of said double-stranded DNA molecules are covalently linked on each of their terminal ends.

13. The method of claim 1, wherein said labeled binding element that recognizes the epitope tag and can detected by PET comprises an antibody or an antigen-binding fragment.

* * * * *

SEQUENCE LISTING

```
<160> NUMBER OF SEQ ID NOS: 7

<210> SEQ ID NO 1
<211> LENGTH: 4098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ccccaactgg ggtaaccttt gggctccccg ggcgcgacta gtaataaaat atctttattt      60
tcattacatc tgtgtgttgg ttttttgtgt gaatcgatag tactaacata cgctctccat     120
caaaacaaaa cgaaacaaaa caaactagca aaataggctg tccccagtgc aagtgcaggt     180
gccagaacat ttctctacta gtgccataga accagagaag tgagtggatg tgatgcccag     240
ctccagaagt gactccagaa caccctgttc caaagcagag gacacactga ttttttttt      300 aataggctgc aggacttact gttggtggga cgccctgctt tgcgaaggga aaggaggagt     360
ttgccctgag cacaggcccc caccctccac tgggctttcc ccagctccct tgtcttctta     420
tcacggtagt ggcccagtcc ctggcccctg actccagaag gtggccctcc tggaaaccca     480
ggtcgtgcag tcaacgatgt actcgccggg acagcgatgt ctgctgcact ccatccctcc     540
cctgttcatt tgtccttcat gcccgtctgg agtagatgct ttttgcagag gtggcaccct     600
```

```
gtaaagctct cctgtctgac ttttttttttt tttttagact gagttttgct cttgttgcct    660
aggctggagt gcaatggcac aatctcagct cactgcaccc tctgcctccc gggttcaagc    720
gattctcctg cctcagcctc ccgagtagtt gggattacag gcatgcacca ccacgcccag    780 ctaattttttg tattttttagt agagacaagg tttcaccgtg atggccaggc tggtcttgaa    840
ctccaggact caagtgatgc tcctgcctag gcctctcaaa gtgttgggat tacaggcgtg    900
agccactgca cccggcctgc acgcgttctt tgaaagcagt cgaggggggcg ctaggtgtgg   960 gcagggacga gctggcgcgg cgtcgctggg tgcaccgcga ccacgggcag agccacgcgg  1020
cgggaggact acaactcccg gcacaccccg cgccgcccg cctctactcc cagaaggccg  1080
cggggggtgg accgcctaag agggcgtgcg ctcccgacat gccccgcggc gcgccattaa  1140
ccgccagatt tgaatcgcgg gacccgttgg cagaggtggg aattcaccgg tcaccatggt  1200 tctgggccc tgcatgctgc tgctgctgct gctgctgggc ctgaggctac agctctccct  1260
gggcatcatc ccagttgagg aggagaaccc ggacttctgg aaccgcgagg cagccgaggc  1320
cctgggtgcc gccaagaagc tgcagcctgc acagacagcc gccaagaacc tcatcatctt  1380
cctgggcgat gggatggggg tgtctacggt gacagctgcc aggatcctaa aagggcagaa  1440
gaaggacaaa ctggggcctg agataccccct ggctatggac cgcttcccat atgtggctct  1500
gtccaagaca tacaatgtag acaaacatgt gccagacagt ggagccacag ccacggccta  1560
cctgtgcggg gtcaagggca acttccagac cattggcttg agtgcagccg cccgcttttaa  1620 ccagtgcaac acgacacgcg gcaacgaggt catctccgtg atgaatcggg ccaagaaagc  1680
agggaagtca gtgggagtgg taaccaccac acgagtgcag cacgcctcgc cagccggcac  1740
ctacgcccac acggtgaacc gcaactggta ctcggacgcc gacgtgcctg cctcggcccg  1800
ccaggagggg tgccaggaca tcgctacgca gctcatctcc aacatggaca ttgatgtgat  1860
cctgggtgga ggccgaaagt acatgttttcg catgggaacc ccagaccctg agtacccaga  1920
tgactacagc caaggtggga ccaggctgga cgggaagaat ctggtgcagg aatggctggc  1980
gaagcgccag ggtgcccggt atgtgtggaa ccgcactgag ctcatgcagg cttccctgga  2040
cccgtctgtg acccatctca tgggtctctt tgagcctgga gacatgaaat acgagatcca  2100
ccgagactcc acactggacc cctccctgat ggagatgaca gaggctgccc tgcgcctgct  2160
gagcaggaac ccccgcggct tcttcctctt cgtggagggt ggtcgcatcg accacggtca  2220
tcacgaaagc agggcttacc gggcactgac tgagacgatc atgttcgacg acgccattga  2280
gagggcgggc cagctcacca gcgaggagga cacgctgagc ctcgtcactg ccgaccactc  2340
ccacgtcttc tccttcggag gctaccccct gcgagggagc tccatcttcg ggctggcccc  2400
tggcaaggcc cggacagga aggcctacac ggtcctccta acggaaacg gtccaggcta  2460 tgtgctcaag gacggcgccc ggccggatgt taccgagagc gagagcggga gccccgagta  2520
tcggcagcag tcagcagtgc ccctggacga agagacccac gcaggcgagg acgtggcggt  2580
gttcgcgcgc ggcccgcagg cgcacctggt tcacggcgtg caggagcaga ccttcatagc  2640
gcacgtcatg gccttcgccg cctgcctgga gccctacacc gcctgcgacc tggcgcccccc  2700 cgccggcacc accgacgccg cgcacccggg gcggtcccgg tccaagcgtc tggattgagc  2760
tagcttcgaa tttaaatcgg atccctgcag gagctcgtcg acaatcaacc tctggattac  2820
aaaatttgtg aaagattgac tggtattctt aactatgttg ctccttttac gctatgtgga  2880
tacgctgctt taatgccttt gtatcatgct attgcttccc gtatggcttt cattttctcc  2940
```

| | |
|---|---:|
| tccttgtata aatcctggtt gctgtctctt tatgaggagt gtggcccgt tgtcaggcaa | 3000 |
| cgtggcgtgg tgtgcactgt gtttgctgac gcaaccccca ctggttgggg cattgccacc | 3060 |
| acctgtcagc tcctttccgg gactttcgct ttcccctcc ctattgccac ggcggaactc | 3120 |
| atcgccgcct gccttgcccg ctgctggaca ggggctcggc tgttgggcac tgacaattcc | 3180 |
| gtggtgttgt cggggaaatc atcgtccttt ccttggctgc tcgcctgtgt tgccacctgg | 3240 |
| attctgcgcg ggacgtcctt ctgctacgtc ccttcggccc tcaatccagc ggaccttcct | 3300 |
| tcccgcggcc tgctgccggc tctgcggcct cttccgcgtc ttcgccttcg ccctcagacg | 3360 |
| agtcggatct cccttgggc cgcctccccg cctggtacct ttaagaccaa tgacttacaa | 3420 |
| ggcagctgta gatcttagcc acttttaaa agaaaagggg ggactggaag ggctaattca | 3480 |
| ctcccaacga aaataagatc tgcttttgc ttgtactggg tctctctggt tagaccagat | 3540 |
| ctgagcctgg gagctctctg gctaactagg gaacccactg cttaagcctc aataaagctt | 3600 |
| gccttgagtg cttcaagtag tgtgtgcccg tctgttgtgt gactctggta actagagatc | 3660 |
| cctcagaccc ttttagtcag tgtggaaaat ctctagcagt agtagttcat gtcatcttat | 3720 |
| tattcagtat ttataacttg caaagaaatg aatatcagag agtgagagga acttgtttat | 3780 |
| tgcagcttat aatggttaca aataaagcaa tagcatcaca aatttcacaa ataaagcatt | 3840 |
| tttttcactg cattctagtt gtggtttgtc caaactcatc aatgtatctt atcatgtctg | 3900 |
| gctctagcta tcccgcccct aactccgccc agttccgccc attctccgcc cctcccgccc | 3960 |
| ctaactccgc ccaatggctg actaattttt tttatttatg cagaggccga ggccgcctcg | 4020 |
| gcctctgagc tattccagaa gtagtgagga ggcttttttg gaggcctaga cttttgcaga | 4080 |
| tcgacccatg ggggcccg | 4098 |

<210> SEQ ID NO 2
<211> LENGTH: 4256
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---:|
| ccccaactgg ggtaaccttt gggctccccg ggcgcgacta gtaataaaat atctttattt | 60 |
| tcattacatc tgtgtgttgg ttttttgtgt gaatcgatag tactaacata cgctctccat | 120 |
| caaaacaaaa cgaaacaaaa caaactagca aaataggctg tccccagtgc aagtgcaggt | 180 |
| gccagaacat ttctctacta gtgaattgat gccatagaac cagagaagtg agtggatgtg | 240 |
| atgcccagct ccagaagtga ctccagaaca ccctgttcca aagcagagga cacactgatt | 300 |
| tttttttaa taggctgcag gacttactgt tggtgggacg ccctgctttg cgaagggaaa | 360 |
| ggaggagttt gccctgagca caggccccca ccctccactg ggctttcccc agctcccttg | 420 |
| tcttcttatc acggtagtgg cccagtccct ggccctgac tccagaaggt ggccctcctg | 480 |
| gaaacccagg tcgtgcagtc aacgatgtac tcgccgggac agcgatgtct gctgcactcc | 540 |
| atccctcccc tgttcatttg tccttcatgc ccgtctggag tagatgcttt ttgcagaggt | 600 |
| ggcaccctgt aaagctctcc tgtctgactt ttttttttt tttagactga gttttgctct | 660 |
| tgttgcctag gctggagtgc aatggcacaa tctcagctca ctgcaccctc tgcctcccgg | 720 |
| gttcaagcga ttctcctgcc tcagcctccc gagtagttgg gattacaggc atgcaccacc | 780 |
| acgcccagct aattttttgta tttttagtag agacaaggtt tcaccgtgat ggccaggctg | 840 |

```
gtcttgaact ccaggactca agtgatgctc ctgcctaggc ctctcaaagt gttgggatta      900
caggcgtgag ccactgcacc cggcctgcac gcgttctttg aaagcagtcg aggggcgct       960 aggtgtgggc agggacgagc tggcgcggcg tcgctgggtg caccgcgacc acgggcagag     1020
ccacgcggcg ggaggactac aactcccggc acacccgcg ccgccccgcc tctactccca      1080
gaaggccgcg gggggtggac cgcctaagag ggcgtgcgct cccgacatgc cccgcggcgc     1140
gccattaacc gccagatttg aatcgcggga cccgttggca gaggtggaag cttggcaatc     1200
cggtactgtt ggtaaagcca ccatggaaga tgccaaaaac attaagaagg gcccagcgcc     1260
attctaccca ctcgaagacg ggaccgccgg cgagcagctg cacaaagcca tgaagcgcta     1320
cgccctggtg cccggcacca tcgcctttac cgacgcacat atcgaggtgg acattaccta     1380
cgccgagtac ttcgagatga cgttcggct ggcagaagct atgaagcgct atgggctgaa      1440
tacaaaccat cggatcgtgg tgtgcagcga gaatagcttg cagttcttca tgcccgtgtt     1500
gggtgccctg ttcatcggtg tggctgtggc cccagctaac gacatctaca cgagcgcga     1560 gctgctgaac agcatgggca tcagccagcc caccgtcgta ttcgtgagca agaaagggct     1620
gcaaaagatc ctcaacgtgc aaaagaagct accgatcata caaagatca tcatcatgga     1680 tagcaagacc gactaccagg gcttccaaag catgtacacc ttcgtgactt cccatttgcc     1740
acccggcttc aacgagtacg acttcgtgcc cgagagcttc gaccgggaca aaccatcgc     1800 cctgatcatg aacagtagtg gcagtaccgg attgcccaag ggcgtagccc taccgcaccg     1860
caccgcttgt gtccgattca gtcatgcccg cgaccccatc ttcggcaacc agatcatccc     1920
cgacaccgct atcctcagcg tggtgccatt tcaccacggc ttcggcatgt tcaccacgct     1980
gggctacttg atctgcggct ttcgggtcgt gctcatgtac cgcttcgagg aggagctatt     2040
cttgcgcagc ttgcaagact ataagattca atctgccctg ctggtgccca cactatttag     2100
cttcttcgct aagagcactc tcatcgacaa gtacgaccta agcaacttgc acgagatcgc     2160
cagcggcggg gcgccgctca gcaaggaggt aggtgaggcc gtggccaaac gcttccacct     2220
accaggcatc cgccagggct acggcctgac agaaacaacc agcgccattc tgatcacccc     2280
cgaaggggac gacaagcctg gcgcagtagg caaggtggtg cccttcttcg aggctaaggt     2340
ggtggacttg gacaccggta agacactggg tgtgaaccag cgcggcgagc tgtgcgtccg     2400
tggccccatg atcatgagcg gctacgttaa caaccccgag gctacaaacg ctctcatcga     2460
caaggacggc tggctgcaca cggcgacat cgcctactgg gacgaggacg agcacttctt      2520
catcgtggac cggctgaaga gcctgatcaa atacaagggc taccaggtag ccccagccga     2580
actggagagc atcctgctgc aacaccccaa catcttcgac gccggggtcg ccggcctgcc     2640
cgacgacgat gccggcgagc tgcccgccgc agtcgtcgtg ctggaacacg gtaaaaccat     2700
gaccgagaag gagatcgtgg actatgtggc cagccaggtt acaaccgcca agaagctgcg     2760
cggtggtgtt gtgttcgtgg acgaggtgcc taaaggactg accggcaagt ggacgcccg      2820 caagatccgc gagattctca ttaaggccaa gaagggcggc aagatcgccg tgtaatctag     2880
agctagcgaa ttcagatctg atatctctag agtcgagcta gcttcgaatt taaatcggat     2940
ccctgcagga gctcgtcgac aatcaacctc tggattacaa aatttgtgaa agattgactg     3000
gtattcttaa ctatgttgct cctttacgc tatgtggata cgctgcttta atgcctttgt      3060
atcatgctat tgcttcccgt atggctttca ttttctcctc cttgtataaa tcctggttgc     3120
tgtctcttta tgaggagttg tggcccgttg tcaggcaacg tggcgtggtg tgcactgtgt     3180
ttgctgacgc aaccccccact ggttgggca ttgccaccac ctgtcagctc ctttccggga     3240
```

```
ctttcgcttt cccctccct attgccacgg cggaactcat cgccgcctgc cttgcccgct   3300
gctggacagg ggctcggctg ttgggcactg acaattccgt ggtgttgtcg gggaaatcat   3360
cgtcctttcc ttggctgctc gcctgtgttg ccacctggat tctgcgcggg acgtccttct   3420
gctacgtccc ttcggccctc aatccagcgg accttccttc ccgcggcctg ctgccggctc   3480
tgcggcctct ccgcgtctt cgccttcgcc ctcagacgag tcggatctcc ctttgggccg   3540
cctccccgcc tggtaccttt aagaccaatg acttacaagg cagctgtaga tcttagccac   3600
tttttaaaag aaaaggggg actggaaggg ctaattcact cccaacgaaa ataagatctg   3660 cttttgctt gtactgggtc tctctggtta gaccagatct gagcctggga gctctctggc   3720
taactaggga acccactgct taagcctcaa taaagcttgc cttgagtgct tcaagtagtg   3780
tgtgcccgtc tgttgtgtga ctctggtaac tagagatccc tcagaccctt ttagtcagtg   3840
tggaaaatct ctagcagtag tagttcatgt catcttatta ttcagtattt ataacttgca   3900
aagaaatgaa tatcagagag tgagaggaac ttgtttattg cagcttataa tggttacaaa   3960
taaagcaata gcatcacaaa tttcacaaat aaagcatttt tttcactgca ttctagttgt   4020
ggtttgtcca aactcatcaa tgtatcttat catgtctggc tctagctatc ccgcccctaa   4080
ctccgcccag ttccgcccat tctccgcccc tcccgcccct aactccgccc aatggctgac   4140 taatttttt tatttatgca gaggccgagg ccgcctcggc ctctgagcta ttccagaagt   4200
agtgaggagg ctttttgga ggcctagact tttgcagatc gacccatggg ggcccg        4256
```

<210> SEQ ID NO 3
<211> LENGTH: 281
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ggcttgttgt ccacaaccgt taaaccttaa aagctttaaa agccttatat attcttttt    60 ttcttataaa acttaaaacc ttagaggcta tttaagttgc tgatttatat taatttatt   120 gttcaaacat gagagcttag tacgtgaaac atgagagctt agtacgttag ccatgagagc   180
ttagtacgtt agccatgagg gtttagttcg ttaaacatga gagcttagta cgttaaacat   240
gagagcttag tacgtactat caacaggttg aactgctgat c                      281
```

<210> SEQ ID NO 4
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gtagaattgg taaagagagt cgtgtaaaat atcgagttcg cacatcttgt tgtctgatta    60
ttgatttttg gcgaaaccat ttgatcatat gacaagatgt gtatctacct taacttaatg   120
attttgataa aaatcatta                                                139
```

<210> SEQ ID NO 5
<211> LENGTH: 3962
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 5

```
gccatagaac cagagaagtg agtggatgtg atgcccagct ccagaagtga ctccagaaca    60
ccctgttcca aagcagagga cacactgatt ttttttttta ataggctgca ggacttactg   120
ttggtgggac gccctgcttt gcgaagggaa aggaggagtt tgccctgagc acaggccccc   180
accctccact gggctttccc cagctccctt gtcttcttat cacggtagtg gcccagtccc   240
tggcccctga ctccagaagg tggccctcct ggaaacccag gtcgtgcagt caacgatgta   300
ctcgccggga cagcgatgtc tgctgcactc catccctccc ctgttcattt gtccttcatg   360
cccgtctgga gtagatgctt tttgcagagg tggcaccctg taaagctctc ctgtctgact   420
tttttttttt ttttagactg agttttgctc ttgttgccta ggctgagtg caatggcaca   480
atctcagctc actgcaccct ctgcctcccg ggttcaagcg attctcctgc ctcagcctcc   540
cgagtagttg ggattacagg catgcaccac cacgcccagc taattttgt attttagta    600
gagacaaggt ttcaccgtga tggccaggct ggtcttgaac tccaggactc aagtgatgct   660
cctgcctagg cctctcaaag tgttgggatt acaggcgtga gccactgcac ccggcctgca   720
cgcgttcttt gaaagcagtc gaggggggcgc taggtgtggg cagggacgag ctggcgcggc   780
gtcgctgggt gcaccgcgac cacgggcaga gccacgcggc gggaggacta caactcccgg   840
cacacccgc gccgccccgc tctactccc agaaggccgc gggggtgga ccgcctaaga     900
gggcgtgcgc tcccgacatg ccccgcggcg cgccattaac cgccagattt gagtcgcggg   960
acccgttggc agaggtggga attcaccggt caccatggtt ctgggccct gcatgctgct   1020
gctgctgctg ctgctgggcc tgaggctaca gctctccctg ggcatcatcc cagttgagga   1080
agagaacccg gacttctgga accgcgaggc agccgaggcc ctgggtgccg ccaagaagct   1140
gcagcctgca cagacagccg ccaagaacct catcatcttc ctgggcgatg ggatgggggt   1200
gtctacggtg acagctgcca ggatcctaaa agggcagaag aaggacaaac tggggcctga   1260
gataccctg gctatggacc gcttcccata tgtggctctg tccaagacat acaatgtaga   1320
caaacatgtg ccagacagtg agccacagc cacgcctac ctgtgcgggg tcaagggcaa    1380
cttccagacc attggcttga gtgcagccgc ccgctttaac cagtgcaaca cgacacgcgg   1440
caacgaggtc atctccgtga tgaatcgggc caagaaagca gggaagtcag tgggagtggt   1500
aaccaccaca cgagtgcagc acgcctcgcc agccggcacc tacgcccaca cggtgaaccg   1560
caactggtac tcggacgccg acgtgcctgc ctcggcccgc caggaggggt gccaggacat   1620
cgctacgcag ctcatctcca acatggacat tgatgtgatc ctgggtggag gccgaaagta   1680
catgtttcgc atgggaaccc cagacccctga gtacccagat gactacagcc aaggtgggac   1740
caggctggac gggaagaatc tggtgcagga atggctggcg aagcgccagg gtgcccggta   1800
tgtgtggaac cgcactgagc tcatgcaggc ttccctggac ccgtctgtga cccatctcat   1860
gggtctcttt gagcctggag acatgaaata cgagatccac cgagactcca cactggaccc   1920
ctcctgatg gagatgacag aggctgccct gcgcctgctg agcaggaacc cccgcggctt   1980
cttcctcttc gtggagggtg gtcgcatcga ccacggtcat cacgaaagca gggcttaccg   2040
ggcactgact gagacgatca tgttcgacga cgccattgag agggcgggcc agctcaccag   2100
cgaggaggac acgctgagcc tcgtcactgc cgaccactcc cacgtcttct ccttcggagg   2160
ctaccccctg cgagggagct ccatcttcgg gctggccccct ggcaaggccc gggacaggaa   2220
```

-continued

| | | | | |
|---|---|---|---|---|
| ggcctacacg | gtcctcctat | acggaaacgg | tccaggctat | gtgctcaagg | acggcgcccg | 2280 |
| gccggatgtt | accgagagcg | agagcgggag | ccccgagtat | cggcagcagt | cagcagtgcc | 2340 |
| cctggacgaa | gagacccacg | caggcgagga | cgtggcggtg | ttcgcgcgcg | gcccgcaggc | 2400 |
| gcacctggtt | cacggcgtgc | aggagcagac | cttcatagcg | cacgtcatgg | ccttcgccgc | 2460 |
| ctgcctggag | ccctacaccg | cctgcgacct | ggcgcccccc | gccggcacca | ccgacgccgc | 2520 |
| gcacccgggg | cggtcccggt | ccaagcgtct | ggattgagct | agcttcgaat | ttaaatcgga | 2580 |
| tccctgcagg | agctcgtcga | caatcaacct | ctggattaca | aaatttgtga | aagattgact | 2640 |
| ggtattctta | actatgttgc | tccttttacg | ctatgtggat | acgctgcttt | aatgcctttg | 2700 |
| tatcatgcta | ttgcttcccg | tatggctttc | attttctcct | ccttgtataa | atcctggttg | 2760 |
| ctgtctcttt | atgaggagtt | gtggcccgtt | gtcaggcaac | gtggcgtggt | gtgcactgtg | 2820 |
| tttgctgacg | caacccccac | tggttggggc | attgccacca | cctgtcagct | cctttccggg | 2880 |
| actttcgctt | tccccctccc | tattgccacg | gcggaactca | tcgccgcctg | ccttgcccgc | 2940 |
| tgctggacag | gggctcggct | gttgggcact | gacaattccg | tggtgttgtc | ggggaaatca | 3000 |
| tcgtcctttc | cttggctgct | cgcctgtgtt | gccacctgga | ttctgcgcgg | gacgtccttc | 3060 |
| tgctacgtcc | cttcggccct | caatccagcg | gaccttcctt | cccgcggcct | gctgccggct | 3120 |
| ctgcggcctc | ttccgcgtct | tcgccttcgc | cctcagacga | gtcggatctc | cctttgggcc | 3180 |
| gcctccccgc | ctggtacaag | taaccgcgaa | ttcctgtgcc | ttctagttgc | cagccatctg | 3240 |
| ttgtttgccc | ctcccccgtg | ccttccttga | ccctggaagg | tgccactccc | actgtccttt | 3300 |
| cctaataaaa | tgaggaaatt | gcatcgcatt | gtctgagtag | gtgtcattct | attctggggg | 3360 |
| gtggggtggg | gcaggacagc | aaggggagg | attgggaaga | caatagcagg | catgctgggg | 3420 |
| atgcggtggg | ctctatggcc | cggacggcc | gctagcccgc | ctaatgagcg | ggcttttttt | 3480 |
| tggcttgttg | tccacaaccg | ttaaacctta | aaagctttaa | aagccttata | tattcttttt | 3540 |
| tttcttataa | aacttaaaac | cttagaggct | atttaagttg | ctgatttata | ttaattttat | 3600 |
| tgttcaaaca | tgagagctta | gtacgtgaaa | catgagagct | tagtacgtta | gccatgagag | 3660 |
| cttagtacgt | tagccatgag | ggtttagttc | gttaaacatg | agagcttagt | acgttaaaca | 3720 |
| tgagagctta | gtacgtacta | tcaacaggtt | gaactgctga | tccacgttgt | ggtagaattg | 3780 |
| gtaaagagag | tcgtgtaaaa | tatcgagttc | gcacatcttg | ttgtctgatt | attgattttt | 3840 |
| ggcgaaacca | tttgatcata | tgacaagatg | tgtatctacc | ttaacttaat | gattttgata | 3900 |
| aaaatcatta | ggtacggccg | cggtgccagg | gcgtgccctt | gggctccccg | ggcgcgacta | 3960 |
| gt | | | | | | 3962 |

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 6
aaauguacug cgcguggaga c                                           21

<210> SEQ ID NO 7
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 7

Asp Tyr Lys Asp Asp Asp Lys
1               5
```